United States Patent
Fang et al.

(10) Patent No.: US 8,101,634 B2
(45) Date of Patent: Jan. 24, 2012

(54) BICYCLIC COMPOUNDS AND USE AS ANTIDIABETICS

(75) Inventors: Jing Fang, Durham, NC (US); Jun Tang, Durham, NC (US); Andrew J Carpenter, Durham, NC (US); Gregory Peckham, Durham, NC (US); Christopher R Conlee, Durham, NC (US); Kien S Du, Durham, NC (US); Subba Reddy Katamreddy, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 223 days.

(21) Appl. No.: 12/517,620

(22) PCT Filed: Dec. 5, 2007

(86) PCT No.: PCT/US2007/086434
§ 371 (c)(1),
(2), (4) Date: Jun. 4, 2009

(87) PCT Pub. No.: WO2008/070692
PCT Pub. Date: Jun. 12, 2008

(65) Prior Publication Data
US 2010/0029650 A1 Feb. 4, 2010

Related U.S. Application Data

(60) Provisional application No. 60/868,789, filed on Dec. 6, 2006.

(51) Int. Cl.
*A61K 31/424* (2006.01)
*A61K 31/445* (2006.01)
*C07D 401/14* (2006.01)
*C07D 413/14* (2006.01)

(52) U.S. Cl. .............. 514/315; 546/184
(58) Field of Classification Search .......... 514/315; 546/184
See application file for complete search history.

(56) References Cited

U.S. PATENT DOCUMENTS

| 6,995,144 B2 | 2/2006 | Ozaki et al. |
| 7,265,108 B2 * | 9/2007 | Ozaki et al. ............ 514/230.5 |
| 2002/0151712 A1 | 10/2002 | Lin et al. |
| 2004/0167224 A1 | 8/2004 | Ozaki et al. |
| 2005/0245527 A1 | 11/2005 | Ozaki et al. |
| 2007/0293496 A1 | 12/2007 | Ozaki et al. |
| 2008/0058339 A1 | 3/2008 | Brandt et al. |
| 2008/0103123 A1 | 5/2008 | Brandt et al. |
| 2008/0103141 A1 | 5/2008 | Brandt et al. |

FOREIGN PATENT DOCUMENTS

| WO | WO 91/03243 | 3/1991 |
| WO | WO 02/49648 | 6/2002 |
| WO | WO 03/084948 | 10/2003 |
| WO | WO 2005/077898 | 8/2005 |
| WO | WO 2006/113704 | 10/2006 |
| WO | WO 2006/129199 | 12/2006 |
| WO | WO 2007/003962 | 1/2007 |
| WO | WO 2008/025798 | 3/2008 |

OTHER PUBLICATIONS

J. Yuan, et al., *Preparation of substituted heteroaryl CB1 antagonists*, retrieved from STN Database accession No. 2006:1124114 RN: 913276-91-2; p. 9, lines 23, 38 (abstract). XP002499851. Database CA (online) Chemical Abstracts Service, Ohio, U.S.

* cited by examiner

*Primary Examiner* — Susannah Chung
(74) *Attorney, Agent, or Firm* — Bonnie L. Deppenbrock

(57) ABSTRACT

The present invention relates to novel compounds that are useful in the treatment of metabolic disorders, particularly type II diabetes mellitus and related disorders, and also to the methods for the making and use of such compounds.

5 Claims, No Drawings

US 8,101,634 B2

BICYCLIC COMPOUNDS AND USE AS ANTIDIABETICS

This application is filed pursuant to 35 U.S.C. §371 as a United States National Phase Application of International Application No. PCT/US2007/086434 filed Dec. 5, 2007, which claims priority from U.S. 60/868,789 filed Dec. 6, 2006.

FIELD OF THE INVENTION

The present invention relates to novel compounds that are useful in the treatment and prevention of metabolic disorders, including diabetes mellitus (type I and type II), obesity, and related disorders, and also includes methods for making, pharmaceutical compositions containing, and therapeutic uses for such compounds.

BACKGROUND OF THE INVENTION

Diabetes mellitus is an ever-increasing threat to human health. For example, in the United States current estimates maintain that about 16 million people suffer from diabetes mellitus.

Type I diabetes, also known as insulin-dependent diabetes mellitus (IDDM), is caused by the autoimmune destruction of the insulin producing pancreatic β-cells, and necessitates regular administration of exogenous insulin. Without insulin, cells cannot absorb sugar (glucose), which they need to produce energy. Symptoms of Type I diabetes usually start in childhood or young adulthood. People often seek medical help because they are seriously ill from sudden symptoms of high blood sugar (hyperglycemia).

Type II diabetes, also known as non-insulin-dependent diabetes mellitus (NIDDM), manifests with an inability to adequately regulate blood-glucose levels. Type II diabetes may be characterized by a defect in insulin secretion or by insulin resistance, namely those that suffer from Type II diabetes have too little insulin or cannot use insulin effectively. Insulin resistance refers to the inability of body tissues to respond properly to endogenous insulin. Insulin resistance develops because of multiple factors, including genetics, obesity, increasing age, and having high blood sugar over long periods of time. Type II diabetes, sometimes called mature or adult onset diabetes, can develop at any age, but most commonly becomes apparent during adulthood. The incidence of Type II diabetes in children, however, is rising.

In diabetics, glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes accounts for approximately 90-95% of diabetes cases, killing about 193,000 U.S. residents each year. Type II diabetes is the seventh leading cause of all deaths. In Western societies, Type II diabetes currently affects 6% of the adult population with world-wide frequency expected to grow by 6% per annum. Although there are certain inheritable traits that may predispose particular individuals to developing Type II diabetes, the driving force behind the current increase in incidence of the disease is the increased sedentary lifestyle, diet, and obesity now prevalent in developed countries. About 80% of diabetics with Type II diabetes are significantly overweight. As noted above, an increasing number of young people are developing the disease. Type II diabetes is now internationally recognized as one of the major threats to human health in the 21$^{st}$ century.

Type II diabetes currently is treated at several levels. A first level of therapy is through the use of diet and/or exercise, either alone or in combination with therapeutic agents. Such agents may include insulin or pharmaceuticals that lower blood glucose levels. About 49% of individuals with Type II diabetes require oral medication(s), about 40% of individuals require insulin injections or a combination of insulin injections and oral medication(s), and about 10% of individuals may use diet and exercise alone.

Current therapies for diabetes mellitus include: insulin; insulin secretagogues, such as sulphonylureas, which increase insulin production from pancreatic ⎯-cells; glucose-lowering effectors, such as metformin which reduce glucose production from the liver; activators of the peroxisome proliferator-activated receptor-☐ (PPAR-☐), such as the thiazolidinediones, which enhances insulin action; and α-glucosidase inhibitors which interfere with gut glucose production. There are, however, deficiencies associated with currently available treatments, including hypoglycemic episodes, weight gain, loss in responsiveness to therapy over time, gastrointestinal problems, and edema.

There are several areas at which research is being targeted in order to bring new, more effective, therapies to the marketplace. For example, on-going research includes exploring a reduction in excessive hepatic glucose production, enhancing the pathway by which insulin transmits its signal to the cells such that they take up glucose, enhancing glucose-stimulated insulin secretion from the pancreatic ☐-cells, and targeting obesity and associated problems with fat metabolism and accumulation.

One particular target is GPR119. GPR119 is a member of the rhodopsin family of G-protein-coupled receptors. In addition to the "GPR119" identifier, several other identifiers exist, including but not limited to RUP 3, Snorf 25, 19 AJ, GPR 116 (believed to be erroneous), AXOR 20, and PS1. GPR119 is expressed in human gastrointestinal regions and in human islets. Activation of GPR119 has been demonstrated to stimulate intracellular cAMP and lead to glucose-dependent GLP-1 and insulin secretion. See, T. Soga et al., *Biochemical and Biophysical Research Communications* 326 (2005) 744-751, herein incorporated by reference with regard to a background understanding of GPR119.

In type 2 diabetes the action of GLP-1 on the β-cell is maintained, although GLP-1 secretion, itself, is reduced. More recently, therefore, much research has been focused on GLP-1. Studies show glucose-lowering effects in addition to GLP-1's ability to stimulate glucose-dependent insulin secretion including, but not limited to, an inhibition of the release of the hormone glucagon following meals, a reduction in the rate at which nutrients are absorbed into the bloodstream, and a reduction of food intake. Studies demonstrate that treatments to increase GLP-1, therefore, may be used for a variety of conditions and disorders including but not limited to metabolic disorders, gastrointestinal disorders, inflammatory diseases, psychosomatic, depressive, and neuropsychiatric disease including but not limited to diabetes mellitus (Type 1 and Type 2), metabolic syndrome, obesity, appetite control and satiety, weight loss, stress, inflammation, myocardial ischemia/reperfusion injury, Alzheimer's Disease, and other diseases of the central nervous system.

The use of exogenous GLP-1 in clinical treatment is severely limited, however, due to its rapid degradation by the protease DPP-IV. There are multiple GLP-1 mimetics in development for type 2 diabetes that are reported in the literature, all are modified peptides, which display longer half-lives than endogenous GLP-1. For example, the product sold under the tradename BYETTA® is the first FDA-approved agent of this new class of medications. These mimetics, however, require injection. An oral medication that is able to elevate GLP-1 secretion is desirable. Orally available inhibitors of DPP-IV, which result in elevation in intact GLP-1, are now available, such as sitagliptin, marketed under the brand name JANUVIA®. Nevertheless, a molecule which may stimulate GLP-1 secretion would provide a therapeutic benefit. A molecule which could stimulate both GLP-1 secretion and insulin secretion through effects on the L-cell and direct effects on the β-cell would hold much promise for type 2 diabetes therapy.

The present invention identifies agonists of GPR119 which increase glucose-disposal in part through elevation of GIP, GLP-1, and insulin. Moreover, studies demonstrate that GPR119 agonists such as the compounds of the present invention can stimulate incretins independently of glucose. GIP and GLP-1 are peptides, known as incretins, secreted from enteroendocrine K and L cells, respectively, in response to ingestion of nutrients, and have a wide variety of physiological effects that have been described in numerous publications over the past two decades. See, for example, Bojanowska, E. et al., *Med. Sci. Monit.*, August 2005, 11(8): RA271-8; Perry, T. et al., *Curr. Alzheimer Res.*, July 2005, 2(3): 377-85; and Meier, J. J. et al., *Diabetes Metab. Res. Rev.*, 2005, March-April; 21(2); 91-117 (each herein incorporated by reference with regard to a background understanding of incretins). Moreover, although the mechanisms regulating GLP-1 secretion remain unclear, the initial rapid rise in GLP-1 following a meal may be a result of hormonal stimulation of neuronal afferents involving GIP. See, for example, J. N. Roberge and P. L. Brubaker, *Endocrinology* 133 (1993), pp. 233-240 (herein incorporated by reference with regard to such teaching). Furthermore, later increases in GLP-1 may involve direct activation of L-cells by nutrients in the distal small-intestine and the colon. GIP and GLP-1 are potent stimulators of the body's ability to produce insulin in response to elevated levels of blood sugar. In Type 2 diabetes, patients display a decreased responsiveness to GIP but not GLP-1, with respect to its ability to stimulate insulin secretion. The mechanism behind the decreased responsiveness to GIP remains unclear since type 2 diabetics retain sensitivity to a bolus administration of GIP but not to a continuous infusion (Meier et al. 2004 Diabetes 53 S220-S224). Moreover recent studies with a long-acting fatty-acid derivative of GIP showed beneficial effects on glucose homeostasis in ob/ob mice following 14 days of treatment (Irwin N. et al. (2006) J. Med. Chem. 49, 1047-1054.)

Agonists to GPR119 may be of therapeutic value for diabetes and associated conditions, particularly type II diabetes, obesity, glucose intolerance, insulin resistance, metabolic syndrome X, hyperlipidemia, hypercholesterolemia, and atherosclerosis.

Pyridazines are disclosed in U.S. Pat. No. 5,231,184, including compound numbers 145, 152, 153 and 163 having 4 rings.

SUMMARY OF THE PRESENT INVENTION

There is provided a compound of the formula (I) or a pharmaceutically acceptable salt thereof:

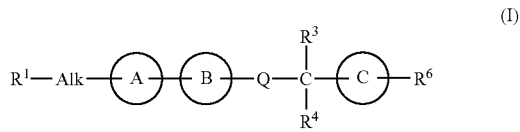

wherein
$R^1$ is selected from the group consisting of halogen, $F_3C-$, $NC-$, $HO-$, $Ar-$, $R^7S-$, $R^7S(O)-$, $R^7S(O)_2-$, $R^7NHS(O)_2-$, $R^7(C_{1-5}alkyl)NS(O)_2-$, $R^7C(O)-$, $R^7OC(O)-$, $R^8R^9NS(O)_2-$, $R^7NHC(O)-$, $R^8R^9NC(O)-$, $R^7S(O)_2NH-$, and $R^7C(O)NH-$;

Alk is a direct bond or alkylene of 1 to 3 carbons;

rings A and B are independently selected from the group consisting of:

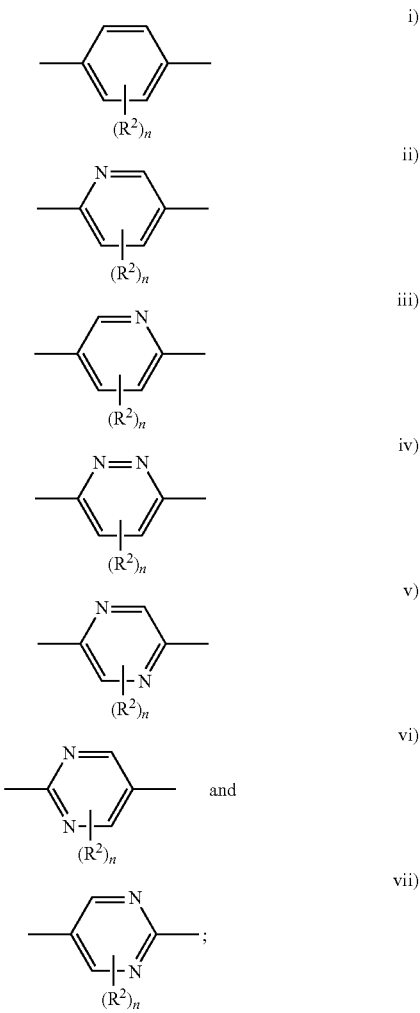

$R^2$ is a replacement for a hydrogen atom and is independently selected from the group consisting of halogen, $-CF_3$, $-OH$, $C_{1-5}$alkyl, $C_{3-7}$ cycloalkyl, and $C_{1-5}$alkoxyl;

n is 0, 1, 2, 3, or 4;

Q is —O—, —S—, —NH—, —NR$^7$—, —S(O)—, or —S(O)$_2$—;

R$^3$ and R$^4$ are independently —H, C$_{1-5}$alkyl, C$_{3-7}$cycloalkyl, or C$_{1-5}$alkyl substituted by a 3-7 membered heterocyclic ring, or R$^3$ and R$^4$ are alkyl and are combined to form a 3-7 membered ring;

ring C is:

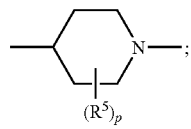
(viii)

R$^5$ is a replacement for a ring hydrogen and is independently selected from the group consisting of halogen, —OH, —CN, C$_{1-5}$alkyl, C$_{3-7}$cycloalkyl, and C$_{1-5}$alkyl substituted by a 3-7 membered heterocyclic ring;

p is 0, 1, 2, or 3;

R$^6$ is —C(O)C(O)R$^7$, —C(O)OR$^{10}$, —C(O)R$^{10}$, —S(O)$_2$C$_{1-5}$alkyl, —S(O)$_2$C$_{3-7}$cycloalkyl, —S(O)$_2$NR$^8$R$^9$, Ar, —CH$_2$Ar, —C(O)NHC$_{1-5}$alkyl, —C(O)NHC$_{3-7}$cycloalkyl, —C(O)NHC$_{1-5}$alkyl-Ar, or —C(O)NR$^{10}$R$^{11}$;

R$^7$ is independently selected from the group consisting of
C$_{1-5}$alkyl,
C$_{3-7}$cycloalkyl,
phenyl,
phenyl(C$_{1-4}$alkylene),
a heterocyclic group of 3-7 ring members, and
C$_{1-5}$alkyl substituted by a heterocyclic group of 3-7 ring members,
which group members may be further optionally substituted by one or more of halogen, —OH, C$_{1-5}$alkoxyl, a heteroaryl ring of 5-6 members, —NR$^8$R$^9$, or —C(O)NR$^8$R$^9$;

R$^8$ and R$^9$ are independently selected from the group consisting of —H, C$_{1-5}$alkyl, C$_{3-7}$cycloalkyl, —C(O)OC$_{1-5}$alkyl and a heterocyclic group of 3-7 members or R$^8$ and R$^9$ are alkyl and together combine to form a ring having 4 to 7 ring atoms and optionally containing a heterogroup selected from —O—, —NH—, and —N(C$_{1-5}$alkyl)- and wherein said ring having 4 to 7 ring atoms is optionally substituted by oxo;

R$^{10}$ and R$^{11}$ are independently selected from the group consisting of
C$_{1-5}$alkyl,
C$_{1-5}$alkenyl,
C$_{3-7}$cycloalkyl, and
Ar,
which group members may be further optionally substituted by halogen,
—OH, C$_{1-5}$alkyl, C$_{1-5}$alkoxyl, —Ar, —CH$_2$Ar or —C(O)NR$^8$R$^9$; and Ar is aryl or a 5- or 6-membered heteroaryl group, which may be substituted by one or more substituents independently selected from halogen, —CF$_3$, C$_{1-5}$alkyl, C$_{3-7}$cycloalkyl, —CN, —OR$^7$, —NR$^8$R$^9$, and —NO$_2$.

Embodiments of the invention include a pharmaceutical composition comprising a compound of the present invention and a compound of the invention for use as an active therapeutic substance.

An aspect of the invention is a compound of the invention for use in the treatment (including prophylaxis) of diseases and conditions mediated through GPR119.

An aspect of the invention is a compound of the invention for use in the treatment (including prophylaxis) of metabolic disorders or conditions, such as diabetes and/or obesity.

An aspect of the invention is the use a compound of the invention in the manufacture of a medicament for use in the treatment (including prophylaxis) of metabolic disorders or conditions, such as diabetes and/or obesity.

An aspect of the invention is a method for the treatment (including prophylaxis) of metabolic disorders or conditions, such as diabetes or obesity, comprising the administration of a compound of the invention.

One embodiment of the invention is a method for increasing GLP-1 secretion in a glucose independent and dependent manner through the administration of a GPR119 agonist, such as a compound of the invention.

One embodiment of the invention is a method for reducing food intake through the administration of a GPR119 agonist, such as a compound of the invention.

The present invention covers all combinations of particular and preferred groups herein described.

DETAILED DESCRIPTION OF THE PREFERRED EMBODIMENTS

A compound of the formula (I) or a pharmaceutically acceptable salt thereof:

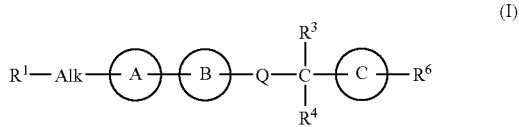
(I)

wherein

R$^1$ is selected from the group consisting of halogen, F$_3$C—, NC—, HO—, Ar—, R$^7$S—, R$^7$S(O)—, R$^7$S(O)$_2$—, R$^7$NHS(O)$_2$—, R$^7$(C$_{1-5}$alkyl)NS(O)$_2$—, R$^7$C(O)—, R$^7$OC(O)—, R$^8$R$^9$NS(O)$_2$—, R$^7$NHC(O)—, R$^8$R$^9$NC(O)—, R$^7$S(O)$_2$NH—, and R$^7$C(O)NH—;

Alk is a direct bond or alkylene of 1 to 3 carbons;

rings A and B are independently selected from the group consisting of:

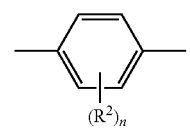
i)

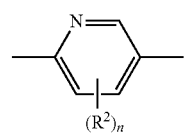
ii)

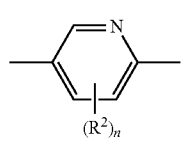
iii)

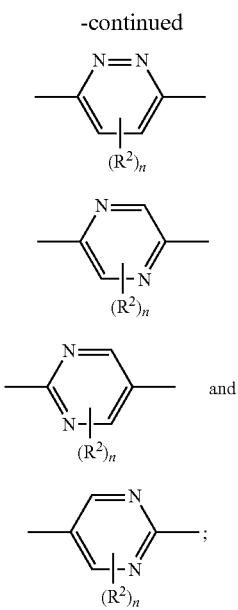

$R^2$ is a replacement for a hydrogen atom and is independently selected from the group consisting of halogen, —CF$_3$, —OH, C$_{1-5}$alkyl, C$_{3-7}$ cycloalkyl and C$_{1-5}$alkoxyl;
n is 0, 1, 2, 3, or 4;
Q is —O—, —S—, —NH—, —NR$^7$—, —S(O)—, or —S(O)$_2$—;
$R^3$ and $R^4$ are independently —H, C$_{1-5}$alkyl, C$_{3-7}$cycloalkyl or C$_{1-5}$alkyl substituted by a 3-7 membered heterocyclic ring or $R^3$ and $R^4$ are alkyl and are combined to form a 3-7 membered ring;
ring C is:

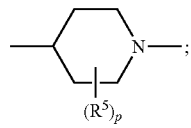

$R^5$ is a replacement for a ring hydrogen and is independently selected from the group consisting of halogen, —OH, —CN, C$_{1-5}$alkyl, C$_{3-7}$cycloalkyl and C$_{1-5}$alkyl substituted by a 3-7 membered heterocyclic ring;
p is 0, 1, 2, or 3;
$R^6$ is —C(O)C(O)R$^7$, —C(O)OR$^{10}$, —C(O)R$^{10}$, —S(O)$_2$C$_{1-5}$alkyl, —S(O)$_2$C$_{3-7}$cycloalkyl, —S(O)$_2$NR$^8$R$^9$, Ar, —CH$_2$Ar, —C(O)NHC$_{1-5}$alkyl, —C(O)NHC$_{3-7}$cycloalkyl, —C(O)NHC$_{1-5}$alkyl-Ar, or —C(O)NR$^{10}$R$^{11}$;
$R^7$ is independently selected from the group consisting of
  C$_{1-5}$alkyl,
  C$_{3-7}$cycloalkyl,
  phenyl,
  phenyl(C$_{1-4}$alkylene),
  a heterocyclic group of 3-7 ring members, and
  C$_{1-5}$alkyl substituted by a heterocyclic group of 3-7 ring members, which group members may be further optionally substituted by one or more of halogen, —OH, C$_{1-5}$alkoxyl, a heteroaryl ring of 5-6 members, —NR$^8$R$^9$, or —C(O)NR$^8$R$^9$;
$R^8$ and $R^9$ are independently selected from the group consisting of —H, C$_{1-5}$alkyl, C$_{3-7}$cycloalkyl, —C(O)OC$_{1-5}$alkyl and a heterocyclic group of 3-7 members or $R^8$ and $R^9$ are alkyl and together combine to form a ring having 4 to 7 ring atoms and optionally containing a heterogroup selected from —O—, —NH— and —N(C$_{1-5}$alkyl)- and wherein said ring having 4 to 7 ring atoms is optionally substituted by oxo;
$R^{10}$ and $R^{11}$ are independently selected from the group consisting of
  C$_{1-5}$alkyl,
  C$_{1-5}$alkenyl,
  C$_{3-7}$cycloalkyl, and
  Ar,
  which group members may be further optionally substituted by halogen,
  —OH, C$_{1-5}$alkyl, C$_{1-5}$alkoxyl, —Ar, —CH$_2$Ar, or —C(O)NR$^8$R$^9$; and
Ar is aryl or a 5- or 6-membered heteroaryl group, which may be substituted by one or more substituents independently selected from halogen, —CF$_3$, C$_{1-5}$alkyl, C$_{3-7}$cycloalkyl, —CN, —OR$^7$, —NR$^8$R$^9$ and —NO$_2$.

In one embodiment of the invention of formula (I), compounds having the formula (Ia) below are provided.

In formula (Ia) $R^1$ is selected from the group consisting of F$_3$C—, NC—, Ar—, R$^7$S—, R$^7$S(O)—, R$^7$S(O)$_2$—, R$^7$NHS(O)$_2$—, R$^7$(C$_{1-5}$alkyl)NS(O)$_2$—, R$^7$C(O)—, R$^7$OC(O)—, R$^8$R$^9$NS(O)$_2$—, R$^7$NHC(O)—, and R$^8$R$^9$NC(O)—.

In formula (Ia), ring B is selected from the group consisting of:

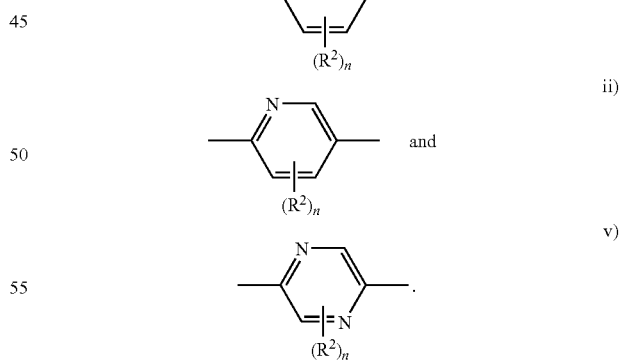

In accordance with formula (Ia), $R^2$ is a replacement for a hydrogen atom and is independently selected from the group consisting of halogen, —CF$_3$, C$_{1-5}$alkyl, C$_{3-7}$ cycloalkyl and C$_{1-5}$alkoxyl; and n is 0, 1, 2.

$R^3$ of formula (Ia) is selected from the group consisting of —H, C$_{1-5}$alkyl, and C$_{3-7}$cycloalkyl.
And $R^6$ of formula (Ia) is —C(O)C(O)R$^7$, —C(O)OR$^{10}$, —C(O)R$^{10}$, —S(O)$_2$C$_{1-5}$ alkyl, —S(O)$_2$C$_{3-7}$cycloalkyl, —S(O)$_2$NR$^8$R$^9$, Ar, —CH$_2$Ar, —C(O)NHC$_{1-5}$alkyl, —C(O)NHC$_{3-7}$cycloalkyl, —C(O)NHC$_{1-5}$alkyl-Ar, or —C(O)NR$^{10}$R$^{11}$.

In formula (Ia), R$^7$ is independently selected from the group consisting of C$_{1-5}$alkyl, C$_{3-7}$cycloalkyl, phenyl, phenyl(C$_{1-4}$alkylene), a heterocyclic group of 3-7 ring members, and C$_{1-5}$alkyl substituted by a heterocyclic group of 3-7 ring members, which group members may be further optionally substituted by one or more of halogen, —OH, C$_{1-5}$alkoxyl, a heteroaryl ring of 5-6 members, —NR$^8$R$^9$, or —C(O)NR$^8$R$^9$.

In formula (Ia), R$^8$ and R$^9$ are independently selected from the group consisting of —H, C$_{1-5}$alkyl, C$_{3-7}$cycloalkyl, —C(O)OC$_{1-5}$alkyl and a heterocyclic group of 3-7 members or R$^8$ and R$^9$ are alkyl and together combine to form a ring having 4 to 7 ring atoms and optionally containing a heterogroup selected from —O—, —NH—, and —N(C$_{1-5}$alkyl)- and wherein said ring having 4 to 7 ring atoms is optionally substituted by oxo.

R$^{10}$ of formula (Ia) is selected from the group consisting of C$_{1-5}$alkyl, C$_{1-5}$ alkenyl, C$_{3-7}$cycloalkyl, and Ar, which group members may be further optionally substituted by halogen, —OH, C$_{1-5}$alkyl, C$_{1-5}$alkoxyl, —Ar, —CH$_2$Ar or —C(O)NR$^8$R$^9$. And, in formula (Ia) Ar is aryl or a 5- or 6-membered heteroaryl group, which may be substituted by one or more substituents independently selected from halogen, —CF$_3$, C$_{1-5}$alkyl, C$_{3-7}$cycloalkyl, —CN, —OR$^7$, —NR$^8$R$^9$ and —NO$_2$.

In one embodiment of formula (Ia), ring B is:

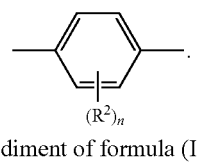

i)

In another embodiment of formula (Ia) ring B is:

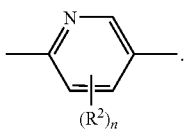

ii)

In still another embodiment of formula (Ia) ring B is:

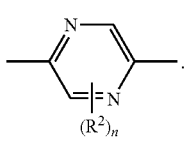

v)

In another embodiment of the invention compounds of formula (I) are provided in accordance with formula (Ib) below:

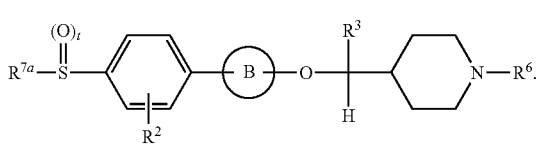

(Ib)

In formula (Ib), ring B is selected from the group consisting of

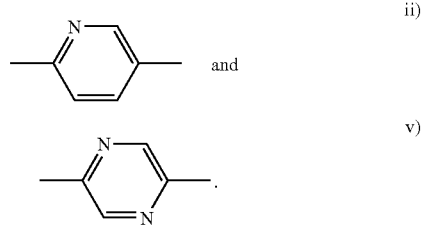

In formula (Ib), R$^2$ is selected from the group consisting of —H, halogen, —CF$_3$, —CH$_3$, and —CH$_2$CH$_3$.

In formula (Ib), t is 1 or 2.

R$^3$ of formula (Ib) is selected from the group consisting of —H, —CH$_3$, and —CH$_2$CH$_3$.

In formula (Ib) R$^6$ is —C(O)OR$^{10}$, —C(O)R$^{10}$, or Ar* where Ar* is selected from the group consisting of:

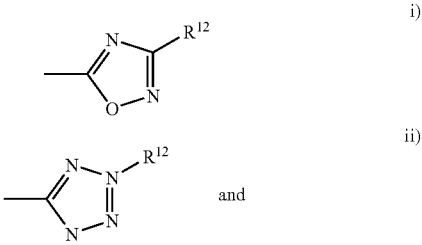

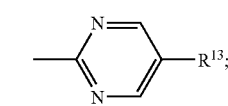

in which R$^{12}$ is selected from a group consisting of C$_{1-5}$alkyl and C$_{3-7}$cycloalkyl;

and R$^{13}$ is selected from a group consisting of —H, halogen, C$_{1-5}$alkyl, and C$_{3-7}$ cycloalkyl.

In formula (Ib) R$^{7a}$ is independently selected from the group consisting of C$_{1-5}$ alkyl and C$_{3-7}$cycloalkyl.

And R$^{10}$ in accordance with formula (Ib) is selected from the group consisting of: C$_{1-5}$alkyl, C$_{1-5}$alkenyl, C$_{3-7}$cycloalkyl, and Ar, which group members may be further optionally substituted by halogen, —OH, C$_{1-5}$alkyl, C$_{1-5}$alkoxyl, —Ar, or —CH$_2$Ar.

And in formula (Ib) Ar is aryl or a 5- or 6-membered heteroaryl group, which may be substituted by one or more substituents independently selected from halogen, —CF$_3$, C$_{1-5}$alkyl, and C$_{3-7}$cycloalkyl.

In one embodiment of formula (Ib), R$^3$ is —CH$_3$. In a preferred embodiment of formula (Ib), R$^3$ is —CH$_3$ and the stereochemistry of the stereogenic carbon is (S).

In an embodiment of formula (Ib), R$^3$ is —C(O)OR$^{10}$ and R$^{10}$ is selected from the group consisting of: C$_{1-5}$alkyl and C$_{3-7}$cycloalkyl.

In one embodiment of formula (Ib) ring B is:

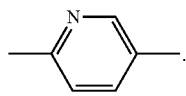
ii)

And in another embodiment of formula (Ib) ring B is:

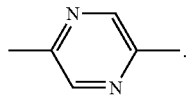
v)

The present invention is described in terms known and appreciated by those skilled in the art. For ease of reference certain terms hereinafter are defined. The fact that certain terms are defined, however, should not be considered as indicative that defined terms are used in a manner inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention. The following definitions are meant to clarify, but not limit, the terms defined.

"Alkyl" refers to a monovalent straight or branched chain hydrocarbon moiety, e.g. of about 1 to 12 carbon atoms, including methyl, ethyl, n-propyl, isopropyl, isobutyl, n-butyl, tert-butyl, isopentyl and n-pentyl.

A specific number of atoms in a group, such as carbon atoms, will be represented by, for example, the phrase "$C_x$-$C_y$ alkyl," which refers to an alkyl group, containing the specified number of carbon atoms.

"Alkenyl" refers to a monovalent straight or branched chain aliphatic hydrocarbon moiety, e.g. of about 1 to 12 carbons, containing one or more carbon-to-carbon double bonds, such as vinyl and allyl.

"Alkylene" refers to a divalent straight or branched chain aliphatic hydrocarbon moiety, e.g. of about 1 to 10 carbon atoms, including methylene, ethylene, n-propylene, and n-butylene.

"Cycloalkyl" refers to a monovalent aliphatic cyclic hydrocarbon ring moiety, e.g. of about 1 to 12 carbons, including cyclopropyl, cyclobutyl, cyclopentyl, cyclohexyl, and cycloheptyl. The term "cycloalkyl" includes a fused ring system where a cycloalkyl ring, such as a cyclopentyl ring, is fused with an aromatic ring, herein an aryl ring, such as a benzene ring, to form groups such as indane.

"Heterocyclic" refers to a monovalent mono- or polycyclic ring system, e.g. of about 3 to 12 members, which may be aromatic, have no unsaturation, or may contain one or more degrees of unsaturation, containing 1 or more heteroatoms including N, O, and/or S, including N-oxides, sulfur oxides, and dioxides. Such rings may be fused to one or more of another heterocyclic ring(s) or cycloalkyl ring(s). Such fused ring systems include a saturated heterocyclic ring (such as a pyrrolidine ring) fused with an aromatic ring, such as a benzene ring to form groups such as indoline. Examples of heterocyclic groups include tetrahydrofuran, pyran, 1,4-dioxane, 1,3-dioxane, piperidine, pyridine, pyrrolidine, morpholine, tetrahydrothiopyran, and tetrahydrothiophene.

"Aryl" refers to a monovalent benzene ring or to a fused benzene ring system, e.g. of about 6 to 14 carbons, such as anthracene, phenanthrene, or naphthalene ring systems, including phenyl, 2-naphthyl and 1-naphthyl.

"Heteroaryl" refers to a monovalent aromatic monocyclic ring, e.g. of 5 to 7 members, or to a fused bicyclic aromatic ring system comprising two aromatic rings that contain one or more N, S, and/or O atoms, including N-oxides, sulfur oxides, and dioxides, including furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl and pyrazolopyrimidinyl.

"Alkoxy" and "alkoxyl" refers to a monovalent group —O-alkyl.

"Halogen" refers to fluorine, chlorine, bromine, or iodine.

Particular aspects of the invention include formula (I) as defined above with the proviso that Ar is other than pyridazine, in particular $R^6$ is not pyridazine attached to the nitrogen of Ring C via the 3-position of pyridazine, or that Ar is not such a pyridazine when Alk is a direct bond and $R^1$ is halogen, $F_3C$—, HO— or $R^7C(O)$—.

$R^1$, in particular, may be $CH_3S(O)_2$—, $(CH_3)_2CHS(O)_2$—, (—$CH_2CH_2$—)CH—NHC(O)—, $(CH_3)_2CHCH_2NHC(O)$—, $HOCH_2CH_2NHS(O)_2$—, $CH_3OCH_2CH_2S(O)_2$—, $HOCH_2CH_2S(O)_2$—, (—$CH_2CH_2CH_2CH_2$—)N—C(O)—, $CH_3OCH_2CH_2NHS(O)_2$—, $CH_3OCH_2C(CH_3)HNHS(O)_2$—, $CH_3OCH_2CH_2CH_2S(O)_2$—, $CH_3CH_2OC(O)$—, $CH_3S(O)$—, $C_6H_5CH_2NHC(O)$—, $C_6H_5NHC(O)$—, $C_6H_5C(O)$—, $HOCH_2$—, $CH_3S(O)_2NH$—, $CH_3CH_2NHC(O)$—, $(CH_3)_2NC(O)$—, $H_2NC(O)$—, $(CH_3CH_2)NC(O)$—, O(—$CH_2CH_2$—)$_2$N—C(O)—, (—$CH_2CH_2CH_2CH_2$—)CH—NHC(O)—, $HOCH_2CH_2NHC(O)$—, (—CH═N—N═CH—)N—NHC(O)—, $(CH_3)_3COC(O)NHCH_2CH_2NHS(O)_2$—, O(—$CH_2CH_2$—)$_2$N—$CH_2CH_2NHS(O)_2$—, O(—$CH_2CH_2$—)$_2$N—$CH_2CH_2N(CH_3)S(O)_2$—, (—$CH_2CH_2CH_2C(O)$—)N—$CH_2CH_2CH_2NHS(O)_2$—, N(—$CH_2CH_2$—)$_2$CH—$CH_2CH_2NHS(O)_2$—, $CH_3OCH_2CH_2CH_2NHS(O)_2$—, $CH_3OCH_2CH_2NHC(O)$—, $CH_3$—, $CH_3S$—, $CF_3$—, $(CH_3)_2CHS$—, $(CH_3)_3C$—, $CH_3CH_2S(O)_2$—, $CH_3CH_2CH_2CH_2NHC(O)$—, O(—$CH_2CH_2$—)N—S(O)_2$—, $(CH_3)_2CHNHS(O)_2$—, $H_2NC(O)CH_2S(O)_2$—, $(CH_3)_2NCH_2CH_2NHS(O)_2$—, (—$CH_2CH_2CH_2CH_2$—)N—$CH_2CH_2NHS(O)_2$—, $H_2NCH_2CH_2NHS(O)_2$—, $HOCH_2CH_2NHC(O)$—, O(—$CH_2CH_2$—)$_2$N—$CH_2CH_2CH_2NHS(O)_2$—, Br—, $H_3COCH_2CH_2S$—, $H_2NC(O)CH_2S$—, $H_3COCH_2CH_2CH_2S$—, (R)—$CH_3S(O)$—, or (S)—$CH_3S(O)$.

Ring A and Ring B, in particular, may be of formula i), ii) or iii); and Ring B, in particular, may be of formula iv), v), vi) or vii), all with n=0. Attachment of Rings A, B and C in the compounds of formula (I) is as depicted in the formulae herein, in particular Ring C is attached with the nitrogen of viii) directly attached to the open valence of $R^6$.

$R^2$, in particular, may be —F, —$OCH_3$ or —OH with n, in particular, being 0, 1 or 2.

$R^6$, in particular, may be —C(O)OC(CH_3)_3, —C(═N—CH—)(═N—CH═)C—$CH_2CH_3$, —C(O)OCH(CH_3)_2, —C(—N═CH—)(═N—CH═)C—Br, —C(═N—)(—O—N═)C—CH(CH_3)_2, —C(═N—)(—O—N═)C—$CH_2CH(CH_3)_2$, —C(═N—)(—O—N═)C—$CH_3$, —C(—N═CH—)(═N—C(CF_3)═)C—H, —C(═N—CH—)(═N—CH═)C—$CH_2CH_2CH_3$, —C(═N—CH—)(═N—CH═)C—F, —C(—N═CH—)(═N—CH═)C—CH(—$CH_2CH_2$—), —$CH_2$—C(═CH—CH═)

(—CH=CH—)C—OCH(CH₃)₂, —C(—CH=CH—)(=N—N=)C—Cl, —C(O)—CH(—CH₂CH₂CH₂—), —C(O)—C(=CH—CH=)(—S—)C—H, —C(O)—CH=C(CH₃)₂, —C(O)—CH₂C(CH₃)₃, —CH₂—C(=CH—CH=)(—CH=CH—)C—F, —CH₂—C(=CH—CH=)(—C(Cl)=CH—)C—H, —CH₂—C(=CH—CH=)(—CH=CH—)C—Cl, —CH₂—C(=CH—CH=)(—CH=C(Cl)—)C—H, —CH₂—C(=CH—CH=)(—CH=C(F)—)C—H, —CH₂—C(=CH—CH=)(—CH=CH—)C—CF₃, —CH₂—C(=C(F)—CH=)(—CH=C(F)—)C—H, —CH₂—C(=CH—CH=)(—CH=C(CH₃)—)C—CH₃, —CH₂—C(=CH—CH=)(—CH=CH—)C—CN, —CH₂—C(=C(F)—CH=)(—CH=C(OCH₃)—)C—H, —CH₂—C(=C(Br)—CH=)(—CH=CH—)C—H, —CH₂—C(=CH—CH=)(—CH=CH—)C—Br, —CH₂—C(=CH—CH=)(—CH=CH—)C—OCH₃, —CH₂—C(=CH—CH=)(—CH=CH—)C—CH₃, —CH₂—C(=CH—C(CH₃)=)(—CH=CH—)C—H, —CH₂—C(=CH—CH=)(—CH=CH—)C—OC(CH₃)₃, —C(=N—)(=N—O—)C—N(CH₃)₂, —C(—CH=CH—)(=N—N=)C—N(CH₃)₂), —C(O)—C(=CH—CH=)(—O—)C—H, —C(O)—N(CH₂CH₃)₂, —C(O)—C(=C—)(—N(CH₃)—N=)C—CH₃, —C(O)—C(CH₃)₂CH₂CH₃, —C(O)—C(—CH=)(=C(CH₃)—O—)C—CH₃, —C(—N=CH—)(=CH—C(Cl)=)N, —C(O)—C(=CH—)(—O—N=)C—H, —C(=CH—CH=)(—N=C(CF₃)—)C—H, —C(O)C(O))CH₃, —C(O)C(O)C(CH₃)₃, —C(O)OCH₂—C(=CH—CH=)(—CH=CH—)C—H, or —C(O)OCH₂CH₂F.

R⁷, in particular, may be —CH₃, —CH(CH₃)₂, —CH(—CH₂CH₂—), —CH₂CH(CH₃)₂, —CH₂CH₂OH, —CH₂CH₂OCH₃, —CH(CH₃)CH₂OCH₃, —CH₂CH₂CH₂OCH₃, —CH₂CH₃, —CH₂C₆H₅, —C₆H₅, —CH(—CH₂CH₂CH₂CH₂—), —N(—CH=N—N=CH—), —CH₂CH₂NHC(O)OC(CH₃)₃, —CH₂CH₂—N(CH₂CH₂)₂O, —CH₂CH₂CH₂—N(—C(O)CH₂CH₂CH₂—), —C(=CH—CH=)(—CH=CH—)N, —CH₂CH₂CH₂CH₃, —CH₂CH₂N(CH₃)₂ or —C(CH₃)₃.

R⁸ and R⁹, in particular, may be both —CH₃, both —H, both —CH₂CH₃, —H and —C(O)OC(CH₃)₃, or may be alkyl and combine to form —CH₂CH₂CH₂CH₂—, —CH₂CH₂CH₂CH₂CH₂—, or —CH₂CH₂OCH₂CH₂—.

R¹⁰ and R¹¹, in particular, may be —C(CH₃)₃, —CH(CH₃)₂, —CH(—CH₂CH₂CH₂—), —CH=C(CH₃)₂, —CH₂C(CH₃)₃ or —CH₂CH₃.

Ar, in particular, may be phenyl substituted by 1 or 2 of —F, —Cl, —CF₃, —CH₃, —CN, —OC(CH₃)₃, —F, —OCH₃ or —Br or Ar may be —C(=N—)(—O—N=)C—C₁₋₅alkyl. Ar, more particularly, may be —C(—N=CH—)(=N—CH=)C—CH₂CH₃, —C(—N=CH—)(=N—CH=)C—Br, —C(=N—)(—O—N=)C—CH(CH₃)₂, —C(=N—)(—O—N=)C—CH₂CH(CH₃)₂, —C(=N—)(—O—N=)C—CH₃, —C(—N=CH—)(=N—C(CF₃)=)C—H, —C(—N=CH—)(=N—CH=)C—CH₂CH₂CH₃, —C(—N=CH—)(=N—CH=)C—F, —C(—N=CH—)(=N—CH=)C—CH(—CH₂CH₂—), —C(=CH—CH=)(—CH=CH—)C—OCH(CH₃)₂, —C(—CH=CH—)(=N—N=)C—Cl, —C(=CH—CH=)(—S—)C—H, —C(=CH—CH=)(—CH=CH—)C—F, —C(=CH—)(—C(Cl)=CH—)C—H, —C(=CH—CH=)(—CH=CH—)C—Cl, —C(=CH—CH=)(—CH=C(Cl)—)C—H, —C(=CH—CH=)(—CH=C(F)—)C—H, —C(=CH—CH=)(—CH=CH—)C—CF₃, —C(=C(F)—CH=)(—CH=C(F)—)C—H, —C(=CH—CH=)(—CH=C(CH₃)—)C—CH₃, —C(=CH—CH=)(—CH=CH—)C—CN, —C(=C(F)—CH=)(—CH=C(OCH₃)—)C—H, —C(=C(Br)—CH=)(—CH=CH—)C—H, —C(=CH—CH=)(—CH=CH—)C—Br, —C(=CH—CH=)(—CH=CH—)C—OCH₃, —C(=CH—CH=)(—CH=CH—)C—CH₃, —C(=CH—)(—CH=CH—)C—H, —C(=CH—CH=)(—CH=CH—)C—OC(CH₃)₃, —C(—N=)(=N—O—)C—N(CH₃)₂, —C(—CH=CH—)(=N—N=)C—N(CH₃)₂, —C(=CH—CH=)(—O—)C—H, —C(=C—)(—N(CH₃)—N=)C—CH₃, —C(—CH=)(=C(CH₃)—O—)C—CH₃, —C(—N=CH—)(=CH—C(Cl)=)N, —C(=CH—)(—O—N=)C—H, —C(=CH—CH=)(—N=C(CF₃)—)C—H, —C(=CH—CH=)(—N=CH)C—CF₃, —C(=N—)(—S—N=)C—CH(CH₃)₂, —C(=N—N=)(—S—)C—CH(CH₃)₂, or —C(=N—)(—N=N—)N—CH(CH₃)₂.

Compounds of formula (I) may crystallize in more than one form, a characteristic known as polymorphism, and such polymorphic forms ("polymorphs") are within the scope of compounds of the invention. Polymorphism generally can occur as a response to changes in temperature, pressure, or both, and can also result from variations in the crystallization process. Polymorphs can be distinguished by various physical characteristics such as x-ray diffraction patterns, solubility, and melting point.

Certain of the compounds described herein may be capable of existing as stereoisomers such as by having a chiral carbon, sulfoxide sulfur or double bond whereby the compounds may exist as R or S enantiomers or E or Z isomers. The scope of the present invention includes all such individual isomers, racemates, purified enantiomers, and enantiomerically enriched mixtures of the compounds of formula (I).

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

Included within the scope of the invention compounds are solvates of compounds of the depicted formula. "Solvate" refers to a complex of variable stoichiometry formed by a solute (in this invention, a compound of Formula (I), or a salt or physiologically functional derivative thereof) and a solvent. Such solvents, for the purpose of the invention, should not interfere with the biological activity of the solute. Preferably the solvent used is a pharmaceutically acceptable solvent such as water, ethanol, and acetic acid.

"Physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5th Edition, Vol. 1: Principles and Practice, which is incorporated herein by reference to the extent that it teaches physiologically functional derivatives.

"Effective amount" means that amount of a drug or pharmaceutical agent that will elicit the biological or medical response of a tissue, system, animal, or human that is being sought, for instance, by a researcher or clinician.

"Therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I), as well as salts, solvates, and physiological functional derivatives thereof, may be administered as the raw chemical. Additionally, the active ingredient may be presented as a pharmaceutical composition.

Accordingly, the invention further provides pharmaceutical compositions that include effective amounts of a compound of the formula (I) or a salt, solvate, or physiological functional derivative thereof, and one or more pharmaceutically acceptable carriers, diluents, or excipients. The carrier(s), diluent(s) or excipient(s) must be acceptable, in the sense of being compatible with the other ingredients of the formulation and not deleterious to the recipient of the pharmaceutical composition.

In another aspect of the invention there is provided a process for the preparation of a pharmaceutical formulation including admixing a compound of the formula (I) or a salt, solvate, or physiological functional derivative thereof, with one or more pharmaceutically acceptable carriers, diluents or excipients.

A therapeutically effective amount of a compound of the present invention will depend upon a number of factors. The species, age, and weight of the recipient, the precise condition requiring treatment and its severity, the nature of the formulation, and the route of administration are all factors to be considered. The therapeutically effective amount ultimately should be at the discretion of the attendant physician or veterinarian. An effective amount of a compound of formula (I) for the treatment of humans or other mammals suffering from metabolic disorders such as diabetes and obesity, generally, should be in the range of about 0.1 to 100 mg/kg body weight of recipient (mammal) per day. More usually the effective amount should be in the range of 0.1 to 10 mg/kg body weight per day. Thus, for a 70 kg adult mammal the actual amount per day would usually be from 7 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein and for prophylaxis.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For oral administration in the form of a tablet or capsule, the active drug component can be combined with an oral, non-toxic pharmaceutically acceptable inert carrier such as ethanol, glycerol or water. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Suitable binders, lubricants, disintegrating agents, and coloring agents can also be incorporated into the mixture. Examples of binders include starch, gelatin, natural sugars such as glucose or beta-lactose, corn sweeteners, natural and synthetic gums such as acacia, tragacanth, or sodium alginate, carboxymethylcellulose, polyethylene glycol and waxes. Lubricants useful in these dosage forms include sodium oleate, sodium stearate, magnesium stearate, sodium benzoate, sodium acetate and sodium chloride. Disintegrators include starch, methyl cellulose, agar, bentonite and xanthan gum.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage, or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. Compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; can also be added.

Where appropriate, dosage unit formulations for oral administration can be microencapsulated. The formulation can also be prepared to prolong or sustain the release as for example by coating or embedding particulate material in polymers or wax.

Compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of formula (I) and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as described in *Pharmaceutical Research,* 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

Compounds of the present invention and their salts, solvates, and physiologically functional derivatives thereof, may be employed alone or in combination with other therapeutic agents. The compound(s) of formula (I) and the other pharmaceutically active agent(s) may be administered together or separately and, when administered separately, administration may occur simultaneously or sequentially, in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Compounds of the present invention may be used in the treatment of a variety of disorders and conditions. As such, the compounds of the present invention may be used in combination with a variety of other therapeutic agents useful in the treatment or prophylaxis of those disorders or conditions. The compounds of the present invention may be used in combination with diet, exercise, insulin, an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, an AXOR 109 agonist, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, antidiarrhoics, cathartics, a hydroxymethylglutaryl coenzyme A reductase inhibitor, a fibric acid derivative, $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent, and a urinary alkalinizer.

Exemplary compounds are hereinafter described, however, a combination within the scope of the present invention should not be limited by this specific description. Rather, any combination within the purview of those skilled in the art is contemplated. In addition, this listing of exemplary compounds includes the free compounds, as well as salts, solvates, and physiologically functional derivatives.

As insulin sensitivity enhancers, peroxisome proliferator-activated receptor-γ agonists such as troglitazone, pioglitazone, rosiglitazone, darglitazone, GI-262570, isaglitazone, LG-100641, NC-2100, T-174, DRF-2189, CLX-0921, CS-011, GW-1929, ciglitazone, englitazone, and NIP-221, peroxisome proliferator-activated receptor-αagonists such as GW-9578 and BM-170744, peroxisome proliferator-activated receptor-α/γ agonists such as GW-409544, KRP-297, NN-622, CLX-0940, LR-90, SB-219994, DRF-4158, and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers may be used for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia. Such compounds are believed to improve the disturbance of insulin signal transduction in peripheral tissues and enhancing glucose uptake into the tissues from the blood, leading to lowering of blood glucose level.

As glucose absorption inhibitors, for example, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors may be used for diabetes, impaired glucose tolerance, diabetic complications, obesity or hyperinsulinemia, and more preferably for impaired glucose tolerance. Such compounds are believed to inhibit the gastrointestinal enzymatic digestion of carbohydrates contained in foods, and inhibit and/or delay the absorption of glucose into the body.

As biguanides, phenformin, buformin, metformin, or the like are illustrated. Biguanides may be used for diabetes, impaired glucose tolerance, diabetic complications or hyperinsulinemia, and more preferably for diabetes, impaired glucose tolerance or hyperinsulinemia. Such compounds are believed to lower blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. In addition, the insulin secretion enhancers include glucokinase activators such as RO-28-1675. Insulin secretion enhancers may be used for diabetes, impaired glucose tolerance or diabetic complications, and more preferably for diabetes or impaired glucose tolerance. Such compounds are believed to lower blood glucose level by acting on pancreatic β-cells and enhancing the insulin secretion.

As SGLT2 inhibitors, compounds described in Japanese patent publications Nos. Hei 10-237089 and 2001-288178, and International Publication Nos. WO1/16147, WO01/27128, WO01/68660, WO01/74834, WO01/74835, WO02/28872, WO02/36602, WO02/44192, WO02/53573, and WO 03/99836 are illustrated. In addition, inhibitors identified as GW869682 and GSK189075 are illustrated as well. SGLT2 inhibitors may be used for diabetes, impaired glucose tolerance, diabetic complications, obesity or hyperinsulinemia, and more preferably for diabetes, impaired glucose tolerance, obesity or hyperinsulinemia. Such compounds are believed to lower blood glucose level by inhibiting the reabsorption of glucose at the kidney's proximal tubule.

As insulin or insulin analogues, human insulin, animal-derived insulin, human or animal-derived insulin analogues or the like are illustrated. These preparations may be used for diabetes, impaired glucose tolerance or diabetic complications, and more preferably for diabetes or impaired glucose tolerance.

AXOR109, also known as TGR5, BG37, M-BAR, or hGPCR19, is a bile acid G-protein coupled receptor primarily expressed in monocytes/macrophages, lung, spleen, and the intestinal tract. AXOR109 agonists may be used for diabetes mellitus, stress, obesity, appetite control and satiety, Alzheimers, inflammation, and diseases of the central nervous system. AXOR109 agonists are believed to moderate blood glucose level by stimulating the release of GLP-1 from enteroendocrine cells.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, vildagliptin, sitigliptin, denagliptin, saxagliptin, TSL-225, P-32/98 or the like are illustrated; as protein tyrosine phosphatase 1 B inhibitors, PTP-112, OC-86839, PNU-177496 or the like are illustrated; as glycogen phosphorylase inhibitors, NN-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 may be used for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors may be used for diabetic complications. Such compounds are believed to inhibit aldose reductase and lowering excessive intracellular accumulation of sorbitol in accelated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride or the like are illustrated. Advanced glycation endproducts formation inhibitors may be used for diabetic complications. Such compounds are believed to inhibit formation of advanced glycation endproducts which are accelated in continuous hyperglycemic condition in diabetes and declining of cellular damage.

As protein kinase C inhibitors, LY-333531, midostaurin or the like are illustrated. Protein kinase C inhibitors may be used for diabetic complications. Such compounds are believed to inhibit protein kinase C activity, which is accelated in continuous hyperglycemic condition in diabetic patients.

As γ-aminobutyric acid receptor antagonists, topiramate or the like are illustrated; as sodium channel antagonists, mexiletine hydrochloride, oxcarbazepine or the like are illustrated; as transcrit factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecarnine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 may be used for diabetic complications.

As antidiarrhoics or cathartics, polycarbophil calcium, albumin tannate, bismuth subnitrate or the like are illustrated. These drugs may be used for diarrhea, constipation or similar conditions that may accompany diabetes or other metabolic disorders.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors may be used for hyperlipidemia, hypercholesterolemia, hypertriglyceridemia, lipid metabolism disorder or atherosclerosis, and more preferably for hyperlipidemia, hypercholesterolemia, or atherosclerosis. Such compounds are believed to lower blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives may be used for hyperinsulinemia, hyperlipidemia, hypercholesterolemia, hypertriglyceridemia, lipid metabolism disorder or atherosclerosis, and more preferably for hyperlipidemia, hypertriglyceridemia, or atherosclerosis. Such compounds are believed to activate hepatic lipoprotein lipase and enhancing fatty acid oxidation, leading to a lowering of blood triglyceride levels.

As $β_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353 (solabegron), N-5984, GW-2696, YM178 or the like are illustrated. $β_3$-adrenoceptor agonists may be used for diabetes, obesity, hyperinsulinemia, hyperlipidemia, hypercholesterolemia, hypertriglyceridemia, lipid metabolism disorder, urinary incontinence, and IBS.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors may be used for hyperlipidemia, hypercholesterolemia, hypertriglyceridemia or lipid metabolism disorder, and more preferably for hyperlipidemia or hypercholesterolemia. Such compounds are believed to lower blood cholesterol levels by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. Probcol, microsomal trigylceride transfer protein inhibitors, lipoxygenase inhibitors, and low-density lipoprotein receptor enhancers may be used for hyperlipidemia, hypercholesterolemia, hypertriglyceridemia, or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, γ-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), α-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. As monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as γ-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors may be used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors may be used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists may be used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. Such drugs may be used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-□, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs may be used for diabetic complications, hypertension, congestive heart failure or edema, and more preferably for hypertension, congestive heart failure or edema. Such compounds are believed to reduce blood pressure or improve edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs may be used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents may be used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs may be used for hyperuricemia or gout.

As noted, the compounds of the present invention may be used alone or may be combined with other medical therapies to treat and/or prevent a variety of disorders and conditions. More particularly, the diseases and conditions metabolic disorders, such as diabetes, including but not limited to diabetes types I and II, obesity, glucose intolerance, insulin resistance, metabolic syndrome X, hyperlipidemia, hypercholesterolemia, artheroscelrosis, neurodegenerative diseases, and other indications such as stroke.

Compounds of this invention may be made by a variety of methods. Illustrative general synthetic methods are set out below followed by a description of exemplary synthesis of specific compounds of the invention as illustrated in the examples.

In the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protective Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be affected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

The novel compounds of the present invention should not be limited by any specific synthetic process herein described.

Experimental Section

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade). All reactions were conducted at room temperature unless otherwise noted. Unless otherwise indicated, definitions for moieties in formulae (II) to (XXVIII) are as defined above for formula (I) and LG represents a leaving group such as hydroxyl. Abbreviations and definitions include HPLC (high pressure liquid chromatography), LC-MS (liquid chromatography-mass spectrometry), NMR (nuclear magnetic resonance), NMP (1-methyl-2-pyrrolidinone), HATU (O-(7-azabenzotriazol-1-yl)-N,N,N',N'-tetramethyluronium hexafluorophosphate), TBTU (O-benzotriazol-1-yl-N,N,N',N'-tetramethyluronium tetrafluoroborate); HOBT (1-hydroxybenzotriazole); TFA (trifluoroacetic acid); DMF (dimethylformamide); DIAD (diisopropyl azodicarboxylate); DME (1,2-dimethoxyethane); THF (tetrahydrofuran); DMSO (dimethylsulfoxide); MeOH (methanol); EtOH (ethanol); $Et_3N$ (triethylamine); AcOH (acetic acid); NMP (1-methyl-2-pyrrolidinone); EtOAc (ethyl acetate); aq (aqueous); and m-CPBA (meta-chloroperbenzoic acid); Tr (retention time); DAST ((diethylamino) sulfur trifluoride); $BOC_2O$ (di-tert-butyl dicarbonate).

$^1$H-NMR spectra were recorded on a Varian VXR-300, a Varian Unity-300, a Varian Unity-400 instrument, or a General Electric QE-300. Chemical shifts are expressed in parts per million (ppm, □ units). Coupling constants are in units of hertz (Hz). Splitting patterns describe apparent multiplicities and are designated as s (singlet), d (doublet), t (triplet), q (quartet), m (multiplet), or bs (broad singlet).

Mass spectra were obtained on Micromass Platform or ZMD mass spectrometers from Micromass Ltd., Altricham, UK, using either Atmospheric Chemical Ionization (APCI) or Electrospray Ionization (ESI).

The microwave reactions were conducted using Emrys™ Optimizer/SmithSynthesizer from Biotage using standard protocols that are known in the art.

The absolute stereochemistry of chiral enantiopure sulfoxides was determined using Vibrational Circular Dichroism (VCD), a spectroscopic technique capable of reliably assigning absolute stereochemistry (Freedman et al., *Chirality*, 2003, 15:743-758). Experimental VCD spectra were acquired using a BioTools ChiralIR™ VCD spectrometer equipped with a dual photoelastic modulator (PEM) and operating at 4 $cm^{-1}$ resolution in the mid-infrared region (2000-800 $cm^{-1}$).

Absolute configurations were assigned by comparing the sign (+/−) of an intense VCD band at 954 $cm^{-1}$ in experimental VCD spectra to the sign of the corresponding band in reference spectra. The sign (+/−) of this VCD band is known to be highly diagnostic for the absolute stereochemistry of the aromatic methyl sulfinyl group (Stephens, P. J. et al. *J. Org. Chem.*, 2001, 66, 3671).

Synthetic Schemes
Scheme 1

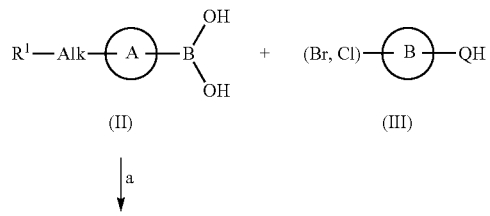

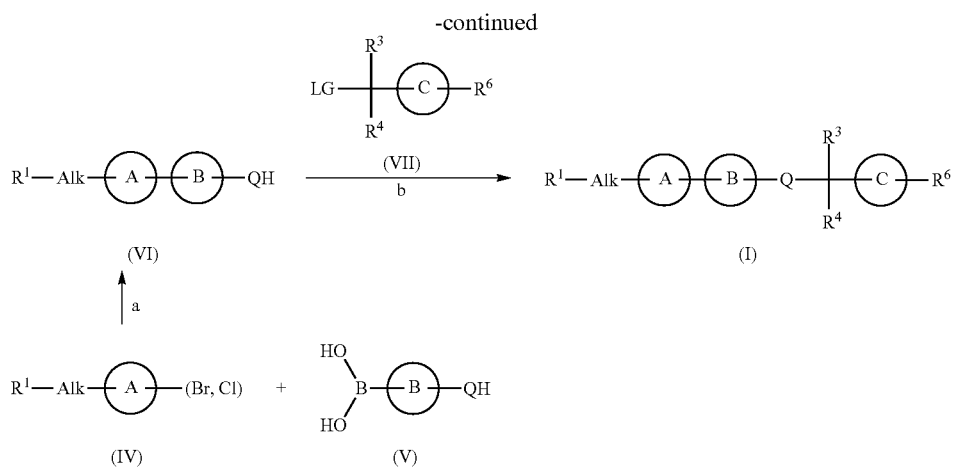

Reagents and conditions: a) Pd(PPh$_3$)$_4$ or PdCl$_2$(PPh$_3$)$_2$, Na$_2$CO$_3$, DME, heating; b) Ph$_3$P, DIAD, THF; or K$_2$CO$_3$, DMF, heating.

Biaryl-based compounds can be prepared by following the general synthetic Scheme 1. A Suzuki coupling reaction under conditions a) between a substituted aryl boronic acid of a base (such as K$_2$CO$_3$) in DMF can also provide the compound (I). For the formation of mesylate (VII) from its corresponding alcohol, see R. K. Crossland and K. L. Servis, *J. Org. Chem.*, 1970, 35, 3195-3196. For reaction conditions for displacement of mesylate, see P. J. Gilligan, et al., *J. Med. Chem.*, 1992, 35, 4344-4361.

Scheme 2

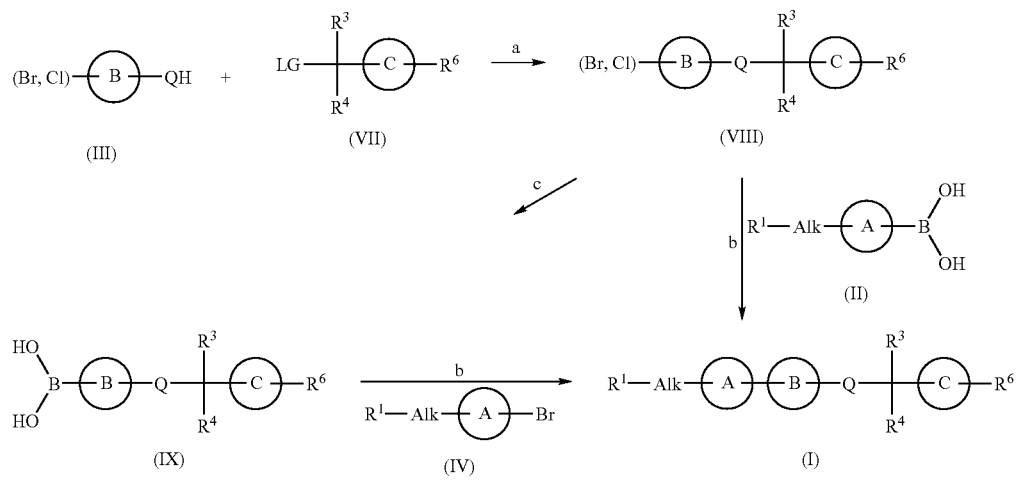

(II) and an appropriately substituted aryl bromide or heteroaryl halide (bromide or chloride) (III) can provide the compound of (VI). For Suzuki reaction conditions, see N. Miyaura and A. Suzuki, *Chem. Rev.*, 1995, 95, 2457-2483; A. Suzuki, *J. Organometallic Chem.* 1999, 576, 147-168; and A. Suzuki, in *Metal-catalyzed Cross-coupling Reactions*, F. Diederich and P. J. Stang., Eds.; Wiley-VCH: New York, 1998, 49-97. Compounds of formula (VI) can also be prepared via a similar Suzuki coupling reaction between (IV) and (V) under a) conditions.

When Q is —O—, the compound (VI) can react with an intermediate (VII) where LG is HO— under Mitsunobu reaction conditions b) to give the compound of formula (I), see Mitsunobu, *Synthesis*, 1981, 1, and for a Mitsunobu reaction review see D. L. Hughes *Organic Reactions* 42, 335. Treatment of the compound (VI) with an intermediate of formula (VII) where LG- is mesyl under b) conditions in the presence Reagents and conditions: a) Ph$_3$P, DIAD, THF; or K$_2$CO$_3$, DMF, heating; b) Pd(PPh$_3$)$_4$ or PdCl$_2$(PPh$_3$)$_2$, Na$_2$CO$_3$, DME, heating; c) (i) nBuLi, −78° C.; (ii) B(O-iPr)$_3$; (iii) HCl.

An alternative synthetic approach for making compounds of formula (I) is shown in Scheme 2. The compound (VIII) can be made from (III) and alcohol (VII) where LG- is HO— using Mitsunobu reaction conditions a), or from (III) and mesylate (VII) wherein LG- is mesyl in the presence of a suitable base such as K$_2$CO$_3$. Suzuki coupling of (VIII) with a boronic acid (II) can provide a compound of formula (I) using reaction conditions regarding Scheme 1 summarized as b). Alternatively, bromide (VIII) can be converted to boronic acid (IX) under c) conditions, which can then couple with bromide (IV) to give (I) under Suzuki coupling conditions b). For formation of boronic acids from bromides, see Yuichi Kobayashi, et al., *Eur. J. Org. Chem.*, 2000, 3825-3834 and Weijie Li, et al., *J. Org. Chem.*, 2002, 67, 5394-5397.

SCHEME 3

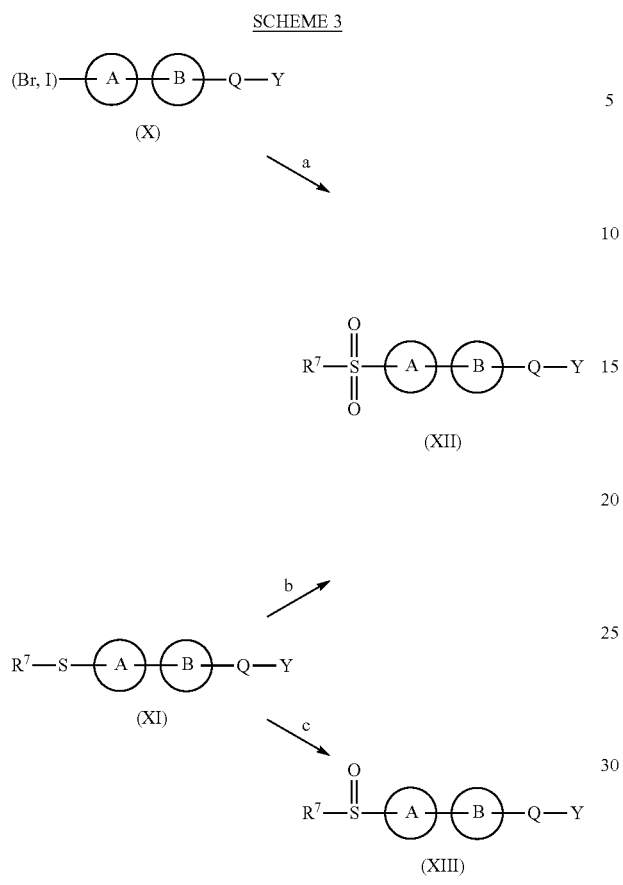

Scheme 4

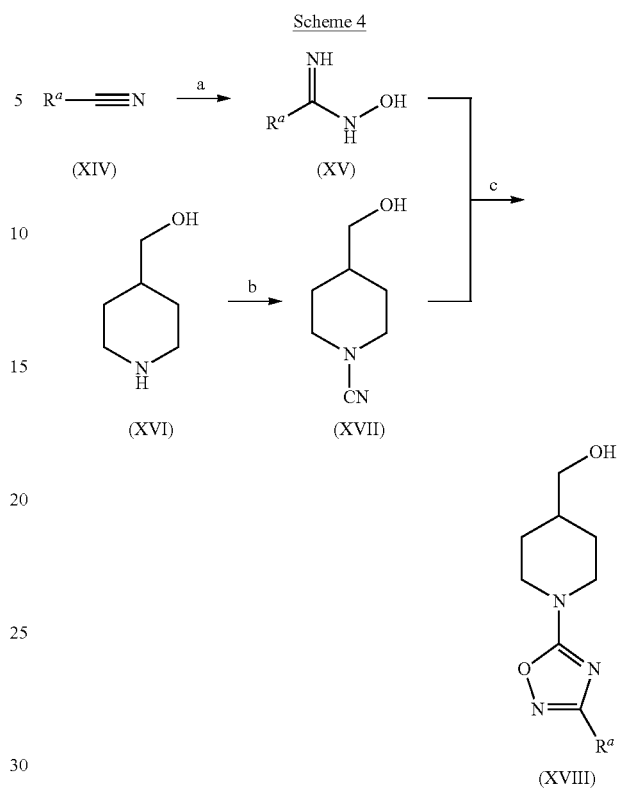

Reagents and conditions: a) H₂NOH, H₂O, EtOH, reflux; b) (i) NaHCO₃, H₂O, CH₂Cl₂, 0° C.; (ii) CNBr, CH₂Cl₂, 0° C. to RT; c) (i) 1N ZnCl₂ in ether, EtOAc, RT; (ii) conc. HCl, EtOH, reflux.

Reagents and conditions: a) CuI, L-proline, NaOH, R⁷SO₂Na, DMSO, 110° C., or CuI, NaOH, R⁷SO₂Na, DMSO, 120° C.; b) Oxone®, acetone (with or without MeOH), water; c) 30% H₂O₂, 1,1,1,3,3,3-hexafluoro-2-propanol.

Sulfones within the R¹ definition on ring "A" can be introduced using a sulfone-containing precursor such as (II) or (IV) in Scheme 1 and Scheme 2. In addition, following Scheme 3, sulfone-containing compound (XII) can be obtained through sulfonation of the compound (X) using a substituted sulphinic acid sodium salt in the presence of CuI depicted as a), see W. Zhu and D. Ma., *J. Org. Chem.*, 2005, 70, 2696-2700, and K. R. Campos, et al., *J. Org. Chem.*, 2005, 70, 268-274, for the conversion of aryl or alkyl halides to the corresponding sulfones. Secondly, sulfide (XI), upon oxidation with Oxone®, also yields the compound (XII), summarized as b), see I. K. Khanna, et al., *J. Med. Chem.*, 1997, 40, 1619-1633. The compound (XI) can also be treated, as summarized by c), with an oxidant such as 30% aqueous H₂O₂ in 1,1,1,3,3,3-hexafluoro-2-propanol to give the racemic sulfoxide (XIII), see K. S. Ravikumar, et al., *Eur. J. Org. Chem.*, 1998, 2937-2940. The racemic sulfoxides can be separated using chiral HPLC methods to give the pure or enriched (R and S) enantiomers.

In Scheme 3, Y is either —H or —C(R³R⁴)-Ring C—R⁶ whereby (XII) and (XIII) are types of (VI) and (I), respectively.

Intermediate (XVIII) can be made according to Scheme 4. Refluxing alkyl nitrile (XIV) where Rᵃ is alkyl or cycloalkyl with hydroxylamine in ethanol and water affords N-hydroxy alkylimidamide (XV). Treatment of 4-hydroxylmethyl piperidine (XVI) with cyanogen bromide gives N-cyano piperidine (XVII). Coupling reaction of (XV) and (XVII) in the presence of ZnCl₂ would result in formation of N-oxadiazol 4-hydroxymethyl piperidine (XVIII) after acidic workup, which can be subsequently used, as a compound of formula (VII), in Scheme 1 and Scheme 2. For reaction conditions, see R. M. Jones, et al., WO 2005/121121A2.

Scheme 5

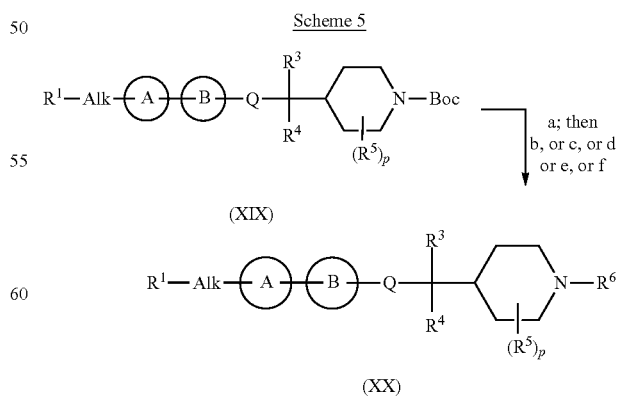

Reagents and conditions: a) TFA, CH₂Cl₂, or HCl, dioxane; b) RSC(=O)Cl, base, CH₂Cl₂; or ROCOCl, base, CH₂Cl₂; or RCOCl, Et$_3$N, CHCl$_3$; or RSO$_2$Cl, Et$_3$N, CH$_2$Cl$_2$; or ArCH$_2$X, base, CH$_3$CN, microwave 120° C. to create —C(O)OR$^{10}$, —C(O)R$^{10}$, —S(O)$_2$R$^{10}$ or —CH$_2$Ar groups as R$^6$; c) R—N=C=X (X is O or S), solvent to create —C(O)NHR$^{10}$ or —C(S)NHR$^{10}$ groups as R$^6$; d) α-halo heteroaryls, base, heating to create —Ar groups as R$^6$; e) (i) CNBr, Et$_3$N, CH$_2$Cl$_2$; (ii) H$_2$NOH—HCl, EtOH, reflux; (iii) RCO$_2$H, TBTU, HOBT, DIPEA, RT to 110° C., or phosgene iminium chloride, Et$_3$N, dichloroethane, 85° C. to create oxadiazolyl as R$^6$; f), or ArCHO, cyanoborohydride resin, catalytic HOAc, CH$_2$Cl$_2$ to create various —CH$_2$Ar groups as R$^6$.

Various groups at R$^6$ of formula (XX) can be introduced by a sequence involving deprotection of a suitable protecting group, such as a Boc group in compound (XIX), with TFA or HCl, summarized as a). Once deprotected, this can be followed by reaction with a variety of electrophiles, including but not limited to benzyl or benzyl-like halides, chloroformates, acyl chlorides and sulfonyl chlorides depicted as b), isocyanates and thioisocyanates depicted as c) and α-halo heteroaryls depicted as d). Reactions with electrophiles can be performed in a suitable solvent such as dichloromethane, chloroform, tetrahydrofuran, acetonitrile or DMSO under conditions known to those skilled in the art.

The deprotected (XIX) can also be reacted with cyanogen bromide to give the corresponding cyanoamine derivative which in turn can be converted to a heterocycle, including but not limited to an oxadiazole, summarized as e). For synthesis of 3-amino-1,2,4-oxadiazole, see R. Cadilla, et al., WO2003/74495A1. For synthesis of 3,5-diamino-1,2,4-oxadiazole, see E. Cohnen and B. Armah, U.S. Pat. No. 4,446,142A1. For a review of the synthesis of tetrazoles, see R. J. Herr, *Bioorg. Med. Chem.*, 2002, 10, 3379-3393. For synthesis of tetrazoles, see G. Bohnart, et al., WO2007/087443A2.

Alternatively, compounds (XX) wherein R$^6$ is ArCH$_2$— can be made from the deprotected (XIX) and aryl aldehydes using a cyanoborohydride resin/AcOH reductive amination protocol, summarized as f).

Scheme 6

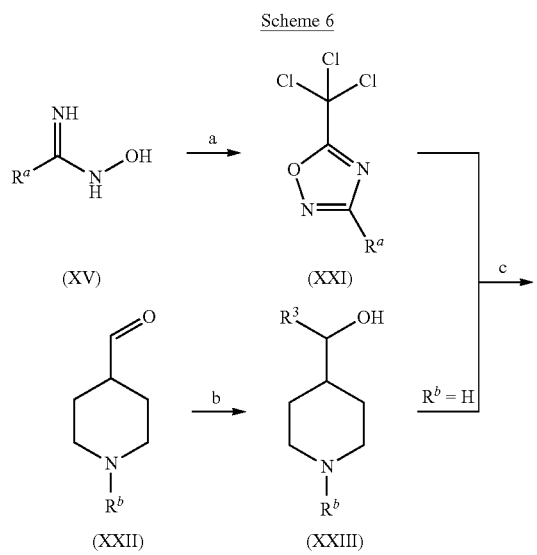

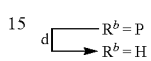

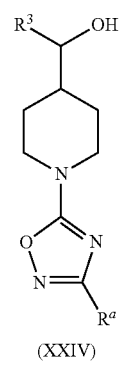

Reagents and conditions: a) Cl$_3$CC(O)Cl [or (Cl$_3$CCO)$_2$O], pyridine, CH$_2$Cl$_2$, −15° C.; b) R$^3$MgBr in ether or THF CH$_2$Cl$_2$, −78 to 0° C.; c) (XXI), MeOH, RT; d) when R$^b$=CBz: H$_2$, Pd/C, EtOH.

Intermediates (XXIII) and (XXIV) can be made according to Scheme 6. Treatment of N-hydroxy alkylimidamide (XV) with trichloroacetyl chloride or its related anhydride in pyridine and dichloromethane at low temperature gives the intermediate (XXI). Alkyl Grignard addition to aldehyde (XXII) affords the secondary alcohol as a racemate. When R$^b$=H, coupling (XXIII) with the intermediate (XXI) in methanol at room temperature affords (XXIV). Preparation of the NH derivative of (XXIII) can be accomplished by the removal of R$^b$ group, providing it is a suitable protecting group (P), such as a benzyl carbamate (CBz), by using hydrogenolysis conditions (hydrogen, Pd/C, solvent).

Scheme 7

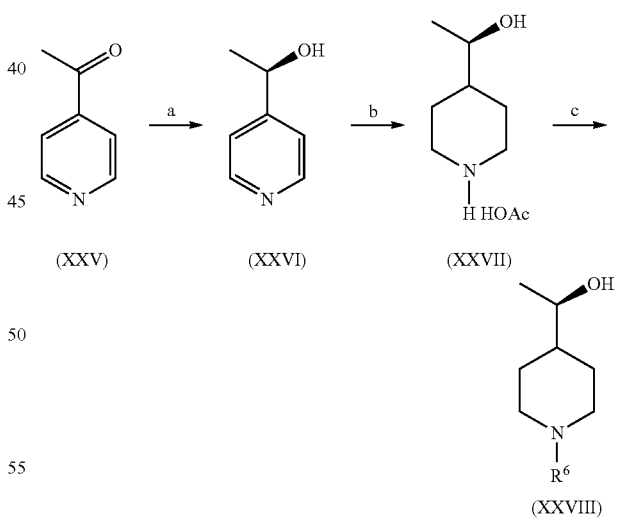

Reagents and conditions: a) [N-[(1R,2R)-2-(amino-N)-1,2-diphenylethyl]-2,4,6-trimethylbenzenesulfonamidato-N] chloro[(1,2,3,4,5,6-n)-1-methyl-4-(1-methylethyl)benzene] ruthenium, Et$_3$N, HCO$_2$H, RT; b) PtO$_2$, H$_2$, HOAc, MeOH, RT; c) (i) when R$^6$=C(O)O-i-Pr: ClC(O)O-i-Pr, K$_2$CO$_3$, H$_2$O, 0° C.; (ii) (XXI), MeOH, K$_2$CO$_3$, RT.

Enantioenriched or enantiopure intermediates of the type (XXVIII) can be prepared according to Scheme 7. 4-Acetylpyridine can be enantioselectively reduced with a ruthenium catalyst (see reference: Uematsu, N.; Fujii, A.; Hashiguchi, S.; Ikariya, T.; Noyori, R; *J. Am. Chem. Soc.* 1996, 118, 4916-4917) and TEA and formic acid to afford secondary alcohol (XXVI). Reduction of the pyridine ring can be performed with a transition-metal catalyst, such as platinum oxide ($PtO_2$), in methanol and acetic acid under an atmosphere of hydrogen. Conversion of the NH into a suitable group (for example, a carbamate) can be accomplished with an alkylchloroformate in dichloromethane in the presence of a base or a heterocycle using a similar sequence described in Scheme 6.

Enantioselective reductions of more general intermediates (ketones other than methyl aryl ketones, such as ethyl ketones) can be accomplished by those skilled in the art using methods described in, but not limited to, reviews on asymmetric reductions; see: Ohkuma, Takeshi; Noyori, Ryoji. "Hydrogenation of carbonyl groups," *Comprehensive Asymmetric Catalysis, Supplement* 2004, 1, 1-41; and Noyori, Ryoji; Hashiguchi, Shohei. "Asymmetric Transfer Hydrogenation Catalyzed by Chiral Ruthenium Complexes," *Accounts of Chemical Research* 1997, 30(2), 97-102; Okana, K.; Murata, K.; Ikariya, T. "Stereoselective synthesis of optically active pyridyl alcohols via asymmetric transfer hydrogenation of pyridyl ketones," *Tetrahedron Lett.* 2000, 41, 9277; Noyori, R; *Asymmetric Catalysis in Organic Synthesis*; John Wiley & Sons: New York, 1994 Chapter 2.

Scheme 8

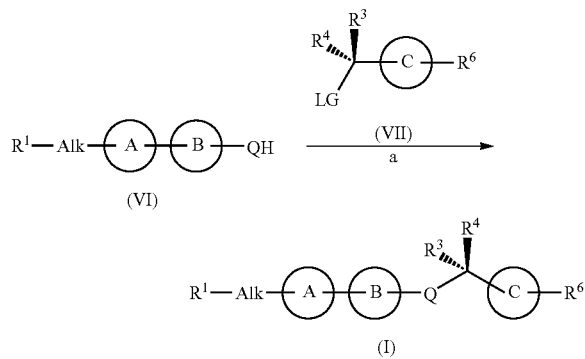

Reagents and conditions: a) $Ph_3P$, DIAD, THF; or $K_2CO_3$, DMF, heating.

Enantioenriched or enantiopure biaryl-based compounds of the type (I) compounds can be prepared by following the general synthetic Scheme 8. As has been described previously, when Q is —O—, the compound (VI) can react with an intermediate (VII) where LG is HO— under Mitsunobu reaction conditions under a) to give the compound of formula (I), see Mitsunobu, *Synthesis*, 1981, 1, and for a Mitsunobu reaction review see D. L. Hughes *Organic Reactions* 42, 335. Treatment of the compound (VI) with an intermediate of formula (VII) where LG- is mesyl under a) conditions in the presence of a base (such as $K_2CO_3$) in DMF can also provide the compound (I). This sequence proceeds with inversion of stereochemistry at the stereogenic carbon under both conditions (LG=OH or OMs).

Compounds of formula (I) can also be prepared in enantioenriched fashion through chiral separation of racemic or enantioenriched material using, but not limited to, preparative chiral SFC technology. For a review, see: Christopher Welch, et al., *LCGC North America* January 2005, 23(1), 16-29.

In addition to the above general synthetic approaches and standard modifications thereto as known in the art, compounds of formula (I) can be obtained by reacting other compounds of formula (I) such as by conversion among the various $R^1$, $R^3$, $R^4$, $R^5$, $R^6$ and $R^7$ groups. For example, see Larock, R. C. In *Comprehensive Organic Transformations: A Guide to Functional Group Preparations*, VCH Publishers: New York, 1990.

Also within the scope of the invention are novel intermediates described above and in the Examples.

Examples

The following specific examples are included as illustrations and are not to be construed as limiting the scope of the present invention.

Example 1

1,1-Dimethylethyl 4-({[4'-(methylsulfonyl)-4-biphenylyl]oxy}methyl)-1-piperidinecarboxylate

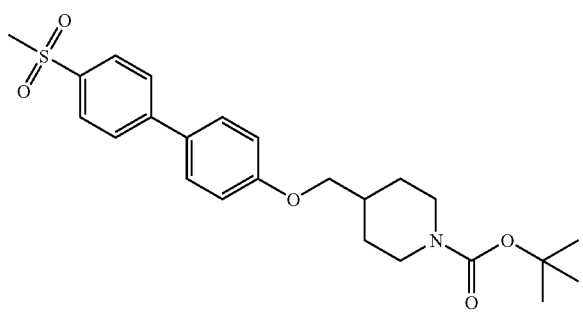

Step 1: [4-(Methylsulfonyl)phenyl]boronic acid (0.69 g, 3.40 mmol) was added to a solution of 4-bromophenol (0.5 g, 2.83 mmol) in DME (25 mL), followed by addition of 2M $Na_2CO_3$ (25 mL) and $Pd(PPh_3)_4$ (0.17 g, 0.14 mmol). The reaction mixture was heated at 90° C. for 3 h, then cooled to ambient temperature, and extracted with ether. The combined organic extract was washed with brine, dried over $Na_2SO_4$, filtered, and the filtrate was concentrated to give the crude product as an off-white solid. The crude product was purified by chromatography on a silica gel column eluted with 50% EtOAc/hexane to give 0.45 g (64%) of 4'-(methylsulfonyl)-4-biphenylol as a white solid. Alternatively, 4'-(methylsulfonyl)-4-biphenylol was prepared from 4-bromophenyl methyl sulfone (2 g, 8.5 mmol), (4-hydroxyphenyl)boronic acid (1.76 g, 12.75 mmol), 2M $Na_2CO_3$ (100 mL) and $Pd(PPh_3)_4$ (0.1 g, 0.08 mmol) in DME (100 mL) in a manner similar to the conditions above. $^1$H NMR (400 MHz, $CDCl_3$): δ 7.97 (d, 2H, J=8.6 Hz), 7.71 (d, 2H, J=8.3 Hz), 7.51 (d, 2H, J=8.6 Hz), 6.94 (d, 2H, J=8.5 Hz), 4.92 (s, 1H), 3.08 (s, 3H); LRMS (ESI), m/z 249 (M+H).

Step 2: A solution of 4'-(methylsulfonyl)-4-biphenylol (0.15 g, 0.60 mmol), N-Boc-4-piperidinemethanol (0.14 g, 0.60 mmol) and $Ph_3P$ (0.16 g, 0.66 mmol) in THF (4 mL) was cooled to -20° C. Diisopropyl azodicarboxylate (0.13 g, 94%, 0.60 mmol) in THF (1 mL) was added dropwise. The reaction mixture was kept between -20° C. and 0° C. for 3 h, then allowed to warm up to ambient temperature, and stirred at ambient temperature overnight. The mixture was diluted with EtOAc, washed with saturated aqueous $NaHCO_3$ and brine, dried over $Na_2SO_4$, filtered, and the filtrate was concentrated to give the crude product as a yellow oil. The crude product was purified by chromatography on a silica gel column eluted with 40% EtOAc/hexane to give 0.20 g (74%) of the title compound as a white solid. $^1$H NMR (400 MHz, CD$_3$OD): δ 7.97 (d, 2H, J=7.6 Hz), 7.83 (d, 2H, J=7.3 Hz), 7.64 (d, 2H, J=7.6 Hz), 7.03 (d, 2H, J=7.8 Hz), 4.15-4.05 (m, 2H), 3.90 (d, 2H, J=6.4 Hz), 3.13 (s, 3H), 2.90-2.70 (bs, 2H), 2.10-1.95 (m, 1H), 1.90-1.80 (m, 2H), 1.46 (s, 9H), 1.35-1.20 (m, 2H); LRMS (ESI), m/z 446 (M+H).

Example 2

5-Ethyl-2-[4-({[4'-(methylsulfonyl)-4-biphenylyl]oxy}methyl)-1-piperidinyl]pyrimidine

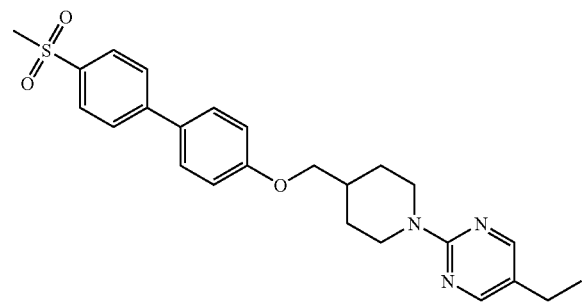

Step 1: 1,1-Dimethylethyl 4-({[4'-(methylsulfonyl)-4-biphenylyl]oxy}methyl)-1-piperidinecarboxylate (Example 1, 87 mg, 0.20 mmol) was dissolved in 1,4-dioxane (4 mL). Ether (3 mL) was added followed by addition of 4M HCl in 1,4-dioxane (3 mL) and 2M HCl in ether (3 mL). The reaction mixture was stirred at ambient temperature overnight. Ether (15 mL) was added, and the white solid was collected via filtration and washed with ether to yield 71 mg (95%) of 4-({[4'-(methylsulfonyl)-4-biphenylyl]oxy}methyl)piperidine hydrochloride as a white solid. $^1$H NMR (400 MHz, CD$_3$OD): δ 7.98 (d, 2H, J=8.5 Hz), 7.83 (d, 2H, J=8.3 Hz), 7.66 (d, 2H, J=8.8 Hz), 7.05 (d, 2H, J=8.8 Hz), 3.97 (d, 2H, J=5.8 Hz), 3.50-3.40 (m, 2H), 3.13 (s, 3H), 3.10-3.00 (m, 2H), 2.25-2.05 (m, 3H), 1.70-1.55 (m, 2H); LRMS (ESI), m/z 346 (M+H).

Step 2: A mixture of 4-({[4'-(methylsulfonyl)-4-biphenylyl]oxy}methyl)piperidine hydrochloride (70 mg, 0.18 mmol), 2-chloro-5-ethylpyrimidine (30 µL, 0.24 mmol) and diisopropylethylamine (0.10 mL, 0.55 mmol) in NMP (3 mL) was heated at 80° C. overnight. After more 2-chloro-5-ethylpyrimidine (0.1 mL) was added, the reaction mixture was heated at 80° C. for 4 h. The mixture was cooled to ambient temperature, and was diluted with EtOAc, washed with water and brine, dried over Na$_2$SO$_4$, filtered, and the filtrate was concentrated to give the crude product as a brown oil. The crude product was purified by chromatography on a silica gel column eluted with 50% EtOAc/hexane followed by trituration with hot hexanes containing 1% MeOH to give 28 mg (34%) of the title compound as a white solid. $^1$H NMR (400 MHz, CDCl$_3$): δ 8.18 (bs, 2H), 7.96 (d, 2H, J=8.3 Hz), 7.72 (d, 2H, J=8.5 Hz), 7.54 (d, 2H, J=8.8 Hz), 6.99 (d, 2H, J=8.8 Hz), 4.85-4.70 (m, 2H), 3.88 (d, 2H, J=6.3 Hz), 3.08 (s, 3H), 3.00-2.85 (m, 2H), 2.55-2.40 (m, 2H), 2.20-2.05 (m, 1H), 2.00-1.90 (m, 2H), 1.45-1.30 (m, 2H), 1.19 (t, 3H, J=7.5 Hz); LRMS (ESI), m/z 452 (M+H).

Example 3

2-[4-({[4'-(Methylsulfonyl)-4-biphenylyl]oxy}methyl)-1-piperidinyl]-4-(trifluoromethyl)pyrimidine trifluoroacetate

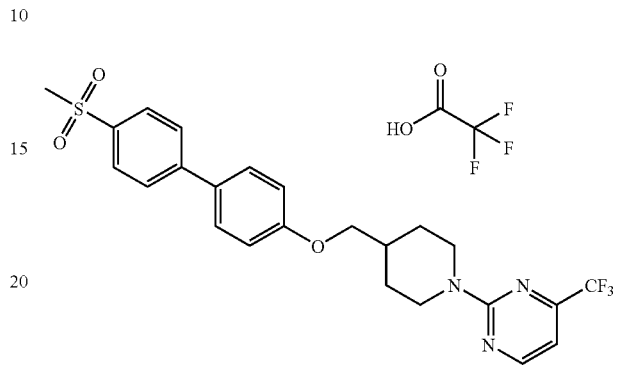

4-({[4'-(Methylsulfonyl)-4-biphenylyl]oxy}methyl)piperidine hydrochloride (prepared as in Example 2, Step 1, 0.05 g, 0.14 mmol) was added to a solution of 2-chloro-4-(trifluoromethyl)pyrimidine (0.03 g, 0.14 mmol) in CH$_3$CN (2 mL), followed by the addition of diisopropylethylamine (0.04 g, 0.28 mmol). The reaction mixture was stirred overnight. The mixture was then concentrated in vacuo and purified by reverse-phase preparative HPLC using CH$_3$CN:H$_2$O gradient (0:100 to 90:10) with 0.05% TFA as a modifier to give the title compound (8 mg, 10%) as a white solid. $^1$H NMR (400 MHz, CDCl$_3$): δ 8.49 (d, 1H, J=5.0 Hz), 7.97 (d, 2H, J=8.7 Hz), 7.72 (d, 2H, J=8.7 Hz), 7.55 (d, 2H, J=8.9 Hz), 7.00 (d, 2H, J=8.9 Hz), 6.73 (d, 1H, J=4.8 Hz), 4.92-4.85 (m, 2H), 3.90 (d, 2H, J=6.4 Hz), 3.08 (s, 3H), 3.02-2.93 (m, 2H), 2.21-2.11 (m, 1H), 2.01-1.95 (m, 2H), 1.45-1.33 (m, 2H); LRMS (ESI), m/z 492 (M+H).

Example 4

2-[4-({[4'-(Methylsulfonyl)-4-biphenylyl]oxy}methyl)-1-piperidinyl]-5-propylpyrimidine trifluoroacetate

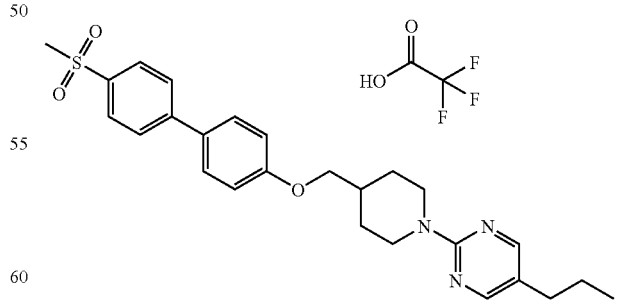

4-({[4'-(Methylsulfonyl)-4-biphenylyl]oxy}methyl)piperidine hydrochloride (prepared as in Example 2, Step 1, 0.05 g, 0.14 mmol) was added to a solution of 2-chloro-5-propylpyrimidine (0.03 g, 0.14 mmol) in CH$_3$CN (2 mL), followed by addition of diisopropylethylamine (0.04 g, 0.28 mmol).

The reaction mixture was stirred overnight. The reaction was then concentrated in vacuo and purified by reverse-phase preparative HPLC using CH$_3$CN:H$_2$O gradient (0:100 to 90:10) with 0.05% TFA as a modifier to give the title compound (18 mg, 20%) as a white solid. $^1$H NMR (400 MHz, CDCl$_3$): δ 8.21 (bs, 2H), 7.97 (d, 2H, J=6.7 Hz), 7.72 (d, 2H, J=8.7 Hz), 7.55 (d, 2H, J=8.9 Hz), 6.99 (d, 2H, J=8.9 Hz), 4.86-4.79 (m, 2H), 3.89 (d, 2H, J=6.4 Hz), 3.08 (s, 3H), 3.04-2.94 (m, 2H), 2.42 (t, 2H, J=7.8 Hz), 2.20-2.08 (m, 1H), 2.03-1.98 (m, 2H), 1.63-1.53 (m, 2H), 1.47-1.35 (m, 2H), 0.94 (t, 3H, J=7.3 Hz); LRMS (ESI), m/z 466 (M+H).

Example 5

5-Fluoro-2-[4-({[4'-(methylsulfonyl)-4-biphenylyl]oxy}methyl)-1-piperidinyl]pyrimidine trifluoroacetate

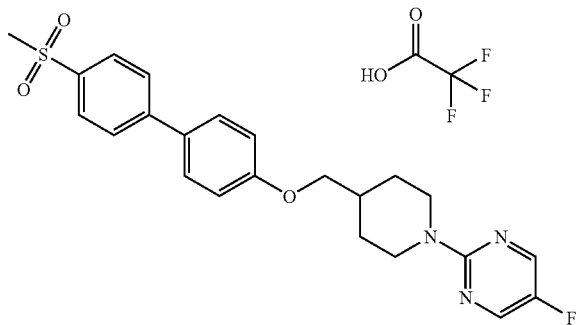

4-({[4'-(Methylsulfonyl)-4-biphenylyl]oxy}methyl)piperidine hydrochloride (prepared as in Example 2, Step 1, 0.05 g, 0.14 mmol) was added to a solution of 2-chloro-5-fluoropyrimidine (0.02 g, 0.14 mmol) in CH$_3$CN (2 mL), followed by addition of diisopropylethylamine (0.04 g, 0.28 mmol). The reaction mixture was heated to 120° C. for 20 min using microwave heating. The reaction was then concentrated in vacuo and purified by reverse-phase preparative HPLC using CH$_3$CN:H$_2$O gradient (0:100 to 90:10) with 0.05% TFA as a modifier to give the title compound (5 mg, 7%) as a white solid. $^1$H NMR (400 MHz, CDCl$_3$): δ 8.23-8.22 (m, 2H), 7.97 (d, 2H, J=8.7 Hz), 7.72 (d, 2H, J=8.7 Hz), 7.55 (d, 2H, J=8.9 Hz), 6.99 (d, 2H, J=8.9 Hz), 4.79-4.73 (m, 2H), 3.89 (d, 2H, J=6.2 Hz), 3.08 (s, 3H), 3.00-2.98 (m, 2H), 2.01-1.93 (m, 2H), 1.63-1.53 (m, 3H); LRMS (ESI), m/z 442 (M+H).

Example 6

3-Chloro-6-[4-({[4'-(methylsulfonyl)-4-biphenylyl]oxy}methyl)-1-piperidinyl]pyridazine trifluoroacetate

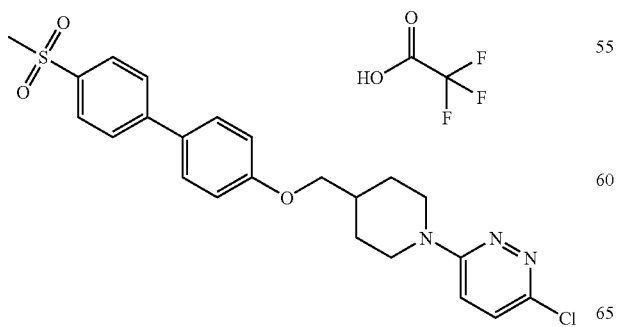

4-({[4'-(Methylsulfonyl)-4-biphenylyl]oxy}methyl)piperidine hydrochloride (prepared as in Example 2, Step 1, 0.1 g, 0.29 mmol) was added to a solution of 3,6-dichloropyridazine (0.04 g, 0.29 mmol) in CH$_3$CN (2 mL), followed by addition of diisopropylethylamine (0.04 g, 0.29 mmol). The reaction mixture was heated at 160° C. using microwave heating for 40 min and then purified by reverse-phase preparative HPLC using CH$_3$CN:H$_2$O gradient (0:100 to 90:10) with 0.05% TFA as a modifier to give the title compound (3 mg, 15%) as a white solid. $^1$H NMR (400 MHz, CDCl$_3$): δ 7.97 (d, 2H, J=8.6 Hz), 7.72 (d, 2H, J=8.6 Hz), 7.55 (d, 2H, J=8.7 Hz), 7.39 (d, 1H, J=9.4 Hz), 7.21 (d, 1H, J=10.5 Hz), 6.99 (d, 2H, J=8.8 Hz), 4.51-4.41 (m, 2H), 3.92 (d, 2H, J=6.3 Hz), 3.28-3.19 (m, 2H), 3.08 (s, 3H), 2.28-2.16 (m, 1H), 2.12-2.05 (m, 2H), 1.69-1.41 (m, 2H); LRMS (ESI), m/z 458 (M+H).

Example 7

4-Chloro-6-[4-({[4'-(methylsulfonyl)-4-biphenylyl]oxy}methyl)-1-piperidinyl]pyrimidine trifluoroacetate

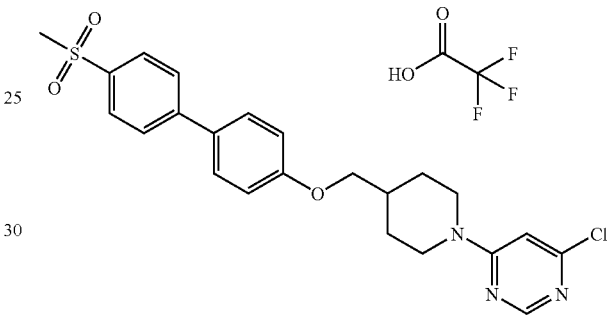

4-({[4'-(Methylsulfonyl)-4-biphenylyl]oxy}methyl)piperidine hydrochloride (prepared as in Example 2, Step 1, 0.1 g, 0.29 mmol) was added to a solution of 4,6-dichloropyrimidine (0.04 g, 0.29 mmol) in CH$_3$CN (2 mL), followed by addition of diisopropylethylamine (0.02 g, 0.14 mmol). The reaction mixture was stirred at room temperature overnight. The reaction was then purified by reverse-phase preparative HPLC using CH$_3$CN:H$_2$O gradient (0:100 to 90:10) with 0.05% TFA as a modifier to give the title compound (3 mg, 12%) as a white solid. $^1$H NMR (400 MHz, CDCl$_3$): δ 8.44 (s, 1H), 7.97 (d, 2H, J=8.5 Hz), 7.72 (d, 2H, J=8.6 Hz), 7.55 (d, 2H, J=8.7 Hz), 6.99 (d, 2H, J=8.9 Hz), 6.56 (s, 1H), 4.55-4.44 (m, 2H), 3.90 (d, 2H, J=6.1 Hz), 3.08 (s, 3H), 3.05-3.00 (m, 2H), 2.27-2.15 (m, 1H), 2.07-1.99 (m, 2H), 1.48-1.37 (m, 2H); LRMS (ESI), m/z 458 (M+H).

Example 8

1-Methylethyl 4-({[4'-(methylsulfonyl)-4-biphenylyl]oxy}methyl)-1-piperidinecarboxylate

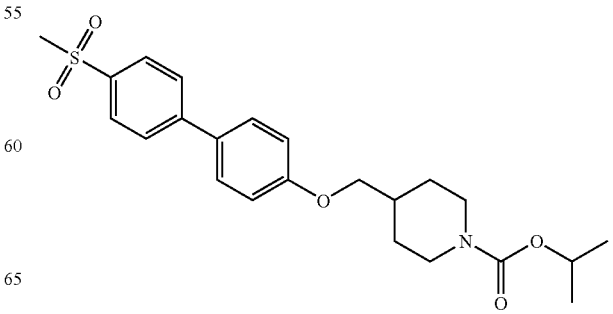

Diisopropylethylamine (0.23 mL, 1.30 mmol) was added to a suspension of 4-({[4'-(methylsulfonyl)-4-biphenylyl]oxy}methyl)piperidine hydrochloride (prepared as in Example 2, Step 1, 0.165 g, 0.43 mmol) in CH$_2$Cl$_2$ (10 mL). The mixture was cooled to 0° C. in an ice bath, and isopropyl chloroformate (1.0M in toluene, 0.48 mL, 0.48 mmol) was added dropwise. The reaction mixture was allowed to warm to ambient temperature, and stirred for 1.5 h, then diluted with ether, washed with water and brine, dried over Na$_2$SO$_4$, filtered, and the filtrate was concentrated. The crude product was purified by chromatography on a silica gel column eluted with 45 to 50% EtOAc/hexane to give 0.152 g (82%) of the title compound as a white solid. $^1$H NMR (400 MHz, CD$_3$OD): δ 7.97 (d, 2H, J=8.3 Hz), 7.83 (d, 2H, J=8.3 Hz), 7.64 (d, 2H, J=8.8 Hz), 7.04 (d, 2H, J=8.8 Hz), 4.90-4.80 (m, 1H), 4.20-4.10 (m, 2H), 3.90 (d, 2H, J=6.1 Hz), 3.13 (s, 3H), 2.95-2.75 (m, 2H), 2.10-1.95 (m, 1H), 1.90-1.80 (m, 2H), 1.35-1.20 (m, 8H); LRMS (ESI), m/z 432 (M+H).

Example 9

1-Methylethyl 4-({[4'-(methylthio)-4-biphenylyl]oxy}methyl)-1-piperidinecarboxylate

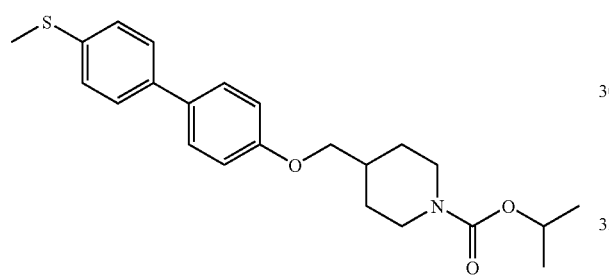

Step 1: Isopropyl chloroformate (1.0M in toluene, 43.4 mL, 43.4 mmol) was added dropwise to a mixture of 4-piperidinemethanol (5 g, 43.4 mmol) and triethylamine (12.1 mL, 86.8 mmol) in CH$_2$Cl$_2$ (150 mL) at 0° C. over 20 min. The mixture was stirred at ambient temperature overnight. The mixture was washed with water, followed by brine. The organic layer was separated and dried over MgSO$_4$, filtered, and the filtrate was concentrated. The crude product was purified by chromatography on a silica gel column using 0 to 5% MeOH/CH$_2$Cl$_2$ to give 7.76 g (89%) of 1-methylethyl 4-(hydroxymethyl)-1-piperidinecarboxylate as a clear oil. $^1$H NMR (400 MHz, CDCl$_3$): δ 4.93-4.78 (m, 1H), 4.19-4.09 (m, 2H), 3.47 (d, 2H, J=6.2 Hz), 2.75-2.65 (m, 2H), 1.75-1.56 (m, 3H), 1.21 (d, 6H, J=6.2 Hz), 1.17-1.06 (m, 2H); LRMS (ESI), m/z 202 (M+H).

Step 2: Diisopropyl azodicarboxylate (9.1 mL, 46.27 mmol) in THF (15 mL) was added dropwise to a solution of 1-methylethyl 4-(hydroxymethyl)-1-piperidinecarboxylate (7.76 g, 38.56 mmol), 4-bromophenol (6.67 g, 38.56 mmol) and Ph$_3$P (13.15 g, 50.12 mmol) in THF (85 mL) at −20° C. The reaction mixture was allowed to warm to ambient temperature and stirred at ambient temperature overnight. The mixture was concentrated, and the residue was purified by chromatography on a silica gel column using 0 to 25% EtOAc/hexane to give the crude product. The crude product was taken up in Et$_2$O (250 mL) and washed with 1N NaOH (aq). The organic extracts were dried over MgSO$_4$, filtered, and the filtrate was concentrated to give 7.5 g (55%) of 1-methylethyl 4-{[(4-bromophenyl)oxy]methyl}-1-piperidinecarboxylate as a white solid. $^1$H NMR (400 MHz, CDCl$_3$): δ 7.35 (d, 2H, J=8.9 Hz), 6.75 (d, 2H, J=8.9 Hz), 4.96-4.83 (m, 1H), 4.24-4.14 (m, 2H), 3.75 (d, 2H, J=6.4 Hz), 2.81-2.71 (m, 2H), 2.02-1.87 (m, 1H), 1.85-1.75 (m, 2H), 1.33-1.13 (m, 8H); LRMS (ESI), m/z 356/358 (M+H).

Step 3: A mixture of [4-(methylthio)phenyl]boronic acid (16.8 mg, 0.1 mmol) and 1-methylethyl 4-{[(4-bromophenyl)oxy]methyl}-1-piperidinecarboxylate (36 mg, 0.10 mmol), Pd(PPh$_3$)$_4$ (5 mg, 0.004 mmol), 2M Na$_2$CO$_3$ (1 mL) and DME (1 mL) was heated at 80° C. overnight. The reaction was cooled to ambient temperature, transferred onto a 1 mL Varian Chem Elut column, eluted with EtOAc, and the filtrate concentrated. The crude product was purified by reverse-phase preparative HPLC using a MeOH:H$_2$O gradient (20:80 to 100:0) with 0.1% formic acid as a modifier to afford the title compound (7.4 mg, 12%). LRMS (ESI), m/z 422 (M+Na).

Example 10

1-Methylethyl 4-({[4'-(trifluoromethyl)-4-biphenylyl]oxy}methyl)-1-piperidinecarboxylate

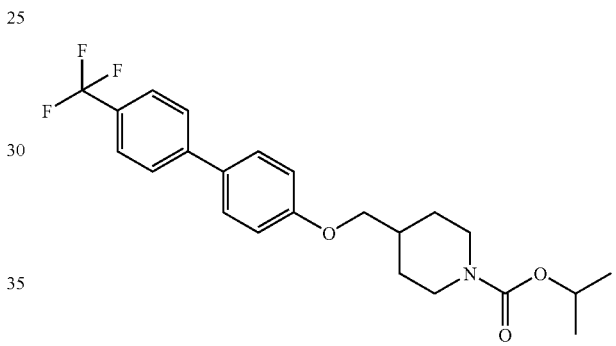

The title compound (2.2 mg, 5%) was prepared from [4-(trifluoromethyl)phenyl]boronic acid (19 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 444 (M+Na).

Example 11

1-Methylethyl 4-[({4'-[(ethyloxy)carbonyl]-4-biphenylyl}oxy)methyl]-1-piperidinecarboxylate

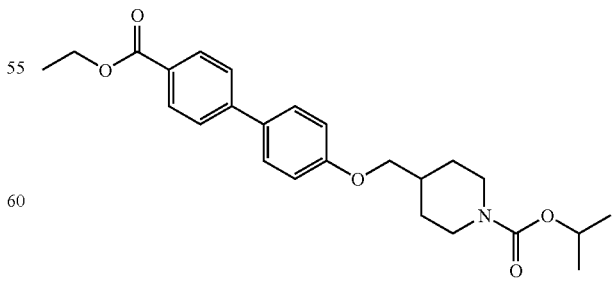

The title compound (2.4 mg, 6%) was prepared from {4-[(ethyloxy)carbonyl]phenyl}boronic acid (19.4 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 448 (M+Na).

Example 12

1-Methylethyl 4-[({4'-[(1-methylethyl)thio]-4-biphenylyl}oxy)methyl]-1-piperidinecarboxylate

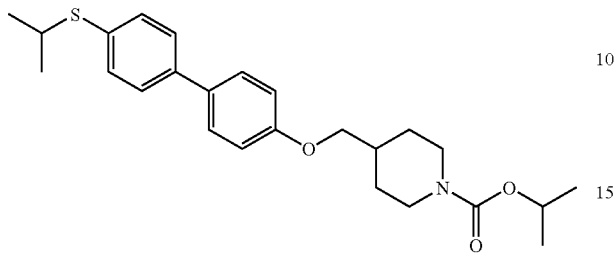

The title compound (7.1 mg, 17%) was prepared from {4-[(1-methylethyl)thio]phenyl}boronic acid (19.6 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 450 (M+Na).

Example 13

(±)-1-Methylethyl 4-({[4'-(methylsulfinyl)-4-biphenylyl]oxy}methyl)-1-piperidinecarboxylate

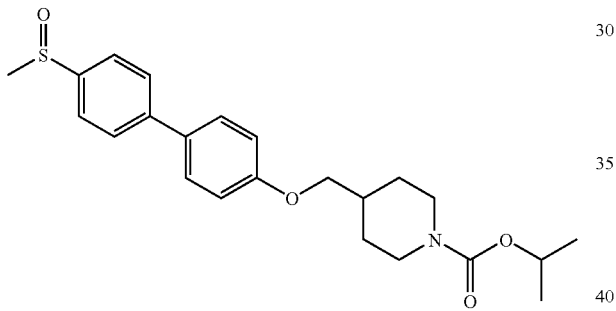

The title compound (6.6 mg, 16%) was prepared from (±)-[4-(methylsulfinyl)phenyl]boronic acid (18.4 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 416 (M+H).

Example 14

1-Methylethyl 4-{[(4'-{[(phenylmethyl)amino]carbonyl}-4-biphenylyl)oxy]methyl}-1-piperidinecarboxylate

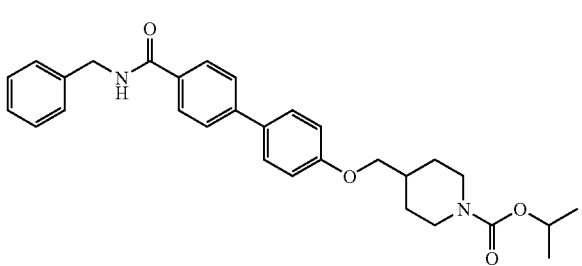

The title compound (7.1 mg, 15%) was prepared from (4-{[(phenylmethyl)amino]carbonyl}phenyl)boronic acid (25.5 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 487 (M+H).

Example 15

1-Methylethyl 4-({[4'-(ethylsulfonyl)-4-biphenylyl]oxy}methyl)-1-piperidinecarboxylate

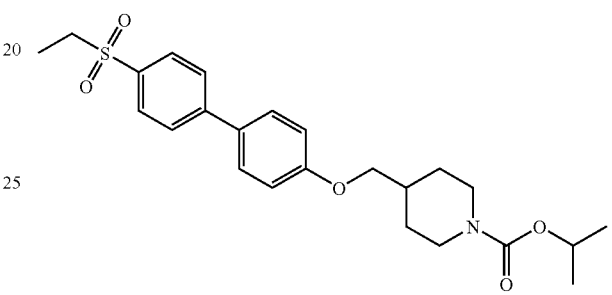

The title compound (8.9 mg, 20%) was prepared from [4-(ethylsulfonyl)phenyl]boronic acid (21.4 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 446 (M+H).

Example 16

1-Methylethyl 4-({[4'-(1-pyrrolidinylcarbonyl)-4-biphenylyl]oxy}methyl)-1-piperidinecarboxylate

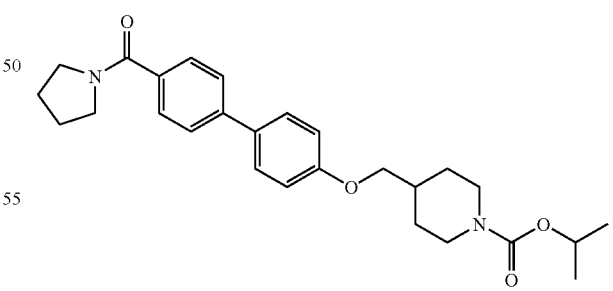

The title compound (8.6 mg, 19%) was prepared from [4-(1-pyrrolidinylcarbonyl)phenyl]boronic acid (21.9 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 451 (M+H).

Example 17

1-Methylethyl 4-[({4'-[(phenylamino)carbonyl]-4-biphenylyl}oxy)methyl]-1-piperidinecarboxylate

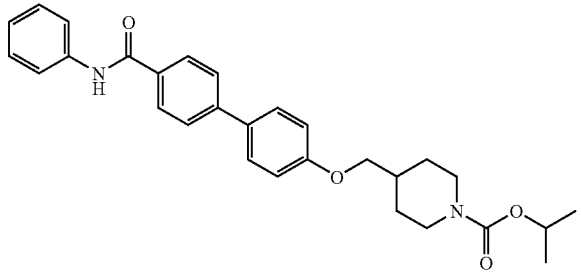

The title compound (7.4 mg, 16%) was prepared from {4-[(phenylamino)carbonyl]phenyl}boronic acid (24.1 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 495 (M+Na).

Example 18

1-Methylethyl 4-({[4'-(phenylcarbonyl)-4-biphenylyl]oxy}methyl)-1-piperidinecarboxylate

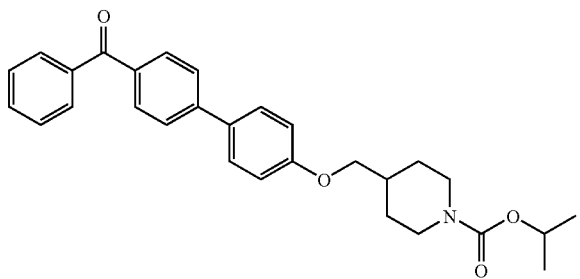

The title compound (3.0 mg, 7%) was prepared from [4-(phenylcarbonyl)phenyl]boronic acid (22.6 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to example 9, Step 3. LRMS (ESI), m/z 480 (M+Na).

Example 19

1-Methylethyl 4-({[4'-(hydroxymethyl)-4-biphenylyl]oxy}methyl)-1-piperidinecarboxylate

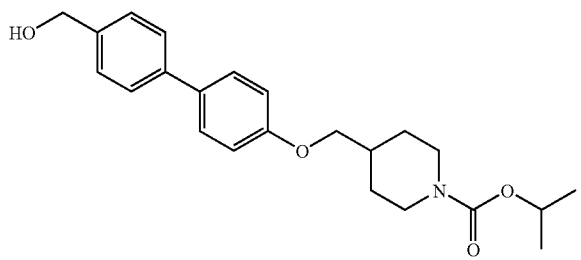

The title compound (1.6 mg, 4%) was prepared from [4-(hydroxymethyl)phenyl]boronic acid (15.2 mg, 0.1 mmol) and 1-methylethyl 4-{[(4-bromophenyl)oxy]methyl}-1-piperidinecarboxylate (Example 9, Step 2, 36 mg, 0.10 mmol) in a manner similar to Example 9, Step 3. LRMS (ESI), m/z 406 (M+Na).

Example 20

1-[3-(1-Methylethyl)-1,2,4-oxadiazol-5-yl]-4-({[4'-(methylsulfonyl)-4-biphenylyl]oxy}methyl)piperidine

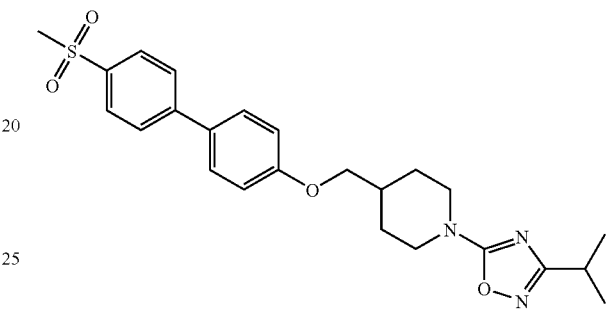

Step 1: A solution of 4-piperidinemethanol (10 g, 86.8 mmol) in CH$_2$Cl$_2$ (20 mL) was added dropwise to a slurry of NaHCO$_3$ (14.6 g, 173.6 mmol) in water (10 mL) at 0° C. The mixture was stirred at 0° C. for 30 min, and then charged with cyanogen bromide (3.0M in CH$_2$Cl$_2$, 32 mL, 95.5 mmol) at 0° C. The reaction mixture was stirred at 0° C. for 30 min, then allowed to warm to ambient temperature, and stirred overnight. The aqueous layer was separated and extracted with CH$_2$Cl$_2$. The combined organic extracts were dried over MgSO$_4$, filtered, and the filtrate was concentrated. The crude product was purified by chromatography on a silica gel column using 0 to 100% EtOAc/hexane to give 7.88 g (65%) of 4-(hydroxymethyl)-1-piperidinecarbonitrile as a tan solid. $^1$H NMR (400 MHz, CDCl$_3$): δ 3.52 (d, 2H, J=6.4 Hz), 3.50-3.40 (m, 2 H), 3.05-2.95 (m, 2H), 1.77 (m, 2H), 1.68-1.54 (m, 1H) 1.44-1.29 (m, 2H); LRMS (ESI), m/z 141 (M+H).

Step 2: A mixture of 2-methylpropanenitrile (10 mL, 110 mmol), 50% hydroxylamine in water (30 mL, 440 mmol) and ethanol (50 mL) was stirred at reflux for 3 h, then cooled to ambient temperature, and concentrated to give N-hydroxy-2-methylpropanimidamide (11.05 g, 98%) as a clear oil. $^1$H NMR (400 MHz, DMSO-d$_6$): δ 8.67 (s, 1H), 5.21 (s, 2H), 2.31-2.11 (m, 1H), 1.02 (d, 6H, J=7.0 Hz); LRMS (ESI), m/z 103 (M+H).

Step 3: A solution of 1N ZnCl$_2$ in Et$_2$O (60.7 mL, 60.7 mmol) was added dropwise over 15 min to a solution of 4-(hydroxymethyl)-1-piperidinecarbonitrile (7.09 g, 50.6 mmol) and N-hydroxy-2-methylpropanimidamide (6.2 g, 60.7 mmol) in EtOAc (150 mL) at ambient temperature. The reaction mixture was left at ambient temperature for 15 min, decanted, and triturated with Et$_2$O to give a white solid. The solid was heated in a solution of concentrated HCl (15 mL) and ethanol (30 mL) for 1 h. Ethanol was removed in vacuo, and the resulting residue was charged with water (150 mL). The mixture was neutralized with Na$_2$CO$_3$, and extracted with CH$_2$Cl$_2$. The organic extracts were dried over MgSO$_4$, filtered and the filtrate was concentrated. The crude product was purified by chromatography on a silica gel column using 0 to 100% EtOAc/hexane to give 4.44 g (39%) of {1-[3-(1- methylethyl)-1,2,4-oxadiazol-5-yl]-4-piperidinyl}methanol as a clear oil. $^1$H NMR (400 MHz, CDCl$_3$): δ 4.20-4.10 (m, 2H), 3.51 (d, 2H, J=6.4 Hz), 3.07-2.97 (m, 2H), 2.90-2.75 (m, 1H), 1.85-1.75 (m, 2H), 1.76-1.62 (m, 1H), 1.36-1.19 (m, 8H); LRMS (ESI), m/z 226 (M+H).

Step 4: Diisopropyl azodicarboxylate (0.102 mL, 0.52 mmol) in THF (1 mL) was added dropwise to a solution of 4'-(methylsulfonyl)-4-biphenylol (prepared as in Example 1, Step 1, 100 mg, 0.40 mmol), {1-[3-(1-methylethyl)-1,2,4-oxadiazol-5-yl]-4-piperidinyl}methanol (as prepared in Example 20, Step 3, 91 mg, 0.40 mmol) and Ph$_3$P (126 mg, 0.48 mmol) in THF (5 mL) at ambient temperature. The reaction mixture was stirred at ambient temperature overnight. The mixture was concentrated, and the crude product was purified by reverse-phase preparative HPLC using a CH$_3$CN:H$_2$O gradient (30:70 to 100:0) with 0.05% TFA as a modifier to give 31 mg (17%) of the title compound as a white solid. $^1$H NMR (400 MHz, CDCl$_3$): δ 7.97 (d, 2H, J=8.6 Hz), 7.72 (d, 2H, J=8.6 Hz), 7.55 (d, 2H, J=8.9 Hz), 6.99 (d, 2 H, J=8.9 Hz), 4.26-4.16 (m, 2H), 3.89 (d, 2H, J=6.4 Hz), 3.22-3.03 (m, 5H), 2.96-2.85 (m, 1H), 2.14-2.03 (m, 1H), 2.03-1.93 (m, 2H), 1.56-1.40 (m, 2H), 1.29 (d, 6H, J=7.0 Hz); LRMS (ESI), m/z 456 (M+H).

Example 21

1-[3-(2-Methylpropyl)-1,2,4-oxadiazol-5-yl]-4-({[4'-(methylsulfonyl)-4-biphenylyl]oxy}methyl)piperidine

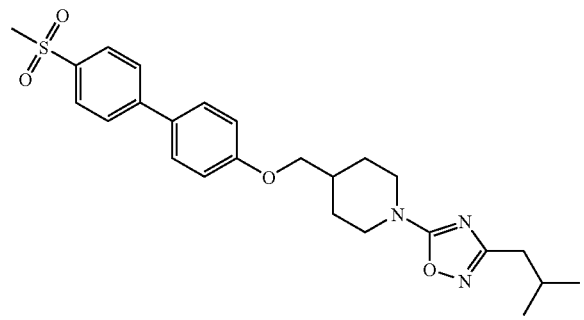

Step 1: A solution of 1N ZnCl$_2$ in Et$_2$O (8.2 mL, 8.2 mmol) was added dropwise over 15 min to a solution of 4-(hydroxymethyl)-1-piperidinecarbonitrile (Example 20, Step 1, 955 mg, 6.8 mmol), N-hydroxy-3-methylbutanimidamide (950 mg, 8.2 mmol) in EtOAc (25 mL) at ambient temperature. The reaction was left at ambient temperature for 15 min. The resulting precipitate was filtered, washed with Et$_2$O, and air-dried to give a white solid. The solid was heated in a solution of concentrated HCl (2.5 mL) and ethanol (5 mL) for 1 h. The mixture was concentrated, and the resulting residue was charged with water (25 mL), neutralized with Na$_2$CO$_3$, and extracted with CH$_2$Cl$_2$. The organics were dried over MgSO$_4$, filtered, and the filtrate was concentrated. The crude product was purified by chromatography on a silica gel column using 0 to 10% MeOH/CH$_2$Cl$_2$ to give 485 mg (30%) of 1-[3-(2-methylpropyl)-1,2,4-oxadiazol-5-yl]-4-piperidinyl}methanol as a clear oil. $^1$H NMR (400 MHz, CDCl$_3$): δ 4.22-4.12 (m, 2H), 3.53 (d, 2H, J=6.4 Hz), 3.11-3.01 (m, 2H), 2.39 (d, 2H, J=7.2 Hz), 2.13-2.00 (m, 1H), 1.88-1.78 (m, 2H), 1.79-1.66 (m, 1H), 1.39-1.23 (m, 2H), 0.96 (d, 2H, J=6.7 Hz); LRMS (ESI), m/z 240 (M+H).

Step 2: 4-{[(4-Bromophenyl)oxy]methyl}-1-[3-(2-methylpropyl)-1,2,4-oxadiazol-5-yl]piperidine (334 mg, 42%) was prepared as a white solid from 1-[3-(2-methylpropyl)-1,2,4-oxadiazol-5-yl]-4-piperidinyl}methanol (485 mg, 2.03 mmol), 4-bromophenol (351 mg, 2.03 mmol) and Ph$_3$P (640 mg, 2.44 mmol) in THF (10 mL) followed by diisopropyl azodicarboxylate (0.52 mL, 2.64 mmol) in a manner similar Example 1, Step 2. $^1$H NMR (400 MHz, CDCl$_3$): δ 7.36 (d, 2H, J=9.1 Hz), 6.76 (d, 2H, J=9.1 Hz), 4.25-4.15 (m, 2H), 3.79 (d, 2H, J=6.4 Hz), 3.15-3.05 (m, 2H), 2.41 (d, 2H, J=7.0 Hz), 2.14-1.99 (m, 2H), 1.98-1.88 (m, 2H), 1.51-1.33 (m, 2 H), 0.97 (d, 6H, J=6.7 Hz); LRMS (ESI), m/z 394/396 (M+H).

Step 3: A mixture of [4-(methylsulfonyl)phenyl]boronic acid (170 mg, 0.85 mmol), 4-{[(4-bromophenyl)oxy]methyl}-1-[3-(2-methylpropyl)-1,2,4-oxadiazol-5-yl]piperidine (334 mg, 0.85 mmol), Pd(PPh$_3$)$_2$Cl$_2$ (50 mg, 0.07 mmol), 2M Na$_2$CO$_3$ (5 mL) and DME (5 mL) was heated at 80° C. for 2 h. The reaction was cooled to ambient temperature, and the organics were partitioned, then concentrated. The crude product was purified by reverse-phase preparative HPLC using a CH$_3$CN:H$_2$O gradient (25:75 to 100:0) with 0.05% TFA as a modifier to give 121 mg (30%) of the title compound as a white solid. $^1$H NMR (400 MHz, CDCl$_3$): δ 7.97 (d, 2H, J=8.2 Hz), 7.72 (d, 2H, J=8.4 Hz), 7.55 (d, 2H, J=8.8 Hz), 6.99 (d, 2H, J=8.8 Hz), 4.25-4.15 (m, 2H), 3.89 (d, 2H, J=6.2 Hz), 3.20-3.10 (m, 2H), 3.08 (s, 3H), 2.43 (d, 2H, J=7.0 Hz), 2.17-2.02 (m, 2H), 2.04-1.94 (m, 2H), 1.59-1.37 (m, 2H), 0.97 (d, 6H, J=6.7 Hz); LRMS (ESI), m/z 470 (M+H).

Example 22

1-(3-Cyclopropyl-1,2,4-oxadiazol-5-yl)-4-({[4'-(methylsulfonyl)-4-biphenylyl]oxy}methyl)piperidine

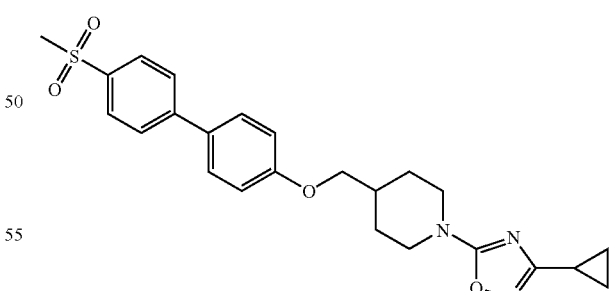

The title compound (8 mg, 0.2%) was prepared from N-hydroxycyclopropanecarboximidamide (1.28 g, 12.8 mmol) in a manner similar to Example 20, Steps 1-4. $^1$H NMR (400 MHz, CDCl$_3$): δ 7.97 (d, 2H, J=8.6 Hz), 7.72 (d, 2H, J=8.8 Hz), 7.55 (d, 2H, J=8.9 Hz), 6.99 (d, 2H, J=8.9 Hz), 4.18 (d, 2H, J=13.2 Hz), 3.88 (d, 2H, J=6.2 Hz), 3.17-2.99 (m, 5H), 2.14-2.02 (m, 1H), 2.00-1.90 (m, 2H), 1.90-1.80 (m, 1H), 1.52-1.37 (m, 2H), 0.95 (d, 4H, J=11.3 Hz); LRMS (ESI), m/z 454 (M+H).

Example 23

1-[3-(1,1-Dimethylethyl)-1,2,4-oxadiazol-5-yl]-4-({[4'-(methylsulfonyl)-4-biphenylyl]oxy}methyl)piperidine

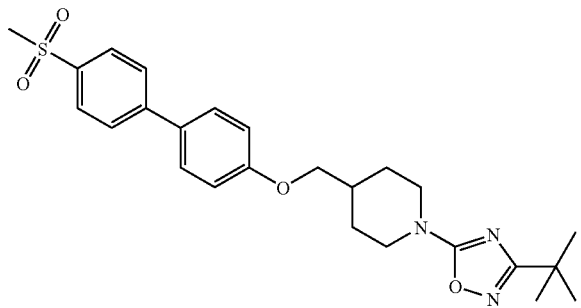

The title compound (105 mg, 3%) was prepared from N-hydroxy-2,2-dimethylpropanimidamide (1 mL, 9.05 mmol) in a manner similar to Example 20, Steps 1-4. $^1$H NMR (400 MHz, CDCl$_3$): δ 7.97 (d, 2H, J=8.6 Hz), 7.72 (d, 2H, J=8.6 Hz), 7.55 (d, 2H, J=8.8 Hz), 6.99 (d, 2H, J=8.8 Hz), 4.22 (d, 2H, J=13.2 Hz), 3.89 (d, 2H, J=6.4 Hz), 3.21-3.01 (m, 5H), 2.15-2.03 (m, 1H), 2.02-1.92 (m, 2H), 1.58-1.41 (m, 2H), 1.32 (s, 9H); LRMS (ESI), m/z 470 (M+H).

Example 24

1-[3-(1-Methylethyl)-1,2,4-oxadiazol-5-yl]-4-[({4'-[(1-methylethyl)sulfonyl]-4-biphenylyl}oxy)methyl]piperidine

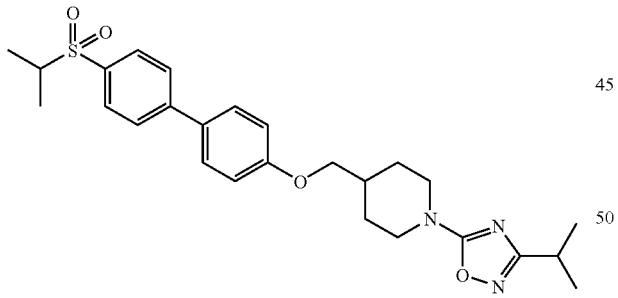

Step 1: 4-{[(4-Bromophenyl)oxy]methyl}-1-[3-(1-methylethyl)-1,2,4-oxadiazol-5-yl]piperidine (322 mg, 42%) was prepared from {1-[3-(1-methylethyl)-1,2,4-oxadiazol-5-yl]-4-piperidinyl}methanol (prepared as in Example 20, Step 3, 450 mg, 2.0 mmol), 4-bromophenol (346 mg, 2.0 mmol) and Ph$_3$P (629 mg, 2.4 mmol) in THF (5 mL) followed by diisopropyl azodicarboxylate (0.512 mL, 2.6 mmol) in a manner similar to Example 1, Step 2. $^1$H NMR (400 MHz, CDCl$_3$): δ 7.36 (d, 2H, J=9.1 Hz), 6.76 (d, 2H, J=8.9 Hz), 4.28-4.18 (m, 2H), 3.79 (d, 2H, J=6.2 Hz), 3.14-3.04 (m, 2H), 2.94-2.82 (m, 1H), 2.10-1.94 (m, 1H), 1.97-1.87 (m, 2H), 1.49-1.36 (m, 2H), 1.28 (d, 6H, J=7.0 Hz); LRMS (ESI), m/z 380/382 (M+H).

Step 2: 1-[3-(1-Methylethyl)-1,2,4-oxadiazol-5-yl]-4-[({4'-[(1-methylethyl)thio]-4-biphenylyl}oxy)methyl]piperidine (20 mg, 5%) was prepared as a white solid from {4-[(1-methylethyl)thio]phenyl}boronic acid (167 mg, 0.85 mmol), 4-{[(4-bromophenyl)oxy]methyl}-1-[3-(1-methylethyl)-1,2,4-oxadiazol-5-yl]piperidine (322 mg, 0.85 mmol), Pd(PPh$_3$)$_2$Cl$_2$ (50 mg, 0.07 mmol), 2M Na$_2$CO$_3$ (5 mL) and DME (5 mL) in a manner similar to Example 21, Step 3. $^1$H NMR (400 MHz, CDCl$_3$): δ 7.57-7.39 (m, 6H), 6.94 (d, 2H, J=8.9 Hz), 4.28-4.18 (m, 2H), 3.87 (d, 2H, J=6.4 Hz), 3.46-3.30 (m, 1H), 3.20-3.08 (m, 2H), 2.98-2.85 (m, 1H), 2.16-2.03 (m, 1H), 2.03-1.93 (m, 2H), 1.55-1.39 (m, 2H), 1.36-1.24 (m, 12H); LRMS (ESI), m/z 452 (M+H).

Step 3: A mixture of 1-[3-(1-methylethyl)-1,2,4-oxadiazol-5-yl]-4-[({4'-[(1-methylethyl)thio]-4-biphenylyl}oxy)methyl]piperidine (20 mg, 0.04 mmol) and m-CPBA (16 mg, 77%, 0.09 mmol) in CH$_2$Cl$_2$ (3 mL) was stirred at 0° C. for 15 min, then at ambient temperature for 4 h. The mixture was concentrated, and the crude product was purified by reverse-phase preparative HPLC using a CH$_3$CN:H$_2$O gradient (30:70 to 100:0) with 0.05% TFA as a modifier to give 10 mg (52%) of the title compound as a white solid. $^1$H NMR (400 MHz, CDCl$_3$): δ 7.90 (d, 2H, J=8.6 Hz), 7.71 (d, 2H, J=8.8 Hz), 7.56 (d, 2H, J=8.8 Hz), 6.99 (d, 2H, J=8.8 Hz), 4.28-4.18 (m, 2H), 3.89 (d, 2H, J=6.4 Hz), 3.29-3.07 (m, 3H), 2.98-2.83 (m, 1H), 2.14-2.04 (m, 1H), 2.02-1.92 (m, 2H), 1.57-1.39 (m, 2H), 1.32 (d, 6H, J=6.9 Hz), 1.29 (d, 6H, J=6.9 Hz); LRMS (ESI), m/z 484 (M+H).

Example 25

N-Cyclopropyl-4'-[({1-[3-(1-methylethyl)-1,2,4-oxadiazol-5-yl]-4-piperidinyl}methyl)oxy]-4-biphenylcarboxamide

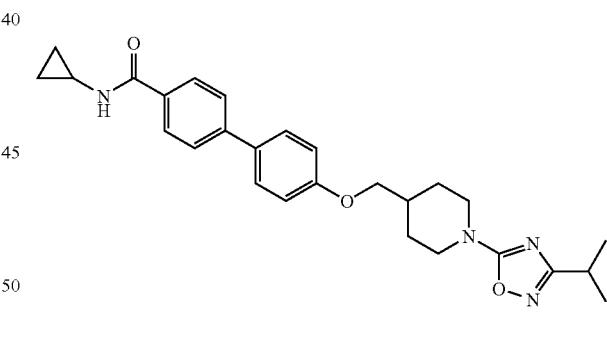

The title compound (9 mg, 5%) was prepared as a white solid from {4-[(cyclopropylamino)carbonyl]phenyl}boronic acid (41 mg, 0.2 mmol), 4-{[(4-bromophenyl)oxy]methyl}-1-[3-(1-methylethyl)-1,2,4-oxadiazol-5-yl]piperidine (prepared as in Example 24, Step 1, 76 mg, 0.2 mmol), Pd(PPh$_3$)$_2$Cl$_2$ (50 mg, 0.07 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.78 (d, 2H, J=8.6 Hz), 7.59 (d, 2H, J=8.6 Hz), 7.54 (d, 2 H, J=8.8 Hz), 6.96 (d, 2H, J=8.8 Hz), 6.26 (s, 1H), 4.28-4.18 (m, 2H), 3.88 (d, 2H, J=6.2 Hz), 3.17-3.07 (m, 2H), 2.98-2.84 (m, 2H), 2.13-2.02 (m, 1H), 2.05-1.92 (m, 2H), 1.55-1.40 (m, 2H), 1.29 (d, 6H, J=6.9 Hz), 0.94-0.84 (m, 2H), 0.67-0.60 (m, 2H); LRMS (ESI), m/z 461 (M+H).

Example 26

1-[3-(1-Methylethyl)-1,2,4-oxadiazol-5-yl]-4-({[4'-(1-pyrrolidinylcarbonyl)-4-biphenylyl]oxy}methyl)piperidine

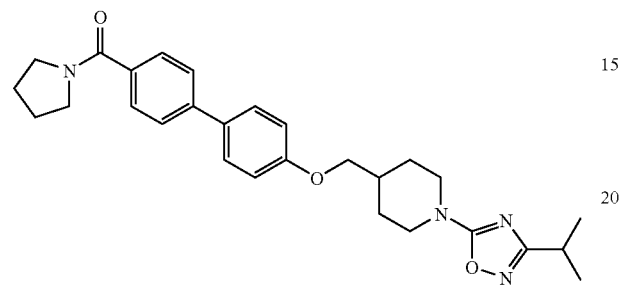

The title compound (4 mg, 4%) was prepared as a yellow solid from [4-(1-pyrrolidinylcarbonyl)phenyl]boronic acid (44 mg, 0.2 mmol), 4-{[(4-bromophenyl)oxy]methyl}-1-[3-(1-methylethyl)-1,2,4-oxadiazol-5-yl]piperidine (prepared as in Example 24, Step 1, 76 mg, 0.2 mmol), Pd(PPh$_3$)$_4$ (50 mg, 0.04 mmol), 2M Na$_2$CO$_3$ (1 mL) and DME (1 mL) in a manner similar to Example 1, Step 1, and worked up in a manner similar to Example 9, Step 3. $^1$H NMR (400 MHz, CDCl$_3$): δ 7.58 (s, 4H), 7.53 (d, 2H, J=8.8 Hz), 6.96 (d, 2H, J=8.8 Hz), 4.26-4.16 (m, 2H), 3.88 (d, 2H, J=6.4 Hz), 3.70 (t, 2H, J=7.0 Hz), 3.52 (t, 2H, J=6.6 Hz), 3.18-3.08 (m, 2H), 2.99-2.84 (m, 1H), 2.15-1.85 (m, 7H), 1.57-1.40 (m, 2H), 1.29 (d, 6H, J=7.0 Hz); LRMS (ESI), m/z 475 (M+H).

Example 27

4'-[({1-[3-(1-Methylethyl)-1,2,4-oxadiazol-5-yl]-4-piperidinyl}methyl)oxy]-N-(phenylmethyl)-4-biphenylcarboxamide

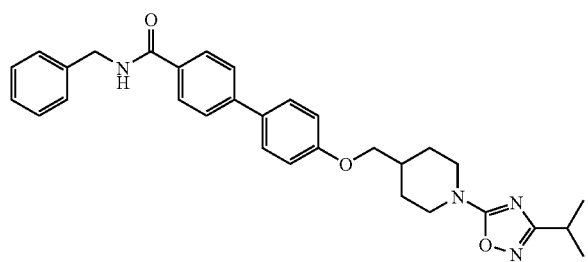

The title compound (2 mg, 2%) was prepared from (4-{[(phenylmethyl)amino]carbonyl}phenyl)boronic acid (51 mg, 0.2 mmol) and 4-{[(4-bromophenyl)oxy]methyl}-1-[3-(1-methylethyl)-1,2,4-oxadiazol-5-yl]piperidine (prepared as in Example 24, Step 1, 76 mg, 0.2 mmol) in a manner similar to Example 1, Step 1, and worked up in a manner similar to Example 9, Step 3. $^1$H NMR (400 MHz, CDCl$_3$): δ 7.83 (d, 2H, J=8.6 Hz), 7.61 (d, 2H, J=8.6 Hz), 7.54 (d, 2H, J=8.9 Hz), 7.39-7.28 (m, 5H), 6.97 (d, 2H, J=8.8 Hz), 6.41 (t, 1H, J=5.7 Hz), 4.68 (d, 2H, J=5.5 Hz), 4.26-4.16 (m, 2H), 3.88 (d, 2H, J=6.4 Hz), 3.18-3.06 (m, 2H), 2.96-2.85 (m, 1H), 2.13-2.01 (m, 1H), 2.02-1.92 (m, 2H), 1.55-1.40 (m, 2H), 1.29 (d, 6H, J=7.0 Hz); LRMS (ESI), m/z 511 (M+H).

Example 28

1-(3-Methyl-1,2,4-oxadiazol-5-yl)-4-({[4'-(methylsulfonyl)-4-biphenylyl]oxy}methyl)piperidine

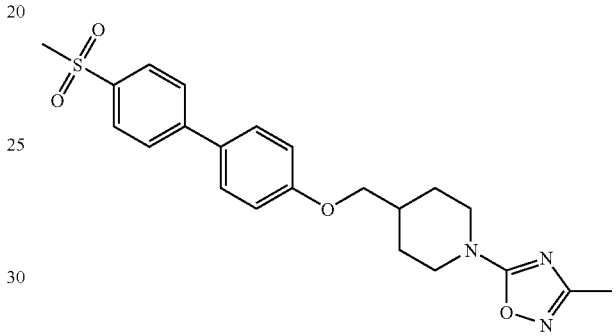

Step 1: [1-(3-Methyl-1,2,4-oxadiazol-5-yl)-4-piperidinyl]methanol (143 mg, 13%) was prepared from a solution of 1N ZnCl$_2$ in Et$_2$O (6.8 mL, 6.8 mmol), 4-(hydroxymethyl)-1-piperidinecarbonitrile (prepared as in Example 20, Step 1, 0.79 g, 5.6 mmol) and N-hydroxyacetamidine (0.5 g, 6.8 mmol) in EtOAc (10 mL) followed by concentrated HCl (2 mL) in EtOH (2 mL) in a manner similar to Example 20, Step 3. $^1$H NMR (400 MHz, CDCl$_3$): δ 4.22-4.10 (m, 2H), 3.54 (d, 2H, J=6.4 Hz), 3.11-3.01 (m, 2H), 2.21 (s, 3H), 1.89-1.79 (m, 2H), 1.78-1.69 (m, 1H), 1.41-1.20 (m, 2H); LRMS (ESI), m/z 198 (M+H).

Step 3: The title compound (43 mg, 21%) was prepared as a white solid from 4'-(methylsulfonyl)-4-biphenylol (prepared as in Example 1, Step 1, 120 mg, 0.48 mmol), [1-(3-methyl-1,2,4-oxadiazol-5-yl)-4-piperidinyl]methanol (143 mg, 0.73 mmol) and Ph$_3$P (191 mg, 0.73 mmol) in THF (5 mL) followed by diisopropyl azodicarboxylate (0.144 mL, 0.73 mmol) in a manner similar to Example 1, Step 2, and worked up in a manner similar to Example 9, Step 3. $^1$H NMR (400 MHz, CDCl$_3$): δ 7.97 (d, 2H, J=8.6 Hz), 7.72 (d, 2H, J=8.4 Hz), 7.55 (d, 2H, J=8.8 Hz), 6.99 (d, 2H, J=8.8 Hz), 4.25-4.15 (m, 2H), 3.89 (d, 2H, J=6.4 Hz), 3.22-3.08 (m, 2H), 3.08 (s, 3 H), 2.24 (s, 3H), 2.04-1.94 (m, 2H), 1.55-1.42 (m, 3H); LRMS (ESI), m/z 428 (M+H).

Example 29

1-Methylethyl 4-[({4'-[(ethylamino)carbonyl]-4-biphenylyl}oxy)methyl]-1-piperidinecarboxylate

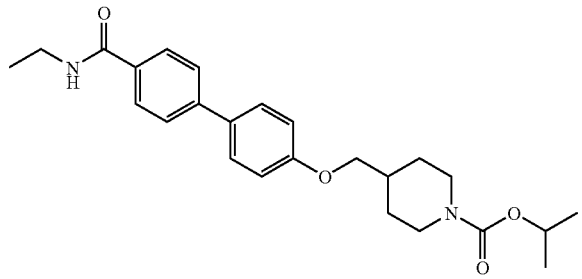

The title compound (11 mg, 26%) was prepared as a tan solid from {4-[(ethylamino)carbonyl]phenyl}boronic acid (19 mg, 0.1 mmol), 1-methylethyl 4-{[(4-bromophenyl)oxy]methyl}-1-piperidinecarboxylate (prepared as in Example 9, Step 2, 36 mg, 0.1 mmol), Pd(PPh$_3$)$_2$Cl$_2$ (10 mg, 0.01 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.80 (d, 2H, J=8.4 Hz), 7.60 (d, 2H, J=8.6 Hz), 7.54 (d, 2H, J=8.8 Hz), 6.96 (d, 2H, J=8.8 Hz), 6.09 (t, 1 H, J=5.4 Hz), 4.98-4.84 (m, 1H), 4.20 (bs, 2H), 3.85 (d, 2H, J=6.4 Hz), 3.61-3.41 (m, 2H), 2.87-2.71 (m, 2H), 2.05-1.95 (m, 1H), 1.90-1.80 (m, 2H), 1.32-1.13 (m, 11H); LRMS (ESI), m/z 425 (M+H).

Example 30

1-Methylethyl 4-[({4'-[(dimethylamino)carbonyl]-4-biphenylyl}oxy)methyl]-1-piperidinecarboxylate

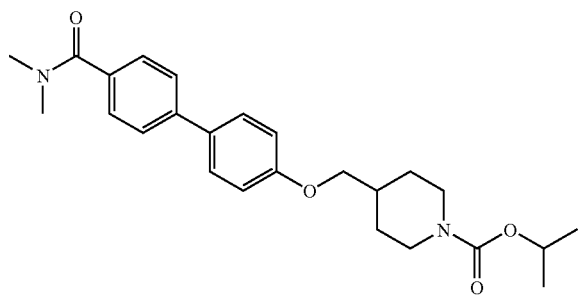

The title compound (29 mg, 27%) was prepared as a white solid from {4-[(dimethylamino)carbonyl]phenyl}boronic acid (39 mg, 0.2 mmol), 1-methylethyl 4-{[(4-bromophenyl)oxy]methyl}-1-piperidinecarboxylate (prepared as in Example 9, Step 2, 71 mg, 0.2 mmol), Pd(PPh$_3$)$_2$Cl$_2$ (50 mg, 0.07 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.63-7.42 (m, 6H), 6.96 (d, 2H, J=8.8 Hz), 4.98-4.81 (m, 1H), 4.20 (bs, 2H), 3.84 (d, 2H, J=6.4 Hz), 3.13 (s, 3H), 3.04 (s, 3H), 2.84-2.74 (m, 2H), 2.08-1.92 (m, 1H), 1.90-1.80 (m, 2H), 1.37-1.14 (m, 8H); LRMS (ESI), m/z 425 (M+H).

Example 31

1-Methylethyl 4-({[4'-(aminocarbonyl)-4-biphenylyl]oxy}methyl)-1-piperidinecarboxylate

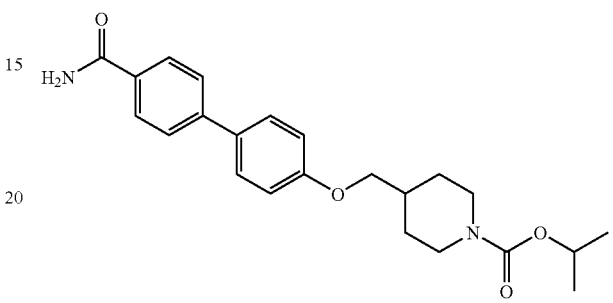

The title compound (15 mg, 15%) was prepared from [4-(aminocarbonyl)phenyl]boronic acid (33 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3 and worked up in a manner similar to Example 9, Step 3. $^1$H NMR (400 MHz, CDCl$_3$): δ 7.86 (d, 2H, J=8.1 Hz), 7.63 (d, 2H, J=8.1 Hz), 7.55 (d, 2H, J=8.8 Hz), 6.97 (d, 2H, J=8.9 Hz), 6.09 (s, 2H), 4.99-4.86 (m, 1H), 4.28-4.14 (m, 2H), 3.85 (d, 2H, J=6.4 Hz), 2.84-2.74 (m, 2H), 2.05-1.95 (m, 1H), 1.90-1.80 (m, 2H), 1.34-1.18 (m, 8H); LRMS (ESI), m/z 419 (M+Na).

Example 32

1-Methylethyl 4-[({4'-[(diethylamino)carbonyl]-4-biphenylyl}oxy)methyl]-1-piperidinecarboxylate

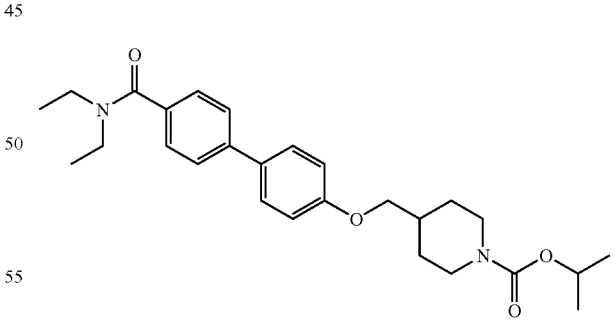

The title compound (39 mg, 34%) was prepared from {4-[(diethylamino)carbonyl]phenyl}boronic acid (44 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3, and worked up in a manner similar to Example 9, Step 3. $^1$H NMR (400 MHz, CDCl$_3$): δ 7.56 (d, 2H, J=8.4 Hz), 7.52 (d, 2H, J=8.8 Hz), 7.41 (d, 2H, J=8.2 Hz), 6.96 (d, 2H, J=8.8 Hz), 4.97-4.86 (m, 1H), 4.21 (bs, 2H), 3.84 (d, 2H, J=6.4 Hz), 3.56 (bs, 2H), 3.32 (bs, 2H), 2.84-2.74 (m, 2H), 2.05-1.95 (m, 1H), 1.90-1.80 (m, 2H), 1.38-1.06 (m, 14H); LRMS (ESI), m/z 453 (M+H).

Example 33

1-Methylethyl 4-({[4'-(4-morpholinylcarbonyl)-4-biphenylyl]oxy}methyl)-1-piperidinecarboxylate

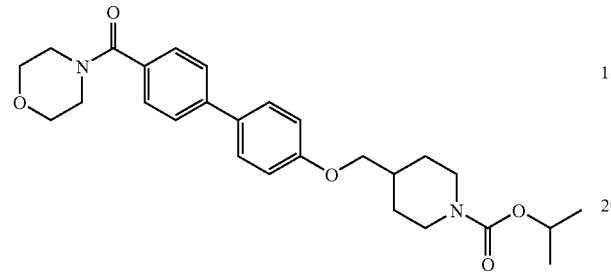

The title compound (37 mg, 32%) was prepared from [4-(4-morpholinylcarbonyl)phenyl]boronic acid (47 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3, and worked up in a manner similar to Example 9, Step 3. $^1$H NMR (400 MHz, CDCl$_3$): δ 7.58 (m, 2H) 7.51 (d, 2H, J=8.8 Hz), 7.46 (d, 2H, J=8.2 Hz), 6.96 (d, 2H, J=8.8 Hz), 4.97-4.86 (m, 1H), 4.21 (bs, 2H), 3.85 (d, 2H, J=6.2 Hz), 3.72 (bs, 6H), 3.53 (bs, 2H), 2.84-2.74 (m, 2H), 2.05-1.95 (m, 1H), 1.90-1.80 (m, 2H), 1.36-1.26 (m, 2H), 1.24 (d, 6H, J=6.4 Hz); LRMS (ESI), m/z 467 (M+H).

Example 34

1-Methylethyl 4-[({4'-[(butylamino)carbonyl]-4-biphenylyl}oxy)methyl]-1-piperidinecarboxylate

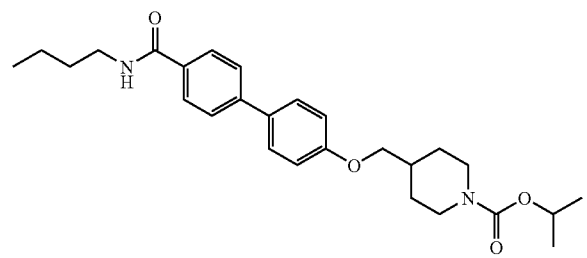

The title compound (26 mg, 23%) was prepared from {4-[(butylamino)carbonyl]phenyl}boronic acid (44 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3, and worked up in a manner similar to Example 9, Step 3. $^1$H NMR (400 MHz, CDCl$_3$): δ 7.80 (d, 2H, J=8.6 Hz), 7.60 (d, 2H, J=8.6 Hz), 7.54 (d, 2H, J=8.9 Hz), 6.96 (d, 2H, J=8.8 Hz), 6.11 (t, 1H, J=5.7 Hz), 5.01-4.83 (m, 1H), 4.21 (bs, 2H), 3.85 (d, 2H, J=6.4 Hz), 3.53-3.39 (m, 2H), 2.83-2.73 (m, 2H), 2.05-1.95 (m, 1H), 1.90-1.80 (m, 2H), 1.67-1.55 (m, 2H), 1.46-1.37 (m, 2H), 1.36-1.25 (m, 2H), 1.24 (d, 6H, J=6.2 Hz), 0.96 (t, 3H, J=7.3 Hz); LRMS (ESI), m/z 453 (M+H).

Example 35

1-Methylethyl 4-[({4'-[(cyclopropylamino)carbonyl]-4-biphenylyl}oxy)methyl]-1-piperidinecarboxylate

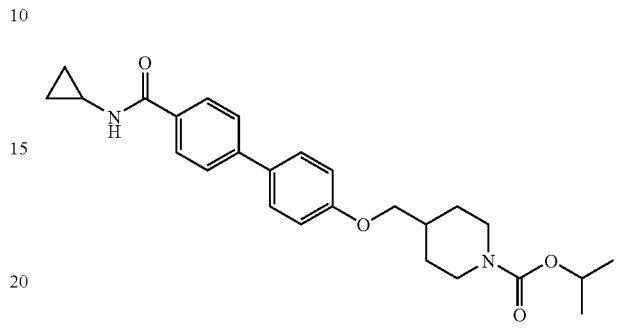

The title compound (13 mg, 12%) was prepared from {4-[(cyclopropylamino)carbonyl]phenyl}boronic acid (41 mg, 0.2 mmol), 1-methylethyl 4-{[(4-bromophenyl)oxy]methyl}-1-piperidinecarboxylate (prepared as in Example 9, Step 2, 71 mg, 0.2 mmol), Pd(PPh$_3$)$_2$Cl$_2$ (50 mg, 0.07 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.77 (d, 2H, J=8.4 Hz), 7.59 (d, 2H, J=8.6 Hz), 7.53 (d, 2H, J=8.8 Hz), 6.96 (d, 2H, J=8.8 Hz), 6.24 (s, 1H), 4.97-4.84 (m, 1H), 4.21 (bs, 2H), 3.84 (d, 2H, J=6.4 Hz), 2.96-2.86 (m, 1H), 2.83-2.73 (m, 2H), 2.05-1.95 (m, 1H), 1.90-1.80 (m, 2H), 1.36-1.26 (m, 2H), 1.24 (d, 6H, J=6.4 Hz), 0.93-0.84 (m, 2H), 0.66-0.60 (m, 2H); LRMS (ESI), m/z 437 (M+H).

Example 36

1-Methylethyl 4-[({4'-[(cyclopentylamino)carbonyl]-4-biphenylyl}oxy)methyl]-1-piperidinecarboxylate

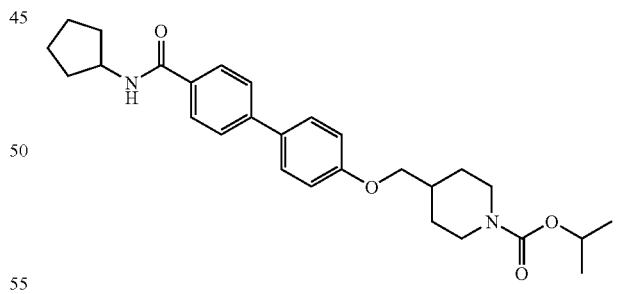

The title compound (14 mg, 12%) was prepared from {4-[(cyclopentylamino)carbonyl]phenyl}boronic acid (47 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3 and worked up in a manner similar to Example 9, Step 3. $^1$H NMR (400 MHz, CDCl$_3$): δ 7.78 (d, 2H, J=8.4 Hz), 7.59 (d, 2H, J=8.4 Hz), 7.53 (d, 2H, J=8.8 Hz), 6.96 (d, 2H, J=8.8 Hz), 6.04 (d, 1 H, J=7.4 Hz), 4.97-4.86 (m, 1H), 4.48-4.37 (m, 1H), 4.21 (bs, 2H), 3.85 (d, 2H, J=6.4 Hz), 2.83-2.73 (m, 2H), 2.17-2.06 (m, 2H), 2.05-1.95 (m, 1H), 1.90-1.80 (m, 2H), 1.78-1.62 (m, 4H), 1.55-1.45 (m, 2H), 1.35-1.26 (m, 2H), 1.24 (d, 6H, J=6.2 Hz); LRMS (ESI), m/z 465 (M+H).

Example 37

1-Methylethyl 4-{[(4'-{[(2-methylpropyl)amino]carbonyl}-4-biphenylyl)oxy]methyl}-1-piperidinecarboxylate

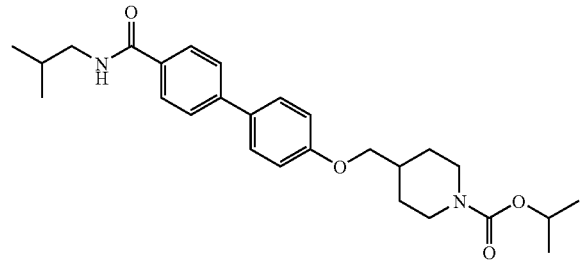

The title compound (21 mg, 19%) was prepared from (4-{[(2-methylpropyl)amino]carbonyl}phenyl)boronic acid (44 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3 and worked up in a manner similar to Example 9, Step 3. $^1$H NMR (400 MHz, CDCl$_3$): δ 7.80 (d, 2H, J=8.6 Hz), 7.60 (d, 2H, J=8.6 Hz), 7.54 (d, 2H, J=8.8 Hz), 6.96 (d, 2H, J=8.9 Hz), 6.17 (t, 1H, J=5.8 Hz), 4.97-4.84 (m, 1H), 4.21 (bs, 2H), 3.85 (d, 2H, J=6.4 Hz), 3.34-3.27 (m, 2H), 2.83-2.73 (m, 2H), 2.05-1.95 (m, 1H), 1.95-1.89 (m, 1H), 1.90-1.80 (m, 2H), 1.35-1.26 (m, 2H), 1.24 (d, 6H, J=6.2 Hz), 0.99 (d, 6H, J=6.7 Hz); LRMS (ESI), m/z 453 (M+H).

Example 38

1-Methylethyl 4-{[(4'-{[(2-hydroxyethyl)amino]carbonyl}-4-biphenylyl)oxy]methyl}-1-piperidinecarboxylate

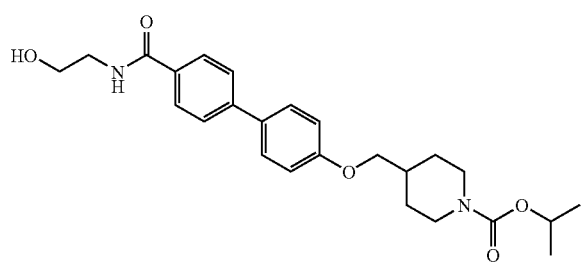

Step 1: A mixture of 4'-{[(1-{[(1-methylethyl)oxy]carbonyl}-4-piperidinyl)methyl]oxy}-4-biphenylcarboxylic acid was prepared from 4-(dihydroxyboranyl)benzoic acid (466 mg, 2.81 mmol), 1-methylethyl 4-{[(4-bromophenyl)oxy]methyl}-1-piperidinecarboxylate (prepared as in Example 9, Step 2, 1 g, 2.81 mmol), Pd(PPh$_3$)$_2$Cl$_2$ (100 mg, 0.14 mmol), 2M Na$_2$CO$_3$ (3 mL) and DME (3 mL) stirred at 80° C. overnight. The mixture was cooled to ambient temperature, charged with MeOH, and the resulting precipitate was filtered off. The filtrate was concentrated, and purified by chromatography on a silica gel column using 0 to 5% MeOH/CH$_2$Cl$_2$, followed by a recrystallization from MeOH to give 100 mg (9%) of 4'-{[(1-{[(1-methylethyl)oxy]carbonyl}-4-piperidinyl)methyl]oxy}-4-biphenylcarboxylic acid as a white solid. $^1$H NMR (400 MHz, CDCl$_3$): δ 8.14 (d, 2H, J=8.6 Hz), 7.65 (d, 2H, J=8.6 Hz), 7.58 (d, 2H, J=8.9 Hz), 6.98 (d, 2H, J=8.8 Hz), 4.97-4.87 (m, 1H), 4.27-4.17 (m, 2H), 3.86 (d, 2H, J=6.4 Hz), 2.84-2.74 (m, 2H), 2.06-1.96 (m, 1H), 1.90-1.80 (m, 2H), 1.37-1.27 (m, 2H), 1.25 (d, 6H, J=6.2 Hz); LRMS (ESI), m/z 398 (M+H).

Step 2: A mixture of 4'-{[(1-{[(1-methylethyl)oxy]carbonyl}-4-piperidinyl)methyl]oxy}-4-biphenylcarboxylic acid (73 mg, 0.18 mmol) and thionyl chloride (1 mL) in CH$_2$Cl$_2$ (3 mL) was heated at reflux for 2 h, then concentrated. The resulting crude was charged with CH$_2$Cl$_2$ (3 mL), followed by a solution of 2-aminoethanol (0.054 mL, 0.09 mmol) in CH$_2$Cl$_2$ (2 mL). The mixture was stirred at ambient temperature for 1 h, and then concentrated. The crude product was purified by reverse-phase preparative HPLC using a CH$_3$CN:H$_2$O gradient (10:90 to 100:0) with 0.05% TFA as a modifier to give 50 mg (50%) of the title compound as a white solid. $^1$H NMR (400 MHz, CDCl$_3$): δ 7.83 (d, 2H, J=8.6 Hz), 7.61 (d, 2H, J=8.6 Hz), 7.54 (d, 2H, J=8.8 Hz), 6.96 (d, 2H, J=8.9 Hz), 5.04-4.81 (m, 1H), 4.21 (bs, 2H), 3.89-3.81 (m, 4H), 3.71-3.60 (m, 2H), 2.84-2.74 (m, 2H), 2.05-1.95 (m, 2H), 1.89-1.79 (m, 2H), 1.36-1.26 (m, 2H), 1.24 (d, 6H, J=6.2 Hz); LRMS (ESI), m/z 441 (M+H).

Example 39

1-Methylethyl 4-[({4'-[(methylsulfonyl)amino]-4-biphenylyl}oxy)methyl]-1-piperidinecarboxylate

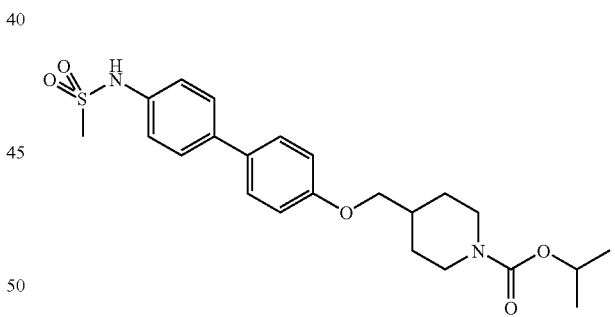

The title compound (11 mg, 25%) was prepared as a tan solid from {4-[(methylsulfonyl)amino]phenyl}boronic acid (22 mg, 0.1 mmol), 1-methylethyl 4-{[(4-bromophenyl)oxy]methyl}-1-piperidinecarboxylate (prepared as in Example 9, Step 2, 36 mg, 0.1 mmol), Pd(PPh$_3$)$_2$Cl$_2$ (25 mg, 0.04 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.55-7.45 (m, 4H), 7.30-7.20 (m, 2H), 6.95 (d, 2H, J=8.6 Hz), 6.38 (s, 1H), 4.99-4.83 (m, 1H), 3.84 (d, 2 H, J=6.4 Hz), 3.03 (s, 3H), 2.84-2.74 (m, 2H), 2.05-1.94 (m, 1H), 1.90-1.80 (m, 2H), 1.37-1.18 (m, 10H); LRMS (ESI), m/z 447 (M+H).

Example 40

N,N-Dimethyl-3-[4-({[4'-(methylsulfonyl)-4-biphenylyl]oxy}methyl)-1-piperidinyl]-1,2,4-oxadiazol-5-amine trifluoroacetate

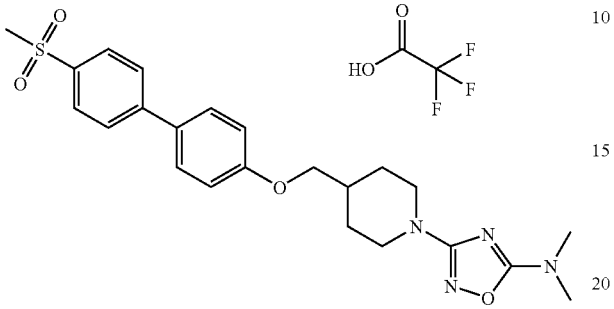

Step 1: Cyanogen bromide (3.0M in CH$_2$Cl$_2$, 0.1 mL, 0.3 mmol) was added dropwise to a mixture of 4-({[4'-(methylsulfonyl)-4-biphenylyl]oxy}methyl)piperidine hydrochloride (prepared as in Example 2, Step 1, 100 mg, 0.3 mmol) and triethylamine (0.083 mL, 0.6 mmol) in CH$_2$Cl$_2$ (5 mL) at ambient temperature. The reaction mixture was stirred at ambient temperature for 1 h and concentrated. The crude product was purified by chromatography on a silica gel column using 0 to 5% MeOH/CH$_2$Cl$_2$ to give 60 mg (54%) of 4-({[4'-(methylsulfonyl)-4-biphenylyl]oxy}methyl)-1-piperidinecarbonitrile as a white solid. $^1$H NMR (400 MHz, CDCl$_3$): δ 7.97 (d, 2H, J=8.4 Hz), 7.72 (d, 2H, J=8.6 Hz), 7.55 (d, 2H, J=8.8 Hz), 6.98 (d, 2H, J=8.6 Hz), 3.87 (d, 2H, J=6.2 Hz), 3.58-3.47 (m, 2H), 3.08 (s, 3H), 1.96-1.86 (m, 2H), 1.53 (bs, 5H); LRMS (ESI), m/z 393 (M+Na).

Step 2: A mixture 4-({[4'-(methylsulfonyl)-4-biphenylyl]oxy}methyl)-1-piperidinecarbonitrile (60 mg, 0.16 mmol) and hydroxylamine hydrochloride (11 mg, 0.16 mmol) in ethanol (5 mL) was heated at 80° C. for 2 h, then cooled to ambient temperature overnight. The mixture was concentrated, and the crude product was purified by chromatography on a silica gel column using 0 to 10% MeOH/CH$_2$Cl$_2$ to give 60 mg (93%) of N-hydroxy-4-({[4'-(methylsulfonyl)-4-biphenylyl]oxy}methyl)-1-piperidinecarboximidamide as a white solid. $^1$H NMR (400 MHz, DMSO-d$_6$): δ 7.93 (m, 2H), 7.87 (m, 2H), 7.69 (d, 2H, J=8.8 Hz), 7.05 (d, 2H, J=8.8 Hz), 3.91 (d, 2H, J=6.0 Hz), 3.84-3.74 (m, 2H), 3.22 (s, 3H), 3.02-2.96 (m, 2H), 2.05 (bs, 2H), 1.86-1.76 (m, 2H), 1.36-1.22 (m, 2H); LRMS (ESI), m/z 404 (M+H).

Step 3: A mixture of N-hydroxy-4-({[4'-(methylsulfonyl)-4-biphenylyl]oxy}methyl)-1-piperidinecarboximidamide (60 mg, 0.15 mmol), phosgene iminium chloride (73 mg, 0.45 mmol) and triethylamine (0.105 mL, 0.75 mmol) in dichloroethane (3 mL) was heated at 85° C. overnight. The mixture was filtered and concentrated. The mixture was cooled to ambient temperature, filtered and concentrated. The crude product was purified by reverse-phase preparative HPLC using a CH$_3$CN:H$_2$O gradient (0.5:99.5 to 90:10) with 0.05% TFA as a modifier to give 1.9 mg (2%) of the title compound as a tan solid. $^1$H NMR (400 MHz, CDCl$_3$): δ 7.97 (d, 2H, J=8.6 Hz), 7.72 (d, 2H, J=8.6 Hz), 7.55 (d, 2H, J=8.8 Hz), 6.99 (d, 2H, J=8.9 Hz), 4.06-3.96 (m, 2H), 3.87 (d, 2H, J=6.4 Hz), 3.11-3.07 (m, 6H), 2.99-2.89 (m, 2H), 2.38 (s, 3H), 2.09-1.99 (m, 1H), 1.96-1.86 (m, 2H), 1.51-1.37 (m, 2H); LRMS (ESI), m/z 457 (M+H).

Example 41

1-Methylethyl 4-({[4'-(4-morpholinylsulfonyl)-4-biphenylyl]oxy}methyl)-1-piperidinecarboxylate

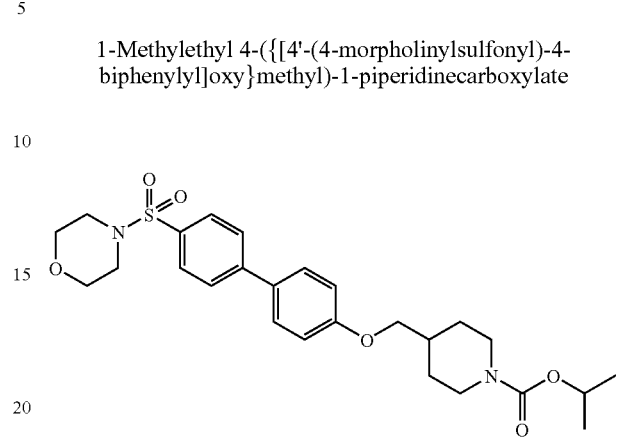

The title compound (10 mg, 8%) was prepared as a white solid from [4-(4-morpholinylsulfonyl)phenyl]boronic acid (54 mg, 0.2 mmol), 1-methylethyl 4-{[(4-bromophenyl)oxy]methyl}-1-piperidinecarboxylate (prepared as in Example 9, Step 2, 71 mg, 0.2 mmol), Pd(PPh$_3$)$_2$Cl$_2$ (50 mg, 0.07 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.78 (m, 2H), 7.70 (m, 2H), 7.54 (d, 2H, J=8.8 Hz), 6.99 (d, 2H, J=8.8 Hz), 4.97-4.86 (m, 1H), 4.22 (bs, 2H), 3.86 (d, 2H, J=6.4 Hz), 3.78-3.73 (m, 4H), 3.07-3.01 (m, 4H), 2.84-2.74 (m, 2H), 2.05-1.95 (m, 1H), 1.91-1.81 (m, 2H), 1.37-1.27 (m, 2H), 1.25 (d, 6H, J=6.4 Hz); LRMS (ESI), m/z 503 (M+H).

Example 42

1-Methylethyl 4-{[(4'-{[(1-methylethyl)amino]sulfonyl}-4-biphenylyl)oxy]methyl}-1-piperidinecarboxylate

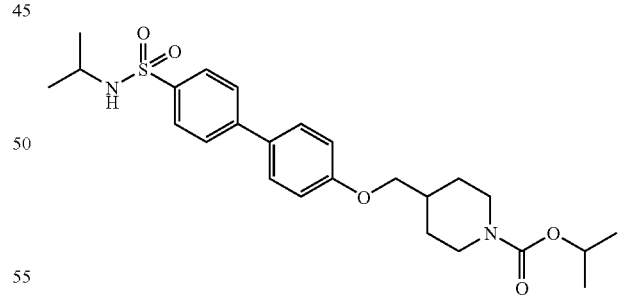

The title compound (9.4 mg, 8%) was prepared from (4-{[(1-methylethyl)amino]sulfonyl}phenyl)boronic acid (49 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3, and worked up in a manner similar to Example 9, Step 3. $^1$H NMR (400 MHz, CDCl$_3$): δ 7.89 (d, 2H, J=8.6 Hz), 7.66 (d, 2H, J=8.6 Hz), 7.54 (d, 2H, J=8.9 Hz), 6.98 (d, 2H, J=8.8 Hz), 4.97-4.87 (m, 1H), 4.28-4.18 (m, 2H), 3.85 (d, 2H, J=6.4 Hz), 3.58-3.45 (m, 1H), 2.84-2.74 (m, 2H), 2.05-1.95 (m, 1H), 1.90-1.80 (m, 2H), 1.37-1.27 (m, 3H), 1.25 (d, 6H, J=6.4 Hz), 1.11 (d, 6H, J=6.5 Hz); LRMS (ESI), m/z 475 (M+H).

Example 43

1-Methylethyl 4-[({4'-[(4H-1,2,4-triazol-4-ylamino)carbonyl]-4-biphenylyl}oxy)methyl]-1-piperidinecarboxylate trifluoroacetate

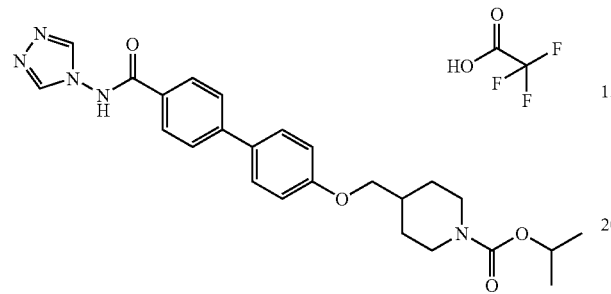

The title compound (8 mg, 7%) was prepared from {4-[(4H-1,2,4-triazol-4-ylamino)carbonyl]phenyl}boronic acid hydrochloride (54 mg, 0.2 mmol) and 1-methylethyl 4-{[(4-bromophenyl)oxy]methyl}-1-piperidinecarboxylate (prepared as in Example 9, Step 2, 71 mg, 0.2 mmol) in a manner similar to Example 21, Step 3, and worked up in a manner similar to Example 9, Step 3. $^1$H NMR (400 MHz, CDCl$_3$): δ 8.35 (s, 2H), 8.08 (d, 2H, J=7.9 Hz), 7.70 (d, 2H, J=8.2 Hz), 7.57 (d, 2H, J=8.6 Hz), 6.97 (d, 2H, J=8.6 Hz), 4.95-4.83 (m, 1H), 4.20 (bs, 2H), 3.84 (d, 2H, J=6.2 Hz), 2.83-2.73 (m, 2H), 2.48 (s, 1H), 2.05-1.95 (m, 1H), 1.89-1.79 (m, 2H), 1.36-1.26 (m, 2H), 1.24 (d, 6H, J=6.4 Hz); LRMS (ESI), m/z 464 (M+H).

Example 44

1-Methylethyl 4-{[(4'-{[(2-hydroxyethyl)amino]sulfonyl}-4-biphenylyl)oxy]methyl}-1-piperidinecarboxylate

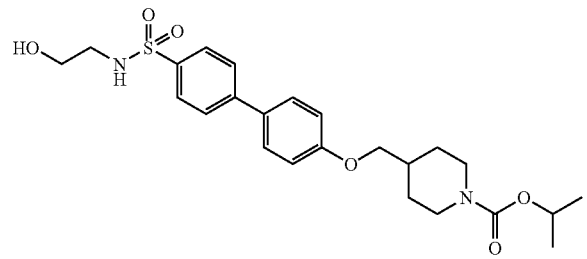

The title compound (25 mg, 26%) was prepared as a white solid from (4-{[(2-hydroxyethyl)amino]sulfonyl}phenyl)boronic acid (49 mg, 0.2 mmol), 1-methylethyl 4-{[(4-bromophenyl)oxy]methyl}-1-piperidinecarboxylate (prepared as in Example 9, Step 2, 71 mg, 0.2 mmol), Pd(PPh$_3$)$_2$Cl$_2$ (50 mg, 0.07 mmol), 2M Na$_2$CO$_3$ (1 mL) and DME (1 mL) in a manner similar to Example 21, Step 3, and worked up in a manner similar to Example 9, Step 3. $^1$H NMR (400 MHz, CDCl$_3$): δ 7.90 (d, 2H, J=8.6 Hz), 7.68 (d, 2H, J=8.6 Hz), 7.54 (d, 2H, J=8.8 Hz), 6.98 (d, 2H, J=8.9 Hz), 4.98-4.86 (m, 2H), 4.21 (bs, 2H), 3.85 (d, 2H, J=6.4 Hz), 3.75-3.69 (m, 2H), 3.19-3.12 (m, 2H), 2.84-2.74 (m, 2H), 2.05-1.95 (m, 1H), 1.90-1.80 (m, 3H), 1.37-1.27 (m, 2H), 1.25 (d, 6H, J=6.4 Hz); LRMS (ESI), m/z 477 (M+H).

Example 45

1-Methylethyl 4-[({4'-[(1-methylethyl)sulfonyl]-4-biphenylyl}oxy)methyl]-1-piperidinecarboxylate

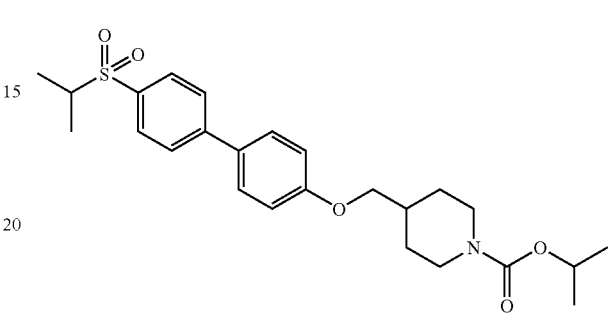

The title compound (188 mg, 60%) was prepared as a white solid from 1-methylethyl 4-[({4'-[(1-methylethyl)thio]-4-biphenylyl}oxy)methyl]-1-piperidinecarboxylate (prepared as in Example 12, 290 mg, 0.68 mmol) and m-CPBA (259 mg, 77%, 1.5 mmol) in CH$_2$Cl$_2$ (10 mL) in a manner similar to Example 24, Step 3. $^1$H NMR (400 MHz, CDCl$_3$): δ 7.90 (d, 2H, J=8.6 Hz), 7.71 (d, 2H, J=8.6 Hz), 7.55 (d, 2H, J=8.8 Hz), 6.98 (d, 2H, J=8.8 Hz), 5.01-4.84 (m, 1H), 4.22 (bs, 2H), 3.85 (d, 2H, J=6.4 Hz), 3.27-3.15 (m, 1H), 2.84-2.74 (m, 2H), 2.08-1.93 (m, 1H), 1.90-1.80 (m, 2H), 1.38-1.15 (m, 14H); LRMS (ESI), m/z 460 (M+H).

Example 46

1-[(4-Fluorophenyl)methyl]-4-({[4'-(methylsulfonyl)-4-biphenylyl]oxy}methyl)piperidine trifluoroacetate

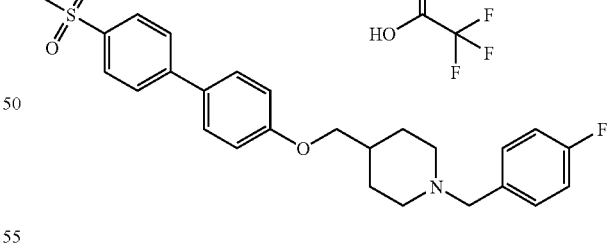

4-({[4'-(Methylsulfonyl)-4-biphenylyl]oxy}methyl)piperidine hydrochloride (prepared as in Example 2, Step 1, 0.05 g, 0.14 mmol) was added to a solution of 4-fluorobenzyl chloride (0.02 g, 0.14 mmol) in CH$_3$CN (2 mL), followed by addition of diisopropylethylamine (0.04 g, 0.28 mmol). The reaction mixture was heated at 120° C. for 20 min using microwave heating. The reaction was then concentrated in vacuo and purified by reverse-phase preparative HPLC using CH$_3$CN:H$_2$O gradient (0:100 to 90:10) with 0.05% TFA as a modifier to give the title compound (40 mg, 50%) as a white solid. $^1$H NMR (400 MHz, CDCl$_3$): δ 7.97 (d, 2H, J=8.5 Hz), 7.71 (d, 2H, J=8.5 Hz), 7.53 (d, 2H, J=8.9 Hz), 7.46 (dd, 2H, $J_a$=8.1 Hz, $J_b$=5.1 Hz), 7.14 (t, 2H, J=8.5 Hz), 6.95 (d, 2H, J=8.9 Hz), 4.19 (s, 2H), 3.89 (d, 2H, J=5.3 Hz), 3.69-3.61 (m, 2H), 3.08 (s, 3H), 2.72-2.61 (m, 2H), 2.13-1.88 (m, 5H); LRMS (ESI), m/z 454 (M+H).

Example 47

1-[(4-Chlorophenyl)methyl]-4-({[4'-(methylsulfonyl)-4-biphenylyl]oxy}methyl)piperidine trifluoroacetate

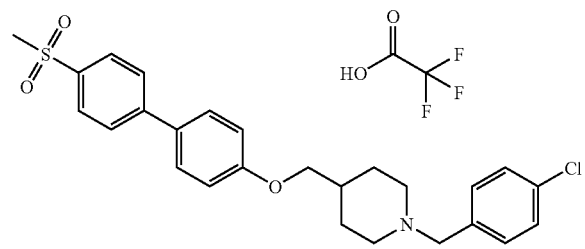

The title compound (33 mg, 40%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-chlorobenzyl chloride (0.02 g, 0.14 mmol), diisopropylethylamine (0.04 g, 0.28 mmol) and $CH_3CN$ (2 mL) in a manner similar to Example 46. $^1$H NMR (400 MHz, CDCl$_3$): δ 7.98 (d, 2H, J=8.3 Hz), 7.73 (d, 2H, J=8.5 Hz), 7.55 (d, 2H, J=8.7 Hz), 7.44 (s, 4H), 6.96 (d, 2H, J=8.9 Hz), 4.19 (s, 2H), 3.91 (d, 2H, J=4.8 Hz), 3.70-3.62 (m, 2H), 3.10 (s, 3H), 2.72-2.61 (m, 2 H), 2.13-1.89 (m, 5H); LRMS (ESI), m/z 470 (M+H).

Example 48

1-[(3-Chlorophenyl)methyl]-4-({[4'-(methylsulfonyl)-4-biphenylyl]oxy}methyl)piperidine trifluoroacetate

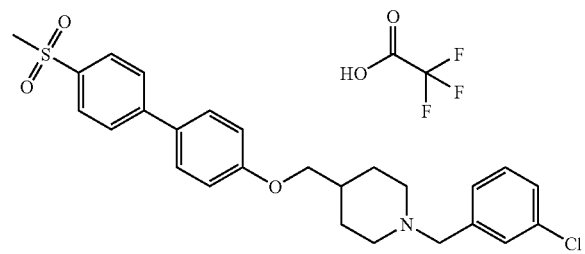

The title compound (33 mg, 40%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 3-chlorobenzyl chloride (0.02 g, 0.14 mmol), diisopropylethylamine (0.04 g, 0.28 mmol) and $CH_3CN$ (2 mL) in a manner similar to Example 46. $^1$H NMR (400 MHz, CDCl$_3$): δ 7.98 (d, 2H, J=8.3 Hz), 7.72 (d, 2H, J=8.3 Hz), 7.55 (d, 2H, J=8.5 Hz), 7.48-7.40 (m, 4H), 6.96 (d, 2H, J=8.7 Hz), 4.18 (s, 2H), 3.91 (d, 2H, J=4.6 Hz), 3.70-3.62 (m, 2H), 3.00 (s, 3H), 2.72-2.61 (m, 2H), 2.12-1.94 (m, 5H); LRMS (ESI), m/z 470 (M+H).

Example 49

1-[(2-Chlorophenyl)methyl]-4-({[4'-(methylsulfonyl)-4-biphenylyl]oxy}methyl)piperidine trifluoroacetate

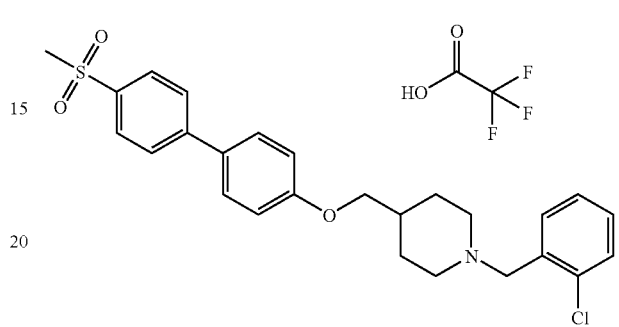

The title compound (28 mg, 34%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 2-chlorobenzyl chloride (0.02 g, 0.14 mmol), diisopropylethylamine (0.04 g, 0.28 mmol) and $CH_3CN$ (2 mL) in a manner similar to Example 46. $^1$H NMR (400 MHz, CDCl$_3$): δ 7.97 (d, 2H, J=8.7 Hz), 7.78-7.76 (m, 1H), 7.72 (d, 2H, J=8.7 Hz), 7.54 (d, 2H, J=8.7 Hz), 7.48-7.40 (m, 1H), 7.42-7.40 (m, 2H), 6.95 (d, 2H, J=8.7 Hz), 4.43 (s, 2H), 3.90 (d, 2H, J=5.7 Hz), 3.72-3.63 (m, 2H), 3.00 (s, 3H), 2.88-2.72 (m, 2H), 2.13-1.91 (m, 5H); LRMS (ESI), m/z 470 (M+H).

Example 50

1-[(3-Fluorophenyl)methyl]-4-({[4'-(methylsulfonyl)-4-biphenylyl]oxy}methyl)piperidine trifluoroacetate

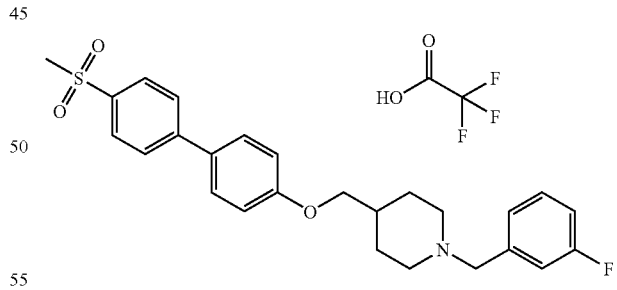

4-({[4'-(Methylsulfonyl)-4-biphenylyl]oxy}methyl)piperidine hydrochloride (prepared as in Example 2, Step 1, 0.05 g, 0.14 mmol) was added to a solution of 3-fluorobenzaldehyde (0.02 g, 0.14 mmol) in $CH_2Cl_2$ (2 mL), followed by addition macroporous cyanoborohydride resin (2.8 mmol) and small amount of acetic acid (0.5 mL). The reaction mixture was stirred at ambient temperature overnight. The reaction mixture was then filtered, concentrated in vacuo and purified by reverse-phase preparative HPLC using $CH_3CN$:$H_2O$ gradient (0:100 to 90:10) with 0.05% TFA as a modifier to give the title compound (11 mg, 14%) as a white solid. $^1$H NMR (400 MHz, CDCl$_3$): δ 7.98 (d, 2H, J=8.3 Hz), 7.72 (d, 2H, J=8.5 Hz), 7.55 (d, 2H, J=8.7 Hz), 7.79-7.42 (m, 1H), 7.35 (d, 1H, J=7.7 Hz), 7.24-7.16 (m, 2H), 6.96 (d, 2H, J=8.7 Hz), 4.21 (s, 2H), 3.91 (d, 2H, J=2.8 Hz), 3.72-3.62 (m, 2H), 3.01 (s, 3H), 2.75-2.64 (m, 2H), 2.14-1.95 (m, 5H); LRMS (ESI), m/z 454 (M+H).

Example 51

4-({[4'-(Methylsulfonyl)-4-biphenylyl]oxy}methyl)-1-{[4-(trifluoromethyl)phenyl]methyl}piperidine trifluoroacetate

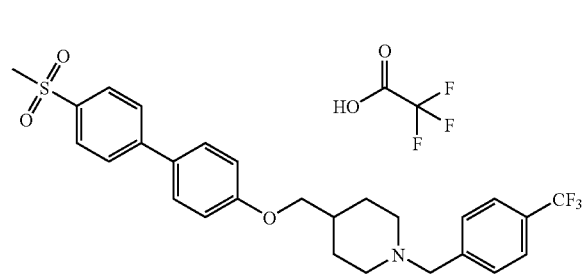

The title compound (5 mg, 6%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-(trifluoromethyl)benzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, DMSO-d$_6$): δ 7.94 (d, 2H, J=8.7 Hz), 7.90-7.85 (m, 4H), 7.76-7.68 (m, 4H), 7.05 (d, 2H, J=8.9 Hz), 4.40 (d, 2H, J=4.6 Hz), 3.91 (d, 2H, J=5.8 Hz), 3.60-3.55 (m, 1H), 3.47-3.37 (m, 2H), 3.22 (s, 3H), 3.07-2.96 (m, 2H), 2.01-1.94 (m, 2H), 1.59-1.47 (m, 2H); LRMS (ESI), m/z 504 (M+H).

Example 52

1-[(2,5-Difluorophenyl)methyl]-4-({[4'-(methylsulfonyl)-4-biphenylyl]oxy}methyl)piperidine trifluoroacetate

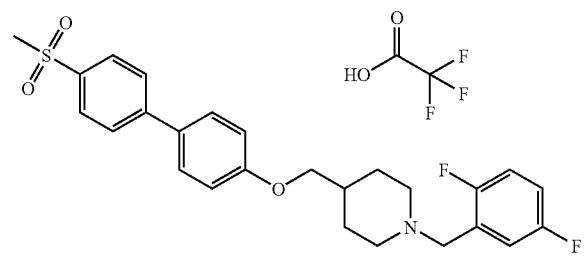

The title compound (20 mg, 25%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 2,5-difluorobenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.97 (d, 2H, J=8.5 Hz), 7.71 (d, 2H, J=8.5 Hz), 7.54 (d, 2H, J=8.7 Hz), 7.36-7.30 (m, 1H), 7.18-7.11 (m, 2H), 4.42 (s, 2H), 3.89 (d, 2H, J=5.7 Hz), 3.72-3.64 (m, 2H), 3.08 (s, 3H), 2.81-2.71 (m, 3H), 2.14-1.99 (m, 3H), 1.97-1.85 (m, 2H), 1.28-1.23 (m, 1H); LRMS (ESI), m/z 472 (M+H).

Example 53

1-[(3,4-Dimethylphenyl)methyl]-4-({[4'-(methylsulfonyl)-4-biphenylyl]oxy}methyl)piperidine trifluoroacetate

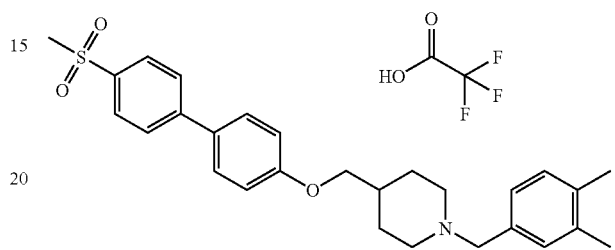

The title compound (20 mg, 25%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 3,4-dimethylbenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.97 (d, 2H, J=8.7 Hz), 7.71 (d, 2H, J=8.7 Hz), 7.53 (d, 2H, J=8.9 Hz), 7.19-7.14 (m, 2H), 7.11-7.07 (m, 1H), 6.94 (d, 2H, J=8.7 Hz), 4.13 (s, 2H), 3.88 (d, 2H, J=5.3 Hz), 3.71-3.62 (m, 2H), 3.08 (s, 3H), 2.71-2.60 (m, 2H), 2.26 (s, 6H), 2.10-1.87 (m, 5H); LRMS (ESI), m/z 464 (M+H).

Example 54

1-{[2-Fluoro-5-(methyloxy)phenyl]methyl}-4-({[4'-(methylsulfonyl)-4-biphenylyl]oxy}methyl)piperidine trifluoroacetate

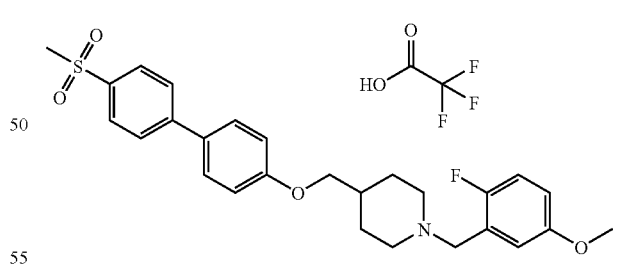

The title compound (25 mg, 30%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 2-fluoro-5-methoxybenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.97 (d, 2H, J=8.7 Hz), 7.71 (d, 2H, J=8.7 Hz), 7.54 (d, 2H, J=8.9 Hz), 7.17-7.13 (m, 1H), 7.05 (t, 1H, J=9.1 Hz), 6.97-6.92 (m, 3H), 4.24 (s, 2H), 3.89 (d, 2H, J=5.7 Hz), 3.78 (s, 3H), 3.71-3.64

(m, 2H), 3.08 (s, 3H), 2.81-2.70 (m, 2H), 2.12-1.87 (m, 5H); LRMS (ESI), m/z 484 (M+H).

Example 55

1-{[4-(Methyloxy)phenyl]methyl}-4-({[4'-(methylsulfonyl)-4-biphenylyl]oxy}methyl)piperidine trifluoroacetate

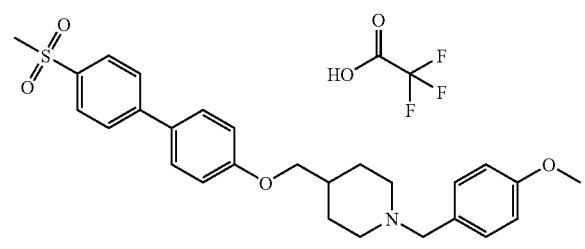

The title compound (23 mg, 28%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-methoxybenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.96 (d, 2H, J=8.5 Hz), 7.70 (d, 2H, J=8.6 Hz), 7.53 (d, 2H, J=8.9 Hz), 7.32 (d, 2H, J=8.7 Hz), 6.96-6.89 (m, 4H), 4.14 (s, 2H), 3.87 (d, 2H, J=5.5 Hz), 3.82 (s, 3H), 3.68-3.60 (m, 2H), 3.08 (s, 3H), 2.69-2.57 (m, 2H), 2.09-1.84 (m, 5H); LRMS (ESI), m/z 466 (M+H).

Example 56

1-[(2-Bromophenyl)methyl]-4-({[4'-(methylsulfonyl)-4-biphenylyl]oxy}methyl)piperidine trifluoroacetate

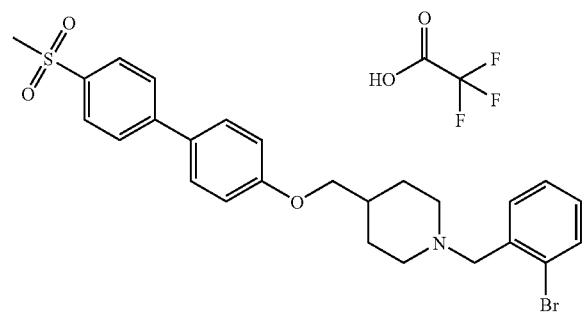

The title compound (26 mg, 29%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 2-bromobenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.96 (d, 2H, J=8.5 Hz), 7.76-7.68 (m, 3H), 7.64 (dd, 1 H, J$_a$=8.0 Hz, J$_b$=1.2 Hz), 7.53 (d, 2H, J=8.7 Hz), 7.43 (m, 1H), 7.31 (m, 1H), 6.95 (d, 2H, J=8.7 Hz), 4.47 (s, 2H), 3.88 (d, 2H, J=5.8 Hz), 3.73-3.62 (m, 2H), 3.08 (s, 3H), 2.92-2.82 (m, 2H), 2.12-2.02 (m, 3H), 1.97-1.84 (m, 2H); LRMS (ESI), m/z 514/516 (M+H).

Example 57

1-[(4-Bromophenyl)methyl]-4-({[4'-(methylsulfonyl)-4-biphenylyl]oxy}methyl)piperidine trifluoroacetate

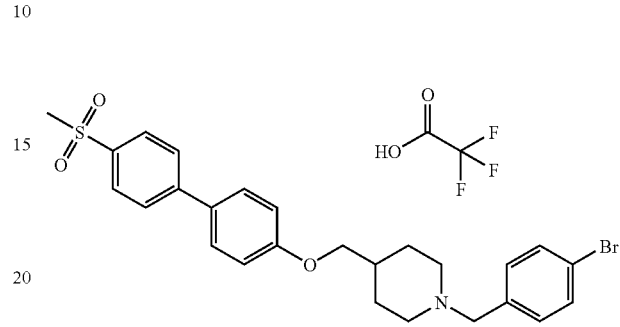

The title compound (30 mg, 34%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-bromobenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.96 (d, 2H, J=8.4 Hz), 7.71 (d, 2H, J=8.4 Hz), 7.57 (d, 2H, J=8.4 Hz), 7.52 (d, 2H, J=8.7 Hz), 7.32 (d, 2H, J=8.4 Hz), 6.94 (d, 2H, J=8.7 Hz), 4.16 (s, 2H), 3.88 (d, 2H, J=5.5 Hz), 3.69-3.59 (m, 2H), 3.08 (s, 3H), 2.71-2.61 (m, 2H), 2.12-1.84 (m, 5H); LRMS (ESI), m/z 514/516 (M+H).

Example 58

4-{[4-({[4'-(Methylsulfonyl)-4-biphenylyl]oxy}methyl)-1-piperidinyl]methyl}benzonitrile trifluoroacetate

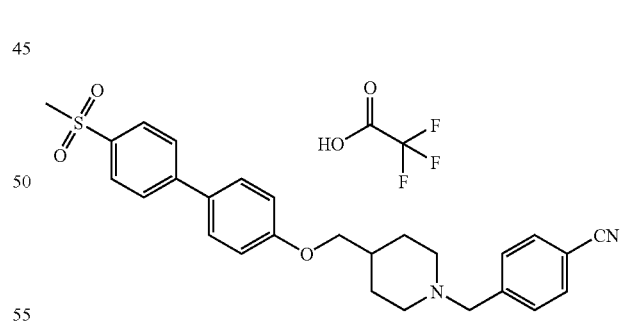

The title compound (25 mg, 31%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-cyanobenzaldehyde (0.02 g, 0.14 mmol) and CH$_2$Cl$_2$ (2 mL) followed by macroporous cyanoborohydride resin (2.8 mmol) and small amount of acetic acid (0.5 mL) in a manner similar to Example 50. $^1$H NMR (400 MHz, CDCl$_3$): δ 7.96 (d, 2H, J=8.6 Hz), 7.75 (d, 2H, J=8.2 Hz), 7.71 (d, 2H, J=8.4 Hz), 7.63 (d, 2H, J=8.2 Hz), 7.53 (d, 2H, J=8.7 Hz), 6.94 (d, 2H, J=8.7 Hz), 4.25 (s, 2H), 3.88 (d, 2H, J=5.5 Hz), 3.70-3.61 (m, 2H), 3.08 (s, 3H), 2.74-2.64 (m, 2H), 2.12-1.86 (m, 5H); LRMS (ESI), m/z 461 (M+H).

Example 59

1-[(3-Methylphenyl)methyl]-4-({[4'-(methylsulfonyl)-4-biphenylyl]oxy}methyl)piperidine trifluoroacetate

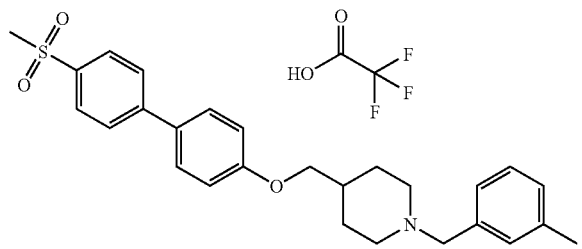

The title compound (16 mg, 20%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 3-methylbenzaldehyde (0.02 g, 0.14 mmol) and $CH_2Cl_2$ (2 mL) followed by macroporous cyanoborohydride resin (2.8 mmol) and small amount of acetic acid (0.5 mL) in a manner similar to Example 50. $^1$H NMR (400 MHz, $CDCl_3$): δ 7.96 (d, 2H, J=8.6 Hz), 7.71 (d, 2H, J=8.6 Hz), 7.52 (d, 2H, J=8.7 Hz), 7.34-7.16 (m, 4H), 6.94 (d, 2H, J=8.9 Hz), 4.15 (s, 2H), 3.88 (d, 2H, J=5.1 Hz), 3.69-3.59 (m, 2H), 3.08 (s, 3H), 2.72-2.60 (m, 2H), 2.37 (s, 3H), 2.08-1.86 (m, 5H); LRMS (ESI), m/z 450 (M+H).

Example 60

1-[(4-Methylphenyl)methyl]-4-({[4'-(methylsulfonyl)-4-biphenylyl]oxy}methyl)piperidine trifluoroacetate

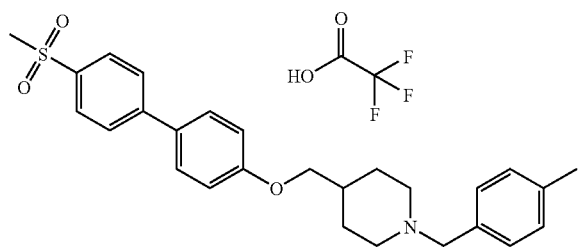

The title compound (23 mg, 30%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-methylbenzaldehyde (0.03 g, 0.14 mmol) and $CH_2Cl_2$ (2 mL) followed by macroporous cyanoborohydride resin (2.8 mmol) and small amount of acetic acid (0.5 mL) in a manner similar to Example 50. $^1$H NMR (400 MHz, $CDCl_3$): δ 7.96 (d, 2H, J=8.7 Hz), 7.70 (d, 2H, J=8.2 Hz), 7.52 (d, 2H, J=8.7 Hz), 7.28 (d, 2H, J=8.0 Hz), 7.22 (d, 2H, J=7.9 Hz), 6.94 (d, 2H, J=8.7 Hz), 4.16 (s, 2H), 3.86 (d, 2H, J=5.5 Hz), 3.68-3.58 (m, 2H), 3.08 (s, 3H), 2.72-2.58 (m, 2H), 2.37 (s, 3H), 2.06-1.89 (m, 5H); LRMS (ESI), m/z 450 (M+H).

Example 61

1-({4-[(1-Methylethyl)oxy]phenyl}methyl)-4-({[4'-(methylsulfonyl)-4-biphenylyl]oxy}methyl)piperidine trifluoroacetate

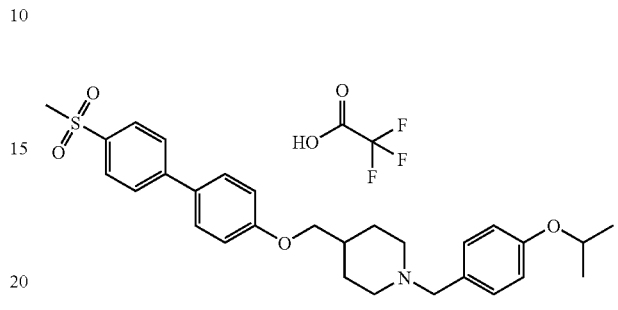

The title compound (38 mg, 45%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-[(1-methylethyl)oxy]benzaldehyde (0.02 g, 0.14 mmol) and $CH_2Cl_2$ (2 mL) followed by macroporous cyanoborohydride resin (2.8 mmol) and small amount of acetic acid (0.5 mL) in a manner similar to Example 50. $^1$H NMR (400 MHz, $CDCl_3$): δ 7.96 (d, 2H, J=8.6 Hz), 7.70 (d, 2H, J=8.7 Hz), 7.52 (d, 2H, J=8.7 Hz), 7.33 (d, 2H, J=8.6 Hz), 6.94 (d, 2H, J=8.9 Hz), 6.90 (d, 2H, J=8.6 Hz), 4.62-4.53 (m, 1H), 4.13 (s, 2H), 3.88 (d, 2H, J=4.2 Hz), 3.68-3.58 (m, 2H), 3.08 (s, 3H), 2.70-2.58 (m, 2H), 2.06-1.89 (m, 5H), 1.84 (d, 6H, J=6.0 Hz); LRMS (ESI), m/z 494 (M+H).

Example 62

1-({4-[(1,1-Dimethylethyl)oxy]phenyl}methyl)-4-({[4'-(methylsulfonyl)-4-biphenylyl]oxy}methyl)piperidine trifluoroacetate

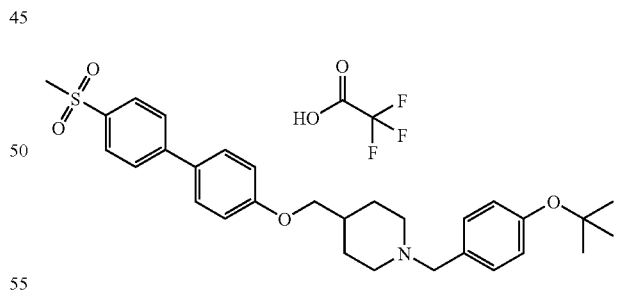

The title compound (20 mg, 30%) was prepared as a white solid from 4-({[4'-(methylsulfonyl)-4-biphenylyl]oxy}methyl)piperidine hydrochloride (prepared as in Example 2, Step 1, 0.05 g, 0.14 mmol), 4-[(1,1-dimethylethyl)oxy]benzaldehyde (0.03 g, 0.14 mmol) and $CH_2Cl_2$ (2 mL) followed by macroporous cyanoborohydride resin (2.8 mmol) and small amount of acetic acid (0.5 mL) in a manner similar to Example 50. $^1$H NMR (400 MHz, $CDCl_3$): δ 7.96 (d, 2H, J=8.6 Hz), 7.71 (d, 2H, J=8.7 Hz), 7.53 (d, 2H, J=8.7 Hz), 7.31 (d, 2H, J=8.4 Hz), 7.02 (d, 2H, J=8.6 Hz), 6.94 (d, 2H, J=8.9 Hz), 4.15 (s, 2H), 3.88 (d, 2H, J=5.3 Hz), 3.63 (d, 2H, J=11.8 Hz), 3.08 (s, 3H), 2.59-2.29 (m, 2H), 2.06-1.89 (m, 5H), 1.36 (s, 9H); LRMS (ESI), m/z 508 (M+H).

Example 63

2-[4-({[4'-(Methylsulfonyl)-4-biphenylyl]oxy}methyl)-1-piperidinyl]-6-(trifluoromethyl)pyridine trifluoroacetate

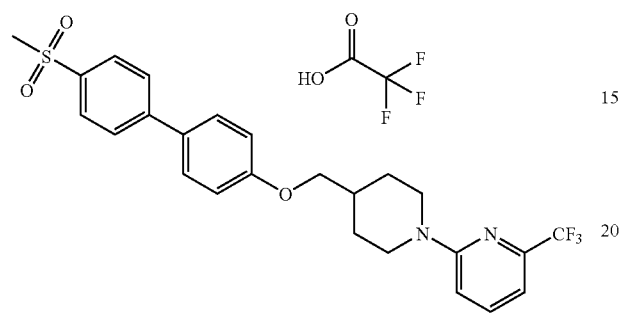

4-({[4'-(Methylsulfonyl)-4-biphenylyl]oxy}methyl)piperidine hydrochloride (prepared as in Example 2, Step 1, 0.05 g, 0.14 mmol) was added to a solution of 2-chloro-6-(trifluoromethyl)pyridine (0.01 g, 0.14 mmol) in DMSO (2 mL), followed by addition of NaO-t-Bu (0.3 g, 0.3 mmol), and a catalytic amount of Pd(P(o-Tol)$_3$)$_2$Cl$_2$. The reaction mixture was heated at 200° C. for 10 min using microwave heating. The reaction was then purified by reverse-phase preparative HPLC using CH$_3$CN:H$_2$O gradient (0:100 to 90:10) with 0.05% TFA as a modifier to give the title compound (3 mg, 4%) as a white solid. $^1$H NMR (400 MHz, CDCl$_3$): δ 7.97 (d, 2H, J=8.6 Hz), 7.72 (d, 2H, J=8.7 Hz), 7.60-7.53 (m, 3H), 7.00 (d, 2H, J=8.9 Hz), 6.94 (d, 1H, J=7.4 Hz), 6.86 (d, 1H, J=8.9 Hz), 4.46-4.40 (m, 2H), 3.90 (d, 2H, J=6.3 Hz), 3.09 (s, 3H), 3.00-2.92 (m, 2H), 2.01-1.95 (m, 3H), 1.51-1.40 (m, 2H); LRMS (ESI), m/z 491 (M+H).

Example 64

1,1-Dimethylethyl 4-({[3-fluoro-4'-(methylsulfonyl)-4-biphenylyl]oxy}methyl)-1-piperidinecarboxylate

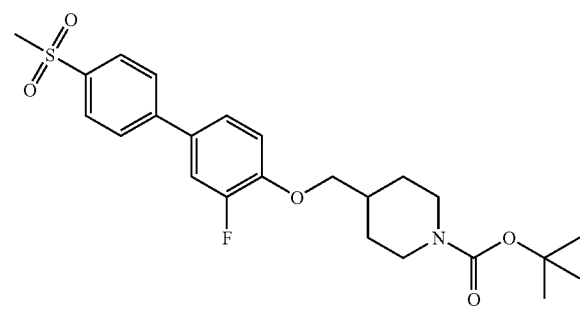

Step 1: 3-Fluoro-4'-(methylsulfonyl)-4-biphenylol (0.42 g, 62%) was prepared as an off-white solid from [4-(methylsulfonyl)phenyl]boronic acid (0.58 g, 2.82 mmol), 4-bromo-2-fluorophenol (0.5 g, 2.57 mmol), 2M Na$_2$CO$_3$ (15 mL) and Pd(PPh$_3$)$_4$ (30 mg 0.03 mmol) in DME (15 mL) in a manner similar to Example 1, Step 1. $^1$H NMR (400 MHz, CDCl$_3$): δ 7.98 (d, 2H, J=8.6 Hz), 7.70 (d, 2H, J=8.5 Hz), 7.40-7.30 (m, 2H), 7.11 (t, 1H, J=8.6 Hz), 5.22 (d, 1H, J=4.1 Hz), 3.08 (s, 3H); LRMS (APCI), m/z 267 (M+H).

Step 2: The title compound (0.32 g, 88%) was prepared as a white solid from 3-fluoro-4'-(methylsulfonyl)-4-biphenylol (0.21 g, 0.79 mmol), N-Boc-4-piperidinemethanol (0.18 g, 0.79 mmol) and Ph$_3$P (0.21 g, 0.79 mmol) in THF (5 mL) followed by diisopropyl azodicarboxylate (0.17 g, 94%, 0.79 mmol) in THF (1.5 mL) in a manner similar to Example 1, Step 2. $^1$H NMR (400 MHz, CDCl$_3$): δ 7.98 (d, 2H, J=8.6 Hz), 7.70 (d, 2H, J=8.6 Hz), 7.40-7.30 (m, 2H), 7.06 (t, 1H, J=8.5 Hz), 4.25-4.15 (m, 2H), 3.92 (d, 2H, J=6.3 Hz), 3.08 (s, 3H), 2.80-2.70 (m, 2H), 2.10-1.95 (m, 1H), 1.90-1.80 (m, 2H), 1.46 (s, 9H), 1.35-1.20 (m, 2H); LRMS (ESI), m/z 464 (M+H).

Example 65

1,1-Dimethylethyl 4-({[2'-fluoro-4'-(methylsulfonyl)-4-biphenylyl]oxy}methyl)-1-piperidinecarboxylate

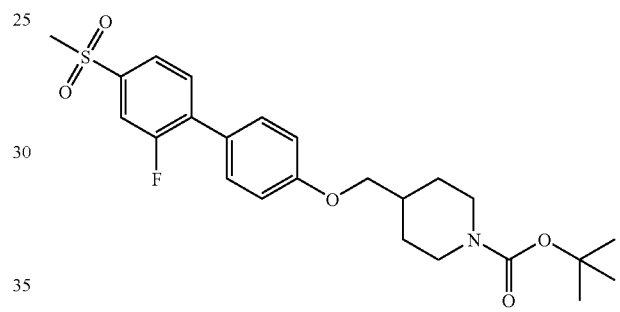

Step 1: Into a flask under N$_2$ were placed CuBr$_2$ (1.49 g, 6.60 mmol), tert-butyl nitrite (1.22 mL, 90%, 9.25 mmol) and CH$_3$CN (15 mL). The solution was heated at 65° C., and 2-fluoro-4-(methylsulfonyl)aniline (1.0 g, 5.29 mmol) in CH$_3$CN (15 mL) was added dropwise over 10 minutes. After the addition was complete, the reaction mixture was left at 65° C. for 1 h, then cooled to ambient temperature, poured into a flask containing 20% HCl (100 mL) and extracted with ether (2×75 mL). The combined organic extract was washed with water and brine, dried over Na$_2$SO$_4$, filtered, and the filtrate was concentrated to give the crude product as a brown solid. The crude product was triturated with hot hexanes to give 1.10 g (82%) of 1-bromo-2-fluoro-4-(methylsulfonyl)benzene as a light brown solid. $^1$H NMR (400 MHz, CDCl$_3$): δ 7.80 (dd, 1H, J$_a$=8.3 Hz, J$_b$=6.3 Hz), 7.70 (dd, 1H, J$_a$=7.5 Hz, J$_b$=2.0 Hz), 7.61 (dd, 1H, J$_a$=8.3 Hz, J$_b$=2.0 Hz), 3.06 (s, 3H); LRMS (ESI), m/z 253/255 (M+H).

Step 2: 2'-Fluoro-4'-(methylsulfonyl)-4-biphenylol (0.34 g, 65%) was prepared as an off-white solid from (4-hydroxyphenyl)boronic acid (0.30 g, 2.07 mmol), 1-bromo-2-fluoro-4-(methylsulfonyl)benzene (0.5 g, 1.98 mmol), 2M Na$_2$CO$_3$ (12 mL) and Pd(PPh$_3$)$_4$ (20 mg, 0.02 mmol) in DME (12 mL) in a manner similar to Example 1, Step 1. $^1$H NMR (400 MHz, CDCl$_3$): δ 7.76 (dd, 1H, J$_a$=8.0 Hz, J$_b$=1.5 Hz), 7.74-7.69 (m, 1H), 7.64-7.58 (m, 1H), 7.47 (d, 2H, J=7.1 Hz), 6.94 (d, 2H, J=8.5 Hz), 4.94 (bs, 1H), 3.10 (s, 3H); LRMS (ESI), m/z 267 (M+H).

Step 3: The title compound (0.51 g, 85%) was prepared as a white solid from 2'-fluoro-4'-(methylsulfonyl)-4-biphenylol (0.34 g, 1.28 mmol), N-Boc-4-piperidinemethanol (0.29 g, 1.28 mmol) and Ph₃P (0.34 g, 1.28 mmol) in THF (8 mL) followed by diisopropyl azodicarboxylate (0.28 g, 94%, 1.28 mmol) in THF (2.5 mL) in a manner similar to Example 1, Step 2. ¹H NMR (400 MHz, CD₃OD): δ 7.85-7.70 (m, 3H), 7.54 (d, 2H, J=7.3 Hz), 7.04 (d, 2H, J=8.8 Hz), 4.15-4.05 (m, 2H), 3.90 (d, 2H, J=6.1 Hz), 3.16 (s, 3H), 2.90-2.75 (m, 2H), 2.10-1.95 (m, 1H), 1.90-1.80 (m, 2H), 1.46 (s, 9H), 1.35-1.20 (m, 2H); LRMS (ESI), m/z 464 (M+H).

Example 66

1-Methylethyl 4-({[2'-fluoro-4'-(methylsulfonyl)-4-biphenylyl]oxy}methyl)-1-piperidinecarboxylate

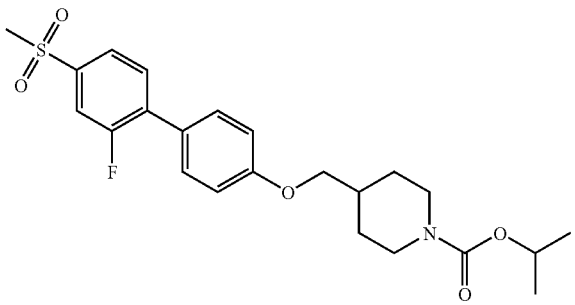

Step 1: 1,1-Dimethylethyl 4-({[2'-fluoro-4'-(methylsulfonyl)-4-biphenylyl]oxy}methyl)-1-piperidinecarboxylate (Example 65, 0.484 g, 1.04 mmol) was dissolved in 1,4-dioxane (20 mL). To this solution was added ether (15 mL), followed by addition of 4.0M HCl in 1,4-dioxane (15 mL) and 2M HCl in ether (15 mL). The reaction mixture was stirred at ambient temperature overnight. The white solid was collected via filtration and washed with ether to yield 0.386 mg (92%) of 4-({[2'-fluoro-4'-(methylsulfonyl)-4-biphenylyl]oxy}methyl)piperidine hydrochloride as a white solid. ¹H NMR (400 MHz, CD₃OD): δ 7.85-7.50 (m, 3H), 7.56 (d, 2H, J=7.3 Hz), 7.06 (d, 2H, J=8.7 Hz), 3.98 (d, 2H, J=5.9 Hz), 3.50-3.40 (m, 2H), 3.17 (s, 3H), 3.10-3.00 (m, 2H), 2.25-2.05 (m, 3H), 1.70-1.55 (m, 2H); LRMS (ESI), m/z 364 (M+H).

Step 2: Diisopropylethylamine (0.14 mL, 0.75 mmol) was added to a suspension of 4-({[2'-fluoro-4'-(methylsulfonyl)-4-biphenylyl]oxy}methyl)piperidine hydrochloride (0.10 g, 0.25 mmol) in CH₂Cl₂ (7 mL). The mixture was cooled to 0° C. in an ice bath, and isopropyl chloroformate (1.0M in toluene, 0.28 mL, 0.28 mmol) was added dropwise. The reaction mixture was allowed to warm to ambient temperature, and stirred overnight. The mixture was then concentrated to give the crude product as a colorless oil. The crude product was purified by chromatography on a silica gel column eluted with 5:6 EtOAc/hexane to give 0.11 g (98%) of the title compound as a white solid. ¹H NMR (400 MHz, CDCl₃): δ 7.80-7.70 (m, 2H), 7.65-7.55 (m, 1H), 7.50 (d, 2H, J=8.8 Hz), 6.98 (d, 2H, J=8.6 Hz), 4.92 (septet, 1H, J=6.1 Hz), 4.25-4.15 (m, 2H), 3.86 (d, 2H, J=6.3 Hz), 3.09 (s, 3H), 2.85-2.75 (m, 2H), 2.10-1.90 (m, 1H), 1.90-1.80 (m, 2H), 1.35-1.10 (m, 8H); LRMS (ESI), m/z 450 (M+H).

Example 67

5-Bromo-2-[4-({[2'-fluoro-4'-(methylsulfonyl)-4-biphenylyl]oxy}methyl)-1-piperidinyl]pyrimidine

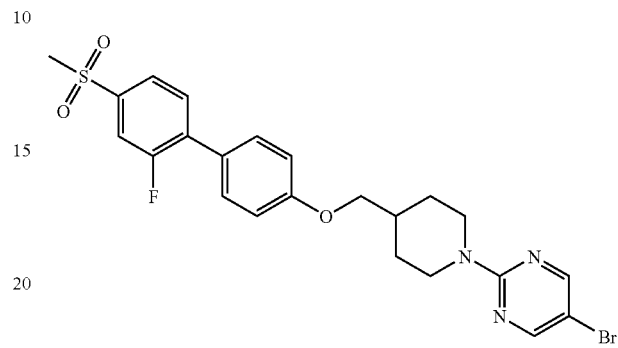

A mixture of 4-({[2'-fluoro-4'-(methylsulfonyl)-4-biphenylyl]oxy}methyl)piperidine hydrochloride (Example 66, Step 1, 0.12 g, 0.30 mmol), 2-chloro-5-bromopyrimidine (89 mg, 0.45 mmol) and K₂CO₃ (0.13 g, 0.90 mmol) in DMSO (5 mL) was degassed, purged with N₂ and heated at 100° C. overnight. The mixture was allowed to cool to ambient temperature, and was poured into water (50 mL) and extracted with EtOAc. The combined organic extract was washed with water and brine, dried over Na₂SO₄, filtered, and the filtrate was concentrated to give the crude product as a yellow solid. The crude product was triturated with hot hexanes containing 1% of MeOH to give 0.142 g (91%) of the title compound as an off-white solid. ¹H NMR (400 MHz, CDCl₃): δ 8.29 (s, 2H), 7.80-7.70 (m, 2H), 7.65-7.55 (m, 1H), 7.50 (d, 2H, J=7.6 Hz), 6.99 (d, 2H, J=8.7 Hz), 4.85-4.75 (m, 2H), 3.88 (d, 2H, J=6.3 Hz), 3.09 (s, 3H), 3.00-2.90 (m, 2H), 2.20-2.05 (m, 1H), 2.00-1.90 (m, 2H), 1.45-1.30 (m, 2H); LRMS (ESI), m/z 520/522 (M+H).

Example 68

1-Methylethyl 4-({[3-fluoro-4'-(methylsulfonyl)-4-biphenylyl]oxy}methyl)-1-piperidinecarboxylate

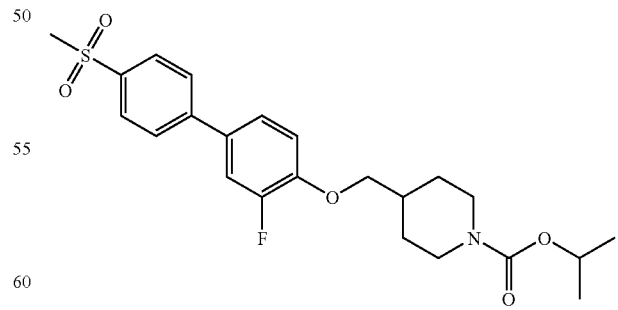

Step 1: 4-({[3-Fluoro-4'-(methylsulfonyl)-4-biphenylyl]oxy}methyl)piperidine hydrochloride (0.23 g, 88%) was prepared as a white solid from 1,1-dimethylethyl 4-({[3-fluoro-4'-(methylsulfonyl)-4-biphenylyl]oxy}methyl)-1-piperidinecarboxylate (Example 64, 0.30 g, 0.65 mmol), 1,4- dioxane (12 mL), ether (9 mL), 4.0M HCl in 1,4-dioxane (9 mL) and 2M HCl in ether (9 mL) in a manner similar to Example 66, Step 1. ¹H NMR (400 MHz, CD₃OD): δ 7.99 (d, 2H, J=8.5 Hz), 7.84 (d, 2H, J=8.5 Hz), 7.55-7.45 (m, 2H), 7.25-7.20 (m, 1H), 4.04 (d, 2H, J=5.9 Hz), 3.50-3.40 (m, 2H), 3.14 (s, 3H), 3.10-3.00 (m, 2H), 2.30-2.15 (m, 1H), 2.15-2.05 (m, 2H), 1.75-1.60 (m, 2H); LRMS (ESI), m/z 364 (M+H).

Step 2: The title compound (83 mg, 92%) was prepared as a white solid from 4-({[3-fluoro-4'-(methylsulfonyl)-4-biphenylyl]oxy}methyl)piperidine hydrochloride (80 mg, 0.20 mmol), diisopropylethylamine (0.11 mL, 0.60 mmol), isopropyl chloroformate (1.0M in toluene, 0.22 mL, 0.22 mmol) and dichloromethane (6 mL) in a manner similar to Example 66, Step 2. ¹H NMR (400 MHz, CDCl₃): δ 7.98 (d, 2H, J=8.3 Hz), 7.70 (d, 2H, J=8.3 Hz), 7.40-7.25 (m, 2H), 7.10-7.00 (m, 1H), 4.92 (septet, 1H, J=6.2 Hz), 4.22 (bs, 2H), 3.92 (d, 2H, J=6.4 Hz), 3.08 (s, 3H), 2.85-2.70 (m, 2H), 2.15-2.00 (m, 1H), 1.95-1.80 (m, 2H), 1.35-1.20 (m, 8H); LRMS (ESI), m/z 450 (M+H).

Example 69

1,1-Dimethylethyl 4-({[2-fluoro-4'-(methylsulfonyl)-4-biphenylyl]oxy}methyl)-1-piperidinecarboxylate

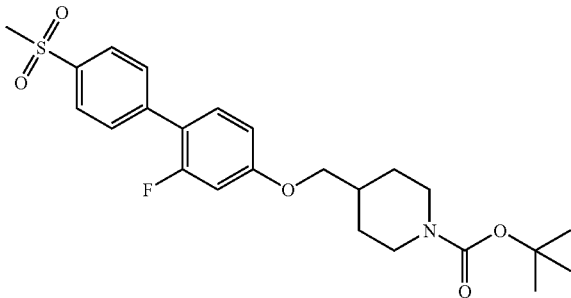

Step 1: 2-Fluoro-4'-(methylsulfonyl)-4-biphenylol (0.58 g, 71%) was prepared as a white solid from [4-(methylsulfonyl)phenyl]boronic acid (0.69 g, 3.38 mmol), 4-bromo-3-fluorophenol (0.6 g, 3.05 mmol), 2M Na₂CO₃ (18 mL) and Pd(PPh₃)₄ (30 mg, 0.03 mmol) in DME (18 mL) in a manner similar to Example 1, Step 1. ¹H NMR (400 MHz, CDCl₃): δ 7.98 (d, 2H, J=8.3 Hz), 7.69 (d, 2H, J=7.4 Hz), 7.40-7.30 (m, 1H), 6.80-6.65 (m, 2H), 5.10 (s, 1H), 3.09 (s, 3H); LRMS (ESI) m/z 267 (M+H).

Step 2: The title compound was prepared as a white solid from 2-fluoro-4'-(methylsulfonyl)-4-biphenylol (0.25 g, 0.94 mmol), N-Boc-4-piperidinemethanol (0.21 g, 0.94 mmol) and Ph₃P (0.25 g, 0.94 mmol) in THF (6 mL) followed by diisopropyl azodicarboxylate (0.20 g, 94%, 0.94 mmol) in THF (2 mL) in a manner similar to Example 1, Step 2. The crude product was triturated with hot hexane containing 1% of MeOH to give 20 mg of the title compound as a white solid. The filtrate was purified by chromatography on a silica gel column eluted with 3:4 EtOAc/hexane to give additional 0.34 g (overall 83%) of the title compound as a white solid. ¹H NMR (400 MHz, CD₃OD): δ 7.99 (d, 2H, J=8.3 Hz), 7.76 (d, 2H, J=7.4 Hz), 7.50-7.40 (m, 1H), 6.90-6.80 (m, 2H), 4.20-4.10 (m, 2H), 3.91 (d, 2H, J=6.4 Hz), 3.14 (s, 3H), 2.90-2.70 (m, 2H), 2.10-1.95 (m, 1H), 1.90-1.80 (m, 2H), 1.45 (s, 9H), 1.35-1.20 (m, 2H); LRMS (ESI), m/z 486 (M+Na).

Example 70

1,1-Dimethylethyl 4-[({5-[4-(methylsulfonyl)phenyl]-2-pyridinyl}oxy)methyl]-1-piperidinecarboxylate

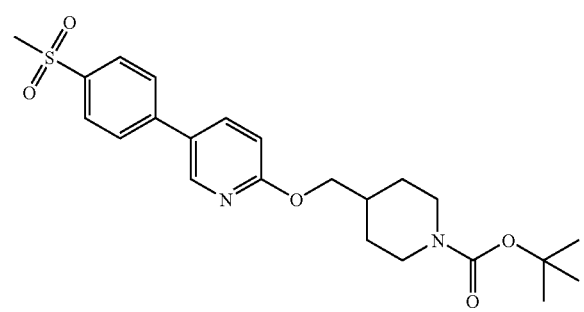

Step 1: A solution of N-Boc-4-piperidinemethanol (1.0 g, 4.50 mmol) in DMSO (2 mL) was added dropwise to a suspension of NaH (60% dispersion in mineral oil, 0.27 g, 6.76 mmol) in DMSO (4 mL). The mixture was stirred at ambient temperature for 1 h, then 30 minutes at 50° C. The mixture was allowed to cool to ambient temperature, and a solution of 2,5-dibromopyridine (1.12 g, 4.73 mmol) in DMSO (4 mL) was added dropwise, and the reaction mixture was stirred at ambient temperature overnight, poured in water, then extracted with EtOAc. The organic extract was washed with water and brine, dried over Na₂SO₄, filtered, and the filtrate was concentrated to give the crude product as an amber oil. The crude product was purified by chromatography on a silica gel column eluted with 1:8 EtOAc/hexane to give 1.40 g (84%) of 1,1-dimethylethyl 4-{[(5-bromo-2-pyridinyl)oxy]methyl}-1-piperidinecarboxylate as a white solid after standing. ¹H NMR (400 MHz, CDCl₃): δ 8.16 (d, 1H, J=2.2 Hz), 7.64 (dd, 1H, J$_a$=8.7 Hz, J$_b$=2.3 Hz), 6.64 (d, 1H, J=8.8 Hz), 7.04 (d, 2H, J=8.8 Hz), 4.20-4.10 (m, 4H), 2.80-2.65 (m, 2H), 2.00-1.85 (m, 1H), 1.85-1.70 (m, 2H), 1.45 (s, 9H), 1.30-1.20 (m, 2H); LRMS (ESI), m/z 371/373 (M+H).

Step 2: The title compound (0.39 g, 93%) was prepared as a white solid from [4-(methylsulfonyl)phenyl]boronic acid (0.23 g, 1.13 mmol), 1,1-dimethylethyl 4-{[(5-bromo-2-pyridinyl)oxy]methyl}-1-piperidinecarboxylate (0.35 g, 0.94 mmol), 2M Na₂CO₃ (5 mL) and Pd(PPh₃)₄ (10 mg, 0.01 mmol) in DME (5 mL) in a manner similar to Example 1, Step 1. ¹H NMR (400 MHz, CD₃OD): δ 8.46 (d, 1H, J=2.7 Hz), 8.05-8.00 (m, 3H), 7.86 (d, 2H, J=8.5 Hz), 6.92 (d, 1H, J=8.6 Hz), 4.21 (d, 2H, J=6.3 Hz), 4.15-4.05 (m, 2H), 3.14 (s, 3H), 2.85-2.70 (m, 2H), 2.00-1.95 (m, 1H), 1.90-1.75 (m, 2H), 1.45 (s, 9H), 1.35-1.20 (m, 2H); LRMS (ESI), m/z 447 (M+H).

Example 71

1-Methylethyl 4-[({5-[4-(methylsulfonyl)phenyl]-2-pyridinyl}oxy)methyl]-1-piperidinecarboxylate

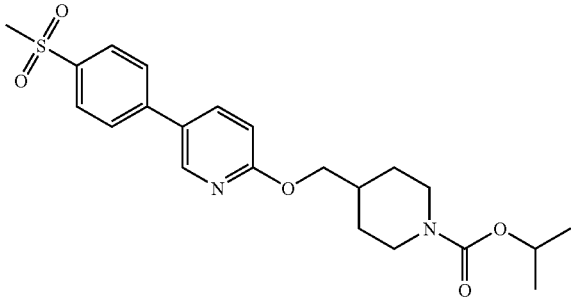

Step 1: 5-[4-(Methylsulfonyl)phenyl]-2-[(4-piperidinylmethyl)oxy]pyridine dihydrochloride (0.32 g, 94%) was prepared as a light yellow solid from 1,1-dimethylethyl 4-[({5-[4-(methylsulfonyl)phenyl]-2-pyridinyl}oxy)methyl]-1-piperidinecarboxylate (Example 70, 0.36 g, 0.81 mmol), 1,4-dioxane (16 mL), ether (12 mL), 4.0M HCl in 1,4-dioxane (12 mL) and 2M HCl in ether (12 mL) in a manner similar to Example 66, Step 1. $^1$H NMR (400 MHz, CD$_3$OD): δ 8.48 (d, 1H, J=2.5 Hz), 8.06 (dd, 1H, J$_a$=8.6 Hz, J$_b$=2.5 Hz), 8.03 (d, 2H, J=8.5 Hz), 7.86 (d, 2H, J=8.4 Hz), 6.94 (d, 1H, J=8.6 Hz), 4.28 (d, 2H, J=6.1 Hz), 3.50-3.40 (m, 2H), 3.14 (s, 3H), 3.10-3.00 (m, 2H), 2.30-2.15 (m, 1H), 2.15-2.05 (m, 2H), 1.70-1.55 (m, 2H); LRMS (ESI), m/z 347 (M+H).

Step 2: The title compound (151 mg, 98%) was prepared as a white solid 5-[4-(methylsulfonyl)phenyl]-2-[(4-piperidinylmethyl)oxy]pyridine dihydrochloride (0.15 g, 0.36 mmol), diisopropylethylamine (0.26 mL, 1.43 mmol), and isopropyl chloroformate (1.0M in toluene, 0.40 mL, 0.40 mmol) in a manner similar to Example 66, Step 2. $^1$H NMR (400 MHz, CD$_3$OD): δ 8.46 (d, 1H, J=2.4 Hz), 8.10-8.00 (m, 3H), 7.86 (d, 2H, J=8.3 Hz), 6.92 (d, 1H, J=8.5 Hz), 4.90-4.80 (m, 1H), 4.21 (d, 2H, J=6.3 Hz), 4.20-4.10 (m, 2H), 3.14 (s, 3H), 2.90-2.75 (m, 2H), 2.10-2.00 (m, 1H), 1.90-1.80 (m, 2H), 1.35-1.20 (m, 8H); LRMS (ESI), m/z 433 (M+H).

Example 72

5-Ethyl-2-{4-[({5-[4-(methylsulfonyl)phenyl]-2-pyridinyl}oxy)methyl]-1-piperidinyl}pyrimidine

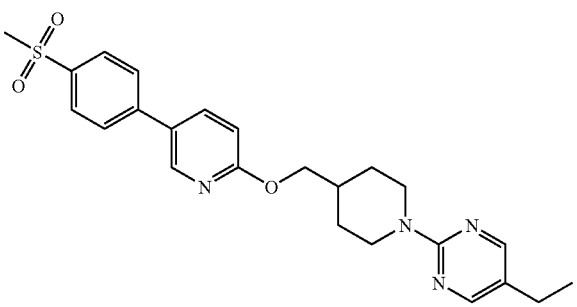

A mixture of 5-[4-(methylsulfonyl)phenyl]-2-[(4-piperidinylmethyl)oxy]pyridine dihydrochloride (Example 71, Step 1, 0.16 g, 0.38 mmol), 2-chloro-5-ethylpyrimidine (0.1 mL, 0.76 mmol) and K$_2$CO$_3$ (0.26 g, 1.91 mmol) in CH$_3$CN (3 mL) was degassed, purged with N$_2$ and heated at 80° C. overnight. After more CH$_3$CN (2 mL) was added, the reaction mixture was heated at 80° C. for two days. The mixture was allowed to cool to ambient temperature, water was added and the mixture was extracted with EtOAc. The combined organic extract was washed with brine, dried over Na$_2$SO$_4$, filtered, and the filtrate was concentrated to give the crude product as a light yellow solid. The crude product was purified by chromatography on a silica gel column eluted with 2:5 EtOAc/CH$_2$Cl$_2$ to give 0.114 g (66%) of the title compound as a white solid. $^1$H NMR (400 MHz, CDCl$_3$): δ 8.39 (d, 1H, J=2.5 Hz), 8.20 (bs, 2H), 8.01 (d, 2H, J=8.3 Hz), 7.82 (dd, 1H, J$_a$=8.7 Hz, J$_b$=2.6 Hz), 7.70 (d, 2H, J=8.3 Hz), 6.85 (d, 1H, J=8.5 Hz), 4.81 (bs, 2H), 4.24 (d, 2H, J=6.3 Hz), 3.08 (s, 3H), 3.05-2.85 (m, 2H), 2.55-2.40 (m, 2H), 2.20-2.05 (m, 1H), 2.00-1.90 (m, 2H), 1.45-1.30 (m, 2H), 1.19 (t, 3H, J=7.5 Hz); LRMS (ESI), m/z 453 (M+H).

Example 73

1,1-Dimethylethyl 4-[({6-[4-(methylsulfonyl)phenyl]-3-pyridinyl}oxy)methyl]-1-piperidinecarboxylate

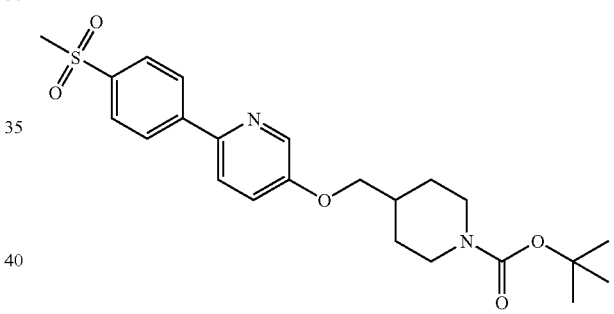

Step 1: 1,1-Dimethylethyl 4-{[(6-chloro-3-pyridinyl)oxy]methyl}-1-piperidinecarboxylate (0.80 g, 54%) was prepared as a white solid from 2-chloro-5-hydroxypyridine (0.60 g, 4.51 mmol), N-Boc-4-piperidinemethanol (1.0 g, 4.51 mmol) and Ph$_3$P (1.20 g, 4.51 mmol) in THF (25 mL) followed by diisopropyl azodicarboxylate (0.97 g, 94%, 4.51 mmol) in THF (8 mL) in a manner similar to Example 1, Step 2. $^1$H NMR (400 MHz, CDCl$_3$): δ 8.04 (bs, 1H), 7.25-7.15 (m, 2H), 4.20-4.10 (m, 2H), 3.82 (d, 2H, J=6.1 Hz), 2.80-2.70 (m, 2H), 2.05-1.90 (m, 1H), 1.85-1.75 (m, 2H), 1.46 (s, 9H), 1.35-1.20 (m, 2H); LRMS (ESI), m/z 327 (M+H).

Step 2: The title compound was prepared as a white solid from [4-(methylsulfonyl)phenyl]boronic acid (0.44 g, 2.15 mmol), 1,1-dimethylethyl 4-{[(6-chloro-3-pyridinyl)oxy]methyl}-1-piperidinecarboxylate (0.54 g, 1.65 mmol), 2M Na$_2$CO$_3$ (5 mL) and PdCl$_2$(PPh$_3$)$_2$ (0.12 g) in DMF (20 mL). The reaction mixture was heated at 85° C. under N$_2$ for 5 h, then cooled to ambient temperature, and extracted with EtOAc (70 mL×2). The combined organic extracts were washed with water, brine, dried over Na$_2$SO$_4$, filtered, and the filtrate was concentrated to give the crude product as a gray solid. The crude product was purified by chromatography on a silica gel column eluted with 25% EtOAc/CH$_2$Cl$_2$ to give the title compound (0.44 g, 60%) as a white solid. $^1$H NMR (400 MHz, CD$_3$OD): δ 8.36 (d, 1H, J=2.9 Hz), 8.18 (d, 2H, J=8.6 Hz), 8.02 (d, 2H, J=8.3 Hz), 7.92 (d, 1H, J=8.8 Hz), 7.49 (dd, 1H, J$_a$=8.8 Hz, J$_b$=2.9 Hz), 4.20-4.10 (m, 2H), 3.99 (d, 2H, J=6.3 Hz), 3.15 (s, 3H), 2.90-2.75 (m, 2H), 2.10-2.00 (m, 1H), 1.90-1.80 (m, 2H), 1.46 (s, 9H), 1.35-1.25 (m, 2H); LRMS (ESI), m/z 447 (M+H).

Example 74

1-Methylethyl 4-[({6-[4-(methylsulfonyl)phenyl]-3-pyridinyl}oxy)methyl]-1-piperidinecarboxylate

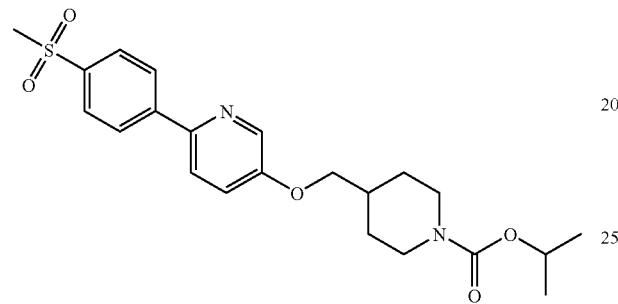

1,1-Dimethylethyl 4-[({6-[4-(methylsulfonyl)phenyl]-3-pyridinyl}oxy)methyl]-1-piperidinecarboxylate (prepared as in Example 73, 0.132 g, 0.30 mmol) was dissolved in CH$_2$Cl$_2$ (9 mL). TFA (0.30 mL) was added to this solution and the mixture was stirred at ambient temperature overnight. The excess TFA and CH$_2$Cl$_2$ were removed under reduced pressure. The residue was redissolved in CH$_2$Cl$_2$ (9 mL). The solution was cooled to 0° C. in an ice bath, and diisopropylethylamine (1.5 mL) was added, followed by addition of isopropyl chloroformate (1.0M in toluene, 0.36 mL, 0.36 mmol). The reaction mixture was allowed to warm to ambient temperature, and stirred for 2 h, then diluted with EtOAc, washed with water and brine, dried over Na$_2$SO$_4$, filtered, and the filtrate was concentrated to give the crude product as a light yellow solid. The crude product was purified by chromatography on a silica gel column eluted with 9:4 EtOAc/hexane to give 0.12 g (93%) of the title compound as a white solid. $^1$H NMR (400 MHz, CDCl$_3$): δ 8.40 (d, 1H, J=2.7 Hz), 8.14 (d, 2H, J=8.3 Hz), 8.01 (d, 2H, J=8.6 Hz), 7.74 (d, 1H, J=8.8 Hz), 7.35-7.25 (m, 1H), 4.92 (septet, 1H, J=6.2 Hz), 4.23 (bs, 2H), 3.92 (d, 2H, J=6.3 Hz), 3.08 (s, 3H), 2.85-2.70 (m, 2H), 2.10-1.95 (m, 1H), 1.90-1.80 (m, 2H), 1.40-1.20 (m, 8H); LRMS (APCI), m/z 433 (M+H).

Alternative preparation: [4-(Methylsulfonyl)phenyl]boronic acid (0.17 g, 0.84 mmol) and 1-methylethyl 4-{[(6-bromo-3-pyridinyl)oxy]methyl}-1-piperidinecarboxylate (prepared as in Example 81, Step 1, 0.25 g, 0.70 mmol) were mixed with DME (4 mL) and 2M Na$_2$CO$_3$ (4 mL). The mixture was degassed with N$_2$, then PdCl$_2$(PPh$_3$)$_2$ (50 mg, 0.07 mmol) was added. The reaction mixture was degassed again with N$_2$ and heated at 80° C. for 6 h, then cooled to ambient temperature, and diluted with EtOAc. The mixture was washed with water and brine and the organic layer was dried over Na$_2$SO$_4$, filtered, and the filtrate was concentrated to give the crude product as a brown solid. The crude product was purified by chromatography on a silica gel column eluted with 25% EtOAc/CH$_2$Cl$_2$ followed by trituration with hexane containing 1% of MeOH to give 0.245 g (81%) of the title compound as a white solid.

Example 75

1,1-Dimethylethyl 4-[({4-[6-(methylsulfonyl)-3-pyridinyl]phenyl}oxy)methyl]-1-piperidinecarboxylate

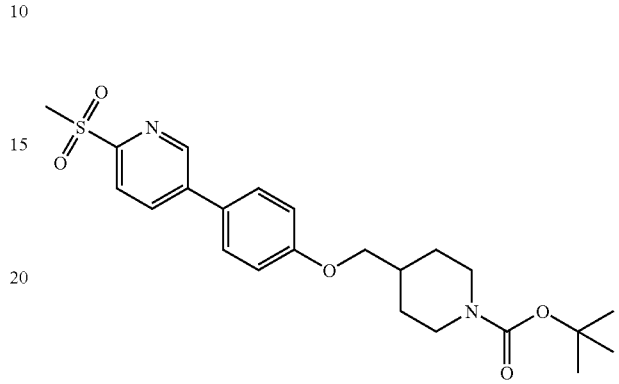

Step 1: A solution of 2,5-dibromopyridine (1.0 g, 4.22 mmol) in DMF (15 mL) was treated with sodium thiomethoxide (0.69 g, 95%, 9.29 mmol) at ambient temperature. The reaction mixture was stirred for 30 minutes, was diluted water and then extracted with ether. The combined organic extract was washed with brine, dried over Na$_2$SO$_4$, filtered, and the filtrate was concentrated to give crude sulfide as a colorless oil. The crude sulfide was dissolved in acetone (120 mL) and was treated with water (50 mL) followed by Oxone® (7.80 g, 12.7 mmol). The reaction mixture was stirred at ambient temperature for 2 h. After more water was added, the mixture was extracted with ether (200 mL) and EtOAc (150 mL). The organic layers were combined and washed with water and brine, dried over Na$_2$SO$_4$, filtered, and the filtrate was concentrated to give the crude product as a light brown oil. The crude product was purified by chromatography on ISCO silica gel column eluted with a 0 to 45% EtOAc:hexane gradient to give 0.54 g (54% from 2,5-dibromopyridine) of 5-bromo-2-(methylsulfonyl)pyridine as a white solid. $^1$H NMR (400 MHz, CDCl$_3$): δ 8.78 (d, 1H, J=2.2 Hz), 8.10 (dd, 1H, J$_a$=8.3 Hz, J$_b$=2.2 Hz), 7.98 (d, 1H, J=8.3 Hz), 3.22 (s, 3H); LRMS (ESI), m/z 236/238 (M+H).

Step 2: 4-[6-(Methylsulfonyl)-3-pyridinyl]phenol was prepared as a brown solid from (4-hydroxyphenyl)boronic acid (0.34 g, 2.40 mmol), 5-bromo-2-(methylsulfonyl)pyridine (0.54 g, 2.29 mmol), 2M Na$_2$CO$_3$ (15 mL) and Pd(PPh$_3$)$_4$ (25 mg, 0.02 mmol) in DME (5 mL) in a manner similar to Example 1, Step 1. The crude product was triturated with 1:1 CH$_2$Cl$_2$/hexane to give 0.45 g (79%) of 4-[6-(methylsulfonyl)-3-pyridinyl]phenol as a brown solid. $^1$H NMR (400 MHz, DMSO-d$_6$): δ 9.88 (s, 1H), 9.01 (d, 1H, J=2.2 Hz), 8.30 (dd, 1H, J$_a$=8.3 Hz, J$_b$=2.2 Hz), 8.02 (d, 1H, J=8.3 Hz), 7.66 (d, 2H, J=8.8 Hz), 6.90 (d, 2H, J=8.5 Hz), 3.27 (s, 3H); LRMS (APCI), m/z 250 (M+H).

Step 3: The title compound (0.34 g, 75%) was prepared as a white solid from 4-[6-(methylsulfonyl)-3-pyridinyl]phenol (0.25 g, 1.00 mmol), N-Boc-4-piperidinemethanol (0.23 g, 1.00 mmol) and Ph$_3$P (0.27 g, 1.00 mmol) in THF (6 mL) followed by diisopropyl azodicarboxylate (0.22 g, 94%, 1.0 mmol) in THF (2 mL) in a manner similar to Example 1, Step 2. $^1$H NMR (400 MHz, CD$_3$OD): δ 8.96 (d, 1H, J=2.2 Hz), 8.28 (dd, 1H, J$_a$=8.3 Hz, J$_b$=2.2 Hz), 8.10 (d, 1H, J=8.1 Hz), 7.70 (d, 2H, 8.8 Hz), 7.08 (d, 2H, J=8.8 Hz), 4.20-4.10 (m, 2H), 3.92 (d, 2H, J=6.1 Hz), 3.24 (s, 3H), 2.90-2.70 (m, 2H), 2.10-1.95 (m, 1H), 1.90-1.80 (m, 2H), 1.46 (s, 9H), 1.35-1.20 (2H); LRMS (APCI), m/z 469 (M+Na).

Example 76

1,1-Dimethylethyl 4-[({6-[2-fluoro-4-(methylsulfonyl)phenyl]-3-pyridinyl}oxy)methyl]-1-piperidinecarboxylate

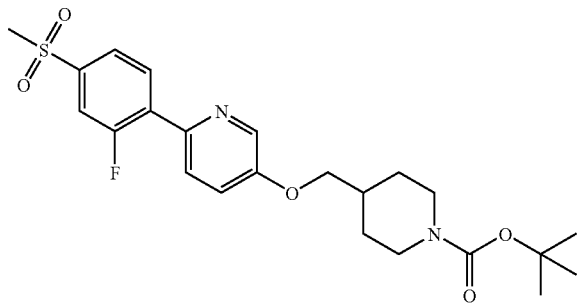

Step 1: 1,1-Dimethylethyl 4-{[(6-bromo-3-pyridinyl)oxy]methyl}-1-piperidinecarboxylate (0.88 g, 83%) was prepared as a light yellow solid from 2-bromo-5-hydroxypyridine (0.50 g, 2.87 mmol), N-Boc-4-piperidinemethanol (0.64 g, 2.87 mmol) and Ph$_3$P (0.77 g, 2.87 mmol) in THF (15 mL) followed by diisopropyl azodicarboxylate (0.62 g, 94%, 2.87 mmol) in THF (5 mL) in a manner similar to Example 1, Step 2. The material was purified by chromatography on a silica gel column eluted with 5 to 20% EtOAc/hexanes. $^1$H NMR (400 MHz, CDCl$_3$): δ 8.04 (bs, 1H), 7.36 (d, 1H, J=8.8 Hz), 7.15-7.05 (m, 1H), 4.25-4.10 (m, 2H), 3.82 (d, 2H, J=6.1 Hz), 2.80-2.70 (m, 2H), 2.05-1.90 (m, 1H), 1.85-1.75 (m, 2H), 1.46 (s, 9H), 1.35-1.20 (m, 2H); LRMS (ESI), m/z 393/395 (M+Na).

Step 2: 1,1-Dimethylethyl 4-({[6-(4-bromo-2-fluorophenyl)-3-pyridinyl]oxy}methyl)-1-piperidinecarboxylate (0.23 g, ~90% purity, 42%) was prepared as a white solid from (4-bromo-2-fluorophenyl)boronic acid (0.30 g, 1.36 mmol), 1,1-dimethylethyl 4-{[(6-bromo-3-pyridinyl)oxy]methyl}-1-piperidinecarboxylate (0.44 g, 1.19 mmol), 2M Na$_2$CO$_3$ (2 mL), and PdCl$_2$(PPh$_3$)$_2$ (85 mg, 0.12 mmol) in DME (4 mL) in a manner similar to Example 21, Step 3. The material was purified by chromatography on a silica gel column eluted with 20% EtOAc/hexanes. $^1$H NMR (400 MHz, CDCl$_3$): δ 8.38 (d, 1H, J=2.7 Hz), 7.90-7.85 (m, 1H), 7.72 (d, 1H, J=8.8 Hz), 7.45-7.30 (m, 2H), 7.30-7.25 (m, 1H), 4.25-4.10 (m, 2H), 3.99 (d, 2H, J=6.4 Hz), 2.95-2.80 (m, 2H), 2.05-1.95 (m, 1H), 1.90-1.80 (m, 2H), 1.46 (s, 9H), 1.35-1.25 (m, 2H); LRMS (ESI), m/z 465/467 (M+H).

Step 3: A mixture of 1,1-dimethylethyl 4-({[6-(4-bromo-2-fluorophenyl)-3-pyridinyl]oxy}methyl)-1-piperidinecarboxylate (0.214 g, 0.46 mmol), methanesulfinic acid sodium salt (71 mg, 80%, 0.55 mmol), L-proline (11 mg, 0.09 mmol), CuI (9 mg, 0.05 mmol) and NaOH (4 mg, 0.09 mmol) in DMSO (2.5 mL) was degassed, purged with N$_2$ and heated at 110° C. for 48 h. The mixture was cooled to ambient temperature and was poured into water and extracted with EtOAc. The combined organic extract was washed with water and brine, dried over Na$_2$SO$_4$, filtered, and the filtrate was concentrated to give the crude product as a yellow solid. The crude product was purified by chromatography on a silica gel column eluted with 25% EtOAc/CH$_2$Cl$_2$ to give 62.5 mg (29%) of the title compound as a white solid. $^1$H NMR (400 MHz, CD$_3$OD): δ 8.40 (d, 1H, J=3.0 Hz), 8.15-8.10 (m, 1H), 7.90-7.75 (m, 3H), 7.50 (dd, 1H, J$_a$=8.8 Hz, J$_b$=2.9 Hz), 4.20-4.10 (m, 2H), 4.00 (d, 2H, J=6.4 Hz), 3.18 (s, 3H), 2.90-2.75 (m, 2H), 2.15-2.00 (m, 1H), 1.90-1.80 (m, 2H), 1.46 (s, 9H), 1.40-1.25 (m, 2H); LRMS (ESI), m/z 465 (M+H).

Example 77

1-Methylethyl 4-[({6-[2-fluoro-4-(methylsulfonyl)phenyl]-3-pyridinyl}oxy)methyl]-1-piperidinecarboxylate

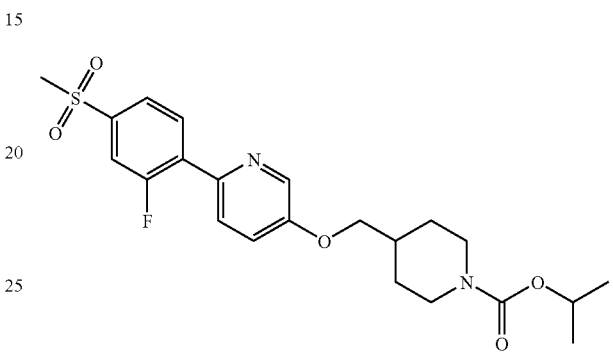

1,1-Dimethylethyl 4-[({6-[2-fluoro-4-(methylsulfonyl)phenyl]-3-pyridinyl}oxy)methyl]-1-piperidinecarboxylate (prepared as in Example 76, 47 mg, 0.10 mmol) was dissolved in CH$_2$Cl$_2$ (3 mL) and treated with TFA (0.20 mL). The mixture was stirred at ambient temperature for 6 h. The mixture was then cooled to 0° C. in an ice bath, and diisopropylethylamine (1.0 mL) was added, followed by addition of isopropyl chloroformate (1.0M in toluene, 0.12 mL, 0.12 mmol). The reaction mixture was allowed to warm to ambient temperature, and stirred overnight, then diluted with EtOAc, washed with water and brine, dried over Na$_2$SO$_4$, filtered, and the filtrate was concentrated to give the crude product as a light brown solid. The crude product was purified by chromatography on a silica gel column eluted with 25% EtOAc/CH$_2$Cl$_2$ to give 32 mg (70%) of the title compound as a white solid. $^1$H NMR (400 MHz, CD$_3$OD): δ 8.40 (d, 1H, J=2.9 Hz), 8.20-8.10 (m, 1H), 7.90-7.75 (m, 3H), 7.50 (dd, 1H, J$_a$=8.8 Hz, J$_b$=3.0 Hz), 4.90-4.80 (m, 1H), 4.25-4.15 (m, 2H), 4.00 (d, 2H, J=6.1 Hz), 3.18 (s, 3H), 2.95-2.80 (m, 2H), 2.15-2.00 (m, 1H), 1.95-1.85 (m, 2H), 1.40-1.20 (m, 8H); LRMS (ESI), m/z 451 (M+H).

Example 78

1,1-Dimethylethyl 4-[({4-[5-(methylsulfonyl)-2-pyridinyl]phenyl}oxy)methyl]-1-piperidinecarboxylate

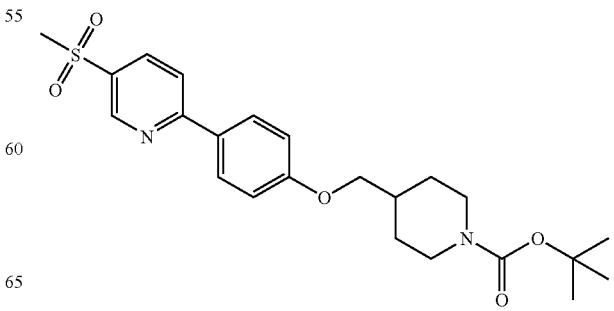

Step 1: 4-(5-Bromo-2-pyridinyl)phenol (0.25 g, 24%) was prepared as a white solid from (4-hydroxyphenyl)boronic acid (0.60 g, 4.22 mmol), 2,5-dibromopyridine (1.0 g, 4.22 mmol), 2M Na$_2$CO$_3$ (6 mL), EtOH (2 mL) and Pd(PPh$_3$)$_4$ (0.15 g, 0.13 mmol) in toluene (4 mL) in a manner similar to Example 1, Step 1, except the reaction was heated overnight. $^1$H NMR (400 MHz, CDCl$_3$): δ 8.68 (d, 1H, J=2.2 Hz), 7.90-7.80 (m, 3H), 7.56 (d, 1H, J=8.5 Hz), 6.92 (d, 2H, J=8.5 Hz), 5.18 (bs, 1H); LRMS (ESI), m/z 250/252 (M+H).

Step 2: 1,1-Dimethylethyl 4-({[4-(5-bromo-2-pyridinyl)phenyl]oxy}methyl)-1-piperidinecarboxylate (0.27 g, 60%) was prepared as a white solid from 4-(5-bromo-2-pyridinyl)phenol (0.25 g, 1.0 mmol), N-Boc-4-piperidinemethanol (0.23 g, 1.0 mmol) and Ph$_3$P (0.27 g, 1.0 mmol) in THF (7 mL) followed by diisopropyl azodicarboxylate (0.22 g, 94%, 1.0 mmol) in THF (3 mL) in a manner similar to Example 1, Step 2. $^1$H NMR (400 MHz, CDCl$_3$): δ 8.69 (s, 1H), 7.92 (d, 2H, J=8.8 Hz), 7.85 (d, 1H, J=8.5 Hz), 7.57 (d, 1H, J=8.5 Hz), 6.97 (d, 2H, J=8.8 Hz), 4.25-4.10 (m, 2H), 3.86 (d, 2H, J=6.4 Hz), 2.85-2.70 (m, 2H), 2.05-1.90 (m, 1H), 1.90-1.80 (m, 2H), 1.46 (s, 9H), 1.35-1.20 (m, 2H); LRMS (ESI), m/z 446/448 (M+H).

Step 3: The title compound (0.20 g, 80%) was prepared as a white solid from 1,1-dimethylethyl 4-({[4-(5-bromo-2-pyridinyl)phenyl]oxy}methyl)-1-piperidinecarboxylate (0.25 g, 0.60 mmol), methanesulfinic acid sodium salt (0.12 g, 80%, 0.91 mmol), L-proline (14 mg, 0.12 mmol), CuI (12 mg, 0.06 mmol) and NaOH (5 mg, 0.12 mmol) in DMSO (3 mL) in a manner similar to Example 76, Step 3. $^1$H NMR (400 MHz, CD$_3$OD): δ 9.05 (d, 1H, J=2.2 Hz), 8.30 (dd, 1H, J$_a$=8.4 Hz, J$_b$=2.3 Hz), 8.09 (d, 2H, J=8.8 Hz), 8.04 (d, 1H, J=8.5 Hz), 7.06 (d, 2H, J=8.8 Hz), 4.20-4.10 (m, 2H), 3.93 (d, 2H, J=6.4 Hz), 3.21 (s, 3H), 2.90-2.70 (m, 2H), 2.10-1.95 (m, 1H), 1.90-1.80 (m, 2H), 1.46 (s, 9H), 1.35-1.20 (m, 2H); LRMS (ESI), m/z 447 (M+H).

Example 79

1-Methylethyl 4-[({4-[5-(methylsulfonyl)-2-pyridinyl]phenyl}oxy)methyl]-1-piperidinecarboxylate

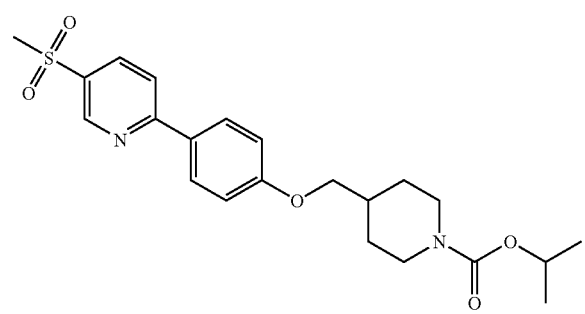

The title compound (53 mg, 91%) was prepared as an off-white solid from 1,1-dimethylethyl 4-[({4-[5-(methylsulfonyl)-2-pyridinyl]phenyl}oxy)methyl]-1-piperidinecarboxylate (Example 78, 60 mg, 0.13 mmol) and TFA (0.25 mL) in CH$_2$Cl$_2$ (4 mL) then diisopropylethylamine (1.5 ml) and isopropyl chloroformate (1.0M in toluene, 0.16 mL, 0.16 mmol) in a manner similar to Example 74. $^1$H NMR (400 MHz, CDCl$_3$): δ 9.12 (s, 1H), 8.21 (d, 1H, J=8.3 Hz), 8.04 (d, 2H, J=8.8 Hz), 7.84 (d, 1H, J=8.3 Hz), 7.00 (d, 2H, J=8.6 Hz), 4.92 (septet, 1H, J=6.3 Hz), 4.21 (bs, 2H), 3.88 (d, 2H, J=6.4 Hz), 3.13 (s, 3H), 2.85-2.70 (m, 2H), 2.10-1.95 (m, 1H), 1.90-1.80 (m, 2H), 1.35-1.20 (m, 8H); LRMS (ESI), m/z 433 (M+H).

Example 80

5-Ethyl-2-{4-[({6-[4-(methylsulfonyl)phenyl]-3-pyridinyl}oxy)methyl]-1-piperidinyl}pyrimidine

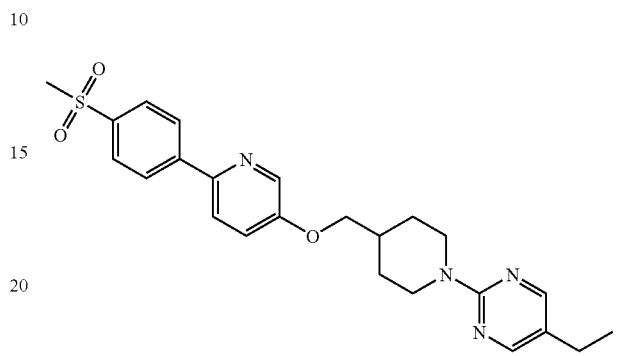

1,1-Dimethylethyl 4-[({6-[4-(methylsulfonyl)phenyl]-3-pyridinyl}oxy)methyl]-1-piperidinecarboxylate (prepared as in Example 73, Step 2, 0.15 g, 0.34 mmol) was dissolved in CH$_2$Cl$_2$ (10 mL). TFA (0.35 mL) was added and the mixture was stirred at ambient temperature for 5 h. An excess of TFA and CH$_2$Cl$_2$ was removed under reduced pressure and the residue was taken up in DMSO (6 mL). Potassium carbonate (1 g) was added, followed by addition of 2-chloro-5-ethylpyrimidine (63 μL, 0.50 mmol). The reaction mixture was degassed, purged with N$_2$ and heated at 100° C. overnight. The mixture was cooled to ambient temperature and poured into water and extracted with EtOAc. The combined organic extract was washed with water and brine, dried over Na$_2$SO$_4$, filtered, and the filtrate was concentrated to give the crude product as a light brown solid. The crude product was triturated with hot hexane containing 1% of MeOH to give 0.14 g (92%) of the title compound as a cream-white solid. $^1$H NMR (400 MHz, CDCl$_3$): δ 8.40 (d, 1H, J=2.7 Hz), 8.19 (bs, 2H), 8.13 (d, 2H, J=8.6 Hz), 8.00 (d, 2H, J=8.6 Hz), 7.73 (d, 1H, J=8.5 Hz), 7.35-7.25 (m, 1H), 4.90-4.75 (m, 2H), 3.94 (d, 2H, J=6.1 Hz), 3.08 (s, 3H), 3.00-2.90 (m, 2H), 2.55-2.40 (m, 2H), 2.25-2.10 (m, 1H), 2.00-1.90 (m, 2H), 1.50-1.30 (m, 2H), 1.19 (t, 3H, J=7.5 Hz); LRMS (APCI), m/z 453 (M+H).

Example 81

1-Methylethyl 4-({[6-(4-{[2-(methoxy)ethyl]sulfonyl}phenyl)-3-pyridinyl]oxy}methyl)-1-piperidinecarboxylate

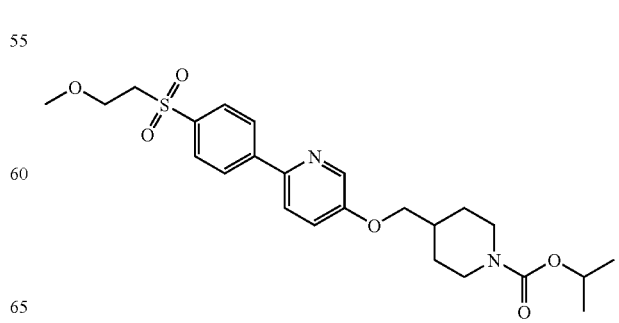

Step 1: 1-Methylethyl 4-{[(6-bromo-3-pyridinyl)oxy]methyl}-1-piperidinecarboxylate (0.71 g, 58%) was prepared as a light yellow solid from 2-bromo-5-hydroxypyridine (0.60 g, 3.45 mmol), 1-methylethyl 4-(hydroxymethyl)-1-piperidinecarboxylate (prepared as in Example 9, Step 1, 0.71 g, 3.45 mmol) and Ph$_3$P (0.92 g, 3.45 mmol) in THF (18 mL) followed by diisopropyl azodicarboxylate (0.75 g, 94%, 3.45 mmol) in THF (6 mL) in a manner similar to Example 1, Step 2. $^1$H NMR (400 MHz, CDCl$_3$): δ 8.04 (bs, 1H), 7.36 (d, 1H, J=8.8 Hz), 7.15-7.05 (m, 1H), 4.91 (septet, 1H, J=6.2 Hz), 4.30-4.10 (m, 2H), 3.82 (d, 2H, J=6.1 Hz), 2.85-2.70 (m, 2H), 2.05-1.90 (m, 1H), 1.90-1.75 (m, 2H), 1.35-1.15 (m, 8H); LRMS (ESI), m/z 357/359 (M+H).

Step 2: A mixture of 4-mercaptophenylboronic acid (1.0 g, 90%, 5.84 mmol), 1-bromo-2-methoxyethane (1.8 g, 13 mmol) and K$_2$CO$_3$ (2.70 g, 19.5 mmol) in CH$_3$CN (20 mL) was stirred at ambient temperature overnight. After CH$_3$CN was removed, water was added to the residue, and the solid was collected via filtration and washed with water to give 0.9 g of the crude (4-{[2-(methoxy)ethyl]thio}phenyl)boronic acid (75% pure by LC-MS). The crude boronic acid was used without further purification.

Step 3: 1-Methylethyl 4-({[6-(4-{[2-(methoxy)ethyl]thio}phenyl)-3-pyridinyl]oxy}methyl)-1-piperidinecarboxylate (0.19 g, 61%) was prepared as a light yellow solid from (4-{[2-(methoxy)ethyl]thio}phenyl)boronic acid (0.23 g, 75% pure, 0.80 mmol), 1-methylethyl 4-{[(6-bromo-3-pyridinyl)oxy]methyl}-1-piperidinecarboxylate (from Step 1, 0.25 g, 0.70 mmol), 2M Na$_2$CO$_3$ (2 mL) and PdCl$_2$(PPh$_3$)$_2$ (50 mg, 0.07 mmol) in DME (3 mL) in a manner similar to Example 21, Step 3. $^1$H NMR (400 MHz, CDCl$_3$): δ 8.34 (d, 1H, J=2.7 Hz), 7.86 (d, 2H, J=8.3 Hz), 7.64 (d, 1H, J=8.7 Hz), 7.42 (d, 2H, J=8.3 Hz), 7.30-7.25 (m, 1H), 4.92 (septet, 1H, J=6.2 Hz), 4.23 (bs, 2H), 3.89 (d, 2H, J=6.3 Hz), 3.59 (t, 2H, J=6.7 Hz), 3.37 (s, 3H), 3.15 (t, 2H, J=6.8 Hz), 2.95-2.80 (m, 2H), 2.10-1.95 (m, 1H), 1.90-1.80 (m, 2H), 1.35-1.20 (m, 8H); LRMS (ESI), m/z 445 (M+H).

Step 4: A solution of 1-methylethyl 4-({[6-(4-{[2-(methyloxy)ethyl]thio}phenyl)-3-pyridinyl]oxy}methyl)-1-piperidinecarboxylate (0.19 g, 0.43 mmol) in acetone (12 mL) and water (5 mL) was treated with Oxone® (0.79 g, 1.28 mmol). The reaction mixture was stirred at ambient temperature for 4 h. After more water was added, the mixture was extracted with EtOAc. The organic extracts were combined and washed with water and brine, dried over Na$_2$SO$_4$, filtered, and the filtrate was concentrated to give the crude product as a white solid. The crude product was triturated with hot hexane containing 1% of MeOH and 1% of CH$_2$Cl$_2$ to give 0.163 g (80%) of the title compound as a white solid. $^1$H NMR (400 MHz, CDCl$_3$): δ 8.40 (d, 1H, J=2.7 Hz), 8.12 (d, 2H, J=8.6 Hz), 7.98 (d, 2H, J=8.6 Hz), 7.74 (d, 1H, J=8.8 Hz), 7.30-7.25 (m, 1H), 4.92 (septet, 1H, J=6.2 Hz), 4.23 (bs, 2H), 3.92 (d, 2H, J=6.1 Hz), 3.75 (t, 2H, J=6.4 Hz), 3.41 (t, 2H, J=6.2 Hz), 3.24 (s, 3H), 2.85-2.70 (m, 2H), 2.10-1.95 (m, 1H), 1.90-1.80 (m, 2H), 1.35-1.20 (m, 8H); LRMS (ESI), m/z 477 (M+H).

Example 82

1-Methylethyl 4-{[(6-{4-[(2-hydroxyethyl)sulfonyl]phenyl}-3-pyridinyl)oxy]methyl}-1-piperidinecarboxylate

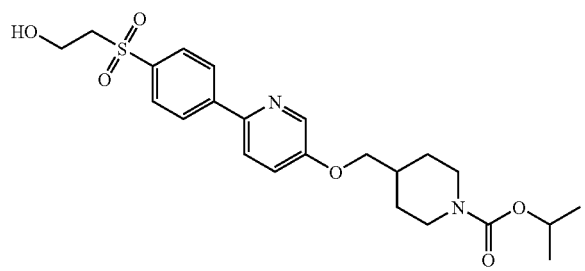

A solution of 1-methylethyl 4-({[6-(4-{[2-(methoxy)ethyl]sulfonyl}phenyl)-3-pyridinyl]oxy}methyl)-1-piperidinecarboxylate (Example 81, 0.13 g, 0.27 mmol) in CH$_2$Cl$_2$ (10 mL) was treated with BBr$_3$ (1.0M in CH$_2$Cl$_2$, 1.64 mL, 1.64 mmol) at −78° C. The reaction mixture was allowed to warm up to 10° C., and poured onto ice and aqueous NaHCO$_3$. The mixture was extracted with EtOAc. The organic extracts were combined and washed with brine, dried over Na$_2$SO$_4$, filtered, and the filtrate was concentrated to give the crude product as a brown solid. The crude product was purified by chromatography on a silica gel column eluted with 2:4:0.1 EtOAc/CH$_2$Cl$_2$/MeOH to give 66 mg (53%) of the title compound as an off-white solid. $^1$H NMR (400 MHz, CD$_3$OD): δ 8.36 (d, 1H, J=2.9 Hz), 8.17 (d, 2H, J=8.5 Hz), 8.00 (d, 2H, J=8.3 Hz), 7.92 (d, 1H, J=8.8 Hz), 7.49 (dd, 1H, J$_a$=8.8 Hz, J$_b$=2.9 Hz), 4.90-4.80 (m, 1H), 4.25-4.10 (m, 2H), 3.99 (d, 2H, J=6.1 Hz), 3.88 (t, 2H, J=6.2 Hz), 3.42 (t, 2H, J=6.2 Hz), 2.95-2.75 (m, 2H), 2.15-2.00 (m, 1H), 1.95-1.80 (m, 2H), 1.35-1.20 (m, 8H); LRMS (ESI), m/z 463 (M+H).

Example 83

2-[2-Fluoro-4-(methylsulfonyl)phenyl]-5-[({1-[3-(1-methylethyl)-1,2,4-oxadiazol-5-yl]-4-piperidinyl}methyl)oxy]pyridine

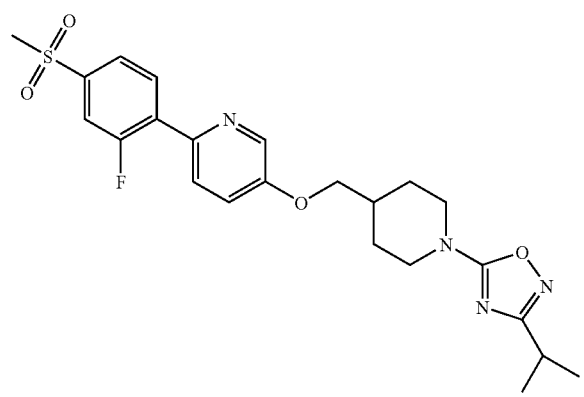

Step 1: A mixture of Pd(PPh$_3$)$_2$Cl$_2$ (0.42 g, 0.57 mmol) and 2-bromo-5-hydroxypyridine (1.0 g, 5.75 mmol) in DME (20 mL) was degassed with N$_2$. 2M Na$_2$CO$_3$ (10 mL) was added, and the mixture was stirred at ambient temperature for 10 minutes. 4-Bromo-2-fluorobenzeneboronic acid (1.48 g, 6.61 mmol) was added. The reaction mixture was degassed again, purged with N$_2$ and heated at 80° C. overnight, then cooled to ambient temperature, and partitioned between water and EtOAc. Concentrated HCl was added carefully to adjust aqueous pH to about 8, the mixture was filtered thought Celite®, and the EtOAc layer was separated and washed with brine, dried over Na$_2$SO$_4$, filtered, and the filtrate was concentrated to give the crude product as a dark brown oil. The crude product was purified by chromatography on a silica gel column eluted with 20% EtOAc/hexane to give 0.168 g of 6-(4-bromo-2-fluorophenyl)-3-pyridinol as an off-white solid. The impure fractions were combined, concentrated and further purified with 1:5 acetone/hexane to give additional 78 mg of 6-(4-bromo-2-fluorophenyl)-3-pyridinol (0.246 g overall, 16% yield). $^1$H NMR (400 MHz, CD$_3$OD): δ 8.20 (d, 1H, J=2.7 Hz), 7.75-7.65 (m, 1H), 7.62 (dd, 1H, J$_a$=8.7 Hz, J$_b$=2.1 Hz), 7.50-7.40 (m, 2H), 7.28 (dd, 1H, J$_a$=8.5 Hz, J$_b$=2.9 Hz); LRMS (ESI), m/z 268/270 (M+H).

Step 2: A mixture of 6-(4-bromo-2-fluorophenyl)-3-pyridinol (0.245 g, 0.91 mmol), methanesulfinic acid sodium salt (0.47 g, 80%, 3.66 mmol), CuI (0.70 g, 3.66 mmol) and NaOH (44 mg, 1.10 mmol) in DMSO (20 mL) was degassed with N$_2$ three times and heated at 120° C. overnight. After the mixture was cooled to ambient temperature, 1N HCl was added to adjust the aqueous pH to about 8. The mixture was extracted with EtOAc. The combined organic extract was washed with water and brine, dried over Na$_2$SO$_4$, filtered, and the filtrate was concentrated to give the crude product as a light brown viscous oil. The crude product was purified by chromatography on a silica gel column eluted with 2:4:0.1 EtOAc/CH$_2$Cl$_2$/MeOH to give 0.166 g (68%) of 6-[2-fluoro-4-(methylsulfonyl)phenyl]-3-pyridinol as a white solid. $^1$H NMR (400 MHz, CD$_3$OD): δ 8.26 (d, 1H, J=2.7 Hz), 8.15-8.05 (m, 1H), 7.90-7.75 (m, 2H), 7.74 (dd, 1H, J$_a$=8.6 Hz, J$_b$=2.1 Hz), 7.32 (dd, 1H, J$_a$=8.6 Hz, J$_b$=2.8 Hz), 3.18 (s, 3H); LRMS (ESI), m/z 268 (M+H).

Step 3: The title compound (54 mg, 38%) was prepared as a white solid from 6-[2-fluoro-4-(methylsulfonyl)phenyl]-3-pyridinol (80 mg, 0.30 mmol), 1-[3-(1-methylethyl)-1,2,4-oxadiazol-5-yl]-4-piperidinyl}methanol (prepared as in Example 20, Steps 1-3, 71 mg, 0.30 mmol) and Ph$_3$P (80 mg, 0.30 mmol) in THF (3 mL) followed by diisopropyl azodicarboxylate (65 mg, 94%, 0.30 mmol) in THF (1 mL) in a manner similar to Example 1, Step 2. $^1$H NMR (400 MHz, CD$_3$OD): δ 8.40 (d, 1H, J=2.9 Hz), 8.15-8.10 (m, 1H), 7.90-7.75 (m, 3H), 7.51 (dd, 1H, J$_a$=8.8 Hz, J$_b$=2.9 Hz), 4.20-4.10 (m, 2H), 4.04 (d, 2H, J=6.4 Hz), 3.25-3.10 (m, 5H), 2.85 (septet, 1H, J=6.9 Hz), 2.25-2.10 (m, 1H), 2.05-1.95 (m, 2H), 1.55-1.40 (m, 2H), 1.26 (d, 6H, J=6.9 Hz); LRMS (ESI), m/z 475 (M+H).

Example 84

1-Methylethyl 4-{[(6-{4-[(2-amino-2-oxoethyl)sulfonyl]phenyl}-3-pyridinyl)oxy]methyl}-1-piperidinecarboxylate

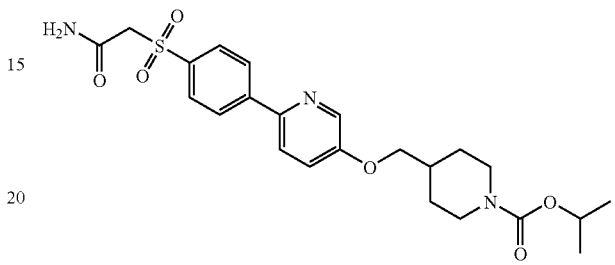

Step 1: A mixture of 4-mercaptophenylboronic acid (1.0 g, 90%, 5.84 mmol), 2-bromoacetamide (1.8 g, 13 mmol) and K$_2$CO$_3$ (2.70 g, 19.5 mmol) in CH$_3$CN (20 mL) was stirred at ambient temperature overnight. After CH$_3$CN was removed, water was added to the residue, and the solid was collected via filtration and washed with water to give 0.6 g (49%) of {4-[(2-amino-2-oxoethyl)thio]phenyl}boronic acid as a white solid. The boronic acid was used without further purification. $^1$H NMR (400 MHz, DMSO-d$_6$): δ 8.00 (s, 2H), 7.68 (d, 2H, J=8.2 Hz), 7.55 (bs, 1H), 7.24 (d, 2H, J=8.2 Hz), 7.15 (bs, 1H), 3.61 (s, 2H); LRMS (APCI), m/z 210 (M−H).

Step 2: 1-Methylethyl 4-{[(6-{4-[(2-amino-2-oxoethyl)thio]phenyl}-3-pyridinyl)oxy]methyl}-1-piperidinecarboxylate (0.139 g, 75%) was prepared as a light yellow solid from {4-[(2-amino-2-oxoethyl)thio]phenyl}boronic acid (0.11 g, 0.50 mmol), 1-methylethyl 4-{[(6-bromo-3-pyridinyl)oxy]methyl}-1-piperidinecarboxylate (Example 81, Step 1, 0.15 g, 0.42 mmol), 2M Na$_2$CO$_3$ (2 mL), Pd(PPh$_3$)$_2$Cl$_2$ (30 mg, 0.04 mmol) and DME (2 mL) in a manner similar to Example 21, Step 3. $^1$H NMR (400 MHz, CDCl$_3$): δ 8.36 (d, 1H, J=2.5 Hz), 7.90 (d, 2H, J=8.2 Hz), 7.65 (d, 1H, J=8.8 Hz), 7.38 (d, 2H, J=8.2 Hz), 7.35-7.25 (m, 1H), 6.65 (bs, 1H), 5.41 (bs, 1H), 4.92 (septet, 1H, J=6.2 Hz), 4.23 (bs, 2H), 3.90 (d, 2H, J=6.3 Hz), 3.67 (s, 2H), 2.85-2.70 (m, 2H), 2.10-1.95 (m, 1H), 1.90-1.80 (m, 2H), 1.35-1.20 (m, 8H); LRMS (ESI), m/z 444 (M+H).

Step 3: The title compound (67 mg, 51%) was prepared as a white solid from 1-methylethyl 4-{[(6-{4-[(2-amino-2-oxoethyl)thio]phenyl}-3-pyridinyl)oxy]methyl}-1-piperidinecarboxylate (0.123 g, 0.28 mmol) and Oxone® (0.52 g, 0.83 mmol) in acetone (7 mL), MeOH (15 mL) and water (4 mL) in a manner similar to Example 81, Step 4, except that MeOH was added. The crude product was loaded onto a silica gel column. After washing with 50% EtOAc/CH$_2$Cl$_2$, 2:5 acetone/CH$_2$Cl$_2$ and 1:1:0.1 EtOAc/CH$_2$Cl$_2$/MeOH, the silica gel was transferred into a beaker, stirred with a solution of 1:1:0.1 EtOAc/CH$_2$Cl$_2$/MeOH (300 mL). The silica gel was filtered off, and the filtrate was concentrated to an off-white solid, which was triturated with hot hexane containing 1% of MeOH to give the title compound as a white solid. $^1$H NMR (400 MHz, CDCl$_3$): δ 8.40 (d, 1H, J=2.6 Hz), 8.16 (d, 2H, J=8.3 Hz), 7.99 (d, 2H, J=8.5 Hz), 7.74 (d, 1H, J=8.8 Hz), 7.30-7.25 (m, 1H), 6.76 (bs, 1H), 5.57 (bs, 1H), 4.92 (septet, 1H, J=6.2 Hz), 4.23 (bs, 2H), 4.04 (s, 2H), 3.92 (d, 2H, J=6.4 Hz), 2.85-2.70 (m, 2H), 2.10-1.95 (m, 1H), 1.90-1.80 (m, 2H), 1.35-1.20 (m, 8H); LRMS (ESI), m/z 476 (M+H).

Example 85

1,1-Dimethylethyl 4-({[6-(4-{[3-(methoxy)propyl]sulfonyl}phenyl)-3-pyridinyl]oxy}methyl)-1-piperidinecarboxylate

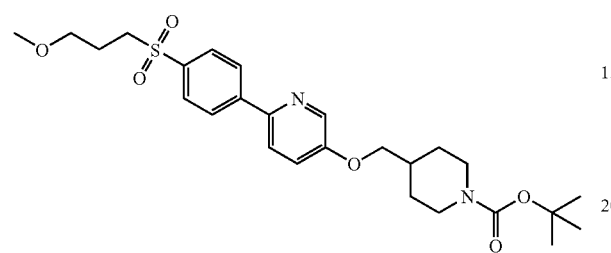

Step 1: A mixture of 4-mercaptophenylboronic acid (1.0 g, 90%, 5.84 mmol), 1-bromo-3-methoxypropane (1.83 g, 11.7 mmol), K$_2$CO$_3$ (2.45 g, 17.5 mmol) and catalytic amount of NaI in CH$_3$CN (20 mL) was stirred at ambient temperature overnight. After CH$_3$CN was removed, water was added to the residue, and the mixture was extracted with CH$_2$Cl$_2$. The combined organic extract was washed with brine, dried over Na$_2$SO$_4$, filtered, and the filtrate was concentrated to give a milky oil. Water was added to this oily residue, and the aqueous layer was acidified to pH about 2 with concentrated HCl. The mixture was let stand at ambient temperature overnight, and the off-white solid was collected via filtration and washed with water and hexane to give 1.07 g (81%) of (4-{[3-(methoxy)propyl]thio}phenyl)boronic acid as an off-white solid. $^1$H NMR (400 MHz, DMSO-d$_6$): δ 7.98 (s, 2H), 7.68 (d, 2H, J=8.0 Hz), 7.22 (d, 2H, J=8.1 Hz), 3.38 (t, 2H, J=6.1 Hz), 3.19 (s, 3H), 2.98 (t, 2H, J=7.2 Hz), 1.85-1.70 (m, 2H); LRMS (ESI), m/z 225 (M−H).

Step 2: 1,1-Dimethylethyl 4-({[6-(4-{[3-(methoxy)propyl]thio}phenyl)-3-pyridinyl]oxy}methyl)-1-piperidinecarboxylate (0.384 g, 86%) was prepared as a yellow solid from (4-{[3-(methoxy)propyl]thio}phenyl)boronic acid (0.27 g, 1.13 mmol), 1,1-dimethylethyl 4-{[[(6-bromo-3-pyridinyl)oxy]methyl}-1-piperidinecarboxylate (prepared as in Example 76, Step 1, 0.35 g, 0.94 mmol), 2M Na$_2$CO$_3$ (5 mL) and PdCl$_2$(PPh$_3$)$_2$ (68 mg, 0.09 mmol) in DME (6 mL) in a manner similar to Example 21, Step 3. $^1$H NMR (400 MHz, CDCl$_3$): δ 8.34 (d, 1H, J=2.2 Hz), 7.84 (d, 2H, J=8.3 Hz), 7.63 (d, 1H, J=8.8 Hz), 7.39 (d, 2H, J=8.3 Hz), 7.25-7.20 (m, 1H), 4.17 (bs, 2H), 3.88 (d, 2H, J=6.3 Hz), 3.48 (t, 2H, J=6.0 Hz), 3.32 (s, 3H), 3.04 (t, 2H, J=7.2 Hz), 2.85-2.70 (m, 2H), 2.05-1.80 (m, 5H), 1.46 (s, 9H), 1.35-1.20 (m, 2H); LRMS (ESI), m/z 473 (M+H).

Step 3: The title compound (0.347 g, 85%) was prepared as a white solid from 1,1-dimethylethyl 4-({[6-(4-{[3-(methoxy)propyl]thio}phenyl)-3-pyridinyl]oxy}methyl)-1-piperidinecarboxylate (0.382 g, 0.81 mmol) and Oxone® (1.49 g, 2.43 mmol) in acetone (25 mL) and water (10 mL) in a manner similar to Example 81, Step 4. $^1$H NMR (400 MHz, CDCl$_3$): δ 8.40 (d, 1H, J=2.7 Hz), 8.12 (d, 2H, J=8.3 Hz), 7.96 (d, 2H, J=8.3 Hz), 7.73 (d, 1H, J=8.5 Hz), 7.29 (dd, 1H, J$_a$=8.7 Hz, J$_b$=2.8 Hz), 4.18 (bs, 2H), 3.91 (d, 2H, J=6.4 Hz), 3.42 (t, 2H, J=5.9 Hz), 3.26 (s, 3H), 3.25-3.20 (m, 2H), 2.85-2.70 (m, 2H), 2.10-1.95 (m, 3H), 1.90-1.80 (m, 2H), 1.46 (s, 9H), 1.35-1.20 (m, 2H); LRMS (ESI), m/z 505 (M+H).

Example 86

5-({[1-(2-Furanylcarbonyl)-4-piperidinyl]methyl}oxy)-2-[4-(methylsulfonyl)phenyl]pyridine trifluoroacetate

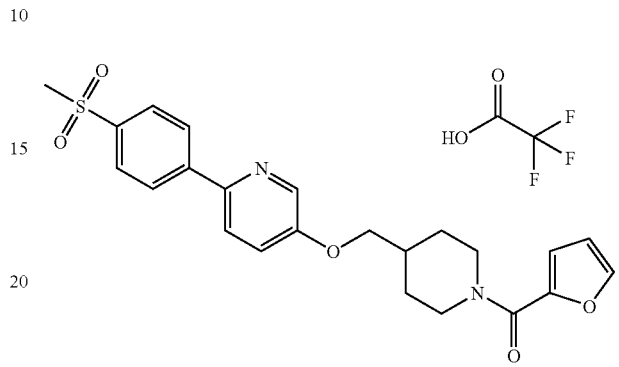

Step 1: 1,1-Dimethylethyl 4-[({6-[4-(methylsulfonyl)phenyl]-3-pyridinyl}oxy)methyl]-1-piperidinecarboxylate (6.87 g, 88%) was prepared as a gray solid from 1,1-dimethylethyl 4-{[(6-chloro-3-pyridinyl)oxy]methyl}-1-piperidinecarboxylate (prepared as in Example 73, Step 1, 5.73 g, 17.5 mmol), [4-(methylsulfonyl)phenyl]boronic acid (3.85 g, 17.53 mmol), Pd(PPh$_3$)$_4$ (10.13 g, 8.76 mmol), 2M Na$_2$CO$_3$ (26 mL) in DME (170 mL) in a manner similar to Example 1, Step 1. $^1$H NMR (400 MHz, CDCl$_3$): δ 8.40 (d, 1H, J=2.9 Hz), 8.15-8.12 (m, 2H), 8.02-7.99 (m, 2H), 7.73 (d, 1H, J=8.7 Hz), 7.28 (dd, 1H, J$_a$=8.7 Hz, J$_b$=3.0 Hz), 4.19 (bs, 2H), 3.91 (d, 2H, J=6.4 Hz), 3.08 (s, 3H), 2.81-2.71 (m, 2H), 2.07-1.96 (m, 1H), 1.87-1.82 (m, 2H), 1.47 (s, 9H), 1.36-1.24 (m, 2H); LRMS (APCI), m/z 447 (M+H).

Step 2: A solution of 1,1-dimethylethyl 4-[({6-[4-(methylsulfonyl)phenyl]-3-pyridinyl}oxy)methyl]-1-piperidinecarboxylate (5.47 g, 12.25 mmol) in 1,4-dioxane (70 mL) was treated with 4.0M HCl in 1,4-dioxane (30 mL, 122 mmol). The reaction mixture was stirred at ambient temperature for 16 h. Diethyl ether was added to the reaction mixture and the resulting solid was collected by filtration. The crude product was then dissolved in methanol and filtered. The filtrate was concentrated to give 4.36 g (85%) of 2-[4-(methylsulfonyl)phenyl]-5-[(4-piperidinylmethyl)oxy]pyridine dihydrochloride as a white solid. $^1$H NMR (400 MHz, CD$_3$OD): δ 8.62 (d, 1H, J=2.7 Hz), 8.31 (d, 1H, J=2.7 Hz), 8.23-8.12 (m, 5H), 4.22 (d, 2H, J=6.1 Hz), 3.51-3.46 (m, 2H), 3.20 (s, 3H), 3.13-3.05 (m, 2H), 2.34-2.23 (m, 1H), 2.16-2.10 (m, 2H), 1.75-1.64 (m, 2H); LRMS (APCI), m/z 347 (M+H).

Step 3: 2-[4-(Methylsulfonyl)phenyl]-5-[(4-piperidinylmethyl)oxy]pyridine dihydrochloride (0.035 g, 0.08 mmol) and triethylamine (0.04 mL, 0.25 mmol) in CHCl$_3$ (1.5 mL) was added to 2-furoyl chloride (0.013 g, 0.1 mmol). The resulting suspension was heated at 40° C. for 16 h and concentrated to dryness. The crude product was purified by reverse-phase preparative HPLC using a CH$_3$CN:H$_2$O gradient (10:90 to 100:0) with 0.1% TFA as a modifier to give 22 mg (60%) of the title compound as a white solid. LRMS (APCI), m/z 441 (M+H).

Example 87

2-[4-(Methylsulfonyl)phenyl]-5-({[1-(2-thienylcarbonyl)-4-piperidinyl]methyl}oxy)pyridine trifluoroacetate

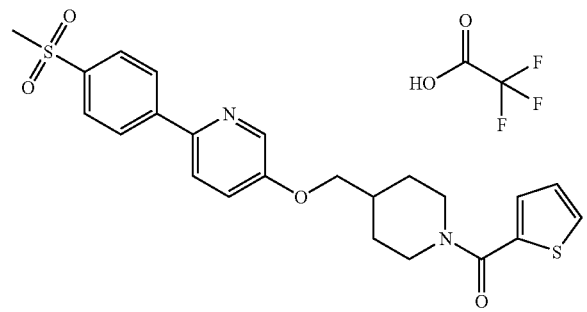

The title compound (27 mg, 57%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), 2-thiophenecarbonyl chloride (0.015 g, 0.1 mmol) and triethylamine (0.04 mL, 0.25 mmol) in CHCl$_3$ (1.5 mL) in a manner similar to Example 86, Step 3. LRMS (APCI), m/z 457 (M+H).

Example 88

5-({[1-(Cyclobutylcarbonyl)-4-piperidinyl]methyl}oxy)-2-[4-(methylsulfonyl)phenyl]pyridine trifluoroacetate

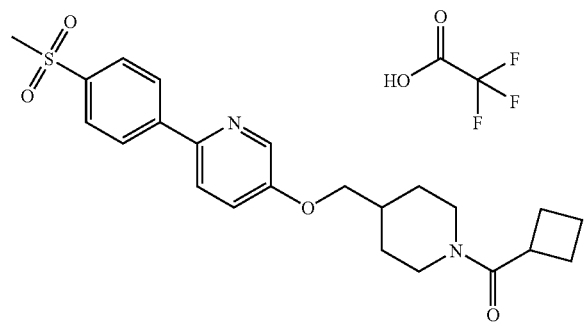

The title compound (25 mg, 55%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), cyclobutanecarbonyl chloride (0.011 g, 0.1 mmol) and triethylamine (0.04 mL, 0.25 mmol) in CHCl$_3$ (1.5 mL) in a manner similar to Example 86, Step 3. LRMS (APCI), m/z 429 (M+H).

Example 89

5-({[1-(3-Methyl-2-butenoyl)-4-piperidinyl]methyl}oxy)-2-[4-(methylsulfonyl)phenyl]pyridine trifluoroacetate

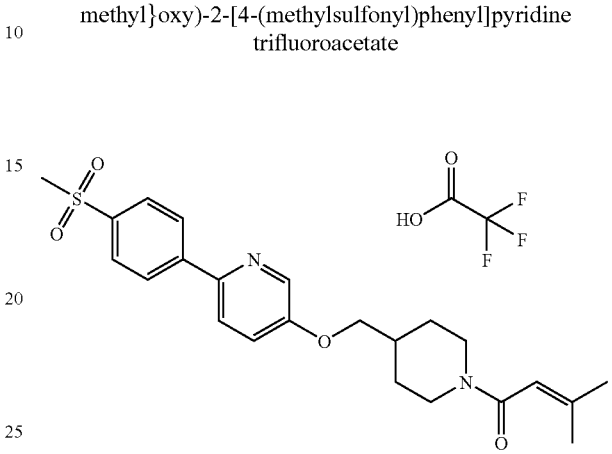

The title compound (19 mg, 42%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), 3,3-dimethylacryl chloride (0.011 g, 0.1 mmol) and triethylamine (0.04 mL, 0.25 mmol) in CHCl$_3$ (1.5 mL) in a manner similar to Example 86, Step 3. LRMS (APCI), m/z 429 (M+H).

Example 90

5-({[1-(2,2-Dimethylbutanoyl)-4-piperidinyl]methyl}oxy)-2-[4-(methylsulfonyl)phenyl]pyridine trifluoroacetate

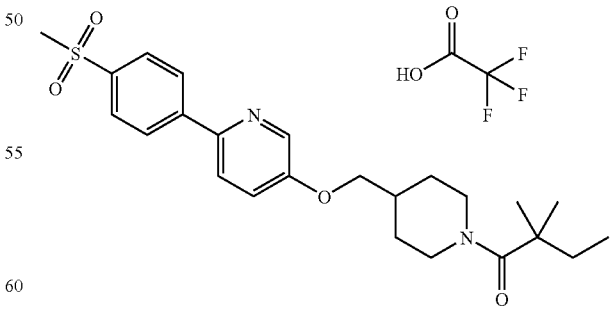

The title compound (19 mg, 41%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), 2,2-dimethylbutyryl chloride (0.014 g, 0.1 mmol) and triethylamine (0.04 mL, 0.25 mmol) in CHCl₃ (1.5 mL) in a manner similar to Example 86, Step 3. LRMS (APCI), m/z 445 (M+H).

Example 91

N,N-Diethyl-4-[({6-[4-(methylsulfonyl)phenyl]-3-pyridinyl}oxy)methyl]-1-piperidinecarboxamide trifluoroacetate

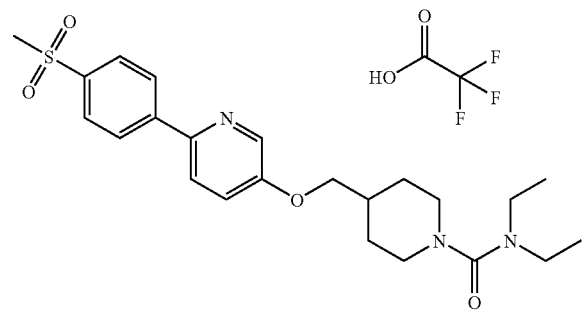

The title compound (9 mg, 19%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), diethylcarbamyl chloride (0.014 g, 0.1 mmol) and triethylamine (0.04 mL, 0.25 mmol) in CHCl₃ (1.5 mL) in a manner similar to Example 86, Step 3. LRMS (APCI), m/z 446 (M+H).

Example 92

5-({[1-(3,3-Dimethylbutanoyl)-4-piperidinyl]methyl}oxy)-2-[4-(methylsulfonyl)phenyl]pyridine trifluoroacetate

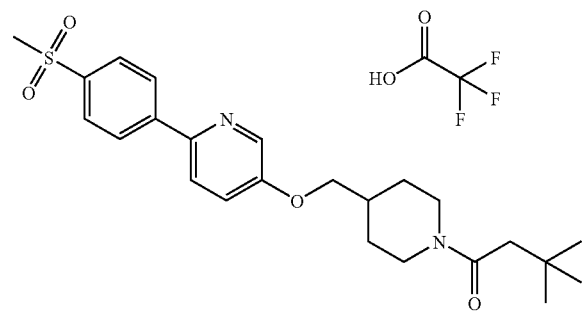

The title compound (3 mg, 6%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), t-butylacetyl chloride (0.014 g, 0.1 mmol) and triethylamine (0.04 mL, 0.25 mmol) in CHCl₃ (1.5 mL) in a manner similar to Example 86, Step 3. LRMS (APCI), m/z 445 (M+H).

Example 93

5-[({1-[(1,3-Dimethyl-1H-pyrazol-5-yl)carbonyl]-4-piperidinyl}methyl)oxy]-2-[4-(methylsulfonyl)phenyl]pyridine trifluoroacetate

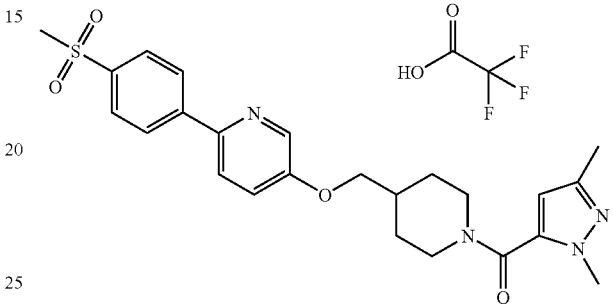

The title compound (15 mg, 31%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), 1,3-dimethylpyrazole-5-carbonyl chloride (0.016 g, 0.1 mmol) and triethylamine (0.04 mL, 0.25 mmol) in CHCl₃ (1.5 mL) in a manner similar to Example 86, Step 3. LRMS (APCI), m/z 469 (M+H).

Example 94

5-[({1-[(2,5-Dimethyl-3-furanyl)carbonyl]-4-piperidinyl}methyl)oxy]-2-[4-(methylsulfonyl)phenyl]pyridine trifluoroacetate

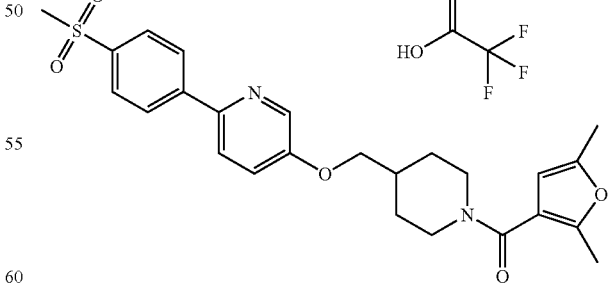

The title compound (12 mg, 25%) was prepared as a white solid from 2-[4-(methylsulfonyl)phenyl]-5-[(4-piperidinylmethyl)oxy]pyridine dihydrochloride (Example 86, Step 2, 0.035 g, 0.1 mmol), 2,5-dimethyl-3-furoyl chloride (0.014 g, 0.1 mmol) and triethylamine (0.04 mL, 0.25 mmol) in CHCl₃ (1.5 mL) in a manner similar to Example 86, Step 3. LRMS (APCI), m/z 469 (M+H).

Example 95

5-({[1-(5-Isoxazolylcarbonyl)-4-piperidinyl] methyl}oxy)-2-[4-(methylsulfonyl)phenyl]pyridine trifluoroacetate

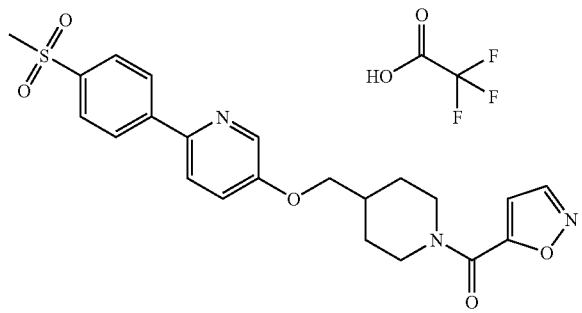

Triethylamine (0.04 mL, 0.25 mmol) was added to a solution of 2-[4-(methylsulfonyl)phenyl]-5-[(4-piperidinylmethyl)oxy]pyridine dihydrochloride (Example 86, Step 2, 0.035 g, 0.1 mmol) in CHCl₃ (1.0 mL), and stirred at ambient temperature for 10 minutes. Isoxazole-5-carbonyl chloride (0.013 g, 0.1 mmol) was added to the reaction mixture and stirred at ambient temperature for 16 h, then concentrated under reduced pressure. The crude product was purified by reverse-phase preparative HPLC using a CH₃CN:H₂O gradient (10:90 to 100:0) with 0.1% TFA as a modifier to give 8 mg (17%) of the title compound as a white solid. ¹H NMR (400 MHz, CDCl₃): δ 8.40 (d, 1H, J=2.7 Hz), 8.31 (d, 1H, J=1.5 Hz), 8.13 (d, 2H, J=8.3 Hz), 8.00 (d, 2H, J=8.3 Hz), 7.73 (d, 1H, J=8.8 Hz), 7.30-7.27 (m, 1H), 6.76 (s, 1H), 4.78-4.74 (m, 1H), 4.26-4.22 (m, 1H), 3.95 (d, 2H, J=4.9 Hz), 3.24-3.18 (m, 1H), 3.07 (s, 3H), 2.91-2.83 (m, 1H), 2.26-2.14 (m, 1H), 2.04-1.97 (m, 2H), 1.56-1.43 (m, 2H); LRMS (APCI), m/z 442 (M+H).

Example 96

1-Methylethyl 4-[({6-[4-(1-pyrrolidinylcarbonyl) phenyl]-3-pyridinyl}oxy)methyl]-1-piperidinecarboxylate

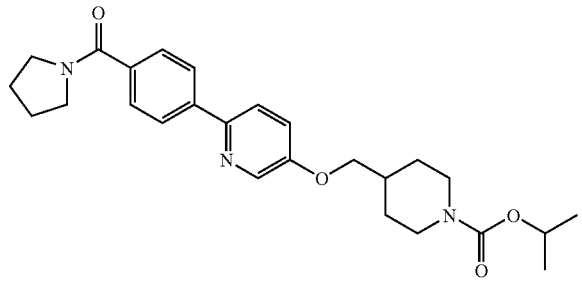

Step 1: 1-Methylethyl-4-{[(6-{4-[(ethyloxy)carbonyl] phenyl}-3-pyridinyl)oxy]methyl}-1-piperidinecarboxylate was prepared as an off-white solid from 1-methylethyl 4-{[(6-bromo-3-pyridinyl)oxy]methyl}-1-piperidinecarboxylate (prepared as in Example 81, Step 1, 0.13 g, 0.67 mmol), {4-[(ethyloxy)carbonyl]phenyl}boronic acid (0.30 g, 0.84 mmol), 2M Na₂CO₃ (10 mL) and Pd(PPh₃)₄ (0.01 g, 0.01 mmol) in DME (10 mL) in a manner similar to Example 1, Step 1. ¹H NMR (400 MHz, CDCl₃): δ 8.39 (d, 1H, J=2.7 Hz), 8.11 (d, 2H, J=8.6 Hz), 7.98 (d, 2H, J=8.6 Hz), 7.72 (d, 1H, J=8.8 Hz), 7.31-7.26 (m, 1H), 4.94-4.87 (m, 1H), 4.38 (q, 2H, J=7.1 Hz), 4.28-4.16 (m, 2H), 3.89 (d, 2H, J=6.4 Hz), 2.82-2.72 (m, 2H), 2.06-1.94 (m, 1H), 1.87-1.80 (m, 4H), 1.39 (t, 3H, J=7.1 Hz), 1.23 (d, 6H, J=6.4 Hz); LRMS (ESI), m/z 427 (M+H).

Step 2: 1-Methylethyl-4-{[(6-{4-[(ethyloxy)carbonyl] phenyl}-3-pyridinyl)oxy]methyl}-1-piperidinecarboxylate (0.3 g, 0.70 mmol) was added to a solution of NaOH (0.06 g, 1.4 mmol) in ethanol (10 mL). The reaction mixture was stirred overnight, neutralized with 1N HCl and freeze-dried to give 4-(5-{[(1-{[(1-methylethyl)oxy]carbonyl}-4-piperidinyl)methyl]oxy}-2-pyridinyl)benzoic acid, which was used without further purification. ¹H NMR (400 MHz, DMSO-d₆): δ 8.38 (d, 1H, J=3.0 Hz), 8.12 (d, 2H, J=8.7 Hz), 8.01-7.97 (m, 3H), 7.53-7.49 (m, 1H), 4.77-4.71 (m, 1H), 4.04-3.94 (m, 4H), 2.07 (bs, 3H), 1.80-1.72 (m, 2H), 1.19-1.13 (m, 8H); LRMS (ESI), m/z 399 (M+H).

Step 3: 4-(5-{[(1-{[(1-Methylethyl)oxy]carbonyl}-4-piperidinyl)methyl]oxy}-2-pyridinyl)benzoic acid (0.05 g, 0.13 mmol) was added to a solution of pyrrolidine (0.01 g, 0.13 mmol) in DMF (2 mL), followed by addition of HATU (0.05 g, 0.13 mmol), and diisopropylethylamine (0.02 g, 0.13 mmol). The reaction mixture was stirred at room temperature for 10 minutes. The reaction was then purified by reverse-phase preparative HPLC using CH₃CN:H₂O gradient (0:100 to 90:10) with 0.05% TFA as a modifier. The resultant lyophilized material was converted to its free base by dissolving the solid in CH₂Cl₂, washing with saturated aqueous NaHCO₃ and concentrating in vacuo to give the title compound (15 mg, 25%) as a white solid. ¹H NMR (400 MHz, CDCl₃): δ 8.44 (d, 1H, J=2.9 Hz), 7.93 (d, 2H, J=8.4 Hz), 7.65 (d, 1H, J=8.6 Hz), 7.68 (d, 2H, J=8.4 Hz), 7.27-7.20 (m, 1H), 4.95-4.85 (m, 1H), 4.29-4.12 (m, 2H), 3.87 (d, 2H, J=6.4 Hz), 3.68-3.59 (m, 2H), 3.47-3.41 (m, 2 H), 2.78-2.72 (m, 2H), 2.04-1.78 (m, 7H), 1.34-1.28 (m, 2H), 1.22 (d, 6H, J=6.2 Hz); LRMS (ESI), m/z 452 (M+H).

Example 97

1-Methylethyl 4-[({6-[4-(4-morpholinylcarbonyl) phenyl]-3-pyridinyl}oxy)methyl]-1-piperidinecarboxylate trifluoroacetate

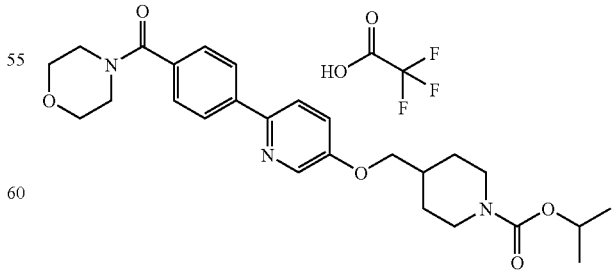

The title compound (5 mg, 6%) was prepared as a clear film from 4-(5-{[(1-{[(1-methylethyl)oxy]carbonyl}-4-piperidinyl)methyl]oxy}-2-pyridinyl)benzoic acid (Example 96, Step 2, 0.05 g, 0.13 mmol), morpholine (0.01 g, 0.13 mmol), HATU (0.05 g, 0.13 mmol), diisopropylethylamine (0.02 g, 0.13 mmol) in DMF (2 mL) in a manner similar to Example 96, Step 3, except that no free base step was used $^1$H NMR (400 MHz, CDCl$_3$): δ 8.66 (d, 1H, J=2.4 Hz), 7.89-7.78 (m, 4H), 7.58 (d, 2H, J=8.2 Hz), 4.97-4.87 (m, 1H), 4.28-4.18 (m, 2H), 4.02 (d, 2H, J=6.0 Hz), 3.85-3.61 (m, 6H), 3.52-3.39 (m, 2H), 2.85-2.71 (m, 2H), 2.11-2.00 (m, 1H), 1.87-1.80 (m, 2H), 1.39-1.26 (m, 2H), 1.24 (d, 6H, J=6.2 Hz); LRMS (ESI), m/z 468 (M+H).

Example 98

1-Methylethyl 4-({[6-(4-{[(2-hydroxyethyl)amino] carbonyl}phenyl)-3-pyridinyl]oxy}methyl)-1-piperidinecarboxylate trifluoroacetate

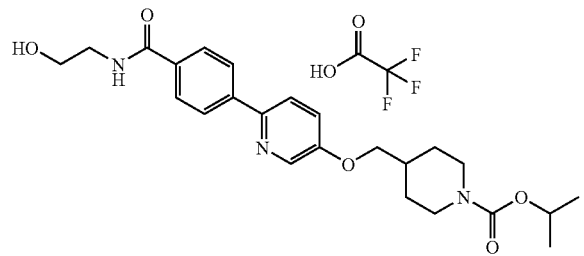

The title compound (5 mg, 7%) was prepared as a clear film from 4-(5-{[(1-{[(1-methylethyl)oxy]carbonyl}-4-piperidinyl)methyl]oxy}-2-pyridinyl)benzoic acid (Example 96, Step 2, 0.05 g, 0.13 mmol), 2-aminoethanol (0.01 g, 0.13 mmol), HATU (0.05 g, 0.13 mmol), diisopropylethylamine (0.02 g, 0.13 mmol) in DMF (2 mL) in a manner similar to Example 96, Step 3, except that no free base step was used. $^1$H NMR (400 MHz, CDCl$_3$): δ 8.61 (d, 1H, J=2.2 Hz), 7.91-7.78 (m, 5H), 7.67-7.60 (m, 1H), 7.12 (s, 1H), 4.97-4.86 (m, 1H), 4.29-4.15 (m, 2H), 3.97 (d, 2H, J=6.2 Hz), 3.85-3.79 (m, 2H), 3.64-3.57 (m, 2H), 2.83-2.72 (m, 2H), 2.09-2.07 (m, 1H), 1.86-1.78 (m, 2H), 1.39-1.26 (m, 2H), 1.23 (d, 6H, J=6.2 Hz); LRMS (ESI), m/z 442 (M+H).

Example 99

1-Methylethyl 4-[({6-[4-({[2-(methyloxy)ethyl] amino}carbonyl)phenyl]-3-pyridinyl}oxy)methyl]-1-piperidinecarboxylate trifluoroacetate

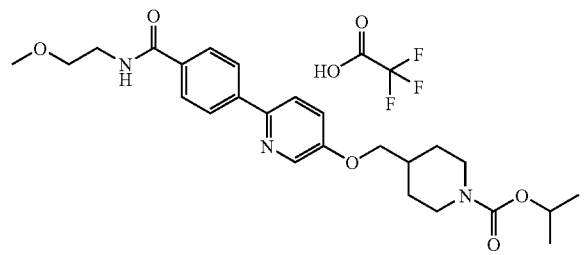

The title compound (5 mg, 7%) was prepared as a white solid from 4-(5-{[(1-{[(1-methylethyl)oxy]carbonyl}-4-piperidinyl)methyl]oxy}-2-pyridinyl)benzoic acid (Example 96, Step 2, 0.05 g, 0.13 mmol), 2-methoxyethylamine (0.01 g, 0.13 mmol), HATU (0.05 g, 0.13 mmol), diisopropylethylamine (0.02 g, 0.13 mmol) in DMF (2 mL) in a manner similar to Example 96, Step 3, except that no free base step was used. $^1$H NMR (400 MHz, CDCl$_3$): δ 8.63 (d, 1H, J=2.5 Hz), 7.92-7.86 (m, 4H), 7.82 (d, 1H, J=8.8 Hz), 7.64-7.60 (m, 1H), 6.77-6.72 (m, 1H), 4.96-4.86 (m, 1H), 4.28-4.16 (m, 2H), 3.97 (d, 2H, J=6.2 Hz), 3.70-3.62 (m, 2H), 3.60-3.55 (m, 2H), 3.39 (s, 3H), 2.83-2.73 (m, 2H), 2.09-2.07 (m, 1H), 1.86-1.79 (m, 2H), 1.39-1.26 (m, 1H), 1.23 (d, 6H, J=6.2 Hz); LRMS (ESI), m/z 456 (M+H).

Example 100

5-[({1-[3-(1-Methylethyl)-1,2,4-oxadiazol-5-yl]-4-piperidinyl}methyl)oxy]-2-[4-(methylsulfonyl)phenyl]pyridine

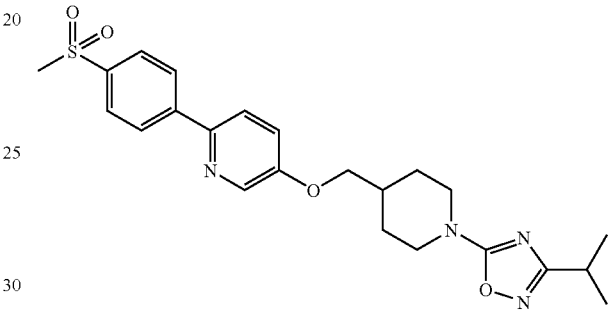

Step 1: A mixture of 2-methylpropanenitrile (100 g, 1.45 mol), hydroxylamine hydrochloride (111 g, 1.59 mol) and NaOH (64 g, 1.59 mol) in EtOH (2 L) and water (500 mL) was stirred at reflux overnight. The mixture was evaporated to dryness and extracted with dichloromethane. The organic extract was dried over Na$_2$SO$_4$ and concentrated to afford the desired N-hydroxy-2-methylpropanimidamide (50 g, 34%).

Step 2: A solution of 4-piperidinemethanol (140 g, 1.22 mol) in CH$_2$Cl$_2$ (1 L) was treated with a slurry of NaHCO$_3$ (205 g, 2.44 mol) in water (1.4 L) at 0° C. The mixture was stirred at 0° C. for 15 min, and then charged with a solution of cyanogen bromide in CH$_2$Cl$_2$, (1.34 mol) at 0° C. The reaction mixture was stirred and allowed to warm to ambient temperature, and stirred overnight. The aqueous layer was separated and extracted with CH$_2$Cl$_2$. The combined organic extracts were dried over Na$_2$SO$_4$, filtered, and the filtrate was concentrated. The crude product was combined with other batches made similarly and purified by chromatography on a silica gel column to give 300 g of 4-(hydroxymethyl)-1-piperidinecarbonitrile.

Step 3: A solution of 1N ZnCl$_2$ in Et$_2$O (182 mL, 182 mmol) was added to a solution of 4-(hydroxymethyl)-1-piperidinecarbonitrile (21.3 g, 152 mmol) and N-hydroxy-2-methylpropanimidamide (18.6 g, 182 mmol) in EtOAc (50 mL) at ambient temperature. The reaction mixture was left at ambient temperature for 30 min, decanted, and was treated with concentrated HCl (45 mL) and ethanol 20 mL). The mixture was heated at reflux for 2 h. The mixture was evaporated to dryness, and the resulting residue was charged with water and the pH was adjusted to basic with K$_2$CO$_3$. The mixture was extracted with EtOAc and the material obtained was combined with 9 other batches prepared similarly and purified by silica gel chromatography to give 150 g of {1-[3-(1-methylethyl)-1,2,4-oxadiazol-5-yl]-4-piperidinyl}methanol.

Step 4: A solution of {1-[3-(1-methylethyl)-1,2,4-oxadiazol-5-yl]-4-piperidinyl}methanol (prepared as in Step 3, 174 g, 0.77 mol) and triethylamine (140 mL, 1.0 mol) in dichloromethane (1 L) at 5° C. was treated with a solution of methanesulfonyl chloride (69 mL, 0.89 mol) in dichloromethane (150 mL) over a 1 h period. The mixture was stirred at 5° C. for 30 min, and then was quenched by the addition of water (400 mL). The mixture was stirred for 30 min, and then the organic extract was washed with water (2×400 mL), dried (MgSO$_4$) and concentrated. The residue was treated with heptane (1 L), stirred for 3 h, and the resulting solid was collected by filtration (heptane wash) and air-dried to afford {1-[3-(1-methylethyl)-1,2,4-oxadiazol-5-yl]-4-piperidinyl}methyl methanesulfonate (219.7 g, 94%) as an off-white solid. $^1$NMR (400 MHz, CDCl$_3$): δ 4.21-4.15 (m, 2H), 4.08 (d, 2H, J=6.6 Hz), 3.04 (m, 2H), 3.01 (s, 3H), 2.86 (septet, 1H, J=6.9 Hz), 2.05-1.93 (m, 1H), 1.88-1.81 (m, 2H), 1.43-1.31 (m, 2H), 1.26 (d, 6H, J=6.8 Hz); LRMS (ESI), m/z 304 (M+H).

Step 5: A mixture of 6-bromo-3-pyridinol (36 g, 207 mmol), [4-(methylsulfonyl)phenyl]boronic acid (50 g, 250 mmol), 2M Na$_2$CO$_3$ (315 mL) and DME (500 mL) was degassed with N$_2$ for 30 min, and then Pd(PPh$_3$)$_4$ (12 g, 10 mmol) was added and the mixture was heated at 80° C. for 18 h. The reaction was allowed to cool to room temperature and was diluted with dichloromethane (500 mL) and water (500 mL) and stirred for 30 min. The reaction was filtered and the solids were rinsed with dichloromethane and the aqueous layer was extracted with dichloromethane. The combined organic extracts were extracted with 1 N NaOH (2×600 mL), and then cooled to 5° C. and the pH was adjusted to ~8 with 6N HCl. The resulting precipitate was collected by filtration (water wash) and air-dried to afford a yellow solid. This procedure was repeated and the solids were combined to provide (71.2 g, 68%) of 6-[4-(methylsulfonyl)phenyl]-3-pyridinol. $^1$H NMR (400 MHz, DMSO-d$_6$): δ 10.27 (s, 1H), 8.25 (d, 1H, J=2.7 Hz), 8.21 (d, 2H, J=8.5 Hz), 8.00-3H), 7.27 (dd, 1H, J$_a$=8.7 Hz, J$_b$=2.8 Hz), 3.21 (s, 3H); LRMS (ESI), m/z 250 (M+H).

Step 6: A mixture of {1-[3-(1-methylethyl)-1,2,4-oxadiazol-5-yl]-4-piperidinyl}methyl methanesulfonate (82.3 g, 271 mmol), 6-[4-(methylsulfonyl)phenyl]-3-pyridinol (71.0 g, 285 mmol), powdered potassium carbonate (118 g, 855 mmol) and N,N-dimethylformamide (750 mL) was mechanically stirred and heated at 80° C. under nitrogen for 20 h. The reaction was cooled to ambient temperature, poured onto ice water (3 L) and allowed to stand for 1 h. The resulting solid was filtered, rinsed with water (2×500 mL) and air-dried. The solid was taken up in dichloromethane (300 mL) and methanol (500 mL). The dichloromethane was slowly removed via rotovap at 55° C. The methanol solution was allowed to stand at ambient temperature for 16 h. The resulting crystalline solid was filtered, rinsed with cold methanol and dried under vacuum at 60° C. for 18 h to afford the desired product (105.7 g, 84%) as a light tan solid. $^1$H NMR (400 MHz, CDCl$_3$): δ 8.41 (d, 1H, J=2.8 Hz), 8.13 (d, 2H, J=8.6 Hz), 8.01 (d, 2H, J=8.6 Hz), 7.74 (d, 1H, J=8.7 Hz), 7.29 (dd, 1H, J$_a$=8.7 Hz, J$_b$=3.0 Hz), 4.24 (d, 2H, J=13.1 Hz), 3.95 (d, 2H, J=6.2 Hz), 3.17-3.04 (m, 5H), 2.94-2.84 (m, 1H), 2.11 (bs, 1H), 1.97 (d, 2H, J=12.6 Hz), 1.54-1.42 (m, 2H), 1.29 (d, 6H, J=7.0 Hz); LRMS (ESI), m/z 457 (M+H).

Alternative preparation: Step 1: 2-Bromo-5-[({1-[3-(1-methylethyl)-1,2,4-oxadiazol-5-yl]-4-piperidinyl}methyl)oxy]pyridine (220 mg, 29%) was prepared as a white solid from {1-[3-(1-methylethyl)-1,2,4-oxadiazol-5-yl]-4-piperidinyl}methanol (prepared as in Example 20, Steps 1-3, 348 mg, 2.0 mmol), 6-bromo-3-pyridinol (348 mg, 2.0 mmol) and Ph$_3$P (629 mg, 2.4 mmol) in THF (5 mL) followed by diisopropyl azodicarboxylate (0.51 mL, 2.6 mmol) in a manner similar to Example 1, Step 2. $^1$H NMR (400 MHz, CDCl$_3$): δ 8.04 (s, 1H), 7.37 (d, 1H, J=8.8 Hz), 7.08 (d, 1H, J=8.8 Hz), 4.26-4.16 (m, 2H), 3.85 (d, 2H, J=6.2 Hz), 3.14-3.04 (m, 2H), 2.95-2.76 (m, 1H), 2.11-1.96 (m, 1H), 1.98-1.88 (m, 2H), 1.52-1.36 (m, 2H), 1.28 (d, 6H, J=6.9 Hz); LRMS (ESI), m/z 381/383 (M+H).

Step 2: 5-[({1-[3-(1-Methylethyl)-1,2,4-oxadiazol-5-yl]-4-piperidinyl}methyl)oxy]-2-[4-(methylsulfonyl)phenyl]pyridine (51 mg, 21%) was prepared from 2-bromo-5-[({1-[3-(1-methylethyl)-1,2,4-oxadiazol-5-yl]-4-piperidinyl}methyl)oxy]pyridine (220 mg, 0.52 mmol), [4-(methylsulfonyl)phenyl]boronic acid (105 mg, 0.52 mmol), 2M Na$_2$CO$_3$ (5 mL), Pd(PPh$_3$)$_4$ (50 mg, 0.04 mmol) and DME (5 mL) in a manner similar to Example 21, Step 3.

Example 101

5-[({1-[3-(1-Methylethyl)-1,2,4-oxadiazol-5-yl]-4-piperidinyl}methyl)oxy]-2-{4-[(1-methylethyl)sulfonyl]phenyl}pyridine hydrochloride

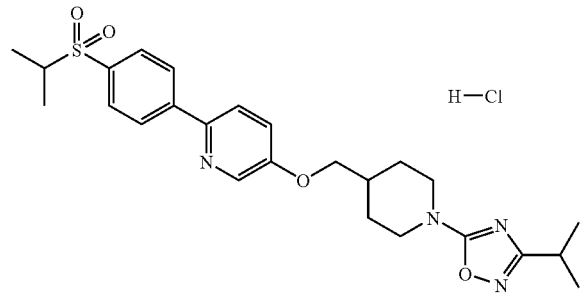

Step 1: 6-{4-[(1-Methylethyl)sulfonyl]phenyl}-3-pyridinol (0.47 g, 29%) was prepared as a tan solid from {4-[(1-methylethyl)sulfonyl]phenyl}boronic acid (1.97 g, 8.62 mmol), 6-bromo-3-pyridinol (1 g, 5.75 mmol), Pd(PPh$_3$)$_2$Cl$_2$ (200 mg, 0.28 mmol), 2M Na$_2$CO$_3$ (5 mL) and DME (5 mL) in a manner similar to Example 21, Step 3. The material was purified by chromatography on a silica gel column eluted with 0 to 5% MeOH/CH$_2$Cl$_2$. $^1$H NMR (400 MHz, CDCl$_3$): δ 8.36 (d, 1H, J=2.9 Hz), 8.06 (d, 2H, J=8.6 Hz), 7.93 (d, 2H, J=8.6 Hz), 7.68 (d, 1H, J=8.8 Hz), 7.30 (dd, 1H, J$_a$=8.8 Hz, J$_b$=2.9 Hz), 3.32-3.16 (m, 1H), 1.30 (d, 6H, J=6.9 Hz); LRMS (ESI), m/z 276 (M−H).

Step 2: The title compound was prepared from 6-{4-[(1-methylethyl)sulfonyl]phenyl}-3-pyridinol (470 mg, 1.69 mmol), {1-[3-(1-methylethyl)-1,2,4-oxadiazol-5-yl]-4-piperidinyl}methanol (prepared as in Example 20, Step 3, 571 mg, 2.54 mmol) and Ph$_3$P (666 mg, 2.54 mmol) in THF (10 mL) followed by diisopropyl azodicarboxylate (0.5 mL, 2.54 mmol) in a manner similar to Example 1, Step 2. The crude product was purified by reverse-phase preparative HPLC using a CH$_3$CN:H$_2$O gradient (10:90 to 100:0) with 0.05% TFA as a modifier and the resulting solid was taken up in CH$_2$Cl$_2$ and free-based with saturated Na$_2$CO$_3$. The resulting solid was taken up in CH$_2$Cl$_2$, treated with 4N HCl in dioxane (0.31 mL), and allowed to stand at ambient temperature for 30 min. The mixture was concentrated to give the title compound (0.67 g, 76%) as a white solid. $^1$H NMR (400 MHz, CDCl$_3$): δ 8.49 (d, 1H, J=2.8 Hz), 8.21 (d, 2H, J=8.6 Hz), 8.01 (d, 2H, J=8.6 Hz), 7.90 (d, 1H, J=8.8 Hz), 7.63 (d, 1H, J=8.8 Hz), 4.32-4.22 (m, 2H), 4.02 (d, 2H, J=6.2 Hz), 3.27-3.19 (m, 1H), 3.18-3.08 (m, 2H), 2.96-2.85 (m, 1H), 2.20-2.09 (m, 1H), 2.04-1.90 (m, 2H), 1.58-1.43 (m, 2H), 1.33-1.27 (m, 12H); LRMS (ESI), m/z 485 (M+H).

Example 102

1-Methylethyl 4-{[(6-{4-[(1-methylethyl)sulfonyl]phenyl}-3-pyridinyl)oxy]methyl}-1-piperidinecarboxylate trifluoroacetate

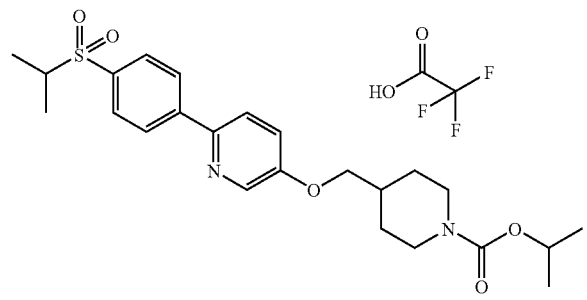

The title compound (40 mg, 19%) was prepared as a white solid from 6-{4-[(1-methylethyl)sulfonyl]phenyl}-3-pyridinol (from additional 0.2 g of impure material obtained from Example 101, Step 1, which was purified by reverse-phase preparative HPLC using a CH$_3$CN:H$_2$O gradient (10:90 to 100:0) with 0.05% TFA as a modifier, 100 mg, 0.36 mmol), 1-methylethyl 4-(hydroxymethyl)-1-piperidinecarboxylate (prepared as in Example 9, Step 1, 109 mg, 0.54 mmol) and Ph$_3$P (141 mg, 0.54 mmol) in THF (2 mL) followed by diisopropyl azodicarboxylate (0.106 mL, 0.54 mmol) in a manner similar to Example 1, Step 2, and purified by reverse-phase preparative HPLC using a CH$_3$CN:H$_2$O gradient (10:90 to 100:0) with 0.05% TFA as a modifier. $^1$H NMR (400 MHz, CDCl$_3$): δ 8.40 (d, 1H, J=2.9 Hz), 8.11 (d, 2H, J=8.8 Hz), 7.94 (d, 2H, J=8.4 Hz), 7.73 (d, 1H, J=8.8 Hz), 7.29 (dd, 1H, J$_a$=8.8 Hz, J$_b$=3.1 Hz), 4.97-4.85 (m, 1H), 4.22 (bs, 2H), 3.91 (d, 2H, J=6.4 Hz), 3.27-3.15 (m, 1H), 2.84-2.74 (m, 2H), 2.08-1.98 (m, 1H), 1.90-1.80 (m, 2H), 1.77 (bs, 2H), 1.31 (d, 6H, J=6.9 Hz), 1.25 (d, 6H, J=6.2 Hz); LRMS (ESI), m/z 461 (M+H).

Example 103

1-Methylethyl 4-({[2-(methoxy)-4'-(methylsulfonyl)-4-biphenylyl]oxy}methyl)-1-piperidinecarboxylate

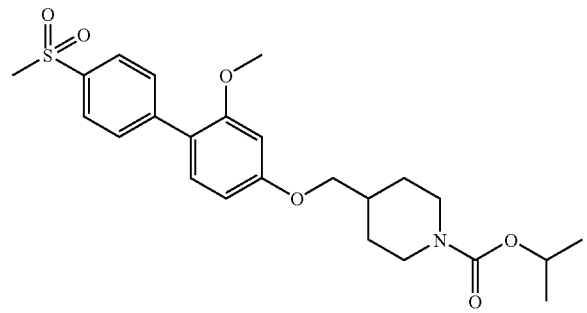

Step 1: 4'-(Methylsulfonyl)-2,4-biphenyldiol (500 mg, 36%) was prepared as a clear oil from [4-(methylsulfonyl)phenyl]boronic acid (1.06 g, 5.29 mmol), 4-bromo-1,3-benzenediol (1 g, 5.29 mmol), Pd(PPh$_3$)$_2$Cl$_2$ (100 mg, 0.14 mmol), 2M Na$_2$CO$_3$ (5 mL) and DME (5 mL) in a manner similar to Example 21, Step 3. $^1$H NMR (400 MHz, DMSO-d$_6$) δ 9.68 (s, 1H), 9.52 (s, 1H), 7.88-7.80 (m, 2H), 7.75-7.69 (m, 2H), 7.13 (d, 1H, J=8.4 Hz), 6.41 (d, 1H, J=2.2 Hz), 6.32 (dd, 1H, J$_a$=8.4 Hz, J$_b$=2.4 Hz), 3.31 (s, 3H); LRMS (ESI), m/z 263 (M−H).

Step 2: 4-({[2-Hydroxy-4'-(methylsulfonyl)-4-biphenylyl]oxy}methyl)-1-piperidinecarboxylate (90 mg, 11%) was prepared as a white solid from 4'-(methylsulfonyl)-2,4-biphenyldiol (500 mg, 1.89 mmol), 1-methylethyl 4-(hydroxymethyl)-1-piperidinecarboxylate (prepared as in Example 9, Step 1, 380 mg, 1.89 mmol) and Ph$_3$P (595 mg, 2.27 mmol) in THF (10 mL) followed by diisopropyl azodicarboxylate (0.484 mL, 2.46 mmol) in a manner similar to Example 1, Step 2. $^1$H NMR (400 MHz, CDCl$_3$): δ 7.90 (d, 2H, J=8.4 Hz), 7.66 (d, 2H, J=8.6 Hz), 7.16 (d, 1H, J=8.1 Hz), 6.56-6.51 (m, 2H), 4.95-4.86 (m, 1H), 4.15 (bs, 3H), 3.77 (bs, 2H), 3.09 (s, 3H), 2.79-2.69 (m, 2H), 1.97-1.87 (m, 1H), 1.76-1.66 (m, 2H), 1.24 (d, 6H, J=6.2 Hz), 1.21-1.14 (m, 2H); LRMS (ESI), m/z 446 (M−H).

Step 3: NaH (60% dispersion in mineral oil, 12 mg, 0.3 mmol) was added to a solution of 1-methylethyl 4-({[2-hydroxy-4'-(methylsulfonyl)-4-biphenylyl]oxy}methyl)-1-piperidinecarboxylate (65 mg, 0.15 mmol) in THF (2 mL). The mixture was stirred at ambient temperature for 30 min. The mixture was charged with 1-chloro-2-(methyloxy)ethane (0.014 mL, 0.15 mmol), and was stirred at ambient temperature for 30 min, then at reflux for 4 h. The reaction did not appear to proceed; therefore, iodomethane (0.014 mL, 0.23 mmol) was added, and the mixture was heated at reflux overnight. The mixture was quenched with MeOH and concentrated. The crude product was taken up in MeOH, filtered, and the filtrate was concentrated and purified by reverse-phase preparative HPLC using a CH$_3$CN:H$_2$O gradient (10:90 to 100:0) with 0.05% TFA as a modifier to give 39 mg (56%) of the title compound as a white solid. $^1$H NMR (400 MHz, CDCl$_3$): δ 7.92 (d, 2H, J=8.6 Hz), 7.68 (d, 2H, J=8.6 Hz), 7.25 (d, 1H, J=8.4 Hz), 6.59 (dd, 1H, J$_a$=8.4 Hz, J$_b$=2.4 Hz), 6.53 (d, 1H, J=2.4 Hz), 4.96-4.83 (m, 1H), 4.20-4.10 (m, 2H), 3.85 (s, 3H), 3.84-3.76 (m, 2H), 3.10 (s, 3H), 2.78-2.68 (m, 2H), 1.97-1.87 (m, 1H), 1.76-1.66 (m, 2H), 1.27-1.11 (m, 8H); LRMS (ESI), m/z 462 (M+H).

Example 104

N-(2-Hydroxyethyl)-4'-[({1-[3-(1-methylethyl)-1,2,4-oxadiazol-5-yl]-4-piperidinyl}methyl)oxy]-4-biphenylsulfonamide

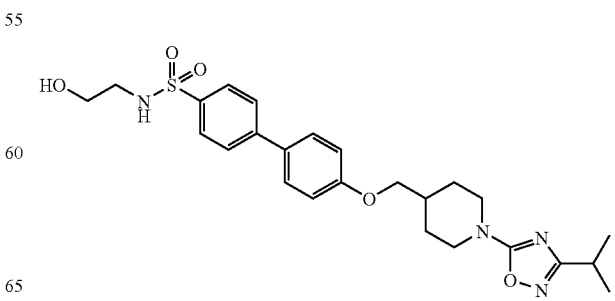

The title compound (4 mg, 2%) was prepared as a white solid from (4-{[(2-hydroxyethyl)amino]sulfonyl}phenyl)boronic acid (98 mg, 0.4 mmol), 4-{[(4-bromophenyl)oxy]methyl}-1-[3-(1-methylethyl)-1,2,4-oxadiazol-5-yl]piperidine (prepared as in Example 24, Step 1, 152 mg, 0.4 mmol), Pd(PPh$_3$)$_2$Cl$_2$ (100 mg, 0.14 mmol), 2M Na$_2$CO$_3$ (2 mL) and DME (2 mL) in a manner similar to Example 21, Step 3. $^1$H NMR (400 MHz, CDCl$_3$): δ 7.90 (d, 2H, J=8.6 Hz), 7.68 (d, 2H, J=8.4 Hz), 7.54 (d, 2H, J=8.8 Hz), 6.98 (d, 2H, J=8.8 Hz), 4.84 (t, 1H, J=6.1 Hz), 4.26-4.16 (m, 2H), 3.89 (d, 2H, J=6.2 Hz), 3.76-3.70 (m, 2H), 3.20-3.07 (m, 4H), 2.98-2.85 (m, 1H), 2.38-2.18 (m, 1H), 2.10-2.04 (m, 1H), 2.03-1.93 (m, 2H), 1.57-1.40 (m, 2H), 1.29 (d, 6H, J=7.0 Hz); LRMS (ESI), m/z 501 (M+H).

Example 105

N-(2-Hydroxyethyl)-4-{5-[({1-[3-(1-methylethyl)-1,2,4-oxadiazol-5-yl]-4-piperidinyl}methyl)oxy]-2-pyridinyl}benzenesulfonamide

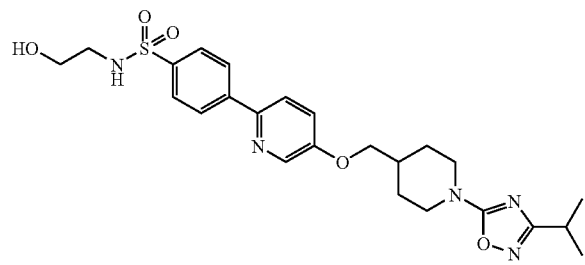

Step 1: 2-Bromo-5-[({1-[3-(1-methylethyl)-1,2,4-oxadiazol-5-yl]-4-piperidinyl}methyl)oxy]pyridine (1 g, 60%) was prepared from {1-[3-(1-methylethyl)-1,2,4-oxadiazol-5-yl]-4-piperidinyl}methanol (prepared as in Example 20, Step 3, 1 g, 4.4 mmol), 6-bromo-3-pyridinol (522 mg, 3 mmol), Ph$_3$P (1.15 g, 4.4 mmol), diisopropyl azodicarboxylate (0.866 mL, 4.4 mmol), diisopropyl azodicarboxylate (0.866 mL, 4.4 mmol), and THF (15 mL) in a manner similar to Example 1, Step 2, and purified by reverse-phase preparative HPLC using a CH$_3$CN:H$_2$O gradient (30:70 to 100:0) with 0.05% TFA as a modifier. $^1$H NMR (400 MHz, CDCl$_3$): δ 8.04 (d, 1H, J=3.1 Hz), 7.37 (d, 1H, J=8.7 Hz), 7.08 (dd, 1H, J$_a$=8.7 Hz, J$_b$=3.2 Hz), 4.22 (d, 2H, J=13.1 Hz), 3.85 (d, 2H, J=6.3 Hz), 3.09 (m, 2H), 2.89 (m, 1H), 2.13-1.99 (m, 1 H), 1.93 (d, 2H, J=12.4 Hz), 1.54-1.35 (m, 2H), 1.28 (d, 6H, J=6.9 Hz); LRMS (ESI) m/z 381/383 (M+H).

Step 2: The title compound (30 mg, 15%) was prepared as an off-white solid from (4-{[(2-hydroxyethyl)amino]sulfonyl}phenyl)boronic acid (98 mg, 0.4 mmol), 2-bromo-5-[({1-[3-(1-methylethyl)-1,2,4-oxadiazol-5-yl]-4-piperidinyl}methyl)oxy]pyridine (153 mg, 0.4 mmol), Pd(PPh$_3$)$_4$ (100 mg, 0.14 mmol), 2M Na$_2$CO$_3$ (2 mL) and DME (4 mL) in a manner similar to Example 21, Step 3. $^1$H NMR (400 MHz, CDCl$_3$): δ 8.39 (s, 1H), 8.07 (d, 2H, J=8.2 Hz), 7.93 (d, 2H, J=8.2 Hz), 7.72 (d, 1H, J=8.6 Hz), 7.30 (d, 1H, J=6.5 Hz), 5.07 (t, 1H, J=5.8 Hz), 4.28-4.18 (m, 2H), 3.94 (d, 2H, J=6.0 Hz), 3.73-3.65 (m, 2H), 3.17-3.04 (m, 4H), 2.96-2.80 (m, 1H), 2.06-1.92 (m, 3H), 1.57-1.40 (m, 2H), 1.28 (d, 6H, J=6.9 Hz); LRMS (ESI), m/z 502 (M+H).

Example 106

2,5-Difluoro-N-(2-hydroxyethyl)-4'-[({1-[3-(1-methylethyl)-1,2,4-oxadiazol-5-yl]-4-piperidinyl}methyl)oxy]-4-biphenylsulfonamide trifluoroacetate

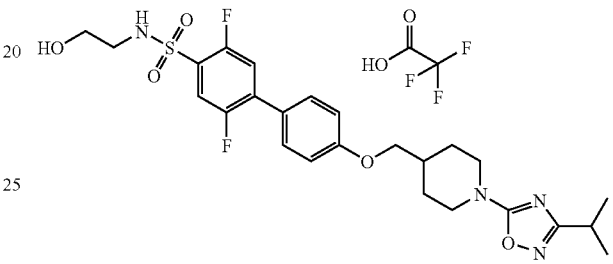

Step 1: A solution of 4-bromo-2,5-difluorobenzenesulfonyl chloride (1.17 g, 4 mmol) in CH$_2$Cl$_2$ (3 mL) was added to a solution of 2-aminoethanol (0.36 mL, 6 mmol) and triethylamine (1.67 mL, 12 mmol) in CH$_2$Cl$_2$ (12 mL) at ambient temperature. The mixture was stirred at ambient temperature for 1 h and concentrated. The crude product was purified by chromatography on a silica gel column using 0 to 10% MeOH/CH$_2$Cl$_2$ to give 884 mg (70%) of 4-bromo-2,5-difluoro-N-(2-hydroxyethyl)benzenesulfonamide as a white solid. $^1$H NMR (400 MHz, CDCl$_3$): δ 7.67 (dd, 1H, J$_a$=7.2 Hz, J$_b$=6.0 Hz), 7.47 (dd, 1H, J$_a$=8.7 Hz, J$_b$=5.1 Hz), 5.39-5.14 (m, 1H), 3.78-3.64 (m, 2H), 3.26-3.10 (m, 2H), 1.73 (bs, 1H); LRMS (ESI), m/z 314/316 (M−H).

Step 2: n-Butyllithium (2.5M in hexanes, 0.56 mL, 1.4 mmol) was added dropwise to a solution of 4-{[(4-bromophenyl)oxy]methyl}-1-[3-(1-methylethyl)-1,2,4-oxadiazol-5-yl]piperidine (prepared as in Example 24, Step 1, 380 mg, 1 mmol) in THF (5 mL) at −78° C. The mixture was stirred at −78° C. for 2 h, and was then charged with a cooled solution (−78° C.) of triisopropylborate (0.46 mL, 2 mmol) in THF (3 mL) at −78° C. The reaction mixture was allowed to warm up to ambient temperature and stirred at ambient temperature overnight. The reaction mixture was charged with 1N HCl (20 mL) and stirred at ambient temperature for 1 h. The mixture was then extracted with Et$_2$O, and the organic extracts were dried over MgSO$_4$, filtered, and the filtrate was concentrated. The crude product was purified by chromatography on a silica gel column using 0 to 7% MeOH/CH$_2$Cl$_2$ to give 120 mg (35%) of the {4-[({1-[3-(1-methylethyl)-1,2,4-oxadiazol-5-yl]-4-piperidinyl}methyl)oxy]phenyl}boronic acid as a white solid. $^1$H NMR (400 MHz, DMSO-d$_6$) δ 7.82 (s, 2H), 7.69 (d, 2H, J=8.8 Hz), 6.86 (d, 2H, J=8.8 Hz), 4.04-3.92 (m, 2H), 3.85 (d, 2H, J=6.4 Hz), 3.15-3.05 (m, 2H), 2.84-2.73 (m, 1H), 2.04-1.94 (m, 1H), 1.88-1.78 (m, 2H), 1.37-1.22 (m, 2H), 1.16 (d, 6H, J=6.9 Hz); LRMS (ESI), m/z 346 (M+H).

Step 3: The title compound (20 mg, 19%) was prepared as a yellow solid from {4-[({1-[3-(1-methylethyl)-1,2,4-oxadiazol-5-yl]-4-piperidinyl}methyl)oxy]phenyl}boronic acid (55 mg, 0.16 mmol), 4-bromo-2,5-difluoro-N-(2-hydroxyethyl)benzenesulfonamide (50 mg, 0.16 mmol), Pd(PPh$_3$)$_4$ (50 mg, 0.023 mmol), 2M Na$_2$CO$_3$ (1 mL) and DME (2 mL) in a manner similar to Example 1, Step 1, and worked up in a manner similar to Example 9, Step 3. $^1$H NMR (400 MHz, CDCl$_3$): δ 7.66 (dd, 1H, J$_a$=9.4 Hz, J$_b$=5.9 Hz), 7.52-7.46 (m, 2H), 7.33-7.24 (m, 1H), 6.98 (d, 2H, J=8.8 Hz), 5.20 (t, 1H, J=6.1 Hz), 4.28-4.16 (m, 2H), 3.89 (d, 2H, J=6.4 Hz), 3.80-3.74 (m, 2H), 3.26-3.18 (m, 2H), 3.19-3.07 (m, 2H), 2.98-2.84 (m, 1H), 2.11 (bs, 2H), 2.02-1.92 (m, 2H), 1.54-1.40 (m, 2H), 1.29 (d, 6H, J=6.9 Hz); LRMS (ESI), m/z 537 (M+H).

Example 107

5-[({1-[5-(1-Methylethyl)-1,2,4-oxadiazol-3-yl]-4-piperidinyl}methyl)oxy]-2-[4-(methylsulfonyl)phenyl]pyridine trifluoroacetate

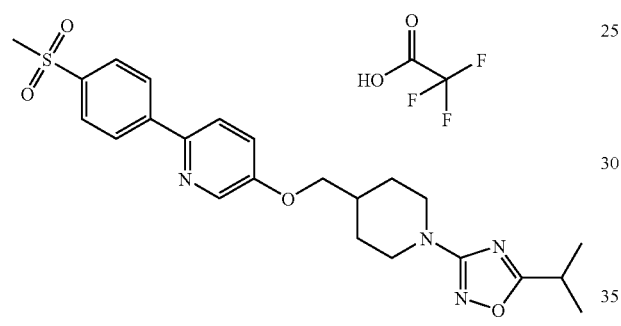

Step 1: N-Hydroxy-4-[({6-[4-(methylsulfonyl)phenyl]-3-pyridinyl}oxy)methyl]-1-piperidinecarboximidamide (35 mg, 29%) was prepared from 2-[4-(methylsulfonyl)phenyl]-5-[(4-piperidinylmethyl)oxy]pyridine dihydrochloride (prepared as in Example 86, Step 2, 113 mg, 0.3 mmol, HCl content undetermined) in the manner similar to Example 40, Steps 1-2. $^1$H NMR (400 MHz, DMSO-d$_6$) δ 10.51 (s, 1H), 9.87 (s, 1H), 8.40 (d, 1H, J=3.1 Hz), 8.29-8.20 (m, 2H), 8.09-7.91 (m, 4H), 7.51 (dd, 1H, J$_a$=8.8 Hz, J$_b$=2.9 Hz), 3.99 (d, 2H, J=6.2 Hz), 3.83-3.71 (m, 2H), 3.21 (s, 3H), 3.10-2.94 (m, 2H), 2.12-2.02 (m, 1H), 1.87-1.74 (m, 2H), 1.37-1.20 (m, 2H); LRMS (ESI), m/z 403 (M−H).

Step 2: A mixture of 2-methylpropanoic acid (0.008 mL, 0.09 mmol), TBTU (29 mg, 0.09 mmol), HOBt (2.7 mg, 0.02 mmol) and N-ethyl-N-(1-methylethyl)-2-propanamine (0.078 mL, 0.45 mmol) in DMF (2 mL) was stirred at ambient temperature for 5 min. The mixture was charged with N-hydroxy-4-[({6-[4-(methylsulfonyl)phenyl]-3-pyridinyl}oxy)methyl]-1-piperidinecarboximidamide (35 mg, 0.09 mmol) and stirred at ambient temperature for 1 h, then at 110° C. for 5 h. The mixture was cooled to ambient temperature, concentrated, and the crude product was purified by reverse-phase preparative HPLC using a CH$_3$CN:H$_2$O gradient (0.5:99.5 to 90:10) with 0.05% TFA as a modifier to give 6 mg (12%) of the title compound as a tan solid. $^1$H NMR (400 MHz, CDCl$_3$): δ 8.49 (d, 1H, J=2.8 Hz), 8.12-7.98 (m, 4H), 7.75 (d, 1H, J=8.8 Hz), 7.40 (dd, 1H, J$_a$=8.6 Hz, J$_b$=2.4 Hz), 4.13-4.03 (m, 2H), 3.95 (d, 2H, J=6.4 Hz), 3.08 (s, 3H), 3.00-2.88 (m, 2H), 2.15 (bs, 2H), 1.98-1.86 (m, 2H), 1.54-1.38 (m, 2H), 1.36-1.30 (m, 6H); LRMS (ESI), m/z 457 (M+H).

Example 108

1,1-Dimethylethyl {2-[({4'-[({1-[3-(1-methylethyl)-1,2,4-oxadiazol-5-yl]-4-piperidinyl}methyl)oxy]-4-biphenylyl}sulfonyl)amino]ethyl}carbamate

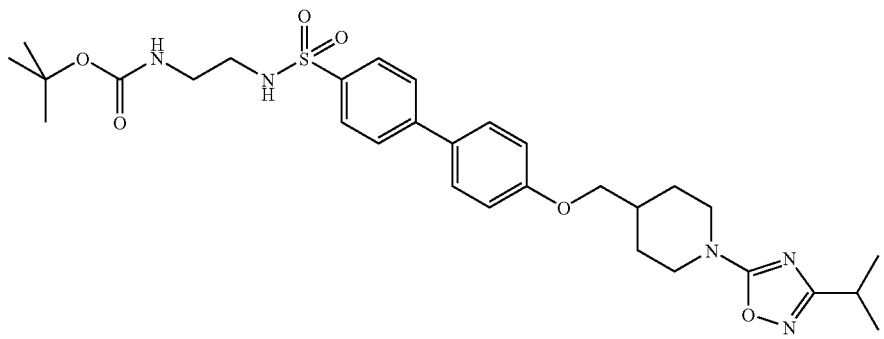

Step 1: 4-Bromobenzenesulfonyl chloride (256 mg, 1 mmol) was added dropwise to a solution of 1,1-dimethylethyl (2-aminoethyl)carbamate (197 mg, 1 mmol) and triethylamine (0.42 mL, 3 mmol) in CH$_2$Cl$_2$ (5 mL) at ambient temperature. The mixture was stirred at ambient temperature overnight. The mixture was then concentrated, and the crude product was purified by chromatography on a silica gel column using 0 to 5% MeOH/CH$_2$Cl$_2$ to give 362 mg (96%) of 1,1-dimethylethyl (2-{[(4-bromophenyl)sulfonyl]amino}ethyl)carbamate as a white solid. $^1$H NMR (400 MHz, CDCl$_3$): δ 7.75-7.68 (m, 2H), 7.67-7.61 (m, 2H), 5.28 (bs, 1H), 4.78 (bs, 1H), 3.26-3.20 (m, 2H), 3.11-3.03 (m, 2H), 1.43 (s, 9H); LRMS (ESI), m/z 379/381 (M+H).

Step 2: 1,1-Dimethylethyl (2-{[(4'-hydroxy-4-biphenylyl)sulfonyl]amino}ethyl)carbamate (246 mg, 65%) was prepared as an off-white solid from (4-hydroxyphenyl)boronic acid (132 mg, 0.96 mmol), 1,1-dimethylethyl (2-{[(4-bromophenyl)sulfonyl]amino}ethyl)carbamate (362 mg, 0.96 mmol), Pd(PPh$_3$)$_2$Cl$_2$ (100 mg, 0.14 mmol), 2M Na$_2$CO$_3$ (2 mL) and DME (4 mL) in a manner similar to Example 21, Step 3, and worked up in a manner similar to Example 9, Step 3. $^1$H NMR (400 MHz, DMSO-d$_6$) δ 9.70 (s, 1H), 7.75 (s, 4H), 7.61 (t, 1H, J=5.9 Hz), 7.54 (d, 2H, J=8.6 Hz), 6.84 (d, 2H, J=8.6 Hz), 6.76 (t, 1H, J=5.6 Hz), 2.97-2.89 (m, 2H), 2.76-2.68 (m, 2H), 1.30 (s, 9H); LRMS (ESI), m/z 391 (M−H).

Step 3: The title compound (169 mg, 45%) was prepared as a white solid from 1,1-dimethylethyl (2-{[(4'-hydroxy-4-biphenylyl)sulfonyl]amino}ethyl)carbamate (246 mg, 0.63 mmol), {1-[3-(1-methylethyl)-1,2,4-oxadiazol-5-yl]-4-piperidinyl}methanol (prepared as in Example 20, Step 3, 214 mg, 0.95 mmol) and Ph$_3$P (249 mg, 0.95 mmol) in THF (5 mL) followed by diisopropyl azodicarboxylate (0.187 mL, 0.95 mmol) in a manner similar to Example 1, Step 2. $^1$H NMR (400 MHz, DMSO-d$_6$) δ 7.84-7.72 (m, 4H), 7.70-7.60 (m, 3H), 7.03 (d, 2H, J=8.8 Hz), 6.76 (t, 1H, J=5.4 Hz), 4.03-3.91 (m, 2H), 3.90 (d, 2H, J=6.4 Hz), 3.15-3.05 (m, 2H), 2.98-2.88 (m, 2H), 2.83-2.67 (m, 3H), 2.06-1.94 (m, 1H), 1.89-1.79 (m, 2H), 1.38-1.24 (m, 11H), 1.14 (d, 6H, J=7.0 Hz); LRMS (ESI), m/z 600 (M+H).

Example 109

4'-[({1-[3-(1-Methylethyl)-1,2,4-oxadiazol-5-yl]-4-piperidinyl}methyl)oxy]-N-[2-(4-morpholinyl)ethyl]-4-biphenylsulfonamide trifluoroacetate

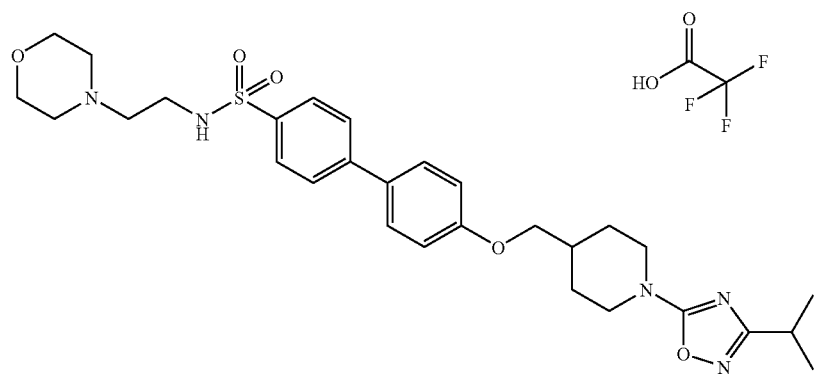

The title compound (146 mg, 21%) was prepared from 2-(4-morpholinyl)ethylamine (0.13 mL, 1 mmol) in a manner similar to Example 108, Steps 1-3. $^1$H NMR (400 MHz, CDCl$_3$): δ 7.86 (d, 2H, J=8.6 Hz), 7.65 (d, 2H, J=8.6 Hz), 7.51 (d, 2H, J=8.8 Hz), 7.02 (bs, 1H), 6.96 (d, 2H, J=8.8 Hz), 4.26-4.14 (m, 2H), 4.04-3.94 (m, 4H), 3.87 (d, 2H, J=6.2 Hz), 3.67-3.57 (m, 2H), 3.45-3.35 (m, 2H), 3.30-3.22 (m, 2H), 3.17-3.05 (m, 2H), 3.02-2.82 (m, 3H), 2.12-2.02 (m, 1H), 2.00-1.90 (m, 2H), 1.52-1.39 (m, 2H), 1.27 (d, 6H, J=7.0 Hz); LRMS (ESI), m/z 570 (M+H).

Example 110

N-[2-(Dimethylamino)ethyl]-4'-[({1-[3-(1-methylethyl)-1,2,4-oxadiazol-5-yl]-4-piperidinyl}methyl)oxy]-4-biphenylsulfonamide trifluoroacetate

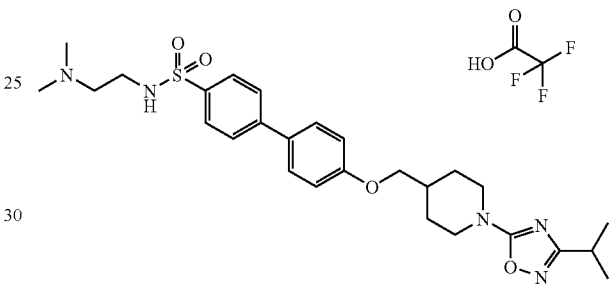

The title compound (116 mg, 18%) was prepared from N,N-dimethyl-1,2-ethanediamine (0.11 mL, 1 mmol) in a manner similar to Example 108, Steps 1-3. $^1$H NMR (400 MHz, CDCl$_3$): δ 7.87 (d, 2H, J=8.4 Hz), 7.65 (d, 2H, J=8.6 Hz), 7.51 (d, 2H, J=8.8 Hz), 7.16 (bs, 1H), 6.96 (d, 2H, J=8.8 Hz), 4.26-4.14 (m, 2H), 3.87 (d, 2H, J=6.2 Hz), 3.40-3.25 (m, 4H), 3.15-3.05 (m, 2H), 2.91 (s, 6H), 2.89 (m, 1H), 2.12-2.01 (m, 1H), 2.00-1.90 (m, 2H), 1.53-1.39 (m, 2H), 1.27 (d, 6H, J=7.0 Hz); LRMS (ESI), m/z 528 (M+H).

Example 111

4'-[({1-[3-(1-Methylethyl)-1,2,4-oxadiazol-5-yl]-4-piperidinyl}methyl)oxy]-N-[2-(1-piperidinyl)ethyl]-4-biphenylsulfonamide trifluoroacetate

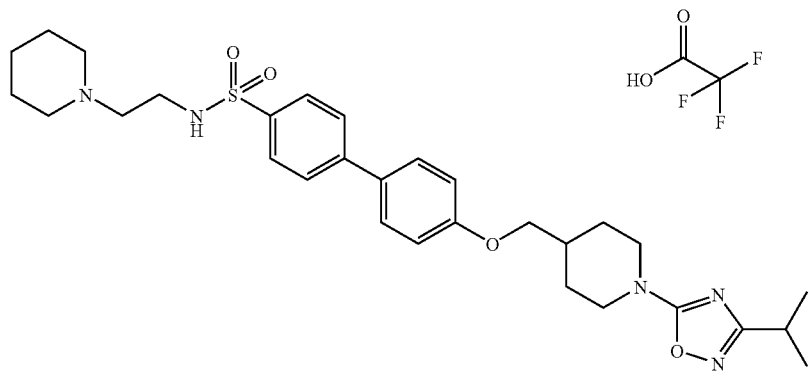

The title compound (68 mg, 10%) was prepared from 2-(1-piperidinyl)ethylamine (0.143 mL, 1 mmol) in a manner similar to Example 108, Steps 1-3. $^1$H NMR (400 MHz, CDCl$_3$): δ 7.86 (d, 2H, J=8.4 Hz), 7.64 (d, 2H, J=8.6 Hz), 7.51 (d, 2H, J=8.8 Hz), 7.06 (bs, 1H), 6.96 (d, 2H, J=8.8 Hz), 4.25-4.15 (m, 2H), 3.87 (d, 2H, J=6.2 Hz), 3.75-3.65 (m, 2H), 3.40-3.33 (m, 2H), 3.28-3.18 (m, 2H), 3.17-3.05 (m, 2H), 2.94-2.85 (m, 1H), 2.80-2.65 (m, 2H), 2.12-2.01 (m, 1H), 2.00-1.80 (m, 7H), 1.54-1.37 (m, 3H), 1.27 (d, 6H, J=7.0 Hz); LRMS (ESI), m/z 568 (M+H).

Example 112

N-(2-aminoethyl)-4'-[({1-[3-(1-methylethyl)-1,2,4-oxadiazol-5-yl]-4-piperidinyl}methyl)oxy]-4-biphenylsulfonamide trifluoroacetate

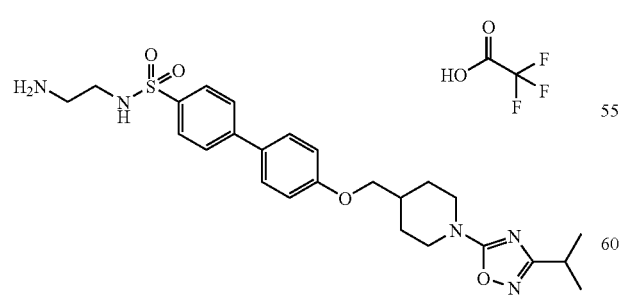

A mixture of 1,1-dimethylethyl{2-[({4'-[({1-[3-(1-methylethyl)-1,2,4-oxadiazol-5-yl]-4-piperidinyl}methyl)oxy]-4-biphenylyl}sulfonyl)amino]ethyl}carbamate (Example 108, 160 mg, 0.27 mmol) and TFA (0.3 mL) in CH$_2$Cl$_2$ (3 mL) was stirred at ambient temperature for 1 h. The crude product was concentrated and purified by reverse-phase preparative HPLC using a CH$_3$CN:H$_2$O gradient (0.5:99.5 to 90:10) with 0.05% TFA as a modifier to give 123 mg (91%) of the title compound as a white solid. $^1$H NMR (400 MHz, CDCl$_3$): δ 8.09 (bs, 2H), 7.86 (d, 2H, J=8.2 Hz), 7.60 (d, 2H, J=8.2 Hz), 7.46 (d, 2H, J=8.8 Hz), 7.33 (bs, 1H), 6.92 (d, 2H, J=8.8 Hz), 4.24-4.14 (m, 2H), 3.84 (d, 2H, J=6.2 Hz), 3.27 (bs, 4H), 3.14-3.04 (m, 2H), 2.94-2.81 (m, 1H), 2.10-2.00 (m, 1H), 1.98-1.88 (m, 2H), 1.51-1.37 (m, 2H), 1.27 (d, 6H, J=7.0 Hz); LRMS (ESI), m/z 500 (M+H).

Example 113

4'-[({1-[3-(1-Methylethyl)-1,2,4-oxadiazol-5-yl]-4-piperidinyl}methyl)oxy]-N-[2-(methoxy)ethyl]-4-biphenylsulfonamide

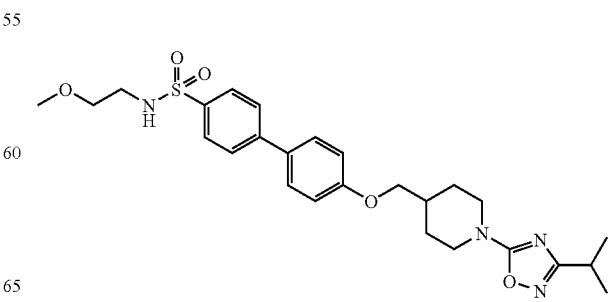

The title compound (124 mg, 24%) was prepared from 2-(methoxy)ethylamine (0.087 mL, 1 mmol) in a manner similar to Example 108, Steps 1-3. $^1$H NMR (400 MHz, CDCl$_3$): δ 7.87 (d, 2H, J=8.6 Hz), 7.65 (d, 2H, J=8.8 Hz), 7.52 (d, 2H, J=8.8 Hz), 6.96 (d, 2H, J=8.8 Hz), 4.83 (t, 1H, J=6.0 Hz), 4.25-4.15 (m, 2H), 3.87 (d, 2H, J=6.4 Hz), 3.45-3.37 (m, 2H), 3.26 (s, 3H), 3.17-3.04 (m, 4H), 2.93-2.81 (m, 1H), 2.12-2.01 (m, 1H), 2.00-1.90 (m, 2H), 1.53-1.38 (m, 2H), 1.27 (d, 6H, J=7.0 Hz); LRMS (ESI), m/z 515 (M+H).

Example 114

(±)-4'-[({1-[3-(1-Methylethyl)-1,2,4-oxadiazol-5-yl]-4-piperidinyl}methyl)oxy]-N-[1-methyl-2-(methoxy)ethyl]-4-biphenylsulfonamide

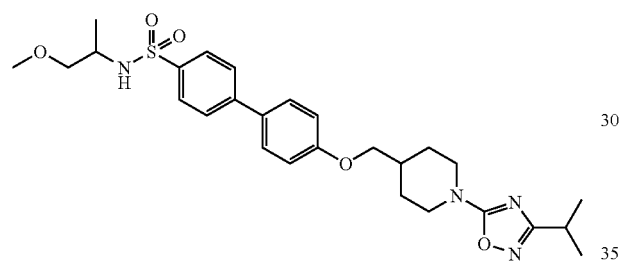

The title compound (149 mg, 28%) was prepared from (±)-1-(methoxy)-2-propylamine (0.105 mL, 1 mmol) in a manner similar to Example 108, Steps 1-3. $^1$H NMR (400 MHz, CDCl$_3$): δ 7.88 (d, 2H, J=8.6 Hz), 7.64 (d, 2H, J=8.6 Hz), 7.53 (d, 2H, J=8.8 Hz), 6.96 (d, 2H, J=9.0 Hz), 4.84 (d, 1H, J=6.8 Hz), 4.24-4.14 (m, 2H), 3.87 (d, 2H, J=6.2 Hz), 3.52-3.41 (m, 1H), 3.22-3.18 (m, 5H), 3.16-3.04 (m, 2H), 2.93-2.83 (m, 1H), 2.12-2.01 (m, 1H), 2.00-1.90 (m, 2H), 1.53-1.38 (m, 2H), 1.27 (d, 6H, J=7.0 Hz), 1.11 (d, 3H, J=6.8 Hz); LRMS (ESI), m/z 529 (M+H).

Example 115

N-Methyl-4'-[({1-[3-(1-methylethyl)-1,2,4-oxadiazol-5-yl]-4-piperidinyl}methyl)oxy]-N-[2-(4-morpholinyl)ethyl]-4-biphenylsulfonamide trifluoroacetate

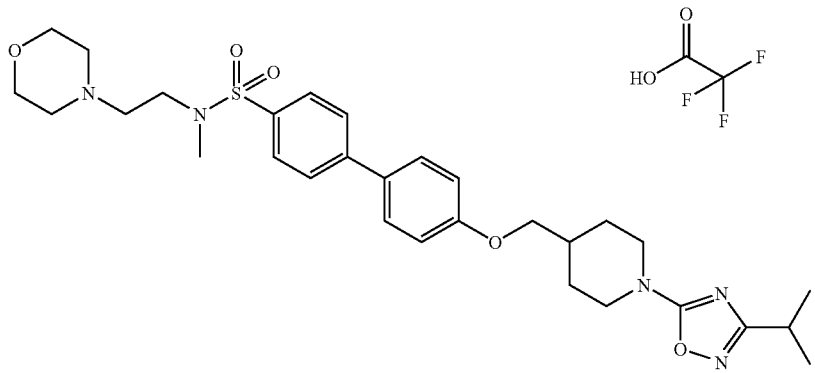

Iodomethane (0.004 mL, 0.07 mmol) was added to a solution of 4'-[({1-[3-(1-methylethyl)-1,2,4-oxadiazol-5-yl]-4-piperidinyl}methyl)oxy]-N-[2-(4-morpholinyl)ethyl]-4-biphenylsulfonamide trifluoroacetate (Example 109, 46 mg, 0.07 mmol) and KOH (12 mg, 0.21 mmol) in EtOH (1 mL) at ambient temperature. The mixture was stirred at ambient temperature overnight. The mixture was charged with additional iodomethane (0.006 mL, 0.11 mmol), and stirred at ambient temperature overnight. The mixture was charged with additional iodomethane (0.006 mL, 0.11 mmol) and stirred at ambient temperature overnight. The mixture was quenched with MeOH and concentrated. The crude product was purified by reverse-phase preparative HPLC using a $CH_3CN:H_2O$ gradient (0.5:99.5 to 90:10) with 0.05% TFA as a modifier to give 19 mg (39%) of the title compound as a white solid. $^1H$ NMR (400 MHz, $CDCl_3$): δ 7.80-7.75 (m, 2H), 7.71-7.66 (m, 2H), 7.52 (d, 2H, J=8.8 Hz), 6.97 (d, 2H, J=8.8 Hz), 4.25-4.15 (m, 2H), 4.07-3.83 (m, 6H), 3.78-3.55 (m, 3H), 3.51-3.32 (m, 4H), 3.17-2.97 (m, 3H), 2.95-2.85 (m, 1H), 2.80 (s, 3H), 2.14-2.02 (m, 1H), 2.01-1.91 (m, 2H), 1.54-1.39 (m, 2H), 1.27 (d, 6H, J=7.0 Hz); LRMS (ESI), m/z 584 (M+H).

Example 116

4'-[({1-[3-(1-Methylethyl)-1,2,4-oxadiazol-5-yl]-4-piperidinyl}methyl)oxy]-N-[3-(4-morpholinyl)propyl]-4-biphenylsulfonamide trifluoroacetate

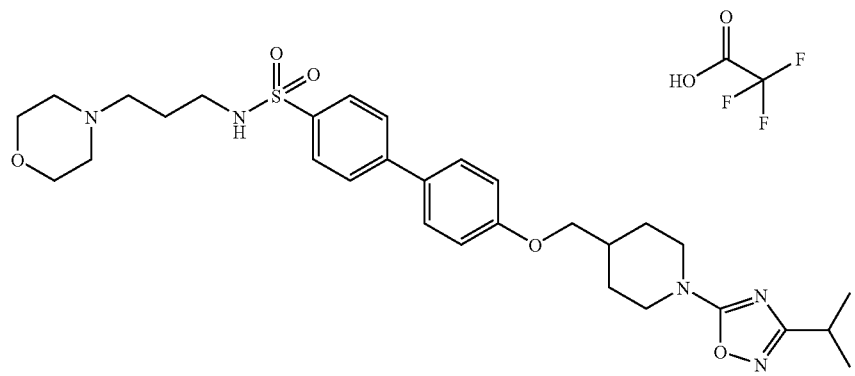

The title compound (87 mg, 12%) was prepared from 3-(4-morpholinyl)-1-propylamine (0.146 mL, 1 mmol) in a manner similar to Example 108, Steps 1-3. $^1$H NMR (400 MHz, CDCl$_3$): δ 7.83 (d, 2H, J=8.4 Hz), 7.64 (d, 2H, J=8.6 Hz), 7.51 (d, 2H, J=8.8 Hz), 6.95 (d, 2H, J=8.8 Hz), 6.19 (bs, 1H), 4.24-4.14 (m, 2H), 4.03-3.79 (m, 6H), 3.60-3.50 (m, 2H), 3.29-3.19 (m, 2H), 3.18-3.08 (m, 2H), 3.03 (t, 2H, J=6.0 Hz), 2.96-2.81 (m, 3H), 2.13-1.85 (m, 5H), 1.55-1.37 (m, 2H), 1.27 (d, 6H, J=7.0 Hz); LRMS (ESI), m/z 584 (M+H).

Example 117

4'-[({1-[3-(1-Methylethyl)-1,2,4-oxadiazol-5-yl]-4-piperidinyl}methyl)oxy]-N-[3-(2-oxo-1-pyrrolidinyl)propyl]-4-biphenylsulfonamide

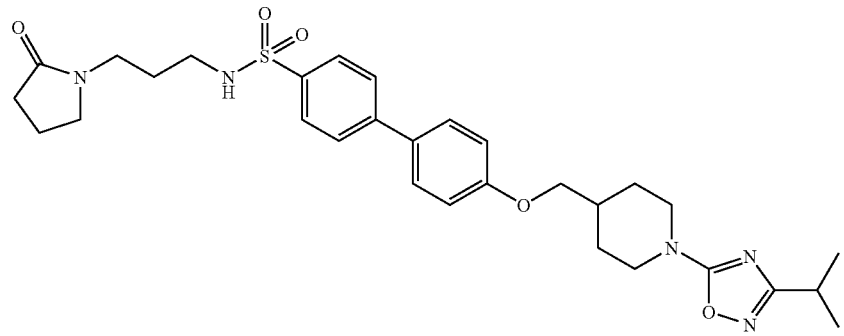

The title compound (116 mg, 20%) was prepared from 1-(3-aminopropyl)-2-pyrrolidinone (142 mg, 1 mmol) in a manner similar to Example 108, Steps 1-3. $^1$H NMR (400 MHz, CDCl$_3$): δ 7.88 (d, 2H, J=8.6 Hz), 7.63 (d, 2H, J=8.8 Hz), 7.52 (d, 2H, J=9.0 Hz), 6.96 (d, 2H, J=8.8 Hz), 5.94 (t, 1H, J=6.6 Hz), 4.27-4.17 (m, 2H), 3.87 (d, 2H, J=6.4 Hz), 3.40-3.26 (m, 4H), 3.16-3.04 (m, 2H), 2.95-2.82 (m, 3H), 2.32 (t, 2H, J=8.2 Hz), 2.14-2.02 (m, 1H), 2.00-1.89 (m, 4H), 1.77-1.63 (m, 2H), 1.54-1.36 (m, 2H), 1.28 (d, 6H, J=7.0 Hz); LRMS (ESI), m/z 582 (M+H).

Example 118

4'-[({1-[3-(1-Methylethyl)-1,2,4-oxadiazol-5-yl]-4-piperidinyl}methyl)oxy]-N-[2-(4-pyridinyl)ethyl]-4-biphenylsulfonamide trifluoroacetate

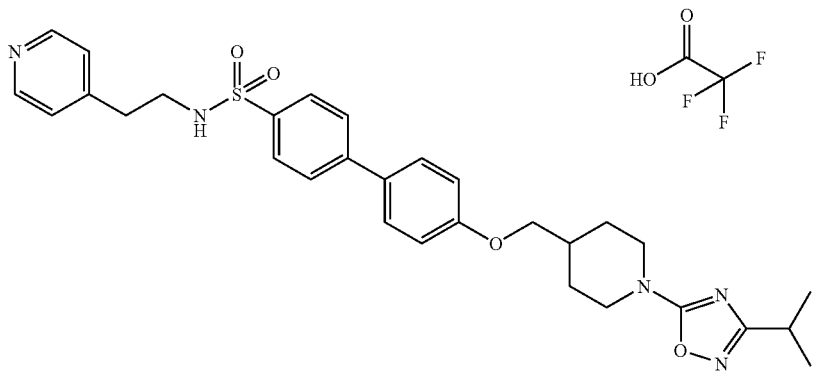

The title compound (82 mg, 12%) was prepared from 2-(4-pyridinyl)ethylamine (122 mg, 1 mmol) in a manner similar to Example 108, Steps 1-3. $^1$H NMR (400 MHz, CDCl$_3$): δ 7.84 (d, 2H, J=8.2 Hz), 7.69-7.60 (m, 5H), 7.53 (d, 2H, J=8.6 Hz), 6.97 (d, 2H, J=8.6 Hz), 5.46 (bs, 1H), 4.25-4.15 (m, 2H), 3.87 (d, 2H, J=6.2 Hz), 3.37 (bs, 2H), 3.17-3.04 (m, 5H), 2.93-2.80 (m, 1H), 2.14-2.01 (m, 1H), 2.00-1.90 (m, 2H), 1.54-1.37 (m, 2H), 1.27 (d, 6H, J=7.0 Hz); LRMS (ESI), m/z 562 (M+H).

Example 119

4'-[({1-[3-(1-Methylethyl)-1,2,4-oxadiazol-5-yl]-4-piperidinyl}methyl)oxy]-N-[3-(methoxy)propyl]-4-biphenylsulfonamide

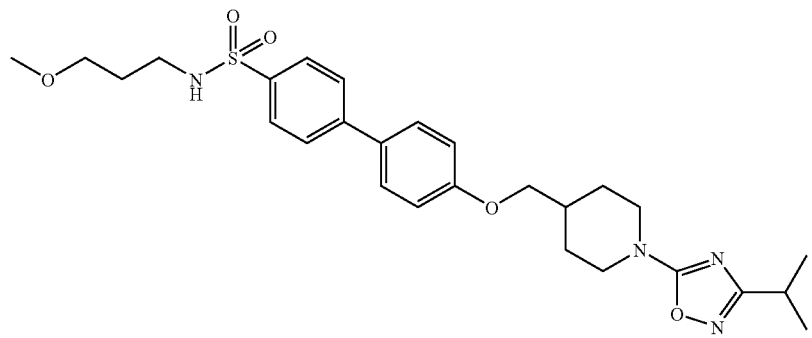

The title compound (200 mg, 38%) was prepared from 3-(methoxy)-1-propylamine (89 mg, 1 mmol) in a manner similar to Example 108, Steps 1-3. $^1$H NMR (400 MHz, CDCl$_3$): δ 7.87 (d, 2H, J=8.6 Hz), 7.65 (d, 2H, J=8.6 Hz), 7.53 (d, 2H, J=8.8 Hz), 6.96 (d, 2H, J=8.8 Hz), 5.08 (t, 1H, J=5.8 Hz), 4.28-4.18 (m, 2H), 3.87 (d, 2H, J=6.4 Hz), 3.44-3.36 (m, 2H), 3.27 (s, 3H), 3.17-3.04 (m, 4H), 2.95-2.82 (m, 1H), 2.14-2.00 (m, 1H), 2.01-1.91 (m, 2H), 1.75-1.67 (m, 2H), 1.55-1.40 (m, 2H), 1.28 (d, 6H, J=7.0 Hz); LRMS (ESI), m/z 529 (M+H).

Example 120

1-Methylethyl 4-({[6-(4-{[(2-hydroxyethyl)amino]sulfonyl}phenyl)-3-pyridinyl]oxy}methyl)-1-piperidinecarboxylate

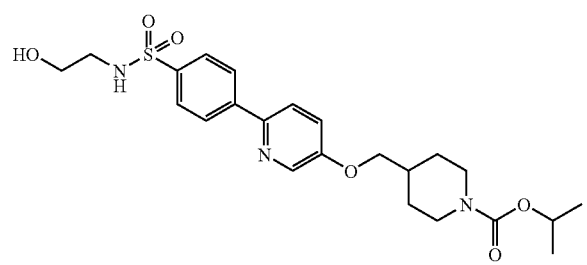

The title compound (70 mg, 27%) was prepared as a white solid from (4-{[(2-hydroxyethyl)amino]sulfonyl}phenyl)boronic acid (130 mg, 0.55 mmol), 1-methylethyl 4-{[(6-bromo-3-pyridinyl)oxy]methyl}-1-piperidinecarboxylate (prepared as in Example 81, Step 1, 197 mg, 0.55 mmol), Pd(PPh$_3$)$_2$Cl$_2$ (100 mg, 0.14 mmol), 2M Na$_2$CO$_3$ (2 mL) and DME (4 mL) in a manner similar to Example 21, Step 3. $^1$H NMR (400 MHz, CDCl$_3$): δ 8.36 (d, 1H, J=2.9 Hz), 8.05 (d, 2H, J=8.6 Hz), 7.91 (d, 2H, J=8.6 Hz), 7.69 (d, 1H, J=8.8 Hz), 7.26 (dd, 1H, J$_a$=8.8 Hz, J$_b$=2.9 Hz), 5.11 (t, 1H, J=6.0 Hz), 4.96-4.83 (m, 1H), 4.20 (bs, 2H), 3.89 (d, 2H, J=6.2 Hz), 3.70-3.61 (m, 2H), 3.13-2.99 (m, 2H), 2.83-2.70 (m, 2H), 2.07-1.92 (m, 1H), 1.89-1.79 (m, 2H), 1.70 (bs, 1H), 1.37-1.17 (m, 8H); LRMS (ESI), m/z 478 (M+H).

Example 121

1-Methylethyl 4-[({6-[4-({[2-(methoxy)ethyl]amino}sulfonyl)phenyl]-3-pyridinyl}oxy)methyl]-1-piperidinecarboxylate trifluoroacetate

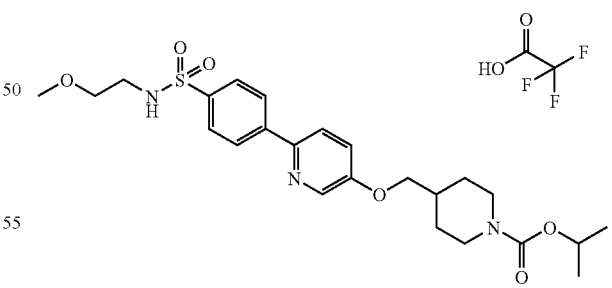

Step 1: 4-Bromo-N-[2-(methoxy)ethyl]benzenesulfonamide (512 mg, 87%) was prepared as a white solid from 4-bromobenzenesulfonyl chloride (511 mg, 2 mmol), 2-(methoxy)ethylamine (0.174 mL, 2 mmol) and triethylamine (0.836 mL, 6 mmol) in CH$_2$Cl$_2$ (10 mL) in a manner similar to Example 108, Step 1. $^1$H NMR (400 MHz, CDCl$_3$): δ 7.77-7.67 (m, 2H), 7.66-7.59 (m, 2H), 4.86 (t, 1H, J=5.7 Hz), 3.45-3.34 (m, 2H), 3.25 (s, 3H), 3.14-3.04 (m, 2H); LRMS (ESI), m/z 294/296 (M+H).

Step 2: n-Butyllithium (2.5M in hexanes, 8.36 mL, 20.89 mmol) was added dropwise to a solution of 4-bromo-N-[2-(methoxy)ethyl]benzenesulfonamide (0.5 g, 1.72 mmol) and triisopropylborate (4.8 mL, 20.89 mmol) in THF (15 mL) at −78° C. The mixture was stirred at −78° C. for 3 h and allowed to warm up to ambient temperature, stirred at ambient temperature overnight. The mixture was quenched with water (5 mL) and concentrated. The crude product was purified by chromatography on a silica gel column using 0 to 30% 2M NH₃ in MeOH/CH₂Cl₂ to give 400 mg (89%) of [4-({[2-(methoxy)ethyl]amino}sulfonyl)phenyl]boronic acid as a white solid. ¹H NMR (400 MHz, DMSO-d₆): δ 8.06-7.28 (m, 4H), 3.25-3.19 (m, 2H), 3.16-3.06 (m, 3H), 2.88-2.74 (m, 2H); LRMS (ESI), m/z 258 (M−H).

Step 3: The title compound (138 mg, 30%) was prepared as a white solid form [4-({[2-(methoxy)ethyl]amino}sulfonyl)phenyl]boronic acid (200 mg, 0.77 mmol), 1-methylethyl 4-{[(6-bromo-3-pyridinyl)oxy]methyl}-1-piperidinecarboxylate (Example 81, Step 1, 276 mg, 0.77 mmol), Pd(PPh₃)₂Cl₂ (100 mg, 0.14 mmol), 2M Na₂CO₃ (2 mL) and DME (4 mL) in a manner similar to Example 21, Step 3. ¹H NMR (400 MHz, CDCl₃): δ 8.49 (d, 1H, J=2.8 Hz), 7.99 (d, 2H, J=8.5 Hz), 7.93 (d, 2H, J=8.4 Hz), 7.73 (d, 1H, J=8.8 Hz), 7.40 (dd, 1H, Jₐ=8.7 Hz, Jᵦ=2.8 Hz), 4.96-4.84 (m 2H), 4.21 (bs, 2H), 3.92 (d, 2H, J=6.2 Hz), 3.41-3.34 (m, 2H), 3.24 (s, 3H), 3.19-3.09 (m, 2H), 2.84-2.72 (m, 2H), 2.10-1.92 (m, 1H), 1.88-1.78 (m, 2H), 1.39-1.17 (m, 8H); LRMS (ESI), m/z 492 (M+H).

Example 122

1-Methylethyl 4-[({6-[2-fluoro-4-({[2-(methoxy)ethyl]amino}sulfonyl)phenyl]-3-pyridinyl}oxy)methyl]-1-piperidinecarboxylate trifluoroacetate

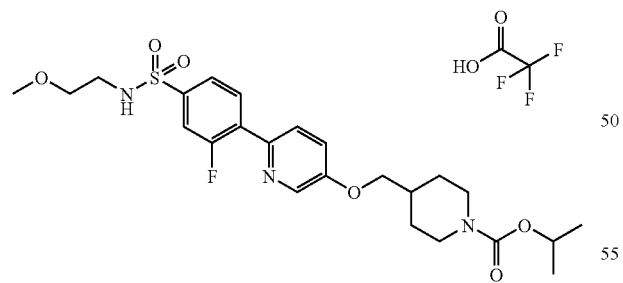

The title compound (78 mg, 6%) was prepared from 4-bromo-3-fluorobenzenesulfonyl chloride (0.296 mL, 2 mmol) and 2-(methoxy)ethylamine (0.174 mL, 2 mmol) in a manner similar to Example 121, Steps 1-3. ¹H NMR (400 MHz, CDCl₃): δ 8.45 (d, 1H, J=2.8 Hz), 8.10-8.00 (m, 1H), 7.77 (dd, 1H, Jₐ=8.9 Hz, Jᵦ=1.9 Hz), 7.70 (dd, 1H, Jₐ=8.2 Hz, Jᵦ=1.7 Hz), 7.64 (dd, 1H, Jₐ=10.4 Hz, Jᵦ=1.7 Hz), 7.32 (dd, 1H, Jₐ=8.8 Hz, Jᵦ=2.9 Hz), 5.10 (t, 1H, J=5.8 Hz), 4.96-4.82 (m, 1H), 4.20 (bs, 2H), 3.90 (d, 2H, J=6.4 Hz), 3.43-3.35 (m, 2H), 3.25 (s, 3H, 3.19-3.09 (m, 2H), 2.82-2.72 (m, 2H), 2.07-1.93 (m, 1H), 1.88-1.78 (m, 2H), 1.39-1.16 (m, 8H); LRMS (ESI), m/z 510 (M+H).

Example 123

2-Fluoro-4'-[({1-[3-(1-methylethyl)-1,2,4-oxadiazol-5-yl]-4-piperidinyl}methyl)oxy]-N-[2-(methoxy)ethyl]-4-biphenylsulfonamide

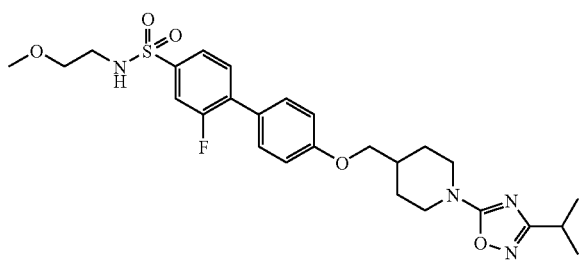

The title compound (11 mg, 2%) was prepared from 4-bromo-3-fluorobenzenesulfonyl chloride (0.148 mL, 1 mmol) and 2-(methoxy)ethylamine (0.087 mL, 1 mmol) in a manner similar to Example 108, Steps 1-3. ¹H NMR (400 MHz, CDCl₃): δ 7.63-7.49 (m, 3H), 7.44 (dd, 2H, Jₐ=8.6 Hz, Jᵦ=1.7 Hz), 6.92 (d, 2H, J=8.8 Hz), 4.19-4.09 (m, 2H), 3.50 (t, 2H, J=5.4 Hz), 3.31 (t, 2H, J=5.4 Hz), 3.26 (s, 3H), 3.10-3.00 (m, 4H), 2.96-2.83 (m, 1H), 2.03-1.90 (m, 1H), 1.90-1.80 (m, 2H), 1.34-1.20 (m, 8H); LRMS (ESI), m/z 533 (M+H).

Example 124

2,5-Difluoro-4'-[({1-[3-(1-methylethyl)-1,2,4-oxadiazol-5-yl]-4-piperidinyl}methyl)oxy]-N-[2-(methoxy)ethyl]-4-biphenylsulfonamide

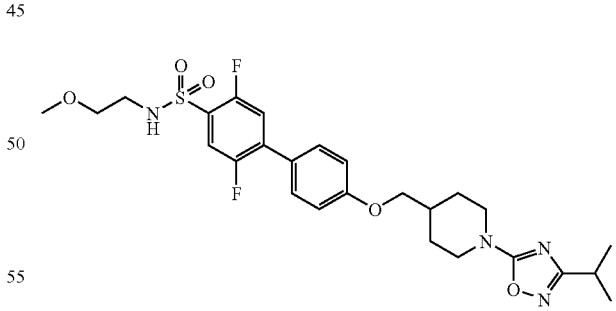

The title compound (60 mg, 11%) was prepared from 4-bromo-2,5-difluorobenzene sulfonyl chloride (292 mg, 1 mmol) and 2-(methoxy)ethylamine (0.087 mL, 1 mmol) in a manner similar to Example 108, Steps 1-3. ¹H NMR (400 MHz, CDCl₃): δ 7.63 (dd, 1H, Jₐ=9.6 Hz, Jᵦ=5.8 Hz), 7.46-7.38 (m, 2H), 7.26-7.19 (m, 1H), 6.92 (d, 2H, J=8.8 Hz), 4.20-4.10 (m, 2H), 3.47 (t, 2H, J=5.0 Hz), 3.40 (t, 2H, J=5.1 Hz), 3.25-3.18 (m, 5H), 3.10-2.98 (m, 2H), 2.96-2.84 (m, 1H), 2.03-1.89 (m, 1H), 1.88-1.78 (m, 2H), 1.35-1.20 (m, 8H); LRMS (ESI), m/z 551 (M+H).

Example 125

2-Fluoro-N-(2-hydroxyethyl)-4'-[({1-[3-(1-methylethyl)-1,2,4-oxadiazol-5-yl]-4-piperidinyl}methyl)oxy]-4-biphenylsulfonamide

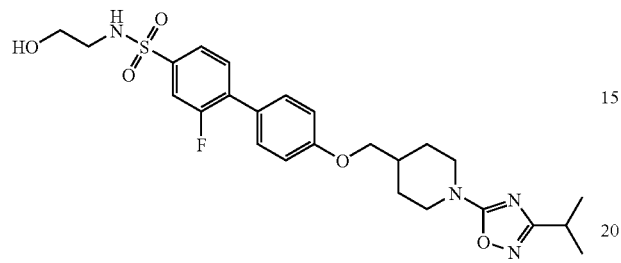

The title compound (25 mg, 5%) was prepared from 4-bromo-3-fluorobenzenesulfonyl chloride (0.148 mL, 1 mmol) and 2-aminoethanol (0.06 mL, 1 mmol) in a manner similar to Example 106, Steps 1-3. $^1$H NMR (400 MHz, CDCl$_3$): δ 7.70-7.59 (m, 2H), 7.57-7.51 (m, 1H), 7.48 (dd, 2H, J$_a$=8.7 Hz, J$_b$=1.6 Hz), 6.96 (d, 2H, J=9.0 Hz), 5.04 (t, 1H, J=5.0 Hz), 4.24-4.14 (m, 2H), 3.87 (d, 2H, J=6.2 Hz), 3.77-3.70 (m, 2H), 3.44-3.36 (m, 1H), 3.20-3.07 (m, 4H), 2.96-2.84 (m, 1H), 2.14-2.01 (m, 1H), 2.01-1.91 (m, 2H), 1.53-1.39 (m, 2H), 1.27 (d, 6H, J=7.0 Hz); LRMS (ESI), m/z 519 (M+H).

Example 126

1,1-Dimethylethyl 4-[({6-[4-(methylsulfonyl)phenyl]-3-pyridazinyl}oxy)methyl]-1-piperidinecarboxylate

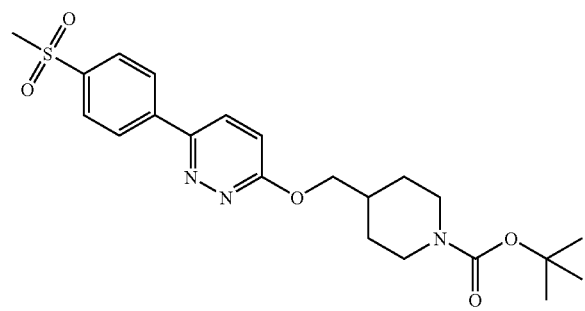

Step 1: A solution of N-Boc-4-piperidinemethanol (1.0 g, 4.50 mmol) was added dropwise to a suspension of NaH (60% in mineral oil, 0.27 g, 6.76 mmol) in DMSO (2 mL). The mixture was stirred at ambient temperature for 1 h, then 30 minutes at 50° C. The mixture was cooled to ambient temperature and a solution of 3,6-dichloropyridazine (0.73 g, 4.73 mmol) in DMSO (4 mL) was added dropwise, and the reaction mixture was stirred at ambient temperature overnight, poured onto water, then extracted with EtOAc, washed with water and brine, dried over Na$_2$SO$_4$, filtered, and the filtrate was concentrated to give the crude product as a dark reddish brown oil. The crude product was purified by chromatography on ISCO silica gel column eluted with a EtOAc: hexane gradient (0 to 30%) to give 0.85 g (56%) of 1,1-dimethylethyl 4-{[(6-chloro-3-pyridazinyl)oxy]methyl}-1-piperidinecarboxylate as a white solid. $^1$H NMR (400 MHz, CDCl$_3$): δ 7.36 (d, 1H, J=9.0 Hz), 6.94 (d, 1H, J=9.1 Hz), 4.34 (d, 2H, J=6.6 Hz), 4.20-4.10 (m, 2H), 2.80-2.65 (m, 2H), 2.10-1.95 (m, 1H), 1.85-1.70 (m, 2H), 1.45 (s, 9H), 1.35-1.20 (m, 2H); LRMS (ESI), m/z 328 (M+H).

Step 2: The title compound (0.22 g, 40%) was prepared as a white solid from [4-(methylsulfonyl)phenyl]boronic acid (0.30 g, 1.46 mmol), 1,1-dimethylethyl 4-{[(6-chloro-3-pyridazinyl)oxy]methyl}-1-piperidinecarboxylate (0.40 g, 1.22 mmol), 2M Na$_2$CO$_3$ (7 mL) and Pd(PPh$_3$)$_4$ (15 mg, 0.01 mmol) in DME (7 mL) in a manner similar to Example 1, Step 1. $^1$H NMR (400 MHz, CD$_3$OD): δ 8.25 (d, 2H, J=8.3 Hz), 8.16 (d, 1H, J=8.3 Hz), 8.09 (d, 2H, J=8.3 Hz), 7.30 (d, 1H, J=8.3 Hz), 4.42 (d, 2H, J=6.3 Hz), 4.15-4.05 (m, 2H), 3.17 (s, 3H), 2.90-2.75 (m, 2H), 2.20-2.05 (m, 1H), 1.90-1.80 (m, 2H), 1.46 (s, 9H), 1.35-1.25 (m, 2H); LRMS (ESI), m/z 448 (M+H).

Example 127

1,1-Dimethylethyl 4-[({5-[4-(methylsulfonyl)phenyl]-2-pyrimidinyl}oxy)methyl]-1-piperidinecarboxylate

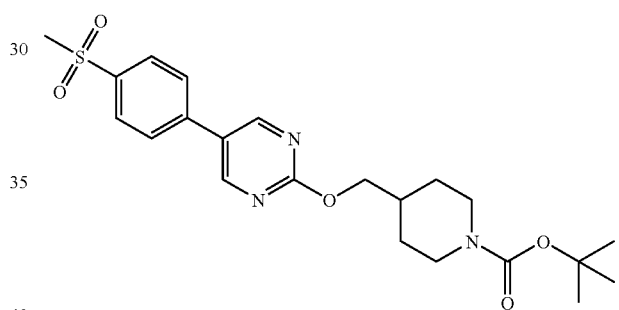

Step 1: A solution of N-Boc-4-piperidinemethanol (1.0 g, 4.50 mmol) in DMSO (2 mL) was added dropwise to a suspension of NaH (60% in mineral oil, 0.27 g, 6.76 mmol) in DMSO (4 mL). The mixture was stirred at ambient temperature for 1 h, then 30 minutes at 50° C. Cooled to ambient temperature, a solution of 5-bromo-2-iodopyrimidine (1.38 g, 4.73 mmol) in DMSO (4 mL) was added dropwise, and the reaction mixture was stirred at ambient temperature overnight, then heated at 100° C. for 5 h. Cooled to ambient temperature, the mixture was poured in water, extracted with EtOAc. The organic extract was washed with water and brine, dried over Na$_2$SO$_4$, filtered, and the filtrate was concentrated to give the crude product as a dark brown oil. The crude product was purified by chromatography on ISCO silica gel column eluted with a EtOAc:hexane gradient (hexane to 15% EtOAc) to give 0.455 g (28%) of 1,1-dimethylethyl 4-{[(5-bromo-2-pyrimidinyl)oxy]methyl}-1-piperidinecarboxylate as a white solid. $^1$H NMR (400 MHz, CDCl$_3$): δ 8.51 (s, 2H), 4.20-4.10 (m, 4H), 2.80-2.65 (m, 2H), 2.05-1.95 (m, 1H), 1.90-1.75 (m, 2H), 1.45 (s, 9H), 1.35-1.20 (m, 2H); LRMS (ESI), m/z 372/374 (M+H).

Step 2: The title compound (0.51 g, 94%) was prepared as a white solid from [4-(methylsulfonyl)phenyl]boronic acid (0.30 g, 1.45 mmol), 1,1-dimethylethyl 4-{[(5-bromo-2-pyrimidinyl)oxy]methyl}-1-piperidinecarboxylate (0.45 g, 1.21 mmol), 2M Na$_2$CO$_3$ (7 mL) and Pd(PPh$_3$)$_4$ (15 mg, 0.013 mmol) in DME (7 mL) in a manner similar to Example 1, Step 1. $^1$H NMR (400 MHz, CD$_3$OD): δ 8.92 (s, 2H), 8.06 (d, 2H, J=8.3 Hz), 7.92 (d, 2H, J=8.5 Hz), 4.33 (d, 2H, J=6.6 Hz), 4.20-4.10 (m, 2H), 3.15 (s, 3H), 2.90-2.70 (m, 2H), 2.15-2.00 (m, 1H), 1.90-1.80 (m, 2H), 1.45 (s, 9H), 1.35-1.25 (m, 2H); LRMS (ESI), m/z 448 (M+H).

Example 128

1,1-Dimethylethyl 4-[({2-[4-(methylsulfonyl)phenyl]-5-pyrimidinyl}oxy)methyl]-1-piperidinecarboxylate

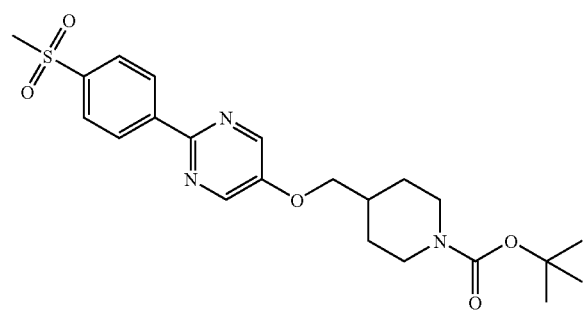

Step 1: 1,1-Dimethylethyl 4-({[2-(4-bromophenyl)-5-pyrimidinyl]oxy}methyl)-1-piperidinecarboxylate was prepared (0.387 g, 76%) as a white solid from 2-(4-bromophenyl)-pyrimidine-5-ol (0.30 g, 1.19 mmol), N-Boc-4-piperidinemethanol (0.27 g, 1.19 mmol) and Ph$_3$P (0.32 g, 1.19 mmol) in THF (8 mL) followed by diisopropyl azodicarboxylate (0.26 g, 94%, 1.19 mmol) in THF (3 mL) in a manner similar to Example 1, Step 2. $^1$H NMR (400 MHz, CDCl$_3$): δ 8.44 (s, 2H), 8.22 (d, 2H, J=8.3 Hz), 7.59 (d, 2H, J=8.3 Hz), 4.25-4.10 (m, 2H), 3.94 (d, 2H, J=6.1 Hz), 2.85-2.70 (m, 2H), 2.10-1.95 (m, 1H), 1.90-1.80 (m, 2H), 1.46 (s, 9H), 1.35-1.20 (m, 2H); LRMS (ESI), m/z 448/450 (M+H).

Step 2: The title compound (0.12 g, 31%) was prepared as a white solid from 1,1-dimethylethyl 4-({[2-(4-bromophenyl)-5-pyrimidinyl]oxy}methyl)-1-piperidinecarboxylate (0.385 g, 0.86 mmol), methanesulfinic acid sodium salt (0.16 g, 80%, 1.29 mmol), L-proline (20 mg, 0.17 mmol), CuI (17 mg, 0.09 mmol) and NaOH (7 mg, 0.17 mmol) in DMSO (5 mL) in a manner similar to Example 76, Step 3. $^1$H NMR (400 MHz, CD$_3$OD): δ 8.60 (s, 2H), 8.57 (d, 2H, J=8.5 Hz), 8.03 (d, 2H, J=8.6 Hz), 4.20-4.10 (m, 2H), 4.08 (d, 2H, J=6.1 Hz), 3.15 (s, 3H), 2.90-2.75 (m, 2H), 2.15-2.00 (m, 1H), 1.90-1.80 (m, 2H), 1.46 (s, 9H), 1.40-1.25 (m, 2H); LRMS (ESI), m/z 448 (M+H).

Example 129

1-Methylethyl 4-[({2-[4-(methylsulfonyl)phenyl]-5-pyrimidinyl}oxy)methyl]-1-piperidinecarboxylate

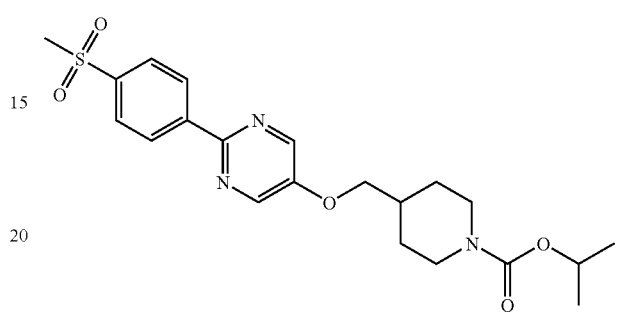

The title compound (80 mg, 92%) was prepared as a white solid from 1,1-dimethylethyl 4-[({2-[4-(methylsulfonyl)phenyl]-5-pyrimidinyl}oxy)methyl]-1-piperidinecarboxylate (Example 128, 90 mg, 0.20 mmol) and TFA (1.0 mL) in CH$_2$Cl$_2$ (6 mL) then diisopropylethylamine (1.0 ml) and isopropyl chloroformate (1.0M in toluene, 0.22 mL, 0.22 mmol) in a manner similar to Example 74. $^1$H NMR (400 MHz, CDCl$_3$): δ 8.56 (d, 2H, J=8.5 Hz), 8.48 (s, 2H), 8.02 (d, 2H, J=8.6 Hz), 4.92 (septet, 1H, J=6.2 Hz), 4.24 (bs, 2H), 3.97 (d, 2H, J=6.3 Hz), 3.08 (s, 3H), 2.85-2.70 (m, 2H), 2.10-1.95 (m, 1H), 1.90-1.80 (m, 2H), 1.40-1.20 (m, 8H); LRMS (APCI), m/z 434 (M+H).

Example 130

5-[({1-[3-(1-Methylethyl)-1,2,4-oxadiazol-5-yl]-4-piperidinyl}methyl)oxy]-2-[4-(methylsulfonyl)phenyl]pyrimidine

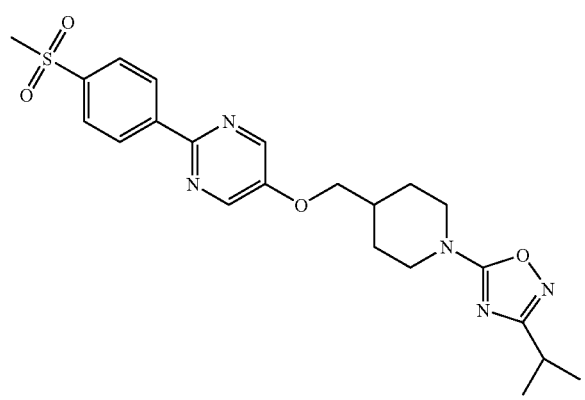

Step 1: 2-[4-(Methylsulfonyl)phenyl]-5-pyrimidinol (0.19 g, 40%) was prepared as a light brown solid from 2-(4-bromophenyl)-pyrimidin-5-ol (0.50 g, 1.89 mmol), methanesulfinic acid sodium salt (0.73 g, 80%, 5.68 mmol) and CuI (1.08 g, 5.68 mmol) in DMSO (15 mL) in a manner similar to Example 83, Step 2. The crude product was purified by chromatography on a silica gel column eluted with 2:4:0.1 EtOAc/ CH₂Cl₂/MeOH to give 0.116 g 2-[4-(methylsulfonyl)phenyl]-5-pyrimidinol as a light brown solid. Impure fractions were combined and further purified by chromatography on a silica gel column eluted with 2:6:0.1 EtOAc/CH₂Cl₂/MeOH to give additional 0.075 g of 2-[4-(methylsulfonyl)phenyl]-5-pyrimidinol as a light brown solid (40% yield overall). ¹H NMR (400 MHz, DMSO-d₆): δ 10.82 (s, 1H), 8.60-8.40 (m, 4H), 8.00 (d, 2H, J=8.5 Hz), 3.23 (s, 3H); LRMS (ESI), m/z 251 (M+H).

Step 2: The title compound (0.145 g, 75%) was prepared as a white solid from 2-[4-(methylsulfonyl)phenyl]-5-pyrimidinol (0.106 g, 0.42 mmol), 1-[3-(1-methylethyl)-1,2,4-oxadiazol-5-yl]-4-piperidinyl}methanol (prepared as in Example 20, Step 3, 0.10 g, 0.42 mmol) and Ph₃P (0.12 g, 0.42 mmol) in THF (3 mL) followed by diisopropyl azodicarboxylate (92 mg, 94%, 0.42 mmol) in THF (1 mL) in a manner similar to Example 1, Step 2. ¹H NMR (400 MHz, CD₃OD): δ 8.61 (s, 2H), 8.58 (d, 2H, J=8.6 Hz), 8.04 (d, 2H, J=8.3 Hz), 4.25-4.10 (m, 2H), 4.12 (d, 2H, J=6.2 Hz), 3.25-3.10 (m, 5H), 2.85 (septet, 1H, J=7.0 Hz), 2.25-2.10 (m, 1H), 2.05-1.90 (m, 2H), 1.55-1.40 (m, 2H), 1.26 (d, 6H, J=7.1 Hz); LRMS (ESI), m/z 458 (M+H).

Example 131

1-Methylethyl 4-[({2-fluoro-4-[5-(methylsulfonyl)-2-pyridinyl]phenyl}oxy)methyl]-1-piperidinecarboxylate

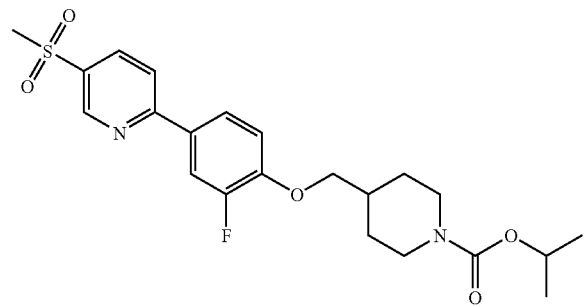

Step 1: (4-Benzyloxy-3-fluorophenyl)boronic acid (1.06 g, 4.22 mmol) was added to a suspension of 2,5-dibromopyridine (1.0 g, 4.22 mmol) in toluene (8 mL), followed by addition of 2M Na₂CO₃ (6 mL) and Pd(PPh₃)₄ (0.15 g, 0.13 mmol) and EtOH (2 mL). The reaction mixture was degassed with N₂ and heated at 90° C. overnight. The mixture was cooled to ambient temperature, water was added, and the mixture was extracted with EtOAc. The combined organic extract was washed with brine, dried over Na₂SO₄, filtered through a pad of silica gel, and the filtrate was concentrated to give a solid, which was recrystallized from MeOH to give 1.16 g (77%) of 5-bromo-2-{3-fluoro-4-[(phenylmethyl)oxy]phenyl}pyridine as a faint yellow solid. ¹H NMR (400 MHz, CDCl₃): δ 8.69 (d, 1H, J=2.2 Hz), 7.85 (dd, 1H, J_a=8.4 Hz, J_b=2.1 Hz), 7.77 (dd, 1H, J_a=12.4 Hz, J_b=2.1 Hz), 7.67 (d, 1H, J=8.6 Hz), 7.54 (d, 1H, J=8.5 Hz), 7.50-7.30 (m, 5H), 7.07 (t, 1H, J=8.4 Hz), 5.20 (s, 2H); LRMS (ESI), m/z 358/360 (M+H).

Step 2: 2-{3-Fluoro-4-[(phenylmethyl)oxy]phenyl}-5-(methylsulfonyl)pyridine (0.168 g, 34%) was prepared as a white solid from 5-bromo-2-{3-fluoro-4-[(phenylmethyl)oxy]phenyl}pyridine (0.50 g, 1.40 mmol), methanesulfinic acid sodium salt (0.72 g, 80%, 5.58 mmol) CuI (0.80 g, 4.19 mmol), NaOH (67 mg, 1.68 mmol) and water (0.4 mL) in DMSO (15 mL) in a manner similar to Example 83, Step 2. The crude product was triturated with hot MeOH containing 5% of CHCl₃. ¹H NMR (400 MHz, CDCl₃): δ 9.14 (d, 1H, J=2.4 Hz), 8.22 (dd, 1H, J_a=8.3 Hz, J_b=2.5 Hz), 7.91 (d, 1H, J=2.2 Hz), 7.90-7.70 (m, 2H), 7.50-7.30 (m, 5H), 7.11 (t, 1H, J=8.6 Hz), 5.23 (s, 2H), 3.13 (s, 3H); LRMS (ESI), m/z 358 (M+H).

Step 3: A solution of 2-{3-fluoro-4-[(phenylmethyl)oxy]phenyl}-5-(methylsulfonyl)pyridine (0.166 g, 0.46 mmol) in CH₂Cl₂ (20 mL) was cooled to −78° C. BBr₃ (0.18 mL, 1.86 mmol) was added dropwise. The reaction mixture was stirred at −78° C. to 0° C. for 2 h, poured into ice and aqueous NaHCO₃ and extracted with EtOAc (60 mL×2). The combined organic extract was washed with brine, dried over Na₂SO₄, filtered, and the filtrate was concentrated to give a solid, which was triturated with hot hexanes containing 1% of CH₂Cl₂ and 1% of MeOH to give 0.115 g (93%) of 2-fluoro-4-[5-(methylsulfonyl)-2-pyridinyl]phenol as a yellow solid. ¹H NMR (400 MHz, CD₃OD): δ 9.05 (d, 1H, J=2.4 Hz), 8.29 (dd, 1H, J_a=8.4 Hz, J_b=2.4 Hz), 8.03 (d, 1H, J=8.3 Hz), 7.92 (dd, 1H, J_a=12.6 Hz, J_b=2.2 Hz), 7.85-7.75 (m, 1H), 7.03 (t, 1H, J=8.6 Hz), 3.21 (s, 3H); LRMS (ESI), m/z 268 (M+H).

Step 4: A solution of 1-methylethyl 4-(hydroxymethyl)-1-piperidinecarboxylate (prepared as in Example 9, Step 1, 0.5 g, 2.36 mmol) in CH₂Cl₂ (5 mL) was cooled to 0° C. Et₃N (0.5 mL, 3.54 mmol) was added, followed by dropwise addition of methanesulfonyl chloride (0.2 mL, 2.60 mmol). The reaction mixture was allowed to warm up to ambient temperature and stirred for 1 h and diluted with CH₂Cl₂. The mixture was washed with water, saturated aqueous NaHCO₃, brine and dried over Na₂SO₄, filtered, and the filtrate was concentrated to give 0.71 g of the crude 1-methylethyl 4-{[(methylsulfonyl)oxy]methyl}-1-piperidinecarboxylate as a light brown solid, which was used without further purification. ¹H NMR (400 MHz, CDCl₃): δ 4.90 (septet, 1H, J=6.2 Hz), 4.25-4.15 (m, 2H), 4.06 (d, 2H, J=6.6 Hz), 3.01 (s, 3H), 2.80-2.65 (m, 2H), 2.00-1.85 (m, 1H), 1.80-1.65 (m, 2H), 1.30-1.15 (m, 8H).

Step 5: A mixture of 2-fluoro-4-[5-(methylsulfonyl)-2-pyridinyl]phenol (0.114 g, 0.43 mmol), 1-methylethyl 4-{[(methylsulfonyl)oxy]methyl}-1-piperidinecarboxylate (0.18 g, 0.55 mmol) and K₂CO₃ (0.12 g, 0.85 mmol) in DMF (5 mL) was stirred at ambient temperature for 30 min, then heated at 70° C. overnight. Cooled to ambient temperature, the mixture was poured into water (30 mL), and the precipitate was collected, washed with water and air dried. The solid was further triturated with hot MeOH to give 0.125 g (65%) of the title compound as a white solid. ¹H NMR (400 MHz, CDCl₃): δ 9.14 (d, 1H, J=1.7 Hz), 8.23 (dd, 1H, J_a=8.4 Hz, J_b=2.0 Hz), 7.90-7.75 (m, 3H), 7.05 (t, 1H, J=8.4 Hz), 4.92 (septet, 1H, J=6.2 Hz), 4.30-4.10 (m, 2H), 3.94 (d, 2H, J=6.6 Hz), 3.13 (s, 3H), 2.85-2.70 (m, 2H), 2.15-2.00 (m, 1H), 1.95-1.80 (m, 2H), 1.40-1.25 (m, 2H), 1.24 (d, 6H, J=6.3 Hz); LRMS (ESI), m/z 451 (M+H).

Example 132

1-Methylethyl 4-{[(6-{4-[(methylsulfonyl)methyl]phenyl}-3-pyridinyl)oxy]methyl}-1-piperidinecarboxylate

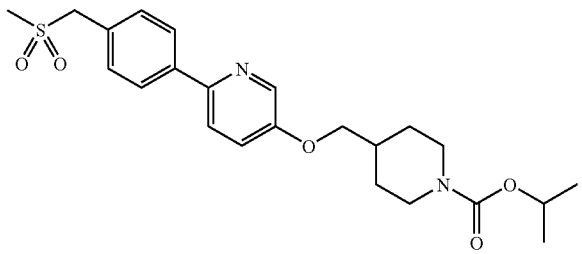

Step 1: 1-Methylethyl 4-[({6-[4-(hydroxymethyl)phenyl]-3-pyridinyl}oxy)methyl]-1-piperidinecarboxylate (208 mg, 77%) was prepared as a white solid from 4-(hydroxy methyl)phenylboronic acid (130 mg, 0.84 mmol), 1-methylethyl 4-{[(6-bromo-3-pyridinyl)oxy]methyl}-1-piperidinecarboxylate (prepared as in Example 81, Step 1, 250 mg, 0.70 mmol), Pd(PPh$_3$)$_2$Cl$_2$ (50 mg, 0.07 mmol), 2M Na$_2$CO$_3$ (4 mL) and DME (4 mL) in a manner similar to Example 21, Step 3. $^1$H NMR (400 MHz, CDCl$_3$): δ 8.37 (bs, 1H), 7.94 (d, 2H, J=7.9 Hz), 7.70 (d, 1H, J=8.6 Hz), 7.46 (d, 2H, J=8.1 Hz), 7.45-7.30 (bs, 1H), 4.91 (septet, 1H, J=6.2 Hz), 4.74 (s, 2H), 4.21 (bs, 2H), 3.90 (d, 2H, J=6.2 Hz), 2.85-2.70 (m, 2H), 2.10-1.95 (m, 1H), 1.90-1.80 (m, 2H), 1.35-1.20 (m, 8H); LRMS (ESI), m/z 385 (M+H).

Step 2: Oxalyl chloride (42 μL, 0.47 mmol) was added to a solution of 1-methylethyl 4-[({6-[4-(hydroxymethyl)phenyl]-3-pyridinyl}oxy)methyl]-1-piperidinecarboxylate (0.165 g, 0.43 mmol) in CH$_2$Cl$_2$ (5 mL) and DMF (0.5 mL) at 0° C. The mixture was warmed to ambient temperature and stirred for 1 h. Removal of CH$_2$Cl$_2$ and excess of oxalyl chloride under reduced pressure gave crude 1-methylethyl 4-[({6-[4-(chloromethyl)phenyl]-3-pyridinyl}oxy)methyl]-1-piperidinecarboxylate as a dark brown oil. Crude 1-methylethyl 4-[({6-[4-(chloromethyl)phenyl]-3-pyridinyl}oxy)methyl]-1-piperidinecarboxylate was mixed with sodium thiomethoxide (64 mg, 0.86 mmol) in DMF and heated at 100° C. overnight. Additional sodium thiomethoxide (64 mg, 0.86 mmol) was added, and the heating was continued at 100° C. overnight. Cooled to ambient temperature, the mixture was poured into water and extracted with Et$_2$O. The combined organic extract was washed with water, brine, dried over Na$_2$SO$_4$, filtered, and the filtrate was concentrated to give a yellow solid. The crude material was purified by chromatography on a silica gel column eluted with 1:11 EtOAc/CH$_2$Cl$_2$ to 1:8 EtOAc/CH$_2$Cl$_2$ to give 32 mg (18%) of 1-methylethyl 4-{[(6-{4-[(methylthio)methyl]phenyl}-3-pyridinyl)oxy]methyl}-1-piperidinecarboxylate as a white solid. LRMS (ESI), m/z 415 (M+H).

Step 3: The title compound (26 mg, 78%) was prepared as a white solid from 1-methylethyl 4-{[(6-{4-[(methylthio)methyl]phenyl}-3-pyridinyl)oxy]methyl}-1-piperidinecarboxylate (31 mg, 0.07 mmol) and Oxone® (0.19 g, 0.3 mmol) in acetone (4 mL) and water (1.5 mL) in a manner similar to Example 81, Step 4. The crude product was triturated with hot hexane containing 1% of MeOH to give the title compound as a white solid. $^1$H NMR (400 MHz, CDCl$_3$): δ 8.37 (d, 1H, J=2.7 Hz), 7.97 (d, 2H, J=8.1 Hz), 7.67 (d, 1H, J=8.8 Hz), 7.49 (d, 2H, J=8.3 Hz), 7.30-7.20 (m, 1H), 4.92 (septet, 1H, J=6.2 Hz), 4.29 (s, 2H), 4.22 (bs, 2H), 3.90 (d, 2H, J=6.3 Hz), 2.85-2.70 (m, 5H), 2.10-1.95 (m, 1H), 1.90-1.80 (m, 2H), 1.40-1.20 (m, 8H); LRMS (ESI), m/z 447 (M+H).

Example 133

1-Methylethyl 4-[({2-fluoro-6-[4-(methylsulfonyl)phenyl]-3-pyridinyl}oxy)methyl]-1-piperidinecarboxylate

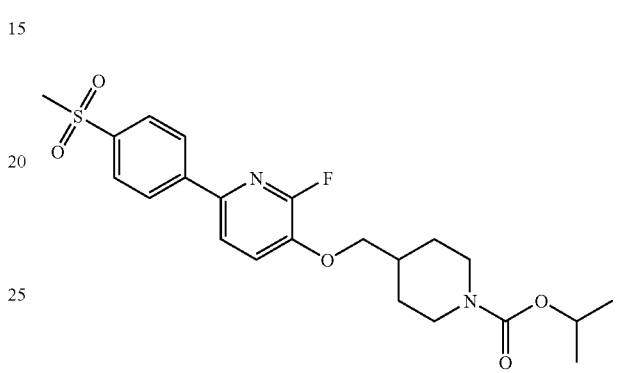

Step 1: A solution of 2-amino-3-hydroxypyridine (2 g, 17.8 mmol) in aqueous 48% HBr (75 mL) was cooled to 0° C. was carefully treated with NaNO$_2$ (10.0 g, 0.14 mol) in portions. The mixture was stirred at 0° C. for 1 h, then neutralized to pH about 7 with 2N NaOH, and extracted with EtOAc (100 mL×3). The combined organic extract was washed with water, brine, dried over Na$_2$SO$_4$, filtered, and the filtrate was concentrated to give a brown solid. The crude material was purified by flash chromatography on a silica gel column eluted with 50% EtOAc/hexanes to give 1.10 g (55%) of 2-fluoro-3-pyridinol as a white solid. $^1$H NMR (400 MHz, CDCl$_3$): δ 7.80-7.70 (m, 1H), 7.60-7.50 (m, 1H), 7.15-7.05 (m, 1H); LRMS (ESI), m/z 114 (M+H).

Step 2: A stirred solution of 2-fluoro-3-pyridinol (1.10 g, 9.73 mmol) and NaOAc (0.80 g, 9.73 mmol) in HOAc (10 mL) was treated with Br$_2$ (1.56 g, 9.73 mmol) at 5° C., and the reaction mixture was allowed to warm to ambient temperature, and stirred at ambient temperature for 4 h. The mixture was poured onto ice and neutralized with 2N NaOH to pH about 7, and then extracted with EtOAc. The combined organic extract was washed with water, brine, dried over Na$_2$SO$_4$, filtered, and the filtrate was concentrated to give a yellow oil. The crude material was purified by flash chromatography on a silica gel column eluted with 1:20 EtOAc/CH$_2$Cl$_2$ to give a colorless oil, which solidified after standing. The solid was recrystallized from hexanes to give 0.2 g (11%) of 6-bromo-2-fluoro-3-pyridinol as a white solid. The filtrate was concentrated to a solid, which was recrystallized from 2:1 hexanes/benzene to give additional 0.57 g (31%) of 6-bromo-2-fluoro-3-pyridinol as a white solid. $^1$H NMR (400 MHz, DMSO-d$_6$): δ 10.77 (s, 1H), 7.40-7.30 (m, 2H); LRMS (ESI), m/z 192/194 (M+H).

Step 3: 1-Methylethyl 4-{[(6-bromo-2-fluoro-3-pyridinyl)oxy]methyl}-1-piperidinecarboxylate (0.238 g, 68%) was prepared as a white solid from 6-bromo-2-fluoro-3-pyridinol (0.18 g, 0.94 mmol), 1-methylethyl 4-{[(methylsulfonyl)oxy]methyl}-1-piperidinecarboxylate (prepared as in Example 131, Step 4, 0.38 g, 1.22 mmol) and K$_2$CO$_3$ (0.26 g, 1.88 mmol) in DMF (10 mL) in a manner similar to Example 131, Step 5. The crude product was purified by flash chromatography on an ISCO silica gel column using 0 to 35% EtOAc/hexanes. $^1$H NMR (400 MHz, CDCl$_3$): δ 7.27 (d, 1H, J=8.3 Hz), 7.20-7.10 (m, 1H), 4.91 (septet, 1H, J=6.2 Hz), 4.30-4.10 (m, 2H), 3.85 (d, 2H, J=6.3 Hz), 2.85-2.70 (m, 2H), 2.10-1.95 (m, 1H), 1.90-1.75 (m, 2H), 1.45-1.20 (m, 8H); LRMS (ESI), m/z 375/377 (M+H).

Step 4: The title compound (197 mg, 70%) was prepared as a light gray solid from [4-(methylsulfonyl)phenyl]boronic acid (160 mg, 0.75 mmol), 1-methylethyl 4-{[(6-bromo-2-fluoro-3-pyridinyl)oxy]methyl}-1-piperidinecarboxylate (235 mg, 0.63 mmol), Pd(PPh$_3$)$_2$Cl$_2$ (45 mg, 0.06 mmol), 2M Na$_2$CO$_3$ (4 mL) and DME (4 mL) in a manner similar to Example 21, Step 3. The crude product was triturated with MeOH to give the title compound as a light gray solid. $^1$H NMR (400 MHz, CDCl$_3$): δ 8.12 (d, 2H, J=8.3 Hz), 7.99 (d, 2H, J=8.6 Hz), 7.63 (d, 1H, J=8.3 Hz), 7.40-7.30 (m, 1H), 4.92 (septet, 1H, J=6.2 Hz), 4.30-4.15 (m, 2H), 3.92 (d, 2H, J=6.4 Hz), 3.07 (s, 3H), 2.85-2.70 (m, 2H), 2.15-2.00 (m, 1H), 1.90-1.80 (m, 2H), 1.40-1.20 (m, 8H); LRMS (ESI), m/z 451 (M+H).

Example 134

1-Methylethyl 4-[({5-[4-(methylsulfonyl)phenyl]-2-pyrazinyl}oxy)methyl]-1-piperidinecarboxylate

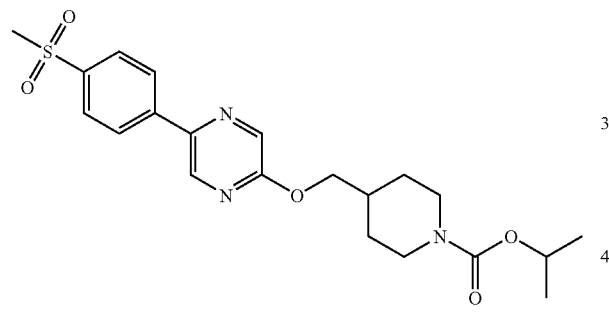

Step 1: Sodium nitrite (0.54 g, 7.53 mmol) was added portionwise to concentrated H$_2$SO$_4$ (3.8 mL) at 0° C. The mixture was heated at 50° C. until all of the NaNO$_2$ had dissolved and the mixture was again cooled to 0° C. A solution of 2-amino-5-bromopyrazine (1 g, 5.57 mmol) in concentrated H$_2$SO$_4$ (5.8 mL) was added dropwise to the nitronium solution. The ice bath was removed, and the mixture was warmed to ambient temperature and stirred for 15 minutes, then heated to 45° C. for 10 minutes. The mixture was cooled to ambient temperature and poured onto ice water (40 mL). The pH was adjusted to about 4 with 2N NaOH. The mixture was extracted with EtOAc (60 mL×3). The combined organic extracts were washed with water, brine, dried over Na$_2$SO$_4$, filtered, and the filtrate was concentrated to a yellow solid, which was triturated with hexanes to give 0.664 g (68%) of 5-bromo-2-pyrazinol (and tautomers thereof) as a yellow solid. $^1$H NMR (400 MHz, CDCl$_3$): δ 8.07 (s, 1H), 7.62 (s, 1H); LRMS (ESI), m/z 175/177 (M+H).

Step 2: A mixture of 5-bromo-2-pyrazinol (and tautomers thereof) (0.2 g, 1.14 mmol), 1-methylethyl 4-{[(methylsulfonyl)oxy]methyl}-1-piperidinecarboxylate (prepared as in Example 131, Step 4, 0.51 g, 1.71 mmol) and K$_2$CO$_3$ (0.32 g, 2.29 mmol) in DMF (12 mL) was stirred at ambient temperature for 30 min, then heated at 70° C. overnight. The mixture was cooled to ambient temperature and poured into water, and then extracted with EtOAc (60 mL×2). The combined organic extract was washed with water, brine and dried over Na$_2$SO$_4$, filtered, and the filtrate was concentrated to give crude 1-methylethyl 4-{[(5-bromo-2-pyrazinyl)oxy]methyl}-1-piperidinecarboxylate a brown oil, which was used without further purification.

Step 3: The title compound (0.303 g, 61%) was prepared as a white solid from [4-(methylsulfonyl)phenyl]boronic acid (0.28 g, 1.37 mmol), 1-methylethyl 4-{[(5-bromo-2-pyrazinyl)oxy]methyl}-1-piperidinecarboxylate (crude material prepared in Step 2), Pd(PPh$_3$)$_2$Cl$_2$ (82 mg, 0.11 mmol), 2M Na$_2$CO$_3$ (8 mL) and DME (8 mL) in a manner similar to Example 21, Step 3. The crude material was purified by flash chromatography on a silica gel column eluted with 1:20 acetone/CH$_2$Cl$_2$ to 1:10 acetone/CH$_2$Cl$_2$ followed by trituration with hot hexanes containing 1% MeOH to give the title compound as a white solid. $^1$H NMR (400 MHz, CDCl$_3$): δ 8.56 (s, 1H), 8.31 (s, 1H), 8.12 (d, 2H, J=8.3 Hz), 8.03 (d, 2H, J=8.3 Hz), 4.92 (septet, 1H, J=6.2 Hz), 4.30-4.10 (m, 4H), 3.09 (s, 3H), 2.85-2.70 (m, 2H), 2.10-1.95 (m, 1H), 1.90-1.80 (m, 2H), 1.40-1.20 (m, 8H); LRMS (ESI), m/z 434 (M+H).

Example 135

Methyl 3-{[(1-{[(1-methylethyl)oxy]carbonyl}-4-piperidinyl)methyl]oxy}-6-[4-(methylsulfonyl)phenyl]-2-pyridinecarboxylate

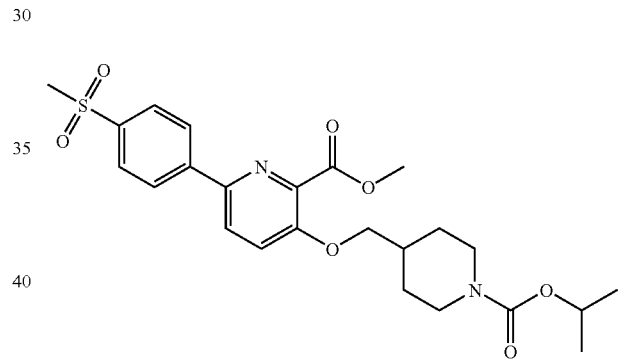

Step 1: A mixture of 3-hydroxypicolinic acid (2 g, 14.1 mmol) in MeOH (100 mL) containing concentrated H$_2$SO$_4$ (4 mL) was refluxed for 18 h. The mixture was concentrated to about 40 mL, diluted with water (150 mL), adjusted to pH around 6 with Na$_2$CO$_3$, and then extracted with CHCl$_3$ (100 mL×3). The combined organic extracts were washed with water, brine and dried over Na$_2$SO$_4$, filtered, and the filtrate was concentrated to give 1.71 g (79%) of methyl 3-hydroxy-2-pyridinecarboxylate as off-white crystals. $^1$H NMR (400 MHz, CDCl$_3$): δ 10.63 (s, 1H), 8.30-8.25 (m, 1H), 7.50-7.35 (m, 2H), 4.06 (s, 3H); LRMS (ESI), m/z 154 (M+H).

Step 2: A stirred solution of methyl 3-hydroxy-2-pyridinecarboxylate (1.69 g, 11.0 mmol) in water (75 mL) at ambient temperature was treated dropwise with bromine (2.39 g, 15.0 mmol). The reaction mixture was stirred at ambient temperature for 3 h, during which time a fine white precipitate formed. The mixture was extracted with CH$_2$Cl$_2$ (100 mL×2). The combined organic extracts were washed with water, brine and dried over Na$_2$SO$_4$, filtered, and the filtrate was concentrated to give 2.11 g (82%) of methyl 6-bromo-3-hydroxy-2-pyridinecarboxylate as an off-white solid. $^1$H NMR (400 MHz, CDCl$_3$): δ 10.69 (s, 1H), 7.55 (d, 1H, J=8.8 Hz), 7.27 (d, 1H, J=8.8 Hz), 4.04 (s, 3H); LRMS (APCI), m/z 232/234 (M+H).

Step 3: Methyl 6-bromo-3-{[(1-{[(1-methylethyl)oxy]carbonyl}-4-piperidinyl)methyl]oxy}-2-pyridinecarboxylate (0.945 g, 86% pure) was prepared as a colorless oil from methyl 6-bromo-3-hydroxy-2-pyridinecarboxylate (0.70 g, 2.78 mmol), 1-methylethyl 4-{[(methylsulfonyl)oxy]methyl}-1-piperidinecarboxylate (prepared as in Example 131, Step 4, 1.23 g, 4.16 mmol) and K$_2$CO$_3$ (0.78 g, 5.55 mmol) in DMF (30 mL) in a manner similar to Example 131, Step 5. The crude product was purified by flash chromatography on an ISCO silica gel column using 0 to 45% EtOAc/hexanes. $^1$H NMR (400 MHz, CDCl$_3$): δ 7.53 (d, 1H, J=8.5 Hz), 7.21 (d, 1H, J=8.8 Hz), 4.91 (septet, 1H, J=6.2 Hz), 4.30-4.10 (m, 2H), 3.93 (s, 3H), 3.86 (d, 2H, J=6.3 Hz), 2.85-2.70 (m, 2H), 2.10-1.95 (m, 1H), 1.90-1.75 (m, 2H), 1.35-1.20 (m, 8H); LRMS (ESI), m/z 415/417 (M+H).

Step 4: The title compound (0.785 g, 82%) was prepared as a light yellow solid from [4-(methylsulfonyl)phenyl]boronic acid (0.48 g, 2.36 mmol), methyl 6-bromo-3-{[(1-{[(1-methylethyl)oxy]carbonyl}-4-piperidinyl)methyl]oxy}-2-pyridinecarboxylate (0.945 g, 86% pure), Pd(PPh$_3$)$_2$Cl$_2$ (0.14 g, 0.20 mmol), 2M Na$_2$CO$_3$ (6 mL) and DME (20 mL) in a manner similar to Example 21, Step 3. The crude material was purified by chromatography on a silica gel column eluted with 1:10 acetone/CH$_2$Cl$_2$ followed by trituration with hot hexanes containing 1% of MeOH to give the title compound. $^1$H NMR (400 MHz, CDCl$_3$): δ 8.15 (d, 2H, J=8.3 Hz), 8.01 (d, 2H, J=8.5 Hz), 7.86 (d, 1H, J=8.8 Hz), 7.41 (d, 1H, J=8.8 Hz), 4.92 (septet, 1H, J=6.2 Hz), 4.30-4.10 (m, 2H), 3.99 (s, 3H), 3.94 (d, 2H, J=6.3 Hz), 3.06 (s, 3H), 2.85-2.70 (m, 2H), 2.15-2.00 (m, 1H), 1.90-1.80 (m, 2H), 1.40-1.20 (m, 8H); LRMS (ESI), m/z 491 (M+H).

Example 136

1-Methylethyl 4-[({2-(fluoromethyl)-6-[4-(methylsulfonyl)phenyl]-3-pyridinyl}oxy)methyl]-1-piperidinecarboxylate

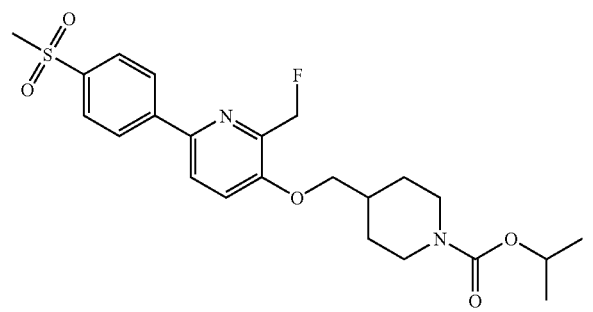

Step 1: NaBH$_4$ (32 mg, 0.82 mmol) was added to a stirred solution of methyl 3-{[(1-{[(1-methylethyl)oxy]carbonyl}-4-piperidinyl)methyl]oxy}-6-[4-(methylsulfonyl)phenyl]-2-pyridinecarboxylate (Example 135, 0.20 g, 0.41 mmol) in THF (4 mL) at 0° C. MeOH (2 mL) was added dropwise. The reaction mixture was stirred at 0° C. for 2 h, then allowed to warm to ambient temperature and stirred overnight. The mixture was heated at 70° C. for 2 h, more NaBH$_4$ (100 mg, 2.56 mmol) was added. Heating was continued at 70° C. for 2 h, then more NaBH$_4$ (100 mg, 2.56 mmol) was added. The mixture was heated at 70° C. for 2 h, cooled to ambient temperature, quenched with saturated aqueous NH$_4$Cl and extracted with EtOAc (70 mL×2). The combined organic extracts were washed with brine and dried over Na$_2$SO$_4$, filtered, and the filtrate was concentrated to a light brown oil.

The crude material was purified by flash chromatography on a silica gel column eluted with 1:8 acetone/CH$_2$Cl$_2$ to give 0.153 g (81%) of 1-methylethyl 4-[({2-(hydroxymethyl)-6-[4-(methylsulfonyl)phenyl]-3-pyridinyl}oxy)methyl]-1-piperidinecarboxylate as a white solid. $^1$H NMR (400 MHz, CDCl$_3$): δ 8.15 (d, 2H, J=8.5 Hz), 8.02 (d, 2H, J=8.5 Hz), 7.71 (d, 1H, J=8.6 Hz), 7.24 (d, 1H, J=8.6 Hz), 4.93 (septet, 1H, J=6.2 Hz), 4.82 (s, 2H), 4.22 (bs, 2H), 3.91 (d, 2H, J=6.1 Hz), 3.09 (s, 3H), 2.85-2.70 (m, 2H), 2.15-2.00 (m, 1H), 1.90_1.80 (m, 2H), 1.40-1.20 (m, 8H); LRMS (ESI), m/z 463 (M+H).

Step 2: A solution of 1-methylethyl 4-[({2-(hydroxymethyl)-6-[4-(methylsulfonyl)phenyl]-3-pyridinyl}oxy)methyl]-1-piperidinecarboxylate (131 mg, 0.28 mmol) in CH$_2$Cl$_2$ (5 mL) was cooled to −78° C. DAST (0.12 mL, 0.85 mmol) was added dropwise. The reaction mixture was allowed to warm to ambient temperature and stirred overnight. The mixture was poured into aqueous NaHCO$_3$ and extracted with EtOAc (50 mL×2). The combined organic extract was washed with brine and dried over Na$_2$SO$_4$, filtered, and the filtrate was concentrated to a purplish-red oil. The crude material was purified by flash chromatography on a silica gel column eluted with 20% EtOAc/CH$_2$Cl$_2$ to give 86 mg (66%) of the title compound as a white solid. $^1$H NMR (400 MHz, CDCl$_3$): δ 8.16 (d, 2H, J=8.6 Hz), 8.00 (d, 2H, J=8.3 Hz), 7.80-7.75 (m, 1H), 7.31 (d, 1H, J=8.8 Hz), 5.58 (d, 2H, J=47.4 Hz), 4.92 (septet, 1H, J=6.2 Hz), 4.22 (bs, 2H), 3.92 (d, 2H, J=6.1 Hz), 3.07 (s, 3H), 2.85-2.70 (m, 2H), 2.15-2.00 (m, 1H), 1.90-1.80 (m, 2H), 1.40-1.20 (m, 8H); LRMS (ESI), m/z 465 (M+H).

Example 137

Methyl {4-[({6-[2-fluoro-4-(methylsulfonyl)phenyl]-3-pyridinyl}oxy)methyl]-1-piperidinyl}(oxo)acetate

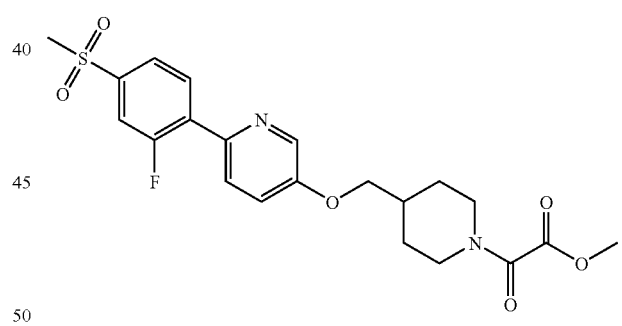

Step 1: A mixture of N-Boc-4-piperidinemethanol (5.0 g, 23.22 mmol), Et$_3$N (4.85 mL, 34.83 mmol) in CH$_2$Cl$_2$ (100 mL) at 0° C. was treated dropwise with methanesulfonyl chloride (2.16 mL, 27.86 mmol). The reaction mixture was stirred at 0° C. for 0.5 h, diluted with CH$_2$Cl$_2$ and washed with water and brine. The CH$_2$Cl$_2$ layer was dried over Na$_2$SO$_4$, filtered, and the filtrate was concentrated. The residue was mixed with 6-bromo-3-pyridinol (6.06 g, 34.83 mmol) and K$_2$CO$_3$ (6.41 g, 46.44 mmol) in DMF. The resulting mixture was heated at 65° C. overnight, cooled to ambient temperature and partitioned between water and EtOAc. The organic layer was separated and washed with 2N NaOH, water, brine, dried over Na$_2$SO$_4$, filtered, and the filtrate was concentrated to give the crude product, which was purified by chromatography on a silica gel column to give 5.88 g (68%) of 1,1-dimethylethyl 4-{[(6-bromo-3-pyridinyl)oxy]methyl}-1-piperidinecarboxylate. $^1$H NMR (400 MHz, CDCl$_3$): δ 8.00 (1H, d, J=3.1 Hz), 7.32 (d, 1H, J=8.6 Hz), 7.05 (dd, 1H, J$_a$=8.7 Hz, J$_b$=3.2 Hz), 4.13 (bs, 2H), 3.79 (d, 2H, J=6.5 Hz), 2.80-2.65 (m, 2H), 2.00-1.85 (m, 1H), 1.80-1.70 (m, 2H), 1.43 (s, 9H), 1.30-1.15 (m, 2H).

Step 2: 4-Bromo-2-fluorobenzeneboronic acid (0.69 g, 3.10 mmol) was added to a solution of 1,1-dimethylethyl 4-{[(6-bromo-3-pyridinyl)oxy]methyl}-1-piperidinecarboxylate (1.0 g, 2.70 mmol) in DME (30 mL), followed by addition of 2M Na$_2$CO$_3$ (8 mL) and Pd(PPh$_3$)$_4$ (0.16 g, 0.13 mmol). The reaction mixture was degassed with N$_2$ and heated at 80° C. for 4 h, then cooled to ambient temperature. Water was added and the mixture was extracted with EtOAc (70 mL×2). The combined organic extract was washed with brine, dried over Na$_2$SO$_4$, filtered, and the filtrate was concentrated to give the crude product. The crude product was purified by chromatography on a silica gel column eluted with 1:5 EtOAc/hexanes to give 0.785 g (63%) of 1,1-dimethylethyl 4-({[6-(4-bromo-2-fluorophenyl)-3-pyridinyl]oxy}methyl)-1-piperidinecarboxylate as an off-white solid. $^1$H NMR (400 MHz, CDCl$_3$): δ 8.38 (d, 1H, J=2.6 Hz), 7.90-7.85 (m, 1H), 7.75-7.65 (m, 1H), 7.40-7.30 (m, 2H), 7.30-7.20 (m, 1H), 4.18 (bs, 2H), 3.89 (d, 2H, J=6.3 Hz), 2.85-2.70 (m, 2H), 2.05-1.95 (m, 1H), 1.90-1.80 (m, 2H), 1.46 (s, 9H), 1.35-1.25 (m, 2H); LRMS m/z 465/467 (M+H).

Step 3: A mixture of 1,1-dimethylethyl 4-({[6-(4-bromo-2-fluorophenyl)-3-pyridinyl]oxy}methyl)-1-piperidinecarboxylate (0.781 g, 1.68 mmol), methanesulphinic acid sodium salt (0.86 g, 80%, 6.71 mmol), CuI (1.28 g, 6.71 mmol) and NaOH (81 mg, 2.02 mmol) in DMSO (20 mL) and water (0.5 mL) was degassed, purged with N$_2$ and heated at 110° C. for 48 h. After cooled to ambient temperature, the mixture was poured into water (75 mL) and EtOAc (75 mL), and filtered through Celite®. The solid on Celite® was further washed with EtOAc. The filtrate and washing were combined and transferred to a separatory funnel. The organic layer was separated and washed with water and brine, dried over Na$_2$SO$_4$, filtered, and the filtrate was concentrated to give the crude product as a yellow solid. The crude product was purified by chromatography on a silica gel column eluted with 25% EtOAc/CH$_2$Cl$_2$ followed by trituration with hot hexanes containing 1% of MeOH to give 0.5 g (64%) of 1,1-dimethylethyl 4-[({6-[2-fluoro-4-(methylsulfonyl)phenyl]-3-pyridinyl}oxy)methyl]-1-piperidinecarboxylate as a white solid. $^1$H NMR (400 MHz, CD$_3$OD): δ 8.40 (d, 1H, J=3.0 Hz), 8.15-8.10 (m, 1H), 7.90-7.75 (m, 3H), 7.50 (dd, 1H, J$_a$=8.8 Hz, J$_b$=3.0 Hz), 4.20-4.10 (m, 2H), 4.00 (d, 2H, J=6.3 Hz), 3.18 (s, 3H), 2.90-2.75 (m, 2H), 2.15-2.00 (m, 1H), 1.90-1.80 (m, 2H), 1.46 (s, 9H), 1.40-1.25 (m, 2H); LRMS (ESI), m/z 465 (M+H).

Step 4: A solution of 1,1-dimethylethyl 4-[({6-[2-fluoro-4-(methylsulfonyl)phenyl]-3-pyridinyl}oxy)methyl]-1-piperidinecarboxylate (0.15 g, 0.32 mmol) in CH$_2$Cl$_2$ (10 mL) was treated with TFA (0.3 mL). The mixture was stirred at ambient temperature overnight. CH$_2$Cl$_2$ and excess of TFA were removed under reduced pressure. The residue was redissolved in CH$_2$Cl$_2$ (5 mL) and cooled in an ice bath. Diisopropylethylamine (1.5 mL) was added, followed by addition of methyl oxalyl chloride (34 µL, 0.36 mmol). The reaction mixture was allowed to warm up to ambient temperature and stirred overnight, quenched with aqueous NaHCO$_3$ and extracted with EtOAc (50 mL×2). The combined organic extract was washed with brine and dried over Na$_2$SO$_4$, filtered, and the filtrate was concentrated to a viscous brown oil. The crude material was purified by chromatography on a silica gel column eluted with 1:5 acetone/CH$_2$Cl$_2$ to give 0.112 g (77%) of the title compound as a white solid. $^1$H NMR (400 MHz, CDCl$_3$): δ 8.42 (d, 1H, J=2.9 Hz), 8.23 (t, 1H, J=7.8 Hz), 7.85-7.80 (m, 2H), 7.73 (dd, 1H, J$_a$=10.3 Hz, J$_b$=1.5 Hz), 7.27 (dd, 1H, J$_a$=10.8 Hz, J$_b$=2.9 Hz), 4.65-4.55 (m, 1H), 4.00-3.90 (m, 2H), 3.88 (s, 3H), 3.80-3.70 (m, 1H), 3.25-3.10 (m, 1H), 3.09 (s, 3H), 2.80-2.70 (m, 1H), 2.25-2.10 (m, 1H), 200-1.90 (m, 2H), 1.50-1.35 (m, 2H); LRMS (APCI), m/z 451 (M+H).

Example 138

1-{4-[({6-[2-Fluoro-4-(methylsulfonyl)phenyl]-3-pyridinyl}oxy)methyl]-1-piperidinyl}-3,3-dimethyl-1-oxo-2-butanone

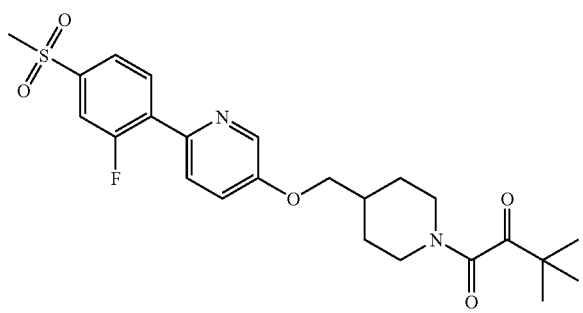

A solution of methyl {4-[({6-[2-fluoro-4-(methylsulfonyl)phenyl]-3-pyridinyl}oxy)methyl]-1-piperidinyl}(oxo)acetate (Example 137, 95 mg, 0.21 mmol) in THF (4 mL) at −78° C. was treated with tert-butylmagnesium chloride (1M in THF, 0.26 mL, 0.26 mmol). The mixture was stirred at −78° C. for 3 h. Additional tert-butylmagnesium chloride (1M in THF, 0.22 mL, 0.22 mmol) was added. The mixture was stirred at −78° C. for 3 h. More tert-butylmagnesium chloride (1M in THF, 0.25 mL, 0.25 mmol) was added. The reaction mixture was stirred at −78° C. for 1 h, quenched with saturated aqueous NH$_4$Cl and extracted with EtOAc (50 mL×2). The combined organic extracts were washed with brine and dried over Na$_2$SO$_4$, filtered, and the filtrate was concentrated to a viscous light brown oil. The crude material was purified by flash chromatography on a silica gel column eluted with 1:10 acetone/CH$_2$Cl$_2$ to give 50 mg (50%) of the title compound as a white solid. $^1$H NMR (400 MHz, CDCl$_3$): δ 8.42 (d, 1H, J=2.9 Hz), 8.23 (t, 1H, J=7.8 Hz), 7.85-7.77 (m, 2H), 7.73 (dd, 1H, J$_a$=10.3 Hz, J$_b$=1.5 Hz), 7.30-7.25 (m, 1H), 4.65-4.55 (m, 1H), 3.95-3.85 (m, 2H), 3.55-3.45 (m, 1H), 3.15-3.05 (m, 4H), 2.80-2.70 (m, 1H), 2.25-2.10 (m, 1H), 2.00-1.85 (m, 2H), 1.50-1.30 (m, 2H), 1.27 (s, 9H); LRMS (ESI), m/z 477 (M+H).

Example 139

(±)-Phenylmethyl 4-[1-({6-[4-(methylsulfonyl)phenyl]-3-pyridinyl}oxy)ethyl]-1-piperidinecarboxylate

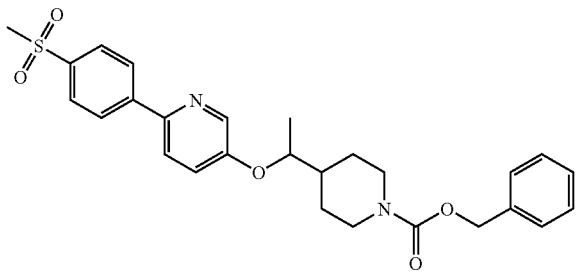

Step 1: A solution of N-(benzyloxycarbonyl)-4-formyl-piperidine (1 g, 3.92 mmol) in $Et_2O$ (40 mL) at −78° C. was treated with methylmagnesium bromide (3M in $Et_2O$, 3.2 mL, 9.60 mmol). The reaction mixture was stirred at −78° C. for 2 h, quenched with saturated aqueous $NH_4Cl$ and extracted with $Et_2O$. The combined organic extract was washed with brine and dried over $Na_2SO_4$, filtered, and the filtrate was concentrated to a colorless oil. The crude product was purified by flash chromatography on an ISCO silica gel column using 0 to 70% EtOAc/hexanes to give 0.64 g (62%) of (±)-phenylmethyl 4-(1-hydroxyethyl)-1-piperidinecarboxylate as a colorless oil. $^1$H NMR (400 MHz, $CDCl_3$): δ 7.40-7.25 (m, 5H), 5.11 (s, 2H), 4.30-4.15 (m, 2H), 3.65-3.55 (m, 1H), 2.80-2.65 (m, 2H), 1.90-1.80 (m, 1H), 1.80-1.70 (m, 1H), 1.70-1.55 (m, 1H), 1.30-1.10 (m, 5H).

Step 2: A mixture of (±)-phenylmethyl 4-(1-hydroxyethyl)-1-piperidinecarboxylate (0.64 g, 2.43 mmol), $Et_3N$ (1.03 mL, 7.29 mmol) in $CH_2Cl_2$ (50 mL) at 0° C. was treated dropwise with methanesulfonyl chloride (0.38 mL, 4.86 mmol). The reaction mixture was stirred at 0° C. for 1 h, then at ambient temperature for 1.5 h, diluted with $CH_2Cl_2$ (100 mL) and washed with 1M $NaH_2PO_4$ (50 mL×2) and brine (25 mL). The $CH_2Cl_2$ layer was dried over $Na_2SO_4$, filtered, and the filtrate was concentrated to give the crude product as a light brown oil. The crude product was purified by flash chromatography on an ISCO silica gel column using 0 to 45% EtOAc/hexanes to give 0.73 g (88%) of (±)-phenylmethyl 4-{1-[(methylsulfonyl)oxy]ethyl}-1-piperidinecarboxylate as a colorless oil. $^1$H NMR (400 MHz, $CDCl_3$): δ 7.40-7.25 (m, 5H), 5.12 (s, 2H), 4.70-4.60 (m, 1H), 4.25 (bs, 2H), 2.99 (s, 3H), 2.80-2.65 (m, 2H), 1.85-1.60 (m, 3H), 1.40 (d, 3H, J=6.4 Hz), 1.35-1.20 (m, 2H).

Step 3: A mixture of 6-bromo-3-pyridinol (0.31 g, 1.78 mmol), (±)-phenylmethyl 4-{1-[(methylsulfonyl)oxy]ethyl}-1-piperidinecarboxylate (0.73 g, 2.14 mmol) and $K_2CO_3$ (0.50 g, 3.57 mmol) in DMF (12 mL) was stirred at ambient temperature for 30 min, then heated at 70° C. overnight, then heated at 100° C. for 27 h. The mixture was cooled to ambient temperature and poured into water, and extracted with EtOAc (60 mL×2). The combined organic extract was washed with water, brine and dried over $Na_2SO_4$, filtered, and the filtrate was concentrated to give crude (±)-phenylmethyl 4-{1-[(6-bromo-3-pyridinyl)oxy]ethyl}-1-piperidinecarboxylate as a brown oil, which was used without further purification.

Step 4: The title compound (0.415 g, 47%) was prepared as a white foam from [(4-methylsulfonyl)phenyl]boronic acid (0.44 g, 2.14 mmol), (±)-phenylmethyl 4-{1-[(6-bromo-3-pyridinyl)oxy]ethyl}-1-piperidinecarboxylate, $Pd(PPh_3)_2Cl_2$ (0.12 g, 0.18 mmol), 2M $Na_2CO_3$ (6 mL) and DME (20 mL) in a manner similar to Example 21, Step 3. The crude material was purified by flash chromatography on a silica gel column eluted with 1:20 acetone/$CH_2Cl_2$ to 1:15 acetone/$CH_2Cl_2$ to give the title compound as a white foam. $^1$H NMR (400 MHz, $CDCl_3$): δ 8.38 (d, 1H, J=2.9 Hz), 8.14 (d, 2H, J=8.5 Hz), 8.01 (d, 2H, J=8.6 Hz), 7.74 (d, 1H, J=8.8 Hz), 7.40-7.25 (m, 6H), 5.13 (s, 2H), 4.40-4.20 (m, 3H), 3.08 (s, 3H), 2.85-2.70 (m, 2H), 1.95-1.65 (m, 3H), 1.45-1.20 (m, 5H); LRMS (ESI), m/z 495 (M+H).

Example 140

(±)-1-Methylethyl 4-[1-({6-[4-(methylsulfonyl)phenyl]-3-pyridinyl}oxy)ethyl]-1-piperidinecarboxylate

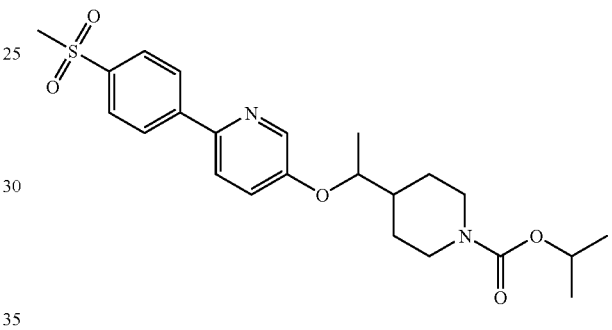

Step 1: (±)-Phenylmethyl 4-[1-({6-[4-(methylsulfonyl)phenyl]-3-pyridinyl}oxy)ethyl]-1-piperidinecarboxylate (Example 139, 0.37 g, 0.75 mmol) was dissolved in MeOH (10 mL) and THF (5 mL). 10% of Pd/C (40 mg, Degussa type) was added, and the mixture was placed under an atmosphere of hydrogen using a $H_2$ balloon at ambient temperature for 4 h. The mixture was filtered through Celite® and the filtrate was concentrated to give 0.27 g (100%) of (±)-2-[4-(methylsulfonyl)phenyl]-5-{[1-(4-piperidinyl)ethyl]oxy}pyridine as a viscous colorless oil. $^1$H NMR (400 MHz, $CDCl_3$): δ 8.38 (d, 1H, J=2.9 Hz), 8.12 (d, 2H, J=8.5 Hz), 8.00 (d, 2H, J=8.3 Hz), 7.72 (d, 1H, J=8.8 Hz), 7.30-7.25 (m, 1H), 4.30-4.20 (m, 1H), 3.20-3.10 (m, 2H), 3.08 (s, 3H), 2.70-2.60 (m, 2H), 1.95-1.65 (m, 3H), 1.45-1.25 (m, 5H); LRMS (ESI), m/z 361 (M+H).

Step 2: A mixture of (±)-2-[4-(methylsulfonyl)phenyl]-5-{[1-(4-piperidinyl)ethyl]oxy}pyridine (0.27 g, 0.75 mmol) in $CH_2Cl_2$ (10 mL) and THF (5 mL) was treated with diisopropylethylamine (0.27 mL, 1.50 mmol). The mixture was cooled to 0° C., and then isopropyl chloroformate (1.0M in toluene, 0.82 mL, 0.82 mmol) was added dropwise. The reaction mixture was allowed to warm to ambient temperature and stirred overnight, diluted with $CH_2Cl_2$ (100 mL) and washed with water, brine and dried over $Na_2SO_4$, filtered, and the filtrate was concentrated to a light brown oil. The crude material was purified by flash chromatography on a silica gel column eluted with 1:5 acetone/$CH_2Cl_2$ to give 0.31 g (93%) of the title compound as a white foam. $^1$H NMR (400 MHz, $CDCl_3$): δ 8.38 (d, 1H, J=2.9 Hz), 8.13 (d, 2H, J=8.5 Hz), 8.01 (d, 2H, J=8.5 Hz), 7.73 (d, 1H, J=8.8 Hz), 7.35-7.25 (m, 1H), 4.91 (septet, 1H, J=6.2 Hz), 4.35-4.15 (m, 3H), 3.08 (s, 3H), 2.80-2.65 (m, 2H), 1.95-1.65 (m, 3H), 1.45-1.25 (m, 5H), 1.23 (d, 6H, J=6.3 Hz); LRMS (ESI), m/z 447 (M+H).

Example 141

1-Methylethyl 4-[(1S)-1-({6-[4-(methylsulfonyl)phenyl]-3-pyridinyl}oxy)ethyl]-1-piperidinecarboxylate

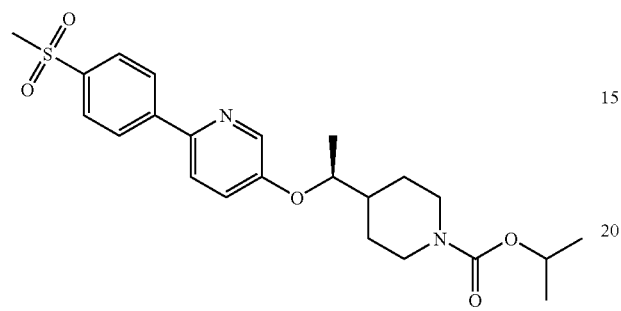

The racemic 1-methylethyl 4-[1-({6-[4-(methylsulfonyl)phenyl]-3-pyridinyl}oxy)ethyl]-1-piperidinecarboxylate (prepared as in Example 140) was subjected to Chiral HPLC [column: AS-H, column mobile phase: 80% CO$_2$: 20% MeOH (2 mL/min), pressure 140 bar, temperature 40° C., 280 nm] analysis and then separated to give two (R and S) enantiomers. The title compound was isolated as a white foam with Tr of 13.23 min (second eluting peak). The (S) absolute stereochemistry was assigned by Ab initio VCD analysis.

Example 142

(±)-1-Methylethyl 4-[1-({6-[4-(methylsulfonyl)phenyl]-3-pyridinyl}oxy)propyl]-1-piperidinecarboxylate

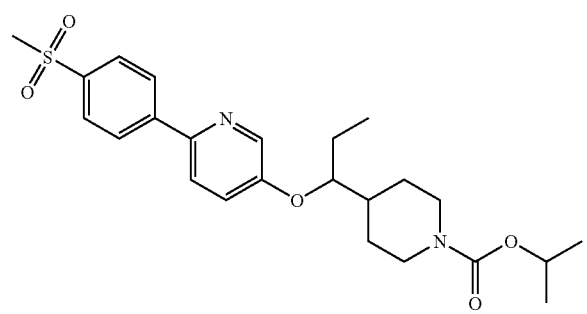

Step 1: (±)-Phenylmethyl 4-[1-({6-[4-(methylsulfonyl)phenyl]-3-pyridinyl}oxy)propyl]-1-piperidinecarboxylate (0.29 g, 18%) was prepared as a white foam from N-(benzyloxycarbonyl)-4-formylpiperidine (1 g, 3.92 mmol) and ethylmagnesium bromide (3M in Et$_2$O, 5.2 mL, 15.6 mmol) in a manner similar to Example 139, Steps 1-4. $^1$H NMR (400 MHz, CDCl$_3$): δ 8.39 (d, 1H, J=2.9 Hz), 8.13 (d, 2H, J=8.3 Hz), 8.01 (d, 2H, J=8.3 Hz), 7.73 (d, 1H, J=8.8 Hz), 7.40-7.25 (m, 6H), 5.12 (s, 2H), 4.26 (bs, 2H), 4.20-4.10 (m, 1H), 3.08 (s, 3H), 2.85-2.65 (m, 2H), 1.95-1.60 (m, 5H), 1.45-1.30 (m, 2H), 0.97 (t, 3H, J=7.5 Hz); LRMS (ESI), m/z 509 (M+H).

Step 2: The title compound (0.147 g, 63%) was prepared as a white foam from (±)-phenylmethyl 4-[1-({6-[4-(methylsulfonyl)phenyl]-3-pyridinyl}oxy)propyl]-1-piperidinecarboxylate (0.26 g, 0.51 mmol) in a manner similar to Example 140, Steps 1-2. The crude product was purified by chromatography on an ISCO silica gel column using 0 to 70% EtOAc/hexanes to give the title compound as a white foam. $^1$H NMR (400 MHz, CDCl$_3$): δ 8.41 (d, 1H, J=2.5 Hz), 8.15 (d, 2H, J=8.1 Hz), 8.03 (d, 2H, J=8.4 Hz), 7.76 (d, 1H, J=8.8 Hz), 7.45-7.30 (m, 1H), 4.90 (septet, 1H, J=6.2 Hz), 4.30-4.10 (m, 3H), 3.09 (s, 3H), 2.80-2.65 (m, 2H), 1.95-1.60 (m, 5H), 1.45-1.25 (m, 2H), 1.23 (d, 6H, J=6.4 Hz), 0.98 (t, 3H, J=7.3 Hz); LRMS (ESI), m/z 461 (M+H).

Example 143

1-Methylethyl 4-[(1R)-1-({6-[4-(methylsulfonyl)phenyl]-3-pyridinyl}oxy)propyl]-1-piperidinecarboxylate

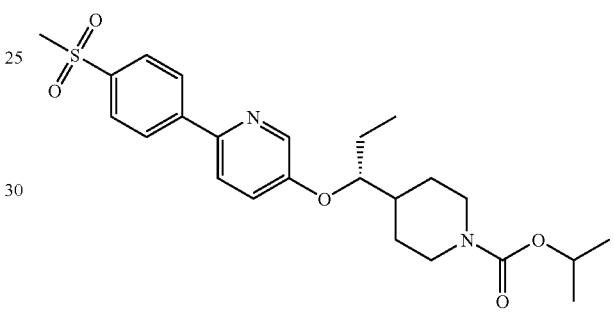

The racemic 1-methylethyl 4-[1-({6-[4-(methylsulfonyl)phenyl]-3-pyridinyl}oxy)propyl]-1-piperidinecarboxylate (prepared as in Example 142) was subjected to Chiral HPLC [column: AS-H, column mobile phase: 80% CO$_2$: 20% MeOH (2 mL/min), pressure 140 bar, temperature 40° C., 215 nm] analysis and then separated to give two (R and S) enantiomers. The title compound was isolated as a white foam with Tr of 10.65 min (first eluting peak). The (R) absolute stereochemistry was assigned by Ab initio VCD analysis.

Example 144

1-Methylethyl 4-[(1S)-1-({6-[4-(methylsulfonyl)phenyl]-3-pyridinyl}oxy)propyl]-1-piperidinecarboxylate

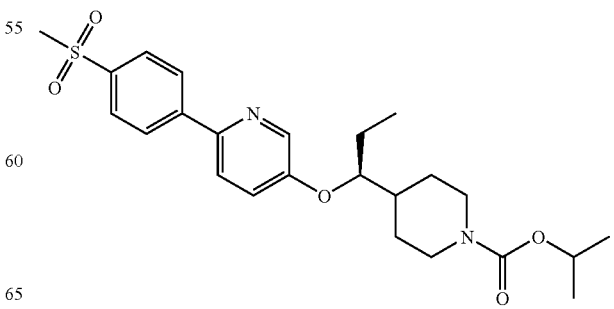

The racemic 1-methylethyl 4-[1-({6-[4-(methylsulfonyl)phenyl]-3-pyridinyl}oxy) propyl]-1-piperidinecarboxylate (prepared as in Example 142) was subjected to Chiral HPLC [column: AS-H, column mobile phase: 80% $CO_2$: 20% MeOH (2 mL/min), pressure 140 bar, temperature 40° C., 215 nm] analysis and then separated to give two (R and S) enantiomers. The title compound was isolated as a white foam with Tr of 14.60 min (second eluting peak). The (S) absolute stereochemistry was assigned by Ab initio VCD analysis.

Example 145

2-[({1-[3-(1-Methylethyl)-1,2,4-oxadiazol-5-yl]-4-piperidinyl}methyl)oxy]-5-[4-(methylsulfonyl)phenyl]pyrazine

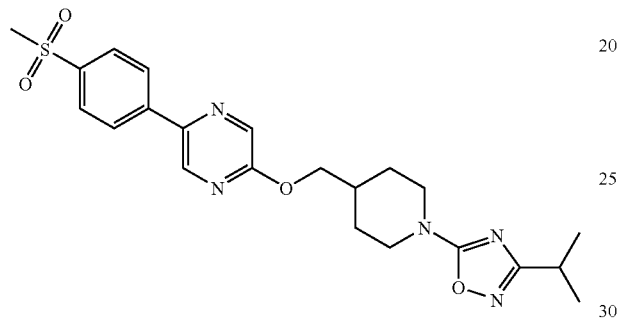

Step 1: A mixture of 2-amino-5-bromopyrazine (0.5 g, 2.79 mmol) and [4-(methylsulfonyl)phenyl]boronic acid (0.57 g, 2.79 mmol) in 1,4-dioxane (10 mL) and MeOH (4 mL) was treated with 2M $Na_2CO_3$ (4 mL) and $Pd(PPh_3)_4$ (65 mg, 0.06 mmol). The reaction mixture was degassed with $N_2$ and heated at 100° C. for 3 h. Most of 1,4-dioxane and MeOH was removed under reduced pressure. Water was added, and the mixture was extracted with EtOAc (50 mL×4). The combined organic extracts were washed with brine, dried over $Na_2SO_4$, filtered, and the filtrate was concentrated to a brown solid, which was triturated with $CH_2Cl_2$ to give 0.465 g (67%) of 5-[4-(methylsulfonyl)phenyl]-2-pyrazinamine as a yellow solid. The filtrate was washed with 1 N HCl (25 mL), and the aqueous layer was separated and basified with 4N NaOH. The mixture was extracted with EtOAc (50 mL×2) and the combined organic extracts were washed with brine, dried over $Na_2SO_4$, filtered, and the filtrate was concentrated to give additional 0.045 g (7%) of 5-[4-(methylsulfonyl)phenyl]-2-pyrazinamine as a yellow solid. $^1$H NMR (400 MHz, DMSO-$d_6$): δ 8.63 (s, 1H), 8.15 (d, 2H, J=8.5 Hz), 7.97 (s, 1H), 7.91 (d, 2H, J=8.5 Hz), 6.81 (s, 2H), 3.20 (s, 3H); LRMS (ESI), m/z 250 (M+H).

Step 2: $NaNO_2$ (0.20 g, 2.76 mmol) was added in portions to concentrated $H_2SO_4$ (1.4 mL) at 0° C. The mixture was heated at 50° C. until all of the $NaNO_2$ had dissolved and the mixture was again cooled to 0° C. A solution of 5-[4-(methylsulfonyl)phenyl]-2-pyrazinamine (0.51 g, 2.05 mmol) in concentrated $H_2SO_4$ (4.2 mL) was added dropwise to the nitronium solution. The ice bath was removed, and the mixture was warmed to ambient temperature and stirred for 15 min, then heated to 45° C. for 30 min. The mixture was cooled to ambient temperature and poured into ice water. The pH was adjusted to about 4 with 4N NaOH and the solid was collected, washed with water, and air dried to give 0.415 g (81%) of 5-[4-(methylsulfonyl)phenyl]-2-pyrazinol (and tautomers thereof) as a brown solid. $^1$H NMR (400 MHz, DMSO-$d_6$): δ 12.77 (bs, 1H), 8.30-8.05 (m, 4H), 7.92 (d, 2H, J=8.6 Hz), 3.21 (s, 3H); LRMS (ESI), m/z 251 (M+H).

Step 3: A mixture of 5-[4-(methylsulfonyl)phenyl]-2-pyrazinol (and tautomers thereof) (0.15 g, 0.60 mmol), {1-[3-(1-methylethyl)-1,2,4-oxadiazol-5-yl]-4-piperidinyl}methyl methanesulfonate (prepared as in Example 100, Step 4, except that on small scale no heptane wash was performed, 0.25 g, 0.81 mmol) and $K_2CO_3$ (0.17 g, 1.20 mmol) in DMF (6 mL) was stirred at ambient temperature overnight, then heated at 100° C. for 5 h. The mixture was cooled to ambient temperature, water was added, and the mixture was extracted with EtOAc (60 mL×2). The combined organic extracts were washed with water, brine and dried over $Na_2SO_4$, filtered, and the filtrate was concentrated to a brown solid. The crude material was purified by chromatography on a silica gel column eluted with 1:20 acetone/$CH_2Cl_2$ to 1:15 acetone/$CH_2Cl_2$ to give 0.14 g (51%) of the title compound as a white solid. $^1$H NMR (400 MHz, CDCl$_3$): δ 8.55 (d, 1H, J=0.9 Hz), 8.31 (s, 1H), 8.11 (d, 2H, J=8.6 Hz), 8.02 (d, 2H, J=8.6 Hz), 4.30-4.20 (m, 4H), 3.10-3.05 (m, 5H), 2.91 (septet, 1H, J=7.0 Hz), 2.10-2.00 (m, 1H), 2.00-1.90 (m, 2H), 1.55-1.40 (m, 2H), 1.27 (d, 6H, J=6.6 Hz); LRMS (ESI), m/z 458 (M+H).

Example 146

(±)-5-[(1-{1-[3-(1-Methylethyl)-1,2,4-oxadiazol-5-yl]-4-piperidinyl}ethyl)oxy]-2-[4-(methylsulfonyl)phenyl]pyridine

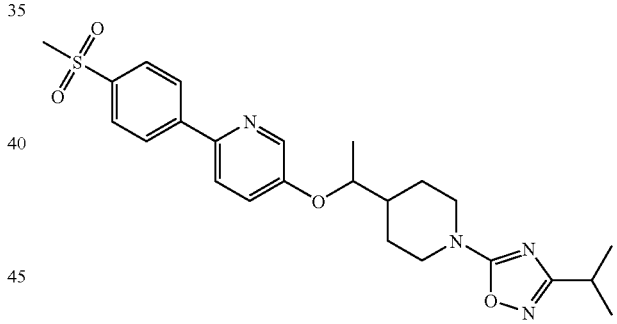

Step 1: A solution of {1-[3-(1-methylethyl)-1,2,4-oxadiazol-5-yl]-4-piperidinyl}methanol (prepared as in Example 20, Step 3, 1.50 g, 6.33 mmol) in $CH_2Cl_2$ (30 mL) was treated with pyridinium chlorochromate (2.09 g, 9.49 mmol). The reaction mixture was stirred at ambient temperature for 5 h. $Et_2O$ (50 mL) was added, and the mixture was stirred for 10 min, filtered through a plug of Celite® on top of a layer of silica gel and the filtrate was concentrated. The resulting brown residue was mixed with $Et_2O$ (100 mL) and filtered. The filtrate was dried over $Na_2SO_4$, filtered and concentrated to give 1.10 g (78%) of 1-[3-(1-methylethyl)-1,2,4-oxadiazol-5-yl]-4-piperidinecarbaldehyde as a light brown oil which was used without further purification. $^1$H NMR (400 MHz, CDCl$_3$): δ 9.69 (s, 1H), 4.15-4.00 (m, 2H), 3.30-3.20 (m, 2H), 2.88 (septet, 1H, J=7.0 Hz), 2.55-2.45 (m, 1H), 2.10-1.95 (m, 2H), 1.80-1.65 (m, 2H), 1.27 (d, 6H, J=6.9 Hz).

Step 2: A solution of 1-[3-(1-methylethyl)-1,2,4-oxadiazol-5-yl]-4-piperidinecarbaldehyde (1.1 g, 4.93 mmol) in THF (25 mL) at −10° C. was treated dropwise with methylmagnesium bromide (3M in Et$_2$O, 3.94 mL, 11.8 mmol). The mixture was stirred at −10° C. to −5° C. over a 2 h period. The reaction was carefully quenched by the addition of saturated aqueous NH$_4$Cl and the aqueous was extracted with ether (6 mL×2). The combined organic extracts were washed with brine, dried over Na$_2$SO$_4$ and concentrated. The crude material was purified by chromatography on a silica gel column eluted with 0 to 70% EtOAc/hexanes to give 0.39 g (33%) of (±)-1-{1-[3-(1-methylethyl)-1,2,4-oxadiazol-5-yl]-4-piperidinyl}ethanol as a light yellow oil.

Step 3: A solution of (±)-1-{1-[3-(1-methylethyl)-1,2,4-oxadiazol-5-yl]-4-piperidinyl}ethanol (0.39 g) in CH$_2$CH$_2$ (35 mL) at 0° C. was treated with methanesulfonyl chloride (0.26 mL, 3.26 mmol) and Et$_3$N (0.69 mL, 4.89 mmol) and stirred at 0° C. for 1 h then room temperature for 15 h. The mixture was diluted with CH$_2$CH$_2$ (80 mL), washed with 1M NaH$_2$PO$_4$ (50 mL×2) and brine (35 mL), and dried over Na$_2$SO$_4$ and concentrated to afford crude (±)-1-{1-[3-(1-methylethyl)-1,2,4-oxadiazol-5-yl]-4-piperidinyl}ethyl methanesulfonate (0.53 g, 100%) as a light brown oil. The crude product was used without further purification. $^1$H NMR (400 MHz, CDCl$_3$): δ 4.75-4.65 (m, 1H), 4.30-4.15 (m, 2H), 3.10-2.95 (m, 5H), 2.89 (septet, 1H, J=7.0 Hz), 1.95-1.70 (m, 3H), 1.55-1.35 (m, 5H), 1.28 (d, 6H, J=6.9 Hz).

Step 4: (4-Methylsulfonylphenyl)boronic acid (4.40 g, 21.55 mmol) was added to a solution of 6-bromo-3-pyridinol (2.5 g, 14.37 mmol) in DME (125 mL), followed by addition of 2M Na$_2$CO$_3$ (75 mL) and Pd(PPh$_3$)$_4$ (0.83 g, 0.72 mmol). The reaction mixture was degassed with N$_2$ and heated at 80° C. overnight, then cooled to ambient temperature. Water (50 mL), 1N NaOH (50 mL), brine (50 mL) and CH$_2$Cl$_2$ (150 mL) were added. The CH$_2$Cl$_2$ layer was separated and the aqueous layer was washed with CH$_2$Cl$_2$ (100 mL). The combined CH$_2$Cl$_2$ extract was further washed with a mixture of water (50 mL), 1N NaOH (50 mL) and brine (50 mL). The aqueous layers were combined and washed with CH$_2$Cl$_2$ (100 mL), neutralized with concentrated HCl and extracted with EtOAc (250 mL×2). The combined EtOAc extract was filtered through celite on top of a layer of silica gel, which was further washed with EtOAc (100 mL). The EtOAc filtrate was washed with brine and dried over Na$_2$SO$_4$, filtered, and concentrated to a light yellow solid, which was triturated with small amount of hot MeOH to give 2.20 g (61%) of 6-[4-(methylsulfonyl)phenyl]-3-pyridinol as a white solid.

Step 5: The title compound (0.295 g, 54%) was prepared as a white foam from 6-[4-(methylsulfonyl)phenyl]-3-pyridinol (0.29 g, 1.16 mmol), (±)-1-{1-[3-(1-methylethyl)-1,2,4-oxadiazol-5-yl]-4-piperidinyl}ethyl methanesulfonate (0.53 g, crude), K$_2$CO$_3$ (0.32 g, 2.32 mmol) in DMF (10 mL) in a manner similar to Example 139, Step 3. The crude material was purified by chromatography on a silica gel column eluted with 1:7 acetone/CH$_2$Cl$_2$ to give the title compound as a white foam. $^1$H NMR (400 MHz, CDCl$_3$): δ 8.38 (d, 1H, J=3.0 Hz), 8.13 (d, 2H, J=8.5 Hz), 8.00 (d, 2H, J=8.6 Hz), 7.74 (d, 1H, J=8.8 Hz), 7.35-7.25 (m, 1H), 4.35-4.25 (m, 1H), 4.25-4.15 (m, 2H), 3.10-3.00 (m, 5H), 2.87 (septet, 1H, J=7.0 Hz), 2.05-1.95 (m, 1H), 1.95-1.75 (m, 2H), 1.40-1.20 (m, 2H), 1.34 (d, 3H, J=6.3 Hz), 1.27 (d, 6H, J=6.9 Hz); LRMS (ESI), m/z 471 (M+H).

Example 147

5-[((1R)-1-{1-[3-(1-Methylethyl)-1,2,4-oxadiazol-5-yl]-4-piperidinyl}ethyl)oxy]-2-[4-(methylsulfonyl)phenyl]pyridine

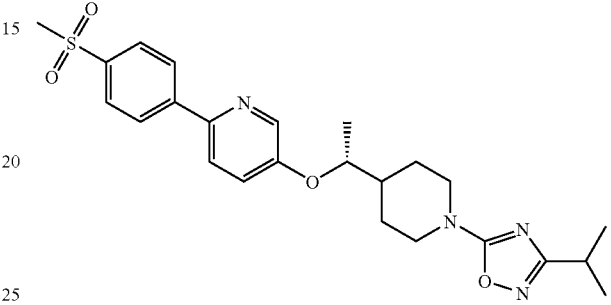

The racemic 5-[(1-{1-[3-(1-methylethyl)-1,2,4-oxadiazol-5-yl]-4-piperidinyl}ethyl)oxy]-2-[4-(methylsulfonyl)phenyl]pyridine (prepared as in Example 146) was subjected to Chiral HPLC [column: AS-H, column mobile phase: 75% CO$_2$: 25% MeOH (2 mL/min), pressure 140 bar, temperature 40° C., 215 nm] analysis and then separated to give two (R and S) enantiomers. The title compound was isolated as a white foam with Tr of 10.25 min (first eluting peak). The (R) absolute stereochemistry was assigned by Ab initio VCD analysis.

Example 148

5-[((1S)-1-{1-[3-(1-Methylethyl)-1,2,4-oxadiazol-5-yl]-4-piperidinyl}ethyl)oxy]-2-[4-(methylsulfonyl)phenyl]pyridine

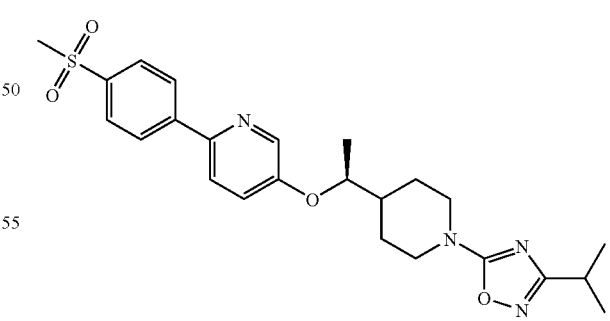

The racemic 5-[(1-{1-[3-(1-methylethyl)-1,2,4-oxadiazol-5-yl]-4-piperidinyl}ethyl)oxy]-2-[4-(methylsulfonyl)phenyl]pyridine (prepared as in Example 146) was subjected to Chiral HPLC [column: AS-H, column mobile phase: 75% CO$_2$: 25% MeOH (2 mL/min), pressure 140 bar, temperature 40° C., 215 nm] analysis and then separated to give two (R and S) enantiomers. The title compound was isolated as a white foam with Tr of 14.89 min (second eluting peak). The (S) absolute stereochemistry was assigned by Ab initio VCD analysis.

Comparative Example 149

1-Methylethyl 4-{[(2'-fluoro-6'-methyl-2,3'-bipyridin-5-yl)oxy]methyl}-1-piperidinecarboxylate

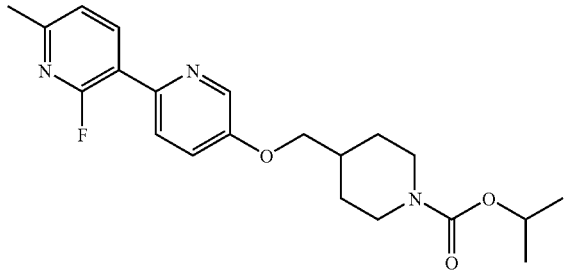

Step 1: 1,1-Dimethylethyl 4-{[(2'-fluoro-6'-methyl-2,3'-bipyridin-5-yl)oxy]methyl}-1-piperidinecarboxylate (0.21 g, 72%) was prepared as an off-white solid from 2-fluoro-6-picoline-3-boronic acid (0.14 g, 0.87 mmol), 1,1-dimethylethyl 4-{[(6-bromo-3-pyridinyl)oxy]methyl}-1-piperidinecarboxylate (prepared as in Example 76, Step 1, 0.27 g, 0.72 mmol), 2M $Na_2CO_3$ (2.5 mL) and $PdCl_2(PPh_3)_2$ (26 mg, 0.04 mmol) DME (8 mL) in a manner similar to Example 21, Step 3. The crude material was purified by chromatography on a silica gel column eluted with 1:10 acetone/$CH_2Cl_2$ to give 1,1-dimethylethyl 4-{[(2'-fluoro-6'-methyl-2,3'-bipyridin-5-yl)oxy]methyl}-1-piperidine carboxylate as an off-white solid. $^1$H NMR (400 MHz, $CDCl_3$): δ 8.45-8.35 (m, 2H), 7.81 (d, 1H, J=8.0 Hz), 7.30-7.25 (m, 1H), 7.15-7.10 (m, 1H), 4.16 (bs, 2H), 3.88 (d, 2H, J=6.4 Hz), 2.80-2.65 (m, 2H), 2.53 (s, 3H), 2.10-1.90 (m, 1H), 1.90-1.80 (m, 2H), 1.45 (s, 9H), 1.35-1.20 (m, 2H); LRMS (ESI), m/z 402 (M+H).

Step 2: The title compound (0.166 g, 96%) was prepared as a white solid from 1,1-dimethylethyl 4-{[(2'-fluoro-6'-methyl-2,3'-bipyridin-5-yl)oxy]methyl}-1-piperidinecarboxylate (0.18 g, 0.45 mmol) and TFA (0.35 mL) in $CH_2Cl_2$ (10 mL) then diisopropylethylamine (2.0 mL) and isopropyl chloroformate (1.0M in toluene, 0.54 mL, 0.54 mmol) in a manner similar to Example 74. The crude material was purified by chromatography on a silica gel column eluted with 1:10 acetone/$CH_2Cl_2$ to give the title compound as a white solid. $^1$H NMR (400 MHz, $CDCl_3$): δ 8.45-8.35 (m, 2H), 7.82 (d, 1H, J=8.6 Hz), 7.30-7.25 (m, 1H), 7.20-7.10 (m, 1H), 4.91 (septet, 1H, J=6.3 Hz), 4.22 (bs, 2H), 3.89 (d, 2H, J=6.4 Hz), 2.85-2.70 (m, 2H), 2.53 (s, 3H), 2.10-1.95 (m, 1H), 1.90-1.80 (m, 2H), 1.40-1.20 (m, 8H); LRMS (ESI), m/z 388 (M+H).

Example 150

2-Fluoroethyl 4-[({6-[4-(methylsulfonyl)phenyl]-3-pyridinyl}oxy)methyl]-1-piperidinecarboxylate

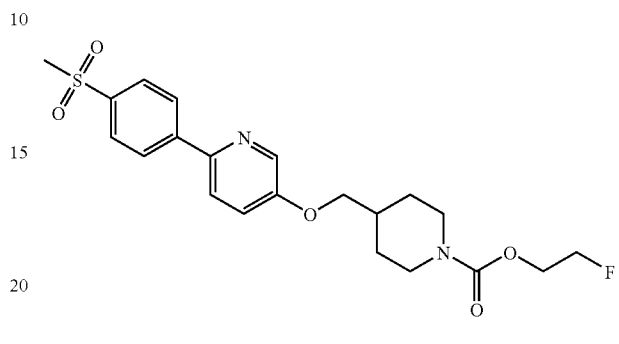

Step 1: A mixture of N-Boc-4-piperidinemethanol (1.0 g, 4.51 mmol), $Et_3N$ (1.30 mL, 9.01 mmol) in $CH_2Cl_2$ (20 mL) at 0° C. was treated dropwise with methanesulfonyl chloride (0.39 mL, 4.96 mmol). The reaction mixture was stirred at 0° C. to 5° C. for 1.5 h, was diluted with $CH_2Cl_2$ (100 mL) and washed with 1M $NaH_2PO_4$ (50 mL×2) and brine (25 mL). The $CH_2Cl_2$ layer was dried over $Na_2SO_4$, filtered, and the filtrate was concentrated to a brown oil, which solidified upon cooling to give 1.35 g (100%) of 1,1-dimethylethyl 4-{[(methylsulfonyl)oxy]methyl}-1-piperidinecarboxylate as a brown solid, which was used without further purification. $^1$H NMR (400 MHz, $CDCl_3$): δ 4.20-4.10 (m, 2H), 4.04 (d, 2H, J=6.5 Hz), 2.99 (s, 3H), 2.75-2.60 (m, 2H), 1.95-1.85 (m, 1H), 1.75-1.65 (m, 2H), 1.43 (s, 9H), 1.30-1.10 (m, 2H).

Step 2: 1,1-Dimethylethyl 4-[({6-[4-(methylsulfonyl)phenyl]-3-pyridinyl}oxy)methyl]-1-piperidinecarboxylate (0.34 g, 95%) was prepared as a white solid from 6-[4-(methylsulfonyl)phenyl]-3-pyridinol (Example 146, Step 4, 0.20 g, 0.80 mmol), 1,1-dimethylethyl 4-{[(methylsulfonyl)oxy]methyl}-1-piperidinecarboxylate (0.33 g, 1.12 mmol), $K_2CO_3$ (0.23 g, 1.60 mmol) in DMF (7 mL) in a manner similar to Example 139, Step 3. The reaction mixture was cooled to ambient temperature, and poured into water (50 mL). The precipitate was collected and washed with water, air dried to give 1,1-dimethylethyl 4-[({6-[4-(methylsulfonyl)phenyl]-3-pyridinyl}oxy)methyl]-1-piperidinecarboxylate as a white solid. $^1$H NMR (400 MHz, $CDCl_3$): δ 8.40 (bs, 1H), 8.14 (d, 2H, J=7.5 Hz), 8.01 (d, 2H, J=7.3 Hz), 7.80-7.70 (m, 1H), 7.34 (bs, 1H), 4.18 (bs, 2H), 3.91 (d, 2H, J=6.1 Hz), 3.07 (s, 3H), 2.85-2.65 (m, 2H), 2.10-1.95 (m, 1H), 1.90-1.80 (m, 2H), 1.45 (s, 9H), 1.40-1.20 (m, 2H); LRMS (ESI), m/z 447 (M+H).

Step 3: The title compound (0.105 g, 90%) was prepared as a white solid from 1,1-dimethylethyl 4-[({6-[4-(methylsulfonyl)phenyl]-3-pyridinyl}oxy)methyl]-1-piperidinecarboxylate (0.12 g, 0.27 mmol) and TFA (0.20 mL) in $CH_2Cl_2$ (6 mL) then diisopropylethylamine (1.2 mL) and 2-fluoroethyl chloroformate (42 μL, 0.32 mmol) in a manner similar to Example 74. The crude material was purified by chromatography on a silica gel column eluted with 1:7 acetone/$CH_2Cl_2$ to give the title compound as a white solid. $^1$H NMR (400 MHz, $CDCl_3$): δ 8.39 (d, 1H, J=2.7 Hz), 8.13 (d, 2H, J=8.3 Hz), 8.00 (d, 2H, J=8.5 Hz), 7.73 (d, 1H, J=8.8 Hz), 7.35-7.25 (m, 1H, 4.70-4.55 (m, 2H), 4.40-4.15 (m, 4H), 3.91 (d, 2H, J=6.4 Hz), 3.06

(s, 3H), 2.84 (bs, 2H), 2.10-1.95 (m, 1H), 1.95-1.80 (m, 2H), 1.40-1.25 (m, 2H); LRMS (ESI), m/z 437 (M+H).

Example 151

5-Fluoro-2-{4-[({6-[4-(methylsulfonyl)phenyl]-3-pyridinyl}oxy)methyl]-1-piperidinyl}pyrimidine

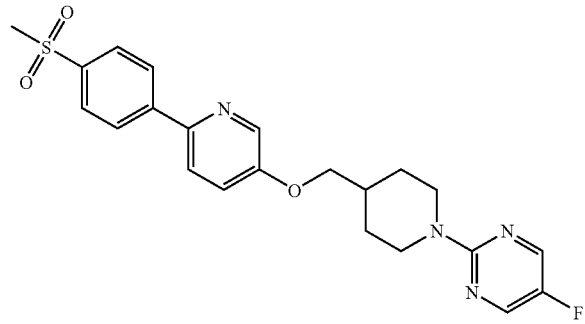

The title compound (91 mg, 84%) was prepared as a white solid from 1,1-dimethylethyl 4-[({6-[4-(methylsulfonyl)phenyl]-3-pyridinyl}oxy)methyl]-1-piperidinecarboxylate (prepared as in Example 150, Step 2, 0.11 g, 0.25 mmol) and TFA (0.20 mL) in CH$_2$Cl$_2$ (6 mL) then K$_2$CO$_3$ (0.75 g) and 2-chloro-5-fluoropyrimidine (47 µL, 0.27 mmol) in DMSO (5 mL) in a manner similar to Example 80. The crude material was purified by chromatography on a silica gel column eluted with 1:15 acetone/CH$_2$Cl$_2$ to give the title compound as a white solid. $^1$H NMR (400 MHz, CDCl$_3$): δ 8.42 (d, 1H, J=2.7 Hz), 8.18 (s, 2H), 8.14 (d, 2H, J=8.3 Hz), 8.02 (d, 2H), J=8.3 Hz), 7.76 (d, 1H, J=8.8 Hz), 7.45-7.35 (m, 1H), 4.80-4.70 (m, 2H), 3.94 (d, 2H, J=6.1 Hz), 3.07 (s, 3H), 3.00-2.85 (m, 2H), 2.10-2.05 (m, 1H), 2.00-1.90 (m, 2H), 1.45-1.30 (m, 2H); LRMS (ESI), m/z 443 (M+H).

Example 152

5-Fluoro-2-{4-[({5-[4-(methylsulfonyl)phenyl]-2-pyrazinyl}oxy)methyl]-1-piperidinyl}pyrimidine

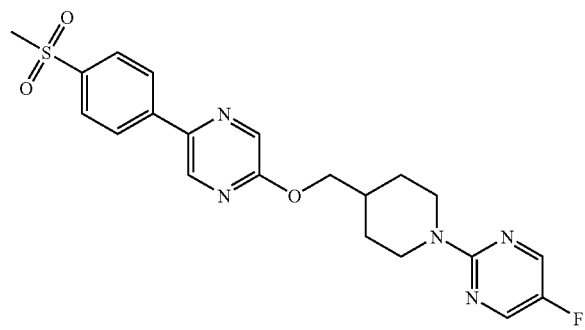

Step 1: A solution of 2-chloro-5-fluoropyrimidine (1.1 g, 8.05 mmol) and 4-piperidinemethanol (1.14 g, 9.66 mmol) in DMSO (20 mL) was treated with K$_2$CO$_3$ (2.23 g, 16.10 mmol). The reaction mixture was heated at 100° C. overnight. The mixture was cooled to ambient temperature and poured into water and extracted with CH$_2$Cl$_2$ (60 mL×3). The organic extracts were combined and washed with brine, dried over Na$_2$SO$_4$, filtered, and the filtrate was concentrated to give crude product as a brown oil. The crude product was purified by chromatography on an ISCO silica gel column using 0 to 40% EtOAc/hexanes to give 1.62 g (95%) of [1-(5-fluoro-2-pyrimidinyl)-4-piperidinyl]methanol as a white solid upon standing. $^1$H NMR (400 MHz, CDCl$_3$): δ 8.18 (s, 2H), 4.75-4.65 (m, 2H), 3.51 (d, 2H, J=6.1 Hz), 2.95-2.80 (m, 2H), 1.85-1.70 (m, 3H), 1.30-1.15 (m, 2H); LRMS (ESI), m/z 212 (M+H).

Step 2: [1-(5-Fluoro-2-pyrimidinyl)-4-piperidinyl]methyl methanesulfonate (0.235 g, 89%) was prepared as a white solid from 1-[1-(5-fluoro-2-pyrimidinyl)-4-piperidinyl] methanol (isolated as a by-product in the methyl Grignard addition step in Example 153, Step 2, but could also be prepared as in Step 1 above, 0.192 g, 0.91 mmol), methanesulfonyl chloride (0.09 mL, 1.09 mmol), Et$_3$N (0.26 mL, 1.82 mmol) and CH$_2$Cl$_2$ (15 mL) in a manner similar to Example 150, Step 1. The crude product was purified by chromatography on an ISCO silica gel column using 0 to 45% EtOAc/hexanes. $^1$H NMR (400 MHz, CDCl$_3$): δ 8.18 (s, 2H), 4.75-4.65 (m, 2H), 4.07 (d, 2H, J=6.3 Hz), 3.00 (s, 3H), 2.95-2.80 (m, 2H), 2.10-1.95 (m, 1H), 1.90-1.80 (m, 2H), 1.35-1.20 (m, 2H); LRMS (ESI), m/z 290 (M+H).

Step 3: A mixture of 5-[4-(methylsulfonyl)phenyl]-2-pyrazinol (and tautomers thereof) (prepared as in Example 145, Step 2, 0.15 g, 0.60 mmol), [1-(5-fluoro-2-pyrimidinyl)-4-piperidinyl]methyl methanesulfonate (0.234 g, 0.81 mmol) and K$_2$CO$_3$ (0.17 g, 1.20 mmol) in DMF (6 mL) was stirred at 100° C. in a preheated oil bath for 2.5 h. The mixture was cooled to ambient temperature, treated with water, and the mixture was extracted with EtOAc (60 mL×2). The combined organic extracts were washed with water, brine and dried over Na$_2$SO$_4$, filtered, and the filtrate was concentrated to give crude product as a light brown solid. The crude product was purified by chromatography on a silica gel column eluted with 1:30 acetone/CH$_2$Cl$_2$ then 1:20 acetone/CH$_2$Cl$_2$ to give 0.132 g (50%) of the title compound as a white solid. $^1$H NMR (400 MHz, CDCl$_3$): δ 8.55 (s, 1H), 8.30 (s, 1H), 8.18 (s, 2H), 8.11 (d, 2H, J=8.0 Hz), 8.02 (d, 2H, J=8.1 Hz), 4.80-4.65 (m, 2H), 4.25 (d, 2H, J=6.6 Hz), 3.07 (s, 3H), 3.00-2.85 (m, 2H), 2.10-2.05 (m, 1H), 2.00-1.85 (m, 2H), 1.45-1.30 (m, 2H); LRMS (ESI), m/z 444 (M+H).

Example 153

(±)-5-Fluoro-2-{4-[1-({6-[4-(methylsulfonyl)phenyl]-3-pyridinyl}oxy)ethyl]-1-piperidinyl}pyrimidine

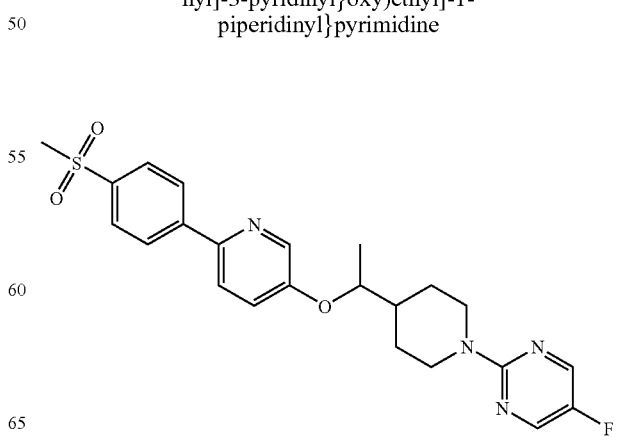

Step 1: 1-(5-Fluoro-2-pyrimidinyl)-4-piperidinecarbaldehyde (0.96 g, 60%) was prepared as a white solid from [1-(5-fluoro-2-pyrimidinyl)-4-piperidinyl]methanol (prepared as in Example 152, Step 1, 1.62 g, 7.67 mmol) and PCC (pyridinium chlorochromate, 2.53 g, 11.50 mmol) in $CH_2Cl_2$ (36 mL) in a manner similar to Example 146, Step 1. The crude product was purified by chromatography on an ISCO silica gel column using 0 to 20% EtOAc/hexanes to give 1-(5-fluoro-2-pyrimidinyl)-4-piperidinecarbaldehyde as a white solid. $^1$H NMR (400 MHz, $CDCl_3$): δ 9.68 (s, 1H), 8.20 (s, 2H), 4.55-4.45 (m, 2H), 3.25-3.10 (m, 2H), 2.60-2.45 (m, 1H), 2.05-1.90 (m, 2H), 1.70-1.55 (m, 2H); LRMS (ESI), m/z 210 (M+H).

Step 2: (±)-1-[1-(5-Fluoro-2-pyrimidinyl)-4-piperidinyl] ethyl methanesulfonate (0.24 g) was prepared as a colorless oil from 1-(5-fluoro-2-pyrimidinyl)-4-piperidinecarbaldehyde and methylmagnesium bromide (3M in $Et_2O$) then methanesulfonyl chloride and $Et_3N$ in a manner similar to Example 139, Steps 1-2. The crude product was purified by chromatography on an ISCO silica gel column using 0 to 40% EtOAc/hexanes to give (±)-1-[1-(5-fluoro-2-pyrimidinyl)-4-piperidinyl]ethyl methanesulfonate as a colorless oil. $^1$H NMR (400 MHz, $CDCl_3$): δ 8.17 (s, 2H), 4.80-4.70 (m, 2H), 4.70-4.60 (m, 1H), 2.99 (s, 3H), 2.90-2.75 (m, 2H), 1.95-1.70 (m, 3H), 1.40 (d, 3H, J=6.3 Hz), 1.35-1.25 (m, 2H); LRMS (ESI), m/z 304 (M+H).

Step 3: The title compound (0.184 g, 51%) was prepared as a white solid from 6-[4-(methylsulfonyl)phenyl]-3-pyridinol (Example 146, Step 3, 0.16 g, 0.63 mmol), (±)-1-[1-(5-fluoro-2-pyrimidinyl)-4-piperidinyl]ethyl methanesulfonate (0.24 g, 0.79 mmol) and $K_2CO_3$ (0.18 g, 1.27 mmol) in DMF (6 mL) in a manner similar to Example 152, Step 3. The crude product was purified by chromatography on an ISCO silica gel column using 0 to 55% EtOAc/hexanes to give the title compound as a white solid. $^1$H NMR (400 MHz, $CDCl_3$): δ 8.37 (d, 1H, J=2.9 Hz), 8.17 (s, 2H), 8.12 (d, 2H, J=8.3 Hz), 8.00 (d, 2H, J=8.3 Hz), 7.72 (d, 1H, J=8.8 Hz), 7.35-7.25 (m, 1H), 4.80-4.70 (m, 2H), 4.35-4.25 (m, 1H), 3.07 (s, 3H), 2.95-2.80 (m, 2H), 2.05-1.75 (m, 3H), 1.45-1.25 (m, 5H); LRMS (ESI), m/z 457 (M+H).

Example 154

5-Fluoro-2-{4-[(1S)-1-({6-[4-(methylsulfonyl)phenyl]-3-pyridinyl}oxy)ethyl]-1-piperidinyl}pyrimidine

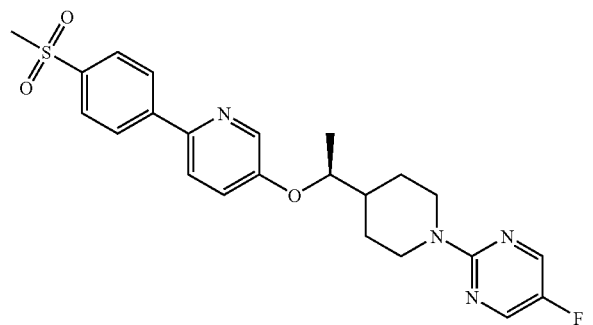

The racemic 5-fluoro-2-{4-[1-({6-[4-(methylsulfonyl)phenyl]-3-pyridinyl}oxy)ethyl]-1-piperidinyl}pyrimidine (prepared as in Example 153) was subjected to Chiral HPLC [column: OJ-H, column mobile phase: 70% $CO_2$: 30% MeOH (2 mL/min), pressure 140 bar, temperature 40° C., 215 nm] analysis and then separated to give two (R and S) enantiomers. The title compound was isolated as an off-white solid with Tr of 21.34 min (first eluting peak). The (S) absolute stereochemistry was assigned by Ab initio VCD analysis.

Example 155

5-Fluoro-2-{4-[(1R)-1-({6-[4-(methylsulfonyl)phenyl]-3-pyridinyl}oxy)ethyl]-1-piperidinyl}pyrimidine

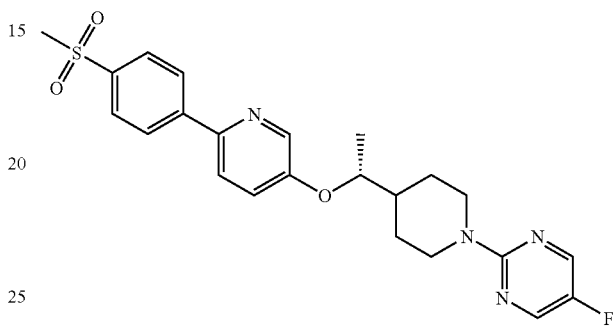

The racemic 5-fluoro-2-{4-[1-({6-[4-(methylsulfonyl)phenyl]-3-pyridinyl}oxy)ethyl]-1-piperidinyl}pyrimidine (prepared as in Example 153) was subjected to Chiral HPLC [column: OJ-H, column mobile phase: 70% $CO_2$: 30% MeOH (2 mL/min), pressure 140 bar, temperature 40° C., 254 nm] analysis and then separated to give two (R and S) enantiomers. The title compound was isolated as an off-white solid with Tr of 30.59 min (second eluting peak). The (R) absolute stereochemistry was assigned by Ab initio VCD analysis.

Example 156

(±)-2-[(1-{1-[3-(1-Methylethyl)-1,2,4-oxadiazol-5-yl]-4-piperidinyl}ethyl)oxy]-5-[4-(methylsulfonyl)phenyl]pyrazine

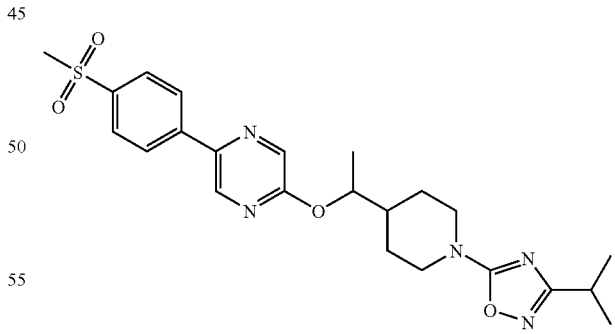

Step 1: A solution of 3-(1-methylethyl)-5-(trichloromethyl)-1,2,4-oxadiazole (prepared as in Example 158, Alternative synthesis, Step 3, 179 g, 0.78 mol) in MeOH (300 mL) was treated with 4-piperidinemethanol (108 g, 0.94 mol) and stirred and heated at 50° C. overnight. The solvent was removed and the residue was purified by flash chromatography on a silica gel column to give {1-[3-(1-methylethyl)-1,2,4-oxadiazol-5-yl]-4-piperidinyl}methanol (60 g, 34%) as a pale yellow oil.

Step 2: A solution of {1-[3-(1-methylethyl)-1,2,4-oxadiazol-5-yl]-4-piperidinyl}methanol (1.50 g, 6.66 mmol) in CH₂Cl₂ (50 mL) at 0° C. was treated with Dess-Martin periodinane (2.91 g, 6.66 mmol). The reaction mixture was warmed to ambient temperature and stirred overnight. The reaction was quenched with aqueous 20% $Na_2S_2O_3$ (100 mL) and aqueous saturated $NaHCO_3$ (100 mL) and then stirred for 10 minutes. The CH₂Cl₂ layer was separated and washed with brine, dried over $Na_2SO_4$, filtered, and the filtrate was concentrated to give the crude product as a cloudy colorless oil. The crude product was dissolved in 100 mL of 1:1 EtOAc/hexanes, filtered through a pad of silica gel, washed with 200 mL of 1:1 EtOAc/hexanes. The filtrate was concentrated to give 1.07 g (72%) of 1-[3-(1-methylethyl)-1,2,4-oxadiazol-5-yl]-4-piperidinecarbaldehyde as a clear colorless oil, which was used without further purification. ¹H NMR (400 MHz, CDCl₃): δ 9.68 (s, 1H), 4.15-4.00 (m, 2H), 3.30-3.20 (m, 2H), 2.86 (septet, 1H, J=7.0 Hz), 2.55-2.45 (m, 1H), 2.10-1.95 (m, 2H), 1.80-1.65 (m, 2H), 1.26 (d, 6H, J=6.8 Hz).

Step 3: (±)-1-{1-[3-(1-Methylethyl)-1,2,4-oxadiazol-5-yl]-4-piperidinyl}ethyl methanesulfonate (0.74 g, 49%) was prepared as a light brown oil from 1-[3-(1-methylethyl)-1,2,4-oxadiazol-5-yl]-4-piperidinecarbaldehyde (1.07 g, 4.79 mmol) and methylmagnesium bromide (3M in Et₂O, 3.51 mL, 10.54 mmol) then methanesulfonyl chloride (0.22 mL, 2.81 mmol) and Et₃N (0.66 mL, 4.68 mmol) in a manner similar to Example 139, Steps 1-2. The crude product was used without further purification. ¹H NMR (400 MHz, CDCl₃): δ 4.70-4.60 (m, 1H), 4.30-4.15 (m, 2H), 3.10-2.95 (m, 5H), 2.87 (septet, 1H, J=7.0 Hz), 1.95-1.70 (m, 3H), 1.55-1.35 (m, 5H), 1.26 (d, 6H, J=6.8 Hz).

Step 4: The title compound (0.212 g, 26%) was prepared as a white foam from 5-[4-(methylsulfonyl)phenyl]-2-pyrazinol (and tautomers thereof) (prepared as in Example 145, Steps 1-2, 0.43 g, 1.72 mmol), (±)-1-{1-[3-(1-methylethyl)-1,2,4-oxadiazol-5-yl]-4-piperidinyl}ethyl methanesulfonate (0.74 g, 2.32 mmol) and $K_2CO_3$ (0.48 g, 3.44 mmol) in DMF (15 mL) in a manner similar to Example 152, Steps 3. The crude product was purified by chromatography on an ISCO silica gel column using 0 to 25% EtOAc/CH₂Cl₂, followed by chromatography on a silica gel column eluted with 50% EtOAc/hexanes to give (±)-2-[(1-{1-[3-(1-methylethyl)-1,2,4-oxadiazol-5-yl]-4-piperidinyl}ethyl)oxy]-5-[4-(methylsulfonyl)phenyl]pyrazine as a white solid. ¹H NMR (400 MHz, CDCl₃): δ 8.53 (s, 1H), 8.25 (s, 1H), 8.10 (d, 2H, J=8.5 Hz), 8.02 (d, 2H, J=8.5 Hz), 5.20-5.10 (m, 1H), 4.35-4.20 (m, 2H), 3.15-3.00 (m, 5H), 2.91 (septet, 1H, J=7.0 Hz), 2.00-1.80 (m, 3H), 1.60-1.40 (m, 2H), 1.34 (d, 3H, J=6.1 Hz), 1.28 (d, 6H, J=7.1 Hz); LRMS (ESI), m/z 472 (M+H).

Example 157

2-[((1R)-1-{1-[3-(1-Methylethyl)-1,2,4-oxadiazol-5-yl]-4-piperidinyl}ethyl)oxy]-5-[4-(methylsulfonyl)phenyl]pyrazine

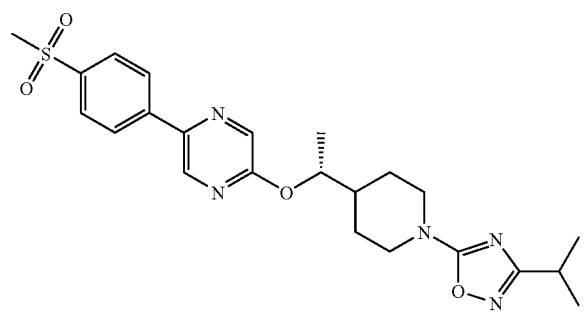

The racemic 2-[(1-{1-[3-(1-methylethyl)-1,2,4-oxadiazol-5-yl]-4-piperidinyl}ethyl)oxy]-5-[4-(methylsulfonyl)phenyl]pyrazine (prepared as in Example 156) was subjected to Chiral HPLC [column: AS-H, column mobile phase: 70% CO₂: 30% MeOH (2 mL/min), pressure 140 bar, temperature 40° C., 215 nm] analysis and then separated to give two (R and S) enantiomers. The title compound was isolated as an off-white solid with Tr of 23.42 min (first eluting peak). The (R) absolute stereochemistry was assigned by Ab initio VCD analysis.

Example 158

2-[((1S)-1-{1-[3-(1-Methylethyl)-1,2,4-oxadiazol-5-yl]-4-piperidinyl}ethyl)oxy]-5-[4-(methylsulfonyl)phenyl]pyrazine

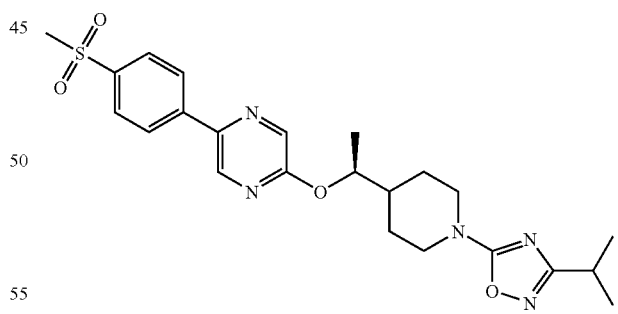

The racemic 2-[(1-{1-[3-(1-methylethyl)-1,2,4-oxadiazol-5-yl]-4-piperidinyl}ethyl)oxy]-5-[4-(methylsulfonyl)phenyl]pyrazine (prepared as in Example 156) was subjected to Chiral HPLC [column: AS-H, column mobile phase: 70% CO₂: 30% MeOH (2 mL/min), pressure 140 bar, temperature 40° C., 215 nm] analysis and then separated to give two (R and S) enantiomers. The title compound was isolated as an off-white solid with Tr of 25.83 min (second eluting peak). The (S) absolute stereochemistry was assigned by Ab initio VCD analysis.

Alternative preparation from enantiomerically enriched material:

Step 1: Triethylamine (315 mL, 2.26 mol) was added dropwise to formic acid (150 mL, 3.91 mol) with overhead stirring while maintaining the internal temperature below 60° C. with ice-bath cooling. Neat 4-acetylpyridine (100 mL, 0.904 mol) was then added rapidly while maintaining the temperature below 50° C. Following this addition, the reaction was allowed to cool to 28° C. and the chiral ruthenium catalyst [N-[(1R,2R)-2-(amino-N)-1,2-diphenylethyl]-2,4,6-trimethylbenzenesulfonamidato-N]chloro[(1,2,3,4,5,6-n)-1-methyl-4-(1-methylethyl)benzene]ruthenium (CAS #177552-91-9; for catalyst preparation, see: Uematsu, N.; Fujii, A.; Hashiguchi, S.; Ikariya, T.; Noyori, R.; *J. Am. Chem. Soc.* 1996, 118, 4916-4917) (3 g, 4.46 mmol) was added. The mixture was stirred under house vacuum for 4 h and then overnight under an atmosphere of nitrogen. The reaction mixture was added dropwise to a stirred solution of 10% $Na_2CO_3$ (4 L) and then extracted with EtOAc (3×1 L). The combined EtOAc layers were washed once with brine (1 L), treated with $MgSO_4$ and Darco G-60 decolorizing charcoal and filtered through a 100 g plug of silica gel washing with 10% MeOH/EtOAc (1 L). The filtrate was concentrated to provide a dark oil that crystallized upon standing. The solid was dissolved in warm t-butyl methyl ether (250 mL) and the warm solution was filtered to remove a small amount of insoluble material. The filtrate was allowed to stir with cooling to room temperature and then to −15° C. The solids were collected by filtration, washing with cold t-butyl methyl ether and heptane, and then dried under high vacuum to yield (1R)-1-(4-pyridinyl)ethanol as a dark beige solid (62 g, 52.9% yield). This solid material was 96% ee based on chiral HPLC (HPLC conditions: AS-H column, 5% MeOH/$CO_2$, 40° C., 140 bar, 2 mL/min). The filtrate was combined with the insoluble solid from the crystallization and concentrated in vacuo to yield additional (1R)-1-(4-pyridinyl)ethanol as a dark oil (37.5 g, 32% yield). This oily material was 78% ee based on chiral HPLC (see HPLC conditions above). $^1$H NMR (400 MHz, DMSO-$d_6$): δ 8.47-8.43 (m, 2H), 7.32-7.28 (m, 2H), 5.37 (d, 1H, J=4.4 Hz), 4.72-4.64 (m, 1H), 1.44 (d, 3H, J=6.6 Hz).

Step 2: A solution of (1R)-1-(4-pyridinyl)ethanol (37 g, 0.3 mol, 78% ee) in MeOH (2 L) was charged with $PtO_2$ (5 g) under nitrogen atmosphere followed by acetic acid (19 mL). The mixture was evacuated and purged with hydrogen several times and then stirred under an atmosphere of hydrogen for 2 d at room temperature. The mixture was filtered to remove catalyst and the filtrate was concentrated in vacuo and triturated with EtOAc to yield a cream-colored solid which was collected by filtration. The filter cake was dissolved in MeOH (500 mL) and 50% NaOH (15.8 g) was added. The resulting solution was stirred at 25° C. for 30 min and concentrated. The resulting solid was triturated with $Et_2O$ (700 mL) and stirred at 25° C. for 30 min, the solids were removed by filtration and the filtrate was dried over $MgSO_4$ and filtered again. The final filtrate was concentrated to yield (1R)-1-(4-piperidinyl)ethanol (22 g, 57% yield) as a light beige solid. $^1$H NMR (400 MHz, CDCl$_3$): δ 3.50 (quint, 1H, J=6.3 Hz), 3.13-3.01 (m, 2H), 2.61-2.47 (m, 2H), 1.88 (br, 2H), 1.84-1.73 (m, 1H), 1.63-1.52 (m, 1H), 1.41-1.27 (m, 1H), 1.23-1.05 (m, 2H), 1.13 (d, 3H, J=6.2 Hz).

Step 3: A stirred solution of N-hydroxy-2-methylpropanimidamide (16.33 g, 160 mmol) in pyridine (16.81 mL, 208 mmol) and dichloromethane (165 mL) at −15° C. was treated with trichloroacetyl chloride (19.63 mL, 176 mmol) over 40 min. The reaction was allowed to warm to ambient temperature and stirred for 42 h. Water (100 mL) was added and the reaction was stirred for 30 min. The dichloromethane was removed and the residue was diluted with water (50 mL) and extracted with ether (300 mL). The ether layer was washed with water, dried over $MgSO_4$ and concentrated to afford 3-(1-methylethyl)-5-(trichloromethyl)-1,2,4-oxadiazole (28.0 g, 76% yield) as an orange liquid. $^1$H NMR (400 MHz, CDCl$_3$): δ 3.13 (septet, 1H, J=7.0 Hz), 1.36 (d, 6H, J=7.0 Hz).

Step 4: A solution of 3-(1-methylethyl)-5-(trichloromethyl)-1,2,4-oxadiazole (25.8 g, 112 mmol) and (1R)-1-(4-piperidinyl)ethanol (13.4 g, 104 mmol) in MeOH (15 mL) was stirred at ambient temperature under a stream of nitrogen for 7 days. The reaction was diluted with MeOH (40 mL), cooled in an ice bath and 1N NaOH (25 mL) was added. The mixture was allowed to warm to ambient temperature and stir for 1 h. The reaction was partitioned in EtOAc (300 mL)/1N NaOH (75 mL) and the layers were separated. The aqueous layer was saturated with NaCl and extracted with EtOAc (200 mL). The combined EtOAc layers were dried over $MgSO_4$, concentrated and placed under high vacuum for 18 h to afford (1R)-1-{1-[3-(1-methylethyl)-1,2,4-oxadiazol-5-yl]-4-piperidinyl}ethanol (16.75 g, 68%) as an orange oil. $^1$H NMR (400 MHz, CDCl$_3$): δ 4.14 (m, 2H), 3.57 (quint, 1H, J=6.3 Hz), 2.98 (m, 2H), 2.83 (septet, 1H, J=7.0 Hz), 1.90 (m, 1H), 1.86 (br, 1H), 1.67 (m, 1H), 1.45 (m, 1H), 1.33 (m, 2H), 1.23 (d, 6H, J=7.0 Hz), 1.16 (d, 3H, J=6.3 Hz); LRMS (ESI), m/z 240 (M+H).

Step 5: A solution of (1R)-1-{1-[3-(1-methylethyl)-1,2,4-oxadiazol-5-yl]-4-piperidinyl}ethanol (1.68 g, 7.0 mmol) in dichloromethane (100 mL) at 0° C. was treated with $Et_3N$ (1.98 mL, 14.0 mmol) followed by methanesulfonyl chloride (0.66 mL, 8.4 mmol). The mixture was stirred at 0° C. for 1 h, then at room temperature for 2 h. The mixture was diluted with dichloromethane (50 mL), washed with 1M $NaH_2PO_4$ (75 mL×2) and brine, and dried over $Na_2SO_4$ and concentrated to give (1R)-1-{1-[3-(1-methylethyl)-1,2,4-oxadiazol-5-yl]-4-piperidinyl}ethyl methanesulfonate (2.23 g, 7.0 mmol, 100% yield) as a brown oil, which was used without further purification.

Step 6: A mixture of 5-[4-(methylsulfonyl)phenyl]-2-pyrazinol (and tautomers thereof) (prepared as in Example 145, Step 2, 1.3 g, 5.19 mmol), (1R)-1-{1-[3-(1-methylethyl)-1,2,4-oxadiazol-5-yl]-4-piperidinyl}ethyl methanesulfonate (2.23 g, 7.0 mmol, 70% ee) and $K_2CO_3$ (1.45 g, 10.4 mmol) in DMF (35 mL) was stirred at 100° C. in a preheated oil bath overnight. The mixture was cooled to ambient temperature, treated with water, and the mixture was extracted with EtOAc (75 mL×2). The combined organic extracts were washed with water, brine and dried over $Na_2SO_4$, filtered, and the filtrate was concentrated to a brown oil, which was by chromatography on a silica gel column eluted with 50% EtOAc/hexanes followed by chromatography on an ISCO silica gel column using 0 to 60% EtOAc/hexanes to give 2-[((1S)-1-{1-[3-(1-methylethyl)-1,2,4-oxadiazol-5-yl]-4-piperidinyl}ethyl)oxy]-5-[4-(methylsulfonyl)phenyl]pyrazine (0.73 g, 70% ee, 30%) as a white solid. The solid was subjected to chiral separation (similar to conditions used above for Example 158) to yield 0.30 g of the title compound as a white solid. $^1$H NMR (400 MHz, CDCl$_3$): δ 8.53 (d, 1H, J=1.3 Hz), 8.25 (d, 1H, J=1.3 Hz), 8.10 (d, 2H, J=8.3 Hz), 8.02 (d, 2H, J=8.5 Hz), 5.20-5.10 (m, 1H), 4.35-4.20 (m, 2H), 3.15-3.00 (m, 5H), 2.90 (septet, 1H, J=7.0 Hz), 2.00-1.80 (m, 3H), 1.60-1.40 (m, 2H), 1.34 (d, 3H, J=6.3 Hz), 1.28 (d, 6H, J=6.9 Hz); LRMS (ESI), m/z 472 (M+H).

Example 159

2-[4-(Methylsulfonyl)phenyl]-5-[({1-[5-(trifluoromethyl)-2-pyridinyl]-4-piperidinyl}methyl)oxy]pyridine

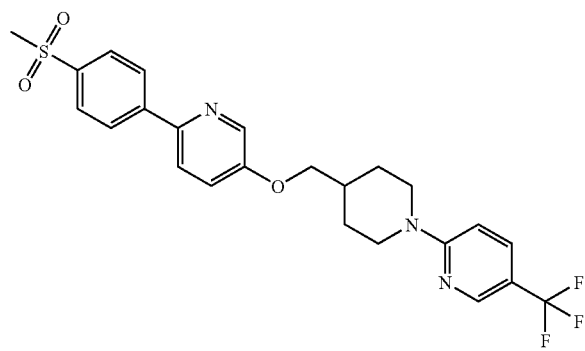

The title compound (73 mg, 66%) was prepared as a white solid from 1,1-dimethylethyl 4-[({6-[4-(methylsulfonyl)phenyl]-3-pyridinyl}oxy)methyl]-1-piperidinecarboxylate (prepared as in Example 150, Step 2, 0.10 g, 0.22 mmol) and TFA (0.18 mL) in CH$_2$Cl$_2$ (6 mL) then K$_2$CO$_3$ (0.62 g) and 2-chloro-5-(trifluoromethyl)pyridine (50 mg, 0.27 mmol) in DMSO (5 mL) in a manner similar to Example 80. The crude material was purified by chromatography on a silica gel column eluted with 1:16 acetone/CH$_2$Cl$_2$ to give the title compound as a white solid. $^1$H NMR (400 MHz, DMSO-d$_6$): δ 8.40 (d, 1H, J=2.9 Hz), 8.36 (s, 1H), 8.24 (d, 2H, J=8.3 Hz), 8.02 (d, 1H, J=8.8 Hz), 7.95 (d, 2H, J=8.3 Hz), 7.75-7.70 (m, 1H), 7.51 (dd, 1H, J$_a$=8.8 Hz, J$_b$=3.0 Hz), 6.94 (d, 1H, J=9.1 Hz), 4.50-4.40 (m, 2H), 3.99 (d, 2H, J=6.4 Hz), 3.21 (s, 3H), 3.00-2.90 (m, 2H), 2.20-2.05 (m, 1H), 1.90-1.80 (m, 2H), 1.35-1.20 (m, 2H); LRMS (ESI), m/z 492 (M+H).

Example 160

(±)-1,1-Dimethylethyl 4-[1-({5-[4-(methylsulfonyl)phenyl]-2-pyrazinyl}oxy)ethyl]-1-piperidinecarboxylate

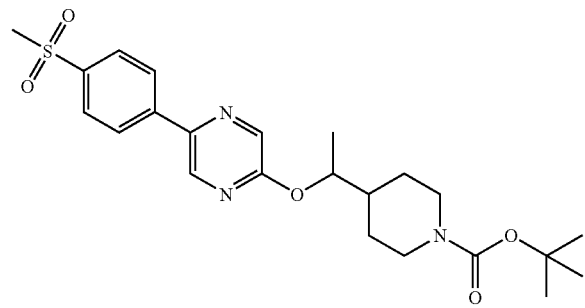

Step 1: (±)-1-(4-Piperidinyl)ethanol (see reference: WO 9725992A, 12.44 g, 65.7 mmol) in 1,2-dichloroethane (500 mL) was stirred at room temperature and BOC$_2$O (14.36 g, 65.8 mmol) was added followed by Et$_3$N (19 mL, 136 mmol). The stirred mixture was heated at gentle reflux for 15 min and then allowed to cool to room temperature and stirred overnight. The solution was washed twice with 10% citric acid, once with 10% Na$_2$CO$_3$, dried over MgSO$_4$, filtered and concentrated to afford (±)-1,1-dimethylethyl 4-(1-hydroxyethyl)-1-piperidinecarboxylate (14 g, 93% yield) as a light amber oil. $^1$H NMR (400 MHz, DMSO-d$_6$): δ 4.35 (d, 1H, J=4.8 Hz), 3.92 (m, 2H), 3.32 (m, 1H), 2.59 (m, 2H), 1.68 (m, 1H), 1.47 (m, 1H), 1.34 (s, 9H), 1.25 (m, 1H), 1.08-0.88 (m, 2H), 0.97 (d, 3H, J=6.4 Hz).

Step 2: (±)-1,1-Dimethylethyl 4-{1-[(methylsulfonyl)oxy]ethyl}-1-piperidinecarboxylate (0.74 g, 49%) was prepared as a light brown oil from (±)-1,1-dimethylethyl 4-(1-hydroxyethyl)-1-piperidinecarboxylate (0.56 g, 2.44 mmol), methanesulfonyl chloride (0.23 mL, 2.93 mmol) and Et$_3$N (0.69 mL, 4.88 mmol) in a manner similar to Example 150, Step 1. The crude product was used without further purification. $^1$H NMR (400 MHz, CDCl$_3$): δ 4.70-4.55 (m, 1H), 4.20-4.10 (m, 2H), 2.99 (s, 3H), 2.70-2.55 (m, 2H), 1.80-1.60 (m, 3H), 1.43 (s, 9H), 1.38 (d, 3H, J=6.4 Hz), 1.35-1.15 (m, 2H).

Step 3: The title compound (0.463 g, 58%) was prepared as a white foam from 5-[4-(methylsulfonyl)phenyl]-2-pyrazinol (and tautomers thereof) (prepared as in Example 145, Step 2, 0.43 g, 1.72 mmol), (±)-1,1-dimethylethyl 4-{1-[(methylsulfonyl)oxy]ethyl}-1-piperidinecarboxylate (0.74 g, 2.41 mmol) and K$_2$CO$_3$ (0.48 g, 3.44 mmol) in DMF (15 mL) in a manner similar to Example 150, Step 3. The crude product was purified by chromatography on a silica gel column eluted with 1:2 EtOAc/hexanes then 40% EtOAc/hexanes to give the title compound as a white foam. $^1$H NMR (400 MHz, CDCl$_3$): δ 8.53 (s, 1H), 8.24 (s, 1H), 8.10 (d, 2H, J=8.3 Hz), 8.02 (d, 2H, J=8.3 Hz), 5.15-5.05 (m, 1H), 4.20-4.10 (m, 2H), 3.07 (s, 3H), 2.75-2.60 (m, 2H), 1.85-1.55 (m, 3H), 1.44 (s, 9H), 1.40-1.20 (m, 5H); LRMS (ESI), m/z 462 (M+H).

Example 161

2-[2-Fluoro-4-(methylsulfonyl)phenyl]-5-[({1-[3-(1-methylethyl)-1,2,4-oxadiazol-5-yl]-4-piperidinyl}methyl)oxy]pyrazine

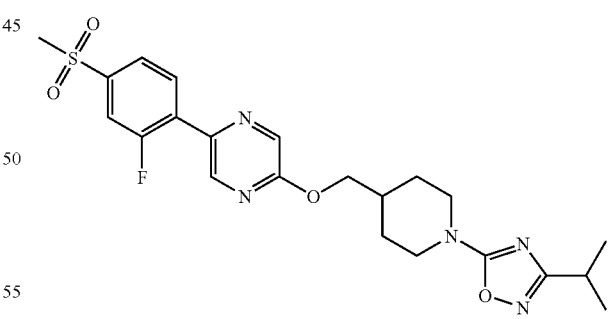

Step 1: 5-[2-Fluoro-4-(methylsulfonyl)phenyl]-2-pyrazinamine (0.30 g, 50%) was prepared as a yellowish brown solid from 2-amino-5-bromopyrazine (0.4 g, 2.23 mmol), [2-fluoro-4-(methylsulfonyl)phenyl]boronic acid (0.50 g, 2.23 mmol), 2M Na$_2$CO$_3$ (4 mL), Pd(PPh$_3$)$_4$ (52 mg, 0.05 mmol) in 1,4-dioxane (8 mL) and MeOH (4 mL) in a manner similar to Example 145, Step 1. The crude product was triturated with CH$_2$Cl$_2$ to give 5-[2-fluoro-4-(methylsulfonyl)phenyl]-2-pyrazinamine as a yellowish brown solid. $^1$H NMR (400 MHz, DMSO-d$_6$): δ 8.41 (s, 1H), 8.11 (t, 1H, J=8.0 Hz), 8.01 (s, 1H), 7.85-7.75 (m, 2H), 6.91 (s, 2H), 3.26 (s, 3H); LRMS (ESI), m/z 268 (M+H).

Step 2: 5-[2-Fluoro-4-(methylsulfonyl)phenyl]-2-pyrazinol (and tautomers thereof) (0.25 g, 86%) was prepared as a yellowish brown solid from 5-[2-fluoro-4-(methylsulfonyl) phenyl]-2-pyrazinamine (0.29 g, 1.09 mmol), NaNO$_2$ (0.104 g, 1.47 mmol) and concentrated H$_2$SO$_4$ (6 mL total) in a manner similar to Example 145, Step 2. $^1$H NMR (400 MHz, DMSO-d$_6$): δ 12.70 (bs, 1H), 8.20-8.05 (m, 2H), 7.93 (bs, 1H), 7.90-7.75 (m, 2H), 3.26 (s, 3H); LRMS (ESI), m/z 269 (M+H).

Step 3: The title compound (0.13 g, 49%) was prepared as a white solid from 5-[2-fluoro-4-(methylsulfonyl)phenyl]-2-pyrazinol (and tautomers thereof) (0.15 g, 0.56 mmol), {1-[3-(1-methylethyl)-1,2,4-oxadiazol-5-yl]-4-piperidinyl}methyl methanesulfonate (prepared as in Example 100, Steps 1-4, 0.23 g, 0.76 mmol) and K$_2$CO$_3$ (0.16 g, 1.12 mmol) in DMF (6 mL) in a manner similar to Example 152, Step 3. The crude product was purified by chromatography on a silica gel column eluted with 50% EtOAc/hexanes to give the title compound as a white solid. $^1$H NMR (400 MHz, CDCl$_3$): δ 8.66 (s, 1H), 8.33 (d, 1H, J=1.0 Hz), 8.23 (t, 1H, J=7.8 Hz), 7.82 (dd, 1H, J$_a$=8.2 Hz, J$_b$=1.7 Hz), 7.76 (dd, 1H, J$_a$=10.2 Hz, J$_b$=1.6 Hz), 4.40-4.30 (m, 2H), 4.29 (d, 2H, J=6.3 Hz), 3.25-3.10 (m, 2H), 3.09 (s, 3H), 2.98 (septet, 1H, J=7.0 Hz), 2.20-2.05 (m, 1H), 2.05-1.90 (m, 2H), 1.60-1.40 (m, 2H), 1.32 (d, 6H, J=6.8 Hz); LRMS (ESI), m/z 476 (M+H).

Alternative Preparation for Example 161

Step 1: A stirred suspension of 1-bromo-2-fluoro-4-iodobenzene (100 g, 332 mmol), NiBr$_2$ (7.26 g, 33.2 mmol), 2,2-dipyridyl (5.19 g, 33.2 mmol) and zinc dust (27.2 g, 415 mmol) in DMF (600 mL) was treated with MeS—SMe (15.65 g, 166 mmol), and the mixture was heated in a sand bath set for 80° C. After 10 min (color changes to black and reaction was complete according to HPLC analysis), the mixture was poured onto water. 1N HCl (100 mL) was added along with Et$_2$O (300 mL), and the suspension was filtered through a glass fritted funnel. The zinc plug was further washed with Et$_2$O and the Et$_2$O layer was separated and the aqueous layer was extracted with Et$_2$O (3×). The organic extracts were then dried over Na$_2$SO$_4$ and the solvent evaporated (note that the product is very volatile) to afford 1-bromo-2-fluoro-4-(methylthio)benzene (180 g), which was used without further purification. $^1$H NMR (400 MHz, CDCl$_3$): δ 7.43-7.38 (m, 1H), 6.97 (dd, 1H, J$_a$=9.1 Hz, J$_b$=2.0 Hz), 6.90-6.86 (m, 1H), 2.46 (s, 3H).

Step 2: A stirred solution of 1-bromo-2-fluoro-4-(methylthio)benzene (180 g, 814 mmol) at −78° C. in THF (500 mL) was treated with n-BuLi (358 mL, 2.5M in hexanes, 895 mmol) over 1.5 h. After 15 min at −78° C., B(OMe)$_3$ (254 g, 244 mol) was added over 1.5 h, and the reaction mixture was slowly warmed to ambient temperature. 10% Aqueous HCl (100 mL) was added and the mixture was stirred for 5 min. Et$_2$O (500 mL) was added and the organic layer was separated and washed with 2M NaOH (300 mL). The aqueous phase was rinsed one more time with Et$_2$O. The aqueous phase was then acidified with 10% aqueous HCl to pH ~4 and the resulting solid was collected to give [2-fluoro-4-(methylthio)phenyl]boronic acid (24.7 g). $^1$H NMR (400 MHz, CDCl$_3$): δ 7.70 (t, 1H, J=7.6 Hz), 7.03 (dd, 1H, J$_a$=8.1 Hz, J$_b$=1.6 Hz), 6.88 (dd, 1H, J$_a$=11.7 Hz, J$_b$=1.6 Hz), 2.49 (s, 3H).

Step 3: A mixture of [2-fluoro-4-(methylthio)phenyl]boronic acid (5 g, 26.9 mmol), 5-bromo-2-pyrazinamine (4.7 g, 26.9 mmol), Pd(PPh$_3$)$_4$ (0.62 g, 0.54 mmol), 2M Na$_2$CO$_3$ (25 mL), 1,4-dioxane (50 mL), and methanol (25 mL) was stirred and heated at 100° C. for 5 h, then at 25° C. overnight. The reaction was charged with water (300 mL) and extracted with EtOAc (100 mL). The organic extracts were dried over MgSO$_4$, filtered, and concentrated to dryness to give a tan solid. The solid was triturated with CH$_2$Cl$_2$, filtered, and the solid air-dried to afford 5-[2-fluoro-4-(methylthio)phenyl]-2-pyrazinamine (3.43 g, 54% yield) as a tan solid. The filtrate was concentrated to dryness to give additional solid (2.5 g) that was purified by SiO$_2$ chromatography (0-25% EtOAc/hexanes, 20 min. gradient; then 25% EtOAc/hexanes, 60 min.; 100 g column) to afford additional product (940 mg, 15% yield) as a tan solid. $^1$H NMR (400 MHz, CDCl$_3$) δ 8.47 (s, 1H), 8.10 (d, 1H, J=1.4 Hz), 7.83 (t, 1H, J=8.3 Hz), 7.10 (dd, 1H, J$_a$=8.3 Hz, J$_b$=1.9 Hz), 7.00 (dd, 1H, J$_a$=12.1 Hz, J$_b$=1.9 Hz), 4.80 (bs, 2H), 2.50 (s, 3H).

Step 4: Sodium nitrite (1.73 g, 25.1 mmol) was added portionwise to concentrated sulfuric acid (20 mL) at 0° C. The mixture was stirred at 45° C. until homogeneous, cooled to 0° C., and charged with a solution of 5-[2-fluoro-4-(methylthio) phenyl]-2-pyrazinamine (4.37 g, 18.6 mmol) in concentrated sulfuric acid (55 mL) at 0° C. The reaction was allowed to warm to 25° C., stirred for 15 min, then at 45° C. for 1 h. The reaction was poured onto ice and the pH was adjusted to ~4 with 10N NaOH. The resulting tan precipitate was filtered, washed with water, and air-dried to afford a tan solid. The solid was refluxed in EtOH (300 mL), hot-filtered, and the filtrate concentrated to afford 5-[2-fluoro-4-(methylthio)phenyl]-2-pyrazinol (and tautomers thereof) (3.16 g, 72% yield, purity=87%) as a tan solid. $^1$H NMR (400 MHz, DMSO-d$_6$) δ 8.14 (d, 1H, J=1.2 Hz), 7.72-7.86 (m, 2H), 7.24-7.15 (m, 2H), 2.52 (s LRMS (ESI), m/z 237 (M+H).

Step 5: A mixture of 5-[2-fluoro-4-(methylthio)phenyl]-2-pyrazinol (and tautomers thereof) (0.35 g, 1.48 mmol), {1-[3-(1-methylethyl)-1,2,4-oxadiazol-5-yl]-4-piperidinyl}methyl methanesulfonate (prepared as in Example 100, Step 4, 0.61 g, 2.0 mmol) and K$_2$CO$_3$ (0.42 g, 2.96 mmol) in DMF (14 mL) was stirred at 100° C. in a preheated oil bath for 5 h. The mixture was cooled to ambient temperature, treated with water, and the mixture was extracted with EtOAc (70 mL×2). The combined organic extracts were washed with water, brine and dried over Na$_2$SO$_4$, filtered, and the filtrate was concentrated to a brown solid, which was purified by chromatography on a silica gel column eluted with 1:25 acetone/CH$_2$Cl$_2$ to give 2-[2-fluoro-4-(methylthio)phenyl]-5-[({1-[3-(1-methylethyl)-1,2,4-oxadiazol-5-yl]-4-piperidinyl}methyl)oxy]pyrazine (0.3 g, 44% yield) as a light beige solid. $^1$H NMR (400 MHz, CDCl$_3$): δ 8.54 (s, 1H), 8.28 (d, 1H, J=1.3 Hz), 7.86 (t, 1H, J=8.3 Hz), 7.10 (dd, 1H, J$_a$=8.3 Hz, J$_b$=1.7 Hz), 7.00 (dd, 1H, J$_a$=12.1 Hz, J$_b$=1.9 Hz), 4.30-4.20 (m, 4H), 3.20-3.05 (m, 2H), 2.92 (septet, 1H, J=7.0 Hz), 2.50 (s, 3H), 2.20-2.05 (m, 1H), 2.00-1.90 (m, 2H), 1.55-1.40 (m, 2H), 1.29 (d, 6H, J=6.9 Hz); LRMS (ESI), m/z 444 (M+H).

Step 6: A mixture of 2-[2-fluoro-4-(methylthio)phenyl]-5-[({1-[3-(1-methylethyl)-1,2,4-oxadiazol-5-yl]-4-piperidinyl}methyl)oxy]pyrazine (0.3 g, 0.66 mmol) in acetone (15 mL), water (8 mL), methanol (10 mL) and THF (10 mL) was treated with Oxone® (1.21 g, 1.97 mmol). The reaction mixture was stirred at ambient temperature overnight. Water (60 mL) was added, the mixture was extracted with EtOAc. The combined organic extracts were washed with water, brine, and dried over Na$_2$SO$_4$, filtered, and the filtrate was concentrated to a light beige solid, which was purified by chromatography on a silica gel column eluted with 50% EtOAc/hexanes to give 0.27 g (87%) of the title compound as a white solid. $^1$H NMR (400 MHz, CDCl$_3$): δ

8.66 (s, 1H), 8.33 (d, 1H, J=1.3 Hz), 8.23 (t, 1H, J=7.8 Hz), 7.82 (dd, 1H, $J_a$=8.2 Hz, $J_b$=1.7 Hz), 7.76 (dd, 1H, $J_a$=10.2 Hz, $J_b$=1.7 Hz), 4.35-4.20 (m, 4H), 3.20-3.05 (m, 5H), 2.93 (septet, 1H, J=6.7 Hz), 2.20-2.05 (m, 1H), 2.00-1.90 (m, 2H), 1.55-1.40 (m, 2H), 1.30 (d, 6H, J=6.8 Hz); LRMS (ESI), m/z 476 (M+H).

Example 162

(±)-1-Methylethyl 4-[1-({5-[4-(methylsulfonyl)phenyl]-2-pyrazinyl}oxy)ethyl]-1-piperidinecarboxylate

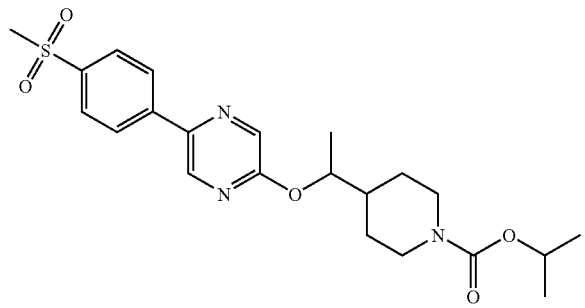

The title compound (0.21 g, 98%) was prepared as a white foam from (±)-1,1-dimethylethyl 4-[1-({5-[4-(methylsulfonyl)phenyl]-2-pyrazinyl}oxy)ethyl]-1-piperidinecarboxylate (Example 160, 0.22 g, 0.48 mmol) and TFA (0.37 mL) in $CH_2Cl_2$ (16 mL) then diisopropylethylamine (1.25 mL) and isopropyl chloroformate (1.0M in toluene, 0.57 mL, 0.57 mmol) in a manner similar to Example 74. The crude material was purified by chromatography on a silica gel column eluted with 50% EtOAc/hexanes to afford (±)-1-methylethyl 4-[1-({5-[4-(methylsulfonyl)phenyl]-2-pyrazinyl}oxy)ethyl]-1-piperidinecarboxylate as a white foam. $^1$H NMR (400 MHz, $CDCl_3$): δ 8.53 (d, 1H, J=1.0 Hz), 8.24 (d, 1H, J=1.2 Hz), 8.10 (d, 2H, J=8.5 Hz), 8.02 (d, 2H, J=8.6 Hz), 5.15-5.05 (m, 1H), 4.89 (septet, 1H, J=6.3 Hz), 4.30-4.15 (m, 2H), 3.07 (s, 3H), 2.75-2.65 (m, 2H), 1.85-1.65 (m, 3H), 1.40-1.25 (m, 5H), 1.22 (d, 6H, J=6.3 Hz); LRMS (ESI), m/z 448 (M+H).

Example 163

1-Methylethyl 4-[(1S)-1-({5-[4-(methylsulfonyl)phenyl]-2-pyrazinyl}oxy)ethyl]-1-piperidinecarboxylate

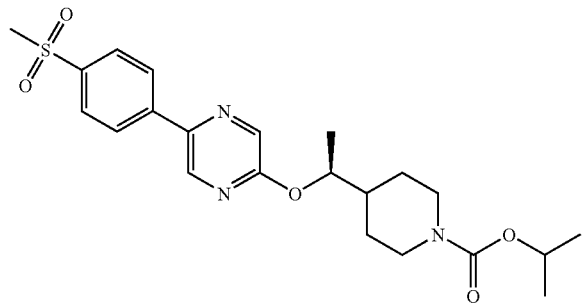

The racemic 1-methylethyl 4-[1-({5-[4-(methylsulfonyl)phenyl]-2-pyrazinyl}oxy)ethyl]-1-piperidinecarboxylate (prepared as in Example 162) was subjected to Chiral HPLC [column: AS-H, column mobile phase: 85% $CO_2$: 15% MeOH (2 mL/min), pressure 140 bar, temperature 40° C., 215 nm] analysis and then separated to give two (R and S) enantiomers, which were further purified by chromatography on an ISCO silica gel column using 0 to 50% EtOAc/hexanes. The title compound was isolated as a white foam with Tr of 13.37 min (first eluting peak). The (S) absolute stereochemistry was assigned by Ab initio VCD analysis.

Example 164

1-Methylethyl 4-[(1R)-1-({5-[4-(methylsulfonyl)phenyl]-2-pyrazinyl}oxy)ethyl]-1-piperidinecarboxylate The racemic 1-methylethyl 4-[1-({5-[4-(methylsulfonyl)phenyl]-2-pyrazinyl}oxy)ethyl]-1-piperidinecarboxylate (prepared as in Example 162) was subjected to Chiral HPLC [column: AS-H, column mobile phase: 85% $CO_2$: 15% MeOH (2 mL/min), pressure 140 bar, temperature 40° C., 215 nm] analysis and then separated to give two (R and S) enantiomers, which were further purified by chromatography on an ISCO silica gel column using 0 to 50% EtOAc/hexanes. The title compound was isolated as a white foam with Tr of 17.00 min (second eluting peak). The (R) absolute stereochemistry was assigned by Ab initio VCD analysis.

Example 165

1-Methylethyl 4-[({5-[2-fluoro-4-(methylsulfonyl)phenyl]-2-pyrazinyl}oxy)methyl]-1-piperidinecarboxylate The title compound (80 mg, 49%) was prepared as a white solid from 5-[2-fluoro-4-(methylsulfonyl)phenyl]-2-pyrazinol (and tautomers thereof) (prepared as in Example 161, Step 2, 98 mg, 0.37 mmol), 1-methylethyl 4-{[(methylsulfonyl)oxy]methyl}-1-piperidinecarboxylate (prepared as in Example 131, Step 4, 0.138 g, 0.49 mmol) and $K_2CO_3$ (0.102 g, 0.73 mmol) in DMF (4 mL) in a manner similar to Example 152, Step 3. The crude product was purified by chromatography on an ISCO silica gel column using 0 to 50% EtOAc/hexanes to give the title compound as a white solid. $^1$H NMR (400 MHz, CDCl$_3$): δ 8.66 (s, 1H), 8.33 (d, 1H, J=1.3 Hz), 8.23 (t, 1H, J=7.8 Hz), 7.85-7.70 (m, 2H), 4.91 (septet, 1H, J=6.2 Hz), 4.30-4.15 (m, 4H), 3.09 (s, 3H), 2.85-2.70 (m, 2H), 2.10-1.95 (m, 1H), 1.85-1.75 (m, 2H), 1.35-1.20 (m, 8H); LRMS (ESI), m/z 452 (M+H).

Example 166

2-[2-Fluoro-4-(methylsulfonyl)phenyl]-5-[((1S)-1-{1-[3-(1-methylethyl)-1,2,4-oxadiazol-5-yl]-4-piperidinyl}ethyl)oxy]pyrazine

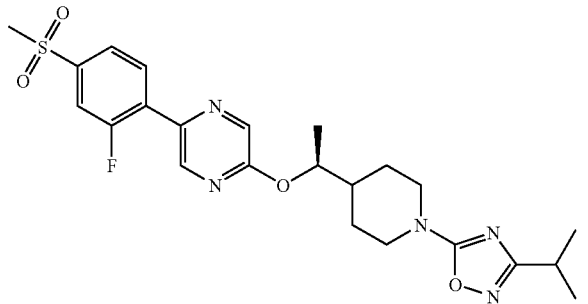

Step 1: (1R)-1-{1-[3-(1-Methylethyl)-1,2,4-oxadiazol-5-yl]-4-piperidinyl}ethyl methanesulfonate (0.75 g, 2.29 mmol) prepared from (1R)-1-{1-[3-(1-methylethyl)-1,2,4-oxadiazol-5-yl]-4-piperidinyl}ethanol (prepared as in Example 158, Alternative synthesis, Step 4, 0.55 g, 2.3 mmol), methanesulfonyl chloride (0.21 mL, 2.7 mmol) and Et$_3$N (0.48 mL, 3.4 mmol) in dichloromethane (30 mL) in a manner similar to Example 139, Step 2, except that no purification step was needed.

Step 2: A mixture of 5-[2-fluoro-4-(methylthio)phenyl]-2-pyrazinol (and tautomers thereof) (prepared as in Example 161, Alternative synthesis, Step 4, 0.40 g, 1.69 mmol), crude (1R)-1-{1-[3-(1-methylethyl)-1,2,4-oxadiazol-5-yl]-4-piperidinyl}ethyl methanesulfonate (0.75 g, 2.29 mmol) and $K_2CO_3$ (0.48 g, 3.39 mmol) in DMF (16 mL) was stirred at 100° C. in a preheated oil bath overnight. The mixture was cooled to ambient temperature, treated with water, and the mixture was extracted with EtOAc (60 mL×2). The combined organic extract was washed with water, brine and dried over Na$_2$SO$_4$, filtered, and the filtrate was concentrated to a brown oil, which was purified by chromatography on an ISCO silica gel column using 0 to 30% EtOAc/hexanes to give 0.335 g (43%) of 2-[2-fluoro-4-(methylthio)phenyl]-5-[(1-{1-[3-(1-methylethyl)-1,2,4-oxadiazol-5-yl]-4-piperidinyl}ethyl)oxy]pyrazine as a yellow viscous oil. $^1$H NMR (400 MHz, CDCl$_3$): δ 8.52 (s, 1H), 8.23 (d, 1H, J=1.0 Hz), 7.85 (t, 1H, J=8.2 Hz), 7.10 (dd, 1H, J$_a$=8.3 Hz, J$_b$=1.7 Hz), 7.00 (dd, 1H, J$_a$=12.1 Hz, J$_b$=1.6 Hz), 5.20-5.05 (m, 1H), 4.25-4.15 (m, 2H), 3.10-2.95 (m, 2H), 2.87 (septet, 1H, J=6.9 Hz), 2.50 (s, 3H), 2.00-1.75 (m, 3H), 1.55-1.40 (m, 2H), 1.33 (d, 3H, J=6.4 Hz), 1.26 (d, 6H, J=6.9 Hz); LRMS (ESI), m/z 458 (M+H).

Step 3: A mixture of 2-[2-fluoro-4-(methylthio)phenyl]-5-[(1-{1-[3-(1-methylethyl)-1,2,4-oxadiazol-5-yl]-4-piperidinyl}ethyl)oxy]pyrazine (0.33 g, 0.72 mmol) in acetone (25 mL) and water (10 mL) was treated with Oxone® (1.33 g, 2.17 mmol). The reaction mixture was stirred at ambient temperature overnight. Water (60 mL) was added, the mixture was extracted with EtOAc. The combined organic extract was washed with water, brine, and dried over Na$_2$SO$_4$, filtered, and the filtrate was concentrated to a light beige solid, which was purified by chromatography on an ISCO silica gel column using 0 to 55% EtOAc/hexanes to give 2-[2-fluoro-4-(methylsulfonyl)phenyl]-5-[((1S)-1-{1-[3-(1-methylethyl)-1,2,4-oxadiazol-5-yl]-4-piperidinyl}ethyl)oxy]pyrazine (0.255 g, 70% ee, 72%) as a white solid. The solid was subjected to chiral separation [column: OJ-H, column mobile phase: 75% $CO_2$: 25% of a 9/1 mixture of MeOH/CHCl$_3$ (2 mL/min), pressure 140 bar, temperature 40° C., 215 nm] to give two (R and S) enantiomers, with the (S)-isomer eluting first. The material was triturated with 9% EtOAc/hexanes to afford the title compound (0.15 g) as a white solid. $^1$H NMR (400 MHz, CDCl$_3$): δ 8.64 (s, 1H), 8.28 (d, 1H, J=1.2 Hz), 8.22 (t, 1H, J=7.7 Hz), 7.82 (dd, 1H, J$_a$=8.2 Hz, J$_b$=1.7 Hz), 7.75 (dd, 1H, J$_a$=10.3 Hz, J$_b$=1.7 Hz), 5.25-5.10 (m, 1H), 4.30-4.15 (m, 2H), 3.10-3.00 (m, 5H), 2.87 (septet, 1H, J=6.9 Hz), 2.00-1.80 (m, 3H), 1.55-1.40 (m, 2H), 1.34 (d, 3H, J=6.1 Hz), 1.26 (d, 6H, J=6.8 Hz); LRMS (ESI), m/z 490 (M+H).

Example 167

1-Methylethyl 4-[(1S)-1-({5-[2-fluoro-4-(methylsulfonyl)phenyl]-2-pyrazinyl}oxy)ethyl]-1-piperidinecarboxylate

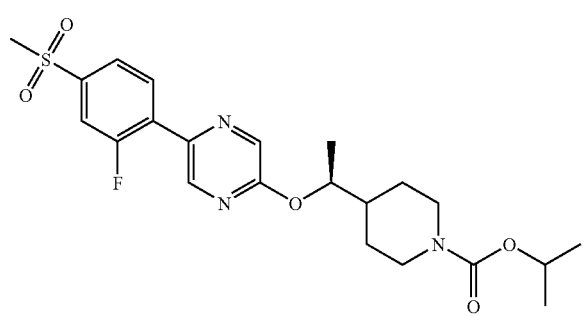

Step 1: (1R)-1-(4-pyridinyl)ethanol (61 g, 495 mmol, 96% ee) was dissolved in MeOH (1.5 L). The mixture was flushed with nitrogen and AcOH (40 mL, 0.7 mol) and PtO$_2$ (15 g) were added. The mixture was stirred overnight under an atmosphere of hydrogen. The catalyst was removed by filtration and washed with MeOH (2×100 mL) and the filtrate was concentrated. The solid residue was mixed with EtOAc (500 mL) and stirred overnight. The resulting solid was collected by filtration, washed with EtOAc (3×100 mL) and dried under vacuum overnight to yield (1R)-1-(4-piperidinyl)ethanol acetic acid salt (74.5 g, 79% yield) as an off-white solid. $^1$H NMR (400 MHz, DMSO-d$_6$): □ 3.30 (m, 1H), 3.03 (m, 2H), 2.55-2.50 (m, 2H), 1.76-1.69 (m, 1H), 1.69 (s, 3H), 1.51-1.44 (m, 1H), 1.27-1.16 (m, 3H), 0.96 (d, 3H, J=6.3 Hz).

Step 2: A solution of (1R)-1-(4-piperidinyl)ethanol acetic acid salt (1 g, 5.28 mmol) in water (10 mL) was cooled to 0° C. in an ice bath. A solution of $K_2CO_3$ (3.65 g, 26.4 mmol) in water (8 mL) was added, followed by dropwise addition of isopropyl chloroformate (1M in toluene, 21.1 mL, 21.1 mmol). The reaction mixture was stirred from 0° C. to ambient temperature over 2 h, then at ambient temperature overnight, diluted with $CH_2Cl_2$ (100 mL), washed with 1N HCl, water and brine, dried over $Na_2SO_4$, filtered, and the filtrate was concentrated to give a brown oil, which was dissolved in MeOH (15 mL). $K_2CO_3$ (1 g, 7.24 mmol) and water (5 mL) were added, and the mixture was stirred at ambient temperature overnight and extracted with $CH_2Cl_2$. The organic extracts were combined and washed with water, brine, dried over $Na_2SO_4$, filtered, and the filtrate was concentrated to give 1.11 g (98%) of 1-methylethyl 4-[(1R)-1-hydroxyethyl]-1-piperidinecarboxylate as a colorless oil, which was used without further purification (% ee not determined). $^1$H NMR (400 MHz, $CDCl_3$): δ 4.88 (septet, 1H, J=6.2 Hz), 4.25-4.10 (m, 2H), 3.60-3.50 (m, 1H), 2.75-2.60 (m, 2H), 1.85-1.75 (m, 1H), 1.65-1.55 (m, 1H), 1.50-1.35 (m, 1H), 1.25-1.10 (m, 11H).

Step 3: 1-Methylethyl 4-{(1R)-1-[(methylsulfonyl)oxy]ethyl}-1-piperidinecarboxylate (0.7 g, 100%) was prepared as a light yellow oil from 1-methylethyl 4-[(1R)-1-hydroxyethyl]-1-piperidinecarboxylate (0.5 g, 2.32 mmol), methanesulfonyl chloride (0.22 mL, 2.79 mmol), $Et_3N$ (0.49 mL, 3.48 mmol) and $CH_2Cl_2$ (30 mL) in a manner similar to Example 150, Step 1. The crude material was used without further purification. $^1$H NMR (400 MHz, $CDCl_3$): δ 4.88 (septet, 1H, J=6.2 Hz), 4.70-4.55 (m, 1H), 4.30-4.10 (m, 2H), 2.99 (s, 3H), 2.75-2.60 (m, 2H), 1.80-1.60 (m, 3H), 1.38 (d, 3H, J=6.3 Hz), 1.35-1.15 (m, 8H).

Step 4: 1-Methylethyl 4-[(1S)-1-({5-[2-fluoro-4-(methylthio)phenyl]-2-pyrazinyl}oxy)ethyl]-1-piperidinecarboxylate (0.334 g, 45%) was prepared as a yellow oil from 5-[2-fluoro-4-(methylthio)phenyl]-2-pyrazinol (and tautomers thereof) (prepared as in Example 161, Alternative synthesis, Step 4, 0.405 g, 1.71 mmol), crude 1-methylethyl 4-{(1R)-1-[(methylsulfonyl)oxy]ethyl}-1-piperidinecarboxylate (0.70 g, 2.32 mmol) and $K_2CO_3$ (0.48 g, 3.43 mmol) in DMF (15 mL) in a manner similar to Example 166, Step 2. The crude product was purified by chromatography on an ISCO silica gel column using 0 to 25% EtOAc/hexanes. $^1$H NMR (400 MHz, $CDCl_3$): δ 8.52 (s, 1H), 8.22 (d, 1H, J=1.3 Hz), 7.85 (t, 1H, J=8.3 Hz), 7.10 (dd, 1H, $J_a$=8.3 Hz, $J_b$=1.7 Hz), 7.01 (dd, 1H, $J_a$=12.1 Hz, $J_b$=1.8 Hz), 5.15-5.05 (m, 1H), 4.89 (septet, 1H, J=6.2 Hz), 4.19 (bs, 2H), 2.80-2.65 (m, 2H), 2.50 (s, 3H), 1.85-1.65 (m, 3H), 1.40-1.15 (m, 11H); LRMS (ESI), m/z 434 (M+H).

Step 5: The title compound (0.195 g) was prepared from 1-methylethyl 4-[(1S)-1-({5-[2-fluoro-4-(methylthio)phenyl]-2-pyrazinyl}oxy)ethyl]-1-piperidinecarboxylate (0.33 g, 0.76 mmol) and Oxone® (1.41 g, 2.29 mmol) in acetone (25 mL) and water (10 mL) in a manner similar to Example 166, Step 2. The crude product was purified by chromatography on an ISCO silica gel column using 0 to 50% EtOAc/hexanes, followed by chiral separation on an AS-H column with 25% MeOH in $CO_2$, 140 bar, 40° C. at 2 mL/min. The first eluting peak was further purified by trituration with 9% EtOAc/hexanes to afford the title compound as a white solid. $^1$H NMR (400 MHz, $CDCl_3$): δ 8.64 (s, 1H), 8.27 (s, 1H), 8.20 (t, 1H, J=7.8 Hz), 7.85-7.70 (m, 2H), 5.20-5.10 (m, 1H), 4.89 (septet, 1H, J=6.2 Hz), 4.30-4.15 (m, 2H), 3.09 (s, 3H), 2.80-2.65 (m, 2H), 1.90-1.65 (m, 3H), 1.40-1.15 (m, 11H); LRMS (ESI), m/z 466 (M+H).

Example 168

(±)-1-Methylethyl 4-[({6-[2-fluoro-4-(methylsulfinyl)phenyl]-3-pyridinyl}oxy)methyl]-1-piperidinecarboxylate

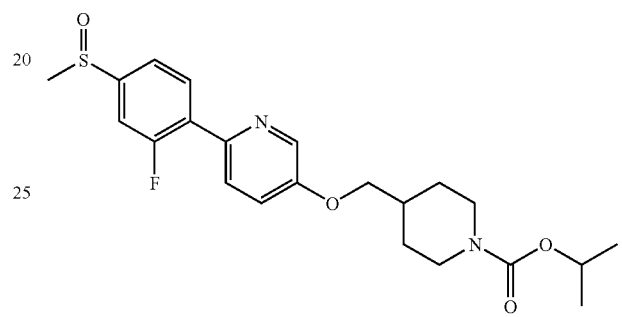

Step 1: 1-Methylethyl 4-[({6-[2-fluoro-4-(methylthio)phenyl]-3-pyridinyl}oxy)methyl]-1-piperidinecarboxylate (0.16 g, 55%) was prepared as a light yellow solid from [2-fluoro-4-(methylthio)phenyl]boronic acid (prepared as in Example 161, Alternative synthesis, Step 2, 0.26 g, 1.4 mmol), 1-methylethyl 4-{[(6-bromo-3-pyridinyl)oxy]methyl}-1-piperidinecarboxylate (prepared as in Example 81, Step 1, 0.25 g, 0.7 mmol), $Na_2CO_3$ (0.148 g, 1.4 mmol), $Pd(PPh_3)_2Cl_2$ (49 mg, 0.07 mmol), water (1 mL) and DME (2 mL) in a manner similar to Example 21, Step 3. LRMS (APCI), m/z 419 (M+H).

Step 2: A mixture of 1-methylethyl 4-[({6-[2-fluoro-4-(methylthio)phenyl]-3-pyridinyl}oxy)methyl]-1-piperidinecarboxylate (50 mg, 0.12 mmol) in 1,1,1,3,3,3-hexafluoro-2-propanol (2 mL) was treated with 30% aqueous $H_2O_2$ (0.027 mL, 0.24 mmol) at ambient temperature. After 2 h, saturated aqueous $Na_2SO_3$ (5 mL) was added carefully and the mixture was stirred for 10 min. EtOAc (3 mL) was added, the organic layer was separated and dried over $Na_2SO_4$ and the solvent evaporated off. The crude product was purified by reverse-phase preparative HPLC using a $CH_3CN$:$H_2O$ gradient (10:90 to 100:0) with 0.1% TFA as a modifier to give 25 mg (48%) of the title compound as a white solid. $^1$HNMR (400 MHz, $CDCl_3$): δ 8.41 (d, 1H, J=2.7 Hz), 8.14 (t, 1H, J=7.8 Hz), 7.78 (dd, 1H, $J_a$=8.7 Hz, $J_b$=1.5 Hz), 7.51 (dd, 1H, $J_a$=10.5 Hz, $J_b$=1.4 Hz), 7.44 (dd, 1H, $J_a$=8.2 Hz, $J_b$=1.5 Hz), 7.30-7.23 (m, 1H), 4.92 (septet, 1H, J=6.2 Hz), 4.30-4.15 (m, 2H), 3.90 (d, 2H, J=6.4 Hz), 2.85-2.74 (m, 2H), 2.76 (s, 3H), 2.06-1.96 (m, 1H), 1.85 (m, 2H), 1.88-1.22 (m, 2H), 1.24 (d, 6H, J=6.4 Hz); LRMS (ESI), m/z 435 (M+H).

Example 169

5-[({1-[3-(1-Methylethyl)-1,2,4-oxadiazol-5-yl]-4-piperidinyl}methyl)oxy]-2-[4-(methylsulfonyl)phenyl]pyridine hydrochloride

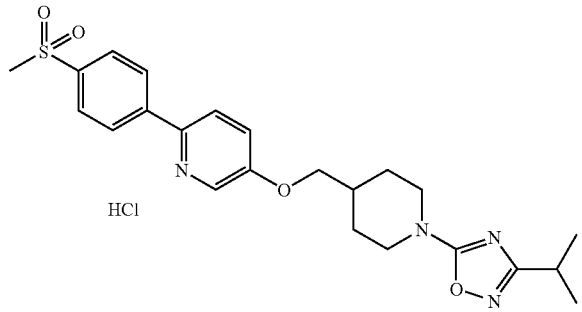

Step 1: A mixture of 6-bromo-3-pyridinol (7 g, 40 mmol), [4-(methylsulfonyl)phenyl]boronic acid (8 g, 40 mmol), 2M $Na_2CO_3$ (30 mL), $PdCl_2(PPh_3)_2$ (1 g) and DME (60 mL) under $N_2$ was heated at 80° C. overnight. The reaction was allowed to cool to room temperature and was diluted with EtOAc and water. The resulting precipitate was filtered off and the aqueous layer was extracted with EtOAc. The combined organic extracts were dried over MgSO4, filtered and concentrated. The aqueous phase was also concentrated. Each of the residues was recrystallized from MeOH. The solid material from the organic phase recrystallization and the mother liquors from both aqueous and organic recrystallizations were combined, concentrated and purified by chromatography on a silica gel column using 0 to 10% MeOH/$CH_2Cl_2$ to give 6-[4-(methylsulfonyl)phenyl]-3-pyridinol (2.9 g, 29%) as a tan solid.

Step 2: Diisopropyl azodicarboxylate (0.175 mL, 0.89 mmol) was added dropwise to a solution of 6-[4-(methylsulfonyl)phenyl]-3-pyridinol (150 mg, 0.59 mmol), {1-[3-(1-methylethyl)-1,2,4-oxadiazol-5-yl]-4-piperidinyl}methanol (prepared as in Example 20, Steps 1-3, 200 mg, 0.89 mmol), $PPh_3$ (233 mg, 0.89 mmol), and THF (10 mL) at ambient temperature. The mixture was stirred at ambient temperature for 4 h. The mixture was concentrated, and the resulting crude was purified by reverse-phase preparative HPLC using a $CH_3CN:H_2O$ gradient (10:90 to 100:0) with 0.05% TFA as a modifier, then taken up in $CH_2Cl_2$ and free-based with saturated $NaHCO_3$ (aq) to give 5-[({1-[3-(1-methylethyl)-1,2,4-oxadiazol-5-yl]-4-piperidinyl}methyl)oxy]-2-[4-(methylsulfonyl)phenyl]pyridine (220 mg) as a white solid.

Step 3: A mixture of the resulting white solid (50 mg, 0.11 mmol) in THF (3 mL) was stirred at ambient temperature as 4N HCl in dioxane (28 μL) was added dropwise. The resulting white precipitate was filtered, air-dried, then triturated with diethyl ether to give 35 mg (65%) of the title compound as a white solid. $^1$H NMR (400 MHz, $CDCl_3$): δ 8.46 (d, 1H, J=0.7 Hz), 8.18 (bs, 2H), 8.05 (bs, 2H), 7.83 (bs, 1H), 7.61-7.45 (m, 1H), 4.24 (d, 2H, J=10.4 Hz), 4.00 (d, 2H, J=0.6 Hz), 3.21-3.03 (m, 5H), 2.89 (m, 1H), 2.15 (d, 1H, J=1.1 Hz), 1.96 (bs, 2H), 1.50 (bs, 2H), 1.28 (d, 6H, J=6.9 Hz); LRMS (ESI), m/z 457 (M+H).

Example 170

1-Methylethyl 4-({[4'-(methylsulfonyl)-4-biphenylyl]thio}methyl)-1-piperidinecarboxylate

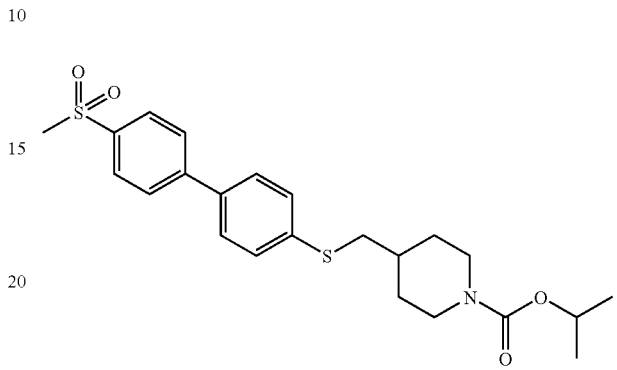

Step 1: Methanesulfonyl chloride (0.28 mL, 3.6 mmol) was added dropwise to a solution of 1-methylethyl 4-(hydroxymethyl)-1-piperidinecarboxylate (prepared as in Example 9, Step 1, 600 mg, 3 mmol), triethylamine (0.627 mL, 4.5 mmol), and $CH_2$—$Cl_2$ (10 mL) at 0° C. The mixture was stirred at 0° C. for 30 min, then at ambient temperature for 2 h. The mixture was washed with water, and the organics were concentrated. The resulting crude material was mixed with 4-bromobenzenethiol (567 mg, 3 mmol) and $K_2CO_3$ (829 mg, 6 mmol) in DMF (10 mL), and the mixture was stirred at ambient temperature overnight. The mixture was charged with water, and extracted with EtOAc. The organics were dried over $MgSO_4$, filtered, and the filtrate was concentrated. The crude product was purified by chromatography on a silica gel column using 0 to 10% EtOAc/hexanes to give 292 mg (26%) of 1-methylethyl 4-{[(4-bromophenyl)thio]methyl}-1-piperidinecarboxylate as a clear oil. $^1$H NMR (400 MHz, $CDCl_3$): δ 7.37 (d, 2H, J=8.5 Hz), 7.15 (d, 2H, J=8.5 Hz), 4.95-4.82 (m, 1H), 4.15-4.09 (m, 2H), 2.80 (d, 2H, J=6.9 Hz), 2.72-2.60 (m, 2H), 1.85-1.77 (m, 2H), 1.70-1.60 (m, 1H), 1.24-1.08 (m, 8H); LRMS (ESI), m/z 372/374 (M+H).

Step 2: A mixture of 1-methylethyl 4-{[(4-bromophenyl)thio]methyl}-1-piperidinecarboxylate (292 mg, 0.78 mmol), [4-(methylsulfonyl)phenyl]boronic acid (157 mg, 0.78 mmol), 2M $Na_2CO_3$ (2 mL), and $Pd(PPh_3)_2Cl_2$ (200 mg, 0.28 mmol) in DME (8 mL) stirred at 80° C. for 3 h, then at ambient temperature overnight. The mixture was poured onto a Varian Chem Elut column, flushed with EtOAc, and the organics concentrated. The crude product was purified by chromatography on a silica gel column using 0 to 30% EtOAc/hexanes to give 105 mg (30%) of the title compound as a tan solid. $^1$H NMR (400 MHz, $CDCl_3$): δ 7.98 (d, 2H, J=8.4 Hz), 7.73 (d, 2H, J=8.4 Hz), 7.51 (d, 2H, J=8.4 Hz), 7.38 (d, 2H, J=8.4 Hz), 4.89 (septet, 1H, J=6.2 Hz), 4.20-4.10 (m, 2H), 3.07 (s, 3H), 2.89 (d, 2H, J=6.8 Hz), 2.75-2.64 (m, 2H), 1.90-1.80 (m, 2H), 1.79-1.65 (m, 1H), 1.28-1.12 (m, 8H); LRMS (ESI), m/z 448 (M+H).

Example 171

(±)-5-[({1-[3-(1-Methylethyl)-1,2,4-oxadiazol-5-yl]-4-piperidinyl}methyl)oxy]-2-[4-(methylsulfinyl)phenyl]pyridine

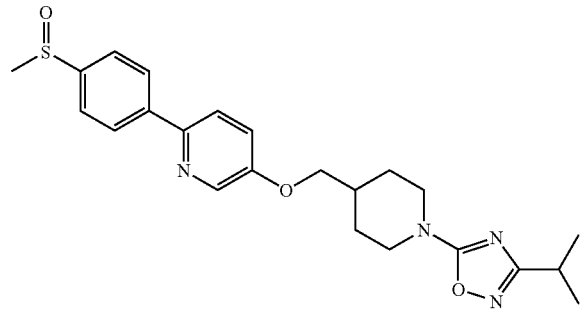

Step 1: A mixture of [4-(methylthio)phenyl]boronic acid (7.2 g, 43.1 mmol), 6-bromo-3-pyridinol (5 g, 28.7 mmol), 2M $Na_2CO_3$ (44 mL), $Pd(PPh_3)_4$ (1.7 g, 1.4 mmol) and DME (70 mL) was degassed with $N_2$ for 30 min, and stirred and heated at 80° C. for 18 h. The mixture was charged with water and $CH_2Cl_2$ and the organic layer was washed with 1N NaOH (100 mL). The basic aqueous layer was washed with $Et_2O$, cooled in an ice bath and the pH was adjusted to about 10 with 6N HCl. The resulting solid was collected, washed with water and air-dried to give 6-[4-(methylthio)phenyl]-3-pyridinol (4.3 g, 69%) as a yellow solid. The reaction was repeated on twice the scale (10 g of 6-bromo-3-pyridinol) to provide 9.1 g (72%) of product. The reaction was repeated on 10× the scale (101.5 g of 6-bromo-3-pyridinol) to provide 53.7 g of product. $^1$H NMR (400 MHz, DMSO-$d_6$): δ 9.96 (s, 1H), 8.15 (d, 1H, J=2.6 Hz), 7.87 (d, 2H, J=8.6 Hz), 7.73 (d, 1H, J=8.7 Hz), 7.27 (d, 2H, J=8.6 Hz), 7.18 (dd, 1H, $J_a$=8.6 Hz, $J_b$=2.9 Hz), 2.46 (s, 3H); LRMS (ESI), m/z 218 (M+H).

Step 2: A mixture of 6-[4-(methylthio)phenyl]-3-pyridinol (53.2 g, 245 mmol), {1-[3-(1-methylethyl)-1,2,4-oxadiazol-5-yl]-4-piperidinyl}methyl methanesulfonate (prepared as in Example 100, Step 4, 74.3 g, 735 mmol), $K_2CO_3$ (101.5 g, 735 mmol) and DMF (500 mL) was stirred at 80° C. for 2 h. The mixture was charged with water, allowed to stand for 30 min, and the resulting precipitate was filtered, washed with water, heptane, and air dried to give 5-[({1-[3-(1-methylethyl)-1,2,4-oxadiazol-5-yl]-4-piperidinyl}methyl)oxy]-2-[4-(methylthio)phenyl]pyridine (93.7 g, 90%) as a tan solid. $^1$H NMR (400 MHz, $CDCl_3$): δ 8.32 (d, 1H, J=2.8 Hz), 7.83 (d, 2H, J=8.5 Hz), 7.61 (d, 1H, J=8.7 Hz), 7.30 (d, 2H, J=8.5 Hz), 7.22 (d, 1H, J=3.0 Hz), 4.30-4.10 (m, 2H), 3.90 (d, 2H, J=6.2 Hz), 3.15-3.05 (m, 2H), 2.92-2.82 (m, 1H), 2.50 (s, 3H), 2.14-1.99 (m, 1H), 2.00-1.90 (m, 2H), 1.55-1.40 (m, 2H), 1.27 (d, 6H, J=6.3 Hz); LRMS (ESI), m/z 425 (M+H).

Step 3: A solution of 5-[({1-[3-(1-methylethyl)-1,2,4-oxadiazol-5-yl]-4-piperidinyl}methyl)oxy]-2-[4-(methylthio)phenyl]pyridine (93.7 g, 221 mol) in 1,1,1,3,3,3-hexafluoro-2-propanol (300 mL) at 5° C. was treated with 30% aqueous $H_2O_2$ (29 mL, 287 mol) over a 1.5 h period at such a rate to maintain temperature between approximately 6-10° C. The reaction was stirred at 5° C. for 2.5 h. The reaction was diluted with $CH_2Cl_2$ (600 mL), quenched by the addition of saturated aqueous $Na_2SO_3$ (400 mL), allowed to warm to room temperature and stirred for 30 min. The organic layer was washed with saturated aqueous $Na_2SO_3$ (400 mL×2), brine and was dried over $MgSO_4$ and concentrated to give a tan solid. The solid was recrystallized from MeOH to provide the title compound (83.5 g, 86%) as a pale yellow solid. $^1$H NMR (400 MHz, $CDCl_3$): δ 8.37 (d, 1H, J=2.7 Hz), 8.07 (d, 2H, J=8.4 Hz), 7.74-7.64 (m, 3H), 7.27 (dd, 1H, $J_a$=8.7 Hz, $J_b$=2.8 Hz), 4.30-4.15 (m, 2H), 3.92 (d, 2H, J=6.2 Hz), 3.20-3.05 (m, 2H), 2.87 (septet, 1H, J=6.9 Hz), 2.74 (s, 3H), 2.19-2.01 (m, 1H), 2.00-1.90 (m, 2H), 1.55-1.40 (m, 2H), 1.27 (d, 6H, J=7.0 Hz); LRMS (ESI), m/z 441 (M+H).

Example 172

1,1-Dimethylethyl 4-[({6-[4-(methylsulfonyl)phenyl]-3-pyridinyl}amino)methyl]-1-piperidinecarboxylate trifluoroacetate

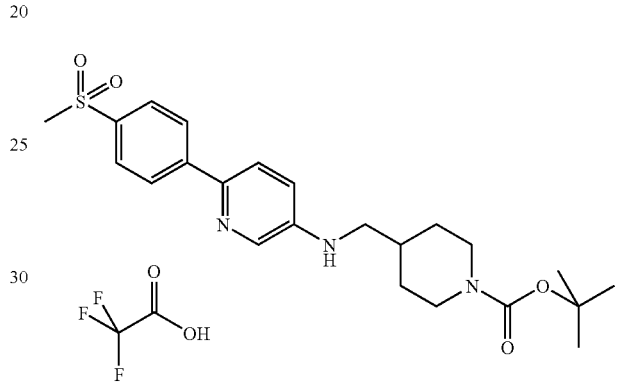

Step 1: TBTU (2.86 g, 8.9 mmol) and diisopropylethylamine (1.55 mL, 8.9 mmol) were added to a mixture of 1-{[(1,1-dimethylethyl)oxy]carbonyl}-4-piperidinecarboxylic acid (1.35 g, 5.9 mmol) in DMF (20 mL) at ambient temperature. The mixture was stirred at ambient temperature for 1 h, charged with 6-bromo-3-pyridinamine (1.13 g, 6.5 mmol), then stirred at 50° C. overnight. The mixture was cooled to ambient temperature, charged with water (200 mL), and extracted with EtOAc. The organics were dried over $MgSO_4$, filtered, and the filtrate was concentrated. The crude product was purified by chromatography on a silica gel column using 0 to 50% EtOAc/hexanes to give 1.75 g (77%) of 1,1-dimethylethyl 4-{[(6-bromo-3-pyridinyl)amino]carbonyl}-1-piperidinecarboxylate as an off-white solid. $^1$H NMR (400 MHz, $CDCl_3$): δ 8.32 (d, 1H, J=2.7 Hz), 8.07 (dd, 1H, $J_a$=8.6 Hz, $J_b$=2.8 Hz), 7.44-7.39 (m, 2H), 4.16 (bs, 2H), 2.90-2.65 (m, 2H), 2.45-2.35 (m, 1H), 1.95-1.80 (m, 2H), 1.79-1.65 (m, 2H), 1.44 (s, 9H); LRMS (ESI), m/z 384 (M+H).

Step 2: A mixture of 1,1-dimethylethyl 4-{[(6-bromo-3-pyridinyl)amino]carbonyl}-1-piperidinecarboxylate (1.75 g, 4.55 mmol), [4-(methylsulfonyl)phenyl]boronic acid (911 mg, 4.55 mmol), 2M $Na_2CO_3$ (5 mL) and $Pd(PPh_3)_2Cl_2$ (400 mg, 0.57 mmol) in DME (10 mL) was stirred at 80° C. overnight. The mixture was cooled to ambient temperature, and the organic phase was separated and concentrated. The crude product was purified by chromatography on a silica gel column using 0 to 5% MeOH/$CH_2Cl_2$ to give 1.41 g (68%) of 1,1-dimethylethyl 4-({6-[4-(methylsulfonyl)phenyl]-3-pyridinyl}amino)carbonyl]-1-piperidinecarboxylate as an off-white solid. $^1$H NMR (400 MHz, $CDCl_3$): δ 8.74 (bs, 1H), 8.57-8.46 (m, 1H), 8.16 (d, 2H, J=8.5 Hz), 8.03 (d, 2H, J=8.4

Hz), 7.81 (d, 1H, J=8.7 Hz), 4.28-4.11 (m, 2H), 3.07 (s, 3H), 2.85-2.74 (m, 2H), 2.55-2.44 (m, 1H), 2.00-1.80 (m, 2H), 1.82-1.69 (m, 2H), 1.45 (s, 9H); LRMS (ESI), m/z 460 (M+H).

Step 3: A suspension of 1,1-dimethylethyl 4-[({6-[4-(methylsulfonyl)phenyl]-3-pyridinyl}amino)carbonyl]-1-piperidinecarboxylate (100 mg, 0.22 mmol) in THF (2 mL) was added dropwise to 1.8M BH$_3$-THF (0.856 mL, 1.54 mmol) at ambient temperature. The mixture was stirred at reflux for 2 h, then at ambient temperature overnight. No reaction appeared to occur. The mixture was then charged with 1.0M BH$_3$-THF (1.54 mL, 1.54 mmol) at ambient temperature and refluxed for 1 h, cooled to ambient temperature, quenched with methanol, and concentrated. The crude product was purified by reverse-phase preparative HPLC using CH$_3$CN:H$_2$O gradient (0.5:99.5 to 90:10) with 0.05% TFA as a modifier to give 30 mg (24%) of the title compound as an off-white solid. $^1$H NMR (400 MHz, CDCl$_3$): δ 8.26 (d, 1H, J=2.6 Hz), 8.05-7.95 (m, 4H), 7.64 (d, 1H, J=8.7 Hz), 7.07 (dd, 1H, J$_a$=8.8 Hz, J$_b$=2.7 Hz), 4.13 (bs, 2H), 3.11 (d, 2H, J=6.3 Hz), 3.06 (s, 3H), 2.80-2.60 (m, 2H), 1.80-1.71 (m, 3H), 1.44 (s, 9H), 1.26-1.11 (m, 2H); LRMS (ESI), m/z 444 (M−H).

Example 173

(±)-1-Methylethyl 4-[({6-[4-(methylsulfinyl)phenyl]-3-pyridinyl}oxy)methyl]-1-piperidinecarboxylate trifluoroacetate

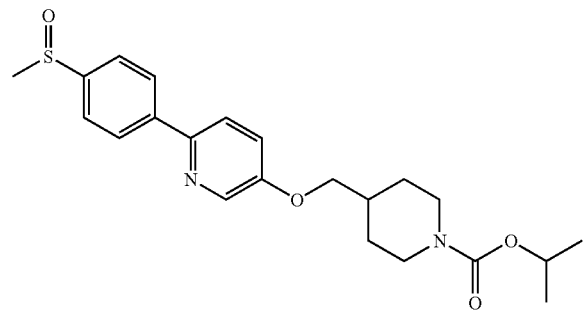

Step 1: A mixture of [4-(methylthio)phenyl]boronic acid (66 mg, 0.39 mmol), 1-methylethyl 4-{[(6-bromo-3-pyridinyl)oxy]methyl}-1-piperidinecarboxylate (prepared as in Example 81, Step 1, 140 mg, 0.39 mmol), PdCl$_2$(PPh$_3$)$_2$ (50 mg), 2M Na$_2$CO$_3$ (1 mL) and DME (2 mL) was stirred and heated in a microwave at 120° C. for 10 min, cooled to ambient temperature, and the organics were separated. The aqueous phase was washed with EtOAc. The organics were combined, dried over MgSO$_4$, filtered, and the filtrate was concentrated. The crude product was purified by chromatography on a silica gel column using 0 to 50% EtOAc/hexanes to give 140 mg (90%) of 1-methylethyl 4-[({6-[4-(methylthio)phenyl]-3-pyridinyl}oxy)methyl]-1-piperidinecarboxylate as a white solid. $^1$H NMR (400 MHz, CDCl$_3$): δ 8.32 (d, 1H, J=2.8 Hz), 7.84 (d, 2H, J=8.5 Hz), 7.60 (d, 1H, J=8.8 Hz), 7.30 (d, 2H, J=8.5 Hz), 7.22 (bs, 1H), 4.90 (septet, 1H, J=6.3 Hz), 4.20 (bs, 2H), 3.87 (d, 2H, J=6.3 Hz), 2.85-2.70 (m, 2H), 2.50 (s, 3H), 2.04-1.94 (m, 1H), 1.90-1.75 (m, 2H), 1.35-1.20 (m, 8H); LRMS (ESI), m/z 401 (M+H).

Step 2: The title compound (370 mg, 99%) was prepared as an off-white solid from 1-methylethyl 4-[({6-[4-(methylthio)phenyl]-3-pyridinyl}oxy)methyl]-1-piperidinecarboxylate (prepared as in Example 173, Step 1, 360 mg, 0.9 mmol), 30% H$_2$O$_2$ (aq) (0.612 mL, 5.4 mmol) and 1,1,1,3,3,3-hexafluoro-2-propanol (3 mL) in a manner similar to Example 171, Step 3. $^1$H NMR (400 MHz, CDCl$_3$): δ 8.50 (d, 1H, J=2.7 Hz), 8.05 (d, 2H, J=8.4 Hz), 7.78-7.71 (m, 3H), 7.45 (dd, 1H, J$_a$=8.7 Hz, J$_b$=2.5 Hz), 4.91 (septet, 1H, J=6.2 Hz), 4.21 (bs, 2H), 3.93 (d, 2H, J=6.3 Hz), 2.84-2.72 (m, 5H), 2.09-1.96 (m, 1H), 1.90-1.80 (m, 2H), 1.37-1.20 (m, 8H); LRMS (ESI), m/z 417 (M+H).

Example 174

(R)-1-Methylethyl 4-[({6-[4-(methylsulfinyl)phenyl]-3-pyridinyl}oxy)methyl]-1-piperidinecarboxylate The racemic sulfoxide 1-methylethyl 4-[({6-[4-(methylsulfinyl)phenyl]-3-pyridinyl}oxy)methyl]-1-piperidinecarboxylate (Example 173, 370 mg) was subjected to Chiral HPLC [column: Chiralpak AS-H, column mobile phase: 65% CO$_2$: 35% MeOH (1 mL/min), pressure 140 bar, temperature 40° C., 215 nm] analysis and then separation to give two (R and S) enantiomers. The title compound (100 mg) was isolated as a white solid with Tr of 3.73 min (first eluting peak). The (R) absolute stereochemistry was assigned by Ab initio VCD analysis.

Example 175

(S)-1-Methylethyl 4-[({6-[4-(methylsulfinyl)phenyl]-3-pyridinyl}oxy)methyl]-1-piperidinecarboxylate The racemic sulfoxide 1-methylethyl 4-[({6-[4-(methylsulfinyl)phenyl]-3-pyridinyl}oxy)methyl]-1-piperidinecarboxylate (Example 173, 370 mg) was subjected to Chiral HPLC [column: Chiralpak AS-H, column mobile phase: 65% CO$_2$: 35% MeOH (1 mL/min), pressure 140 bar, temperature 40° C., 215 nm] analysis and then separation to give two (R and S) enantiomers. The title compound (99 mg) was isolated as an off-white solid with Tr of 7.24 min (second eluting peak). The (S) absolute stereochemistry was assigned by Ab initio VCD analysis.

Example 176

(±)-2-[2-Fluoro-4-(methylsulfinyl)phenyl]-5-[({1-[3-(1-methylethyl)-1,2,4-oxadiazol-5-yl]-4-piperidinyl}methyl)oxy]pyridine

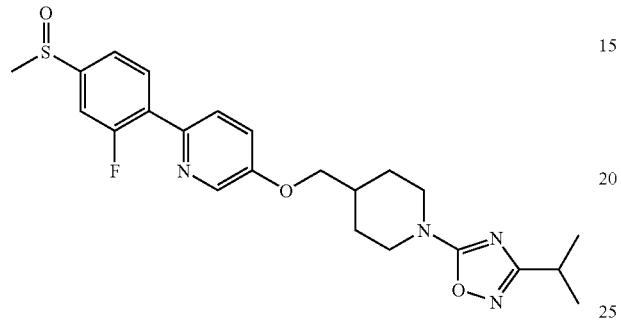

Step 1: A mixture of 6-bromo-3-pyridinol (42.2 g, 242 mmol), [2-fluoro-4-(methylthio)phenyl]boronic acid (prepared as in Example 161, Alternative synthesis, Step 2, 54.1 g, 291 mmol), 2M $Na_2CO_3$ (410 mL), $Pd(PPh_3)_4$ (14 g, 12 mmol) and DME (550 mL) was degassed with $N_2$ for 30 min, and then the mixture was heated at 80° C. for 5 h. The reaction was allowed to cool to room temperature and stirred overnight. The mixture was diluted with dichloromethane (500 mL) and water (200 mL) and stirred for 30 min. The reaction was filtered and the solids were rinsed with dichloromethane and the aqueous layer was extracted with dichloromethane. The combined organic extracts were extracted with 1N NaOH (2×300 mL), and then the basic layer was cooled in an ice bath and the pH was adjusted to ~1 with concentrated HCl. EtOAc was added, the mixture was stirred for 1 h, and the resulting precipitate was collected by filtration (EtOAc wash) and air-dried to give 52.6 g (80%) of 6-[2-fluoro-4-(methylthio)phenyl]-3-pyridinol hydrochloride as a pale yellow solid. $^1H$ NMR (400 MHz, $CDCl_3$): δ 8.36 (d, 1H, J=2.8 Hz), 7.87 (t, 1H, J=8.3 Hz), 7.69 (dd, 1H, $J_a$=8.7 Hz, $J_b$=1.7 Hz), 7.22 (bs, 1H), 7.11-7.07 (m, 1H), 6.98 (dd, 1H, $J_a$=12.1 Hz, $J_b$=1.8 Hz), 4.30-4.10 (m, 2H), 3.90 (d, 2H, J=6.3 Hz), 3.14-3.06 (m, 2H), 2.93-2.79 (m, 1H), 2.49 (s, 3H), 2.11-2.03 (m, 1H), 2.00-1.85 (m, 2H), 1.50-1.38 (m, 2H), 1.27 (d, 6H, J=7.0 Hz); LRMS (ESI), m/z 443 (M+H).

Step 2: A mixture of {1-[3-(1-methylethyl)-1,2,4-oxadiazol-5-yl]-4-piperidinyl}methyl methanesulfonate (prepared as in Example 100, Step 4, 50.4 g, 166 mmol), 6-[2-fluoro-4-(methylthio)phenyl]-3-pyridinol hydrochloride (47.6 g, 175 mmol), powdered potassium carbonate (72.6 g, 525 mmol) and N,N-dimethylformamide (450 mL) was mechanically stirred and heated at 80° C. under nitrogen for 48 h. The reaction was cooled to ambient temperature, poured onto ice water (2.5 L) and allowed to stand for 30 min. The resulting solid was filtered, rinsed with water (500 mL), heptane (500 mL) and air-dried to afford 2-[2-fluoro-4-(methylthio)phenyl]-5-[({1-[3-(1-methylethyl)-1,2,4-oxadiazol-5-yl]-4-piperidinyl}methyl)oxy]pyridine (67.5 g, 92%) as a light tan solid.

Step 3: The title compound (109 g, 76%) was prepared as a white solid from 2-[2-fluoro-4-(methylthio)phenyl]-5-[({1-[3-(1-methylethyl)-1,2,4-oxadiazol-5-yl]-4-piperidinyl}methyl)oxy]pyridine (prepared as in Step 2, 138 g, 312 mmol), 30% $H_2O_2$ (aq) (41 mL, 410 mmol) and 1,1,1,3,3,3-hexafluoro-2-propanol (400 mL) in a manner similar to Example 171, Step 3. $^1H$ NMR (400 MHz, $CDCl_3$): δ 8.39 (d, 1H, J=2.8 Hz), 8.13 (t, 1H, J=7.8 Hz), 7.77 (dd, 1H, $J_a$=8.7 Hz, $J_b$=1.9 Hz), 7.50 (dd, 1H, $J_a$=10.4 Hz, $J_b$=1.6 Hz), 7.43 (dd, 1H, $J_a$=8.1 Hz, $J_b$=1.7 Hz), 7.26 (d, 1H, J=3.0 Hz), 4.27-4.16 (m, 2H), 3.92 (d, 2H, J=6.2 Hz), 3.20-3.00 (m, 2H), 2.87 (septet, 1H, J=7.0 Hz), 2.74 (s, 3H), 2.15-2.03 (m, 1H), 2.00-1.90 (m, 2H), 1.52-1.40 (m, 2H), 1.27 (d, 6H, J=7.0 Hz); LRMS (ESI), m/z 459 (M+H).

Example 177

(R)-2-[2-Fluoro-4-(methylsulfinyl)phenyl]-5-[({1-[3-(1-methylethyl)-1,2,4-oxadiazol-5-yl]-4-piperidinyl}methyl)oxy]pyridine

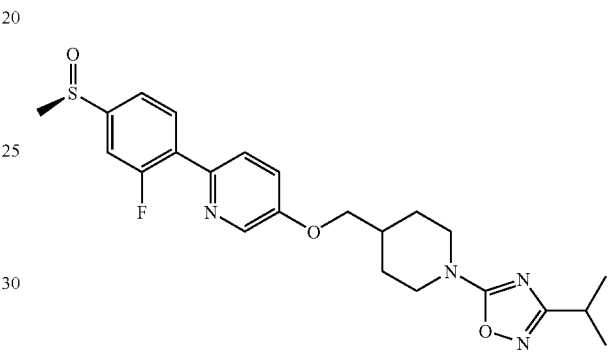

The racemic sulfoxide 2-[2-fluoro-4-(methylsulfinyl)phenyl]-5-[({1-[3-(1-methylethyl)-1,2,4-oxadiazol-5-yl]-4-piperidinyl}methyl)oxy]pyridine (prepared as in Example 176, 195 mg) was subjected to Chiral HPLC [column: Chiralpak AS-H, column mobile phase: 65% $CO_2$: 35% (80% MeOH: 20% $CHCl_3$) (2 mL/min), pressure 140 bar, temperature 30° C., 280 nm] analysis and then separation to give two (R and S) enantiomers. The title compound (32 mg) was isolated as an off-white solid with Tr of 11.25 min (first eluting peak). The (R) absolute stereochemistry was assigned by Ab initio VCD analysis.

Example 178

(S)-2-[2-Fluoro-4-(methylsulfinyl)phenyl]-5-[({1-[3-(1-methylethyl)-1,2,4-oxadiazol-5-yl]-4-piperidinyl}methyl)oxy]pyridine

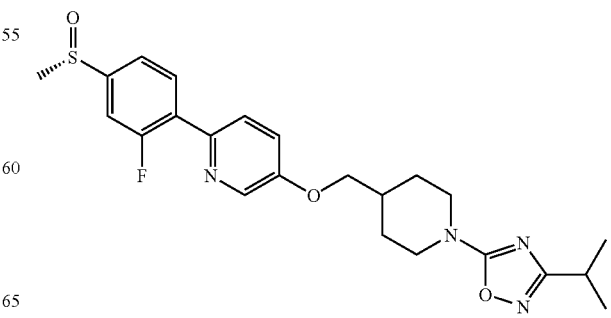

The racemic sulfoxide 2-[2-fluoro-4-(methylsulfinyl)phenyl]-5-[({1-[3-(1-methylethyl)-1,2,4-oxadiazol-5-yl]-4-piperidinyl}methyl)oxy]pyridine (prepared as in Example 176, 195 mg) was subjected to Chiral HPLC [column: Chiralpak AS-H, column mobile phase: 65% CO$_2$: 35% (80% MeOH: 20% CHCl$_3$) (2 mL/min), pressure 140 bar, temperature 30° C., 280 nm] analysis and then separation to give two (R and S) enantiomers. The title compound (39 mg) was isolated as an off-white solid with Tr of 16.69 min (second eluting peak). The (S) absolute stereochemistry was assigned by Ab initio VCD analysis.

Example 179

(R)-5-[({1-[3-(1-Methylethyl)-1,2,4-oxadiazol-5-yl]-4-piperidinyl}methyl)oxy]-2-[4-(methylsulfinyl)phenyl]pyridine

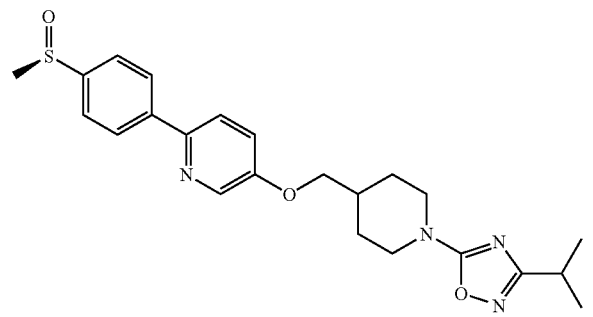

The racemic sulfoxide 5-[({1-[3-(1-methylethyl)-1,2,4-oxadiazol-5-yl]-4-piperidinyl}methyl)oxy]-2-[4-(methylsulfinyl)phenyl]pyridine (prepared as in Example 171, 290 mg) was subjected to Chiral HPLC [column: Chiralcel OJ-H, column mobile phase: 80% CO$_2$: 20% (80% MeOH: 20% CHCl$_3$) (2 mL/min), pressure 140 bar, temperature 30° C., 254 nm] analysis and then separation to give two (R and S) enantiomers. The title compound (25 mg) was isolated a tan solid with Tr of 11.15 min (first eluting peak). The (R) absolute stereochemistry was assigned by Ab initio VCD analysis.

Example 180

(S)-5-[({1-[3-(1-Methylethyl)-1,2,4-oxadiazol-5-yl]-4-piperidinyl}methyl)oxy]-2-[4-(methylsulfinyl)phenyl]pyridine

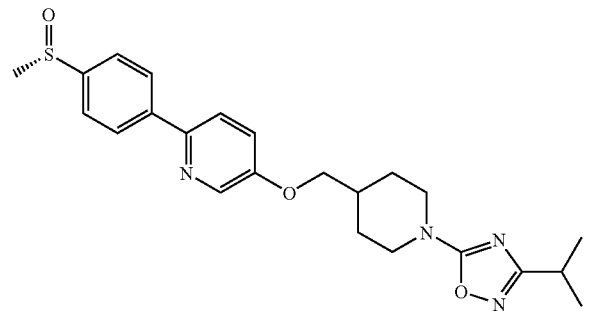

The racemic sulfoxide 5-[({1-[3-(1-methylethyl)-1,2,4-oxadiazol-5-yl]-4-piperidinyl}methyl)oxy]-2-[4-(methylsulfinyl)phenyl]pyridine (prepared as in Example 171, 290 mg) was subjected to Chiral HPLC [column: Chiralcel OJ-H, column mobile phase: 80% CO$_2$: 20% (80% MeOH: 20% CHCl$_3$) (2 mL/min), pressure 140 bar, temperature 30° C., 254 nm] analysis and then separation to give two (R and S) enantiomers. The title compound (28 mg) was isolated a tan solid with Tr of 12.11 min (second eluting peak). The (S) absolute stereochemistry was assigned by Ab initio VCD analysis.

Example 181

1-Methylethyl 4-[({6-[2-fluoro-4-(methylsulfonyl)phenyl]-3-pyridinyl}amino)methyl]-1-piperidinecarboxylate

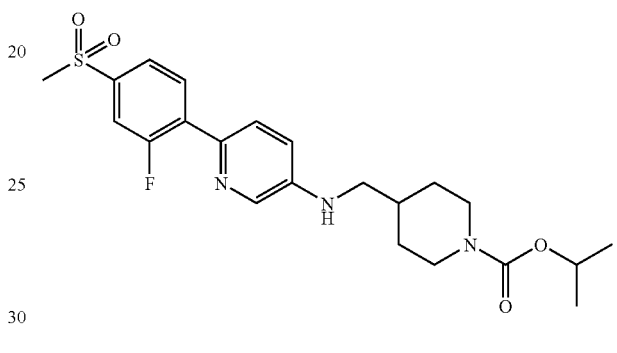

Step 1: Isopropyl chloroformate (1.0M in toluene, 55 mL, 55 mmol) was added dropwise to a mixture of 4-piperidinecarboxylic acid (6.5 g, 50 mmol) and sodium hydroxide (4.4 g, 110 mmol) in water (25 mL) at ambient temperature. The mixture was stirred at ambient temperature overnight. The aqueous phase was separated and adjusted to pH=1 with concentrated HCl. The aqueous phase was extracted with EtOAc, and the organics were dried over MgSO$_4$, filtered, and the filtrate was concentrated to give 10.2 g (95%) of 1-{[(1-methylethyl)oxy]carbonyl}-4-piperidinecarboxylic acid as a white solid. $^1$H NMR (400 MHz, CDCl$_3$): δ 4.89 (septet, 1H, J=6.2 Hz), 4.04 (d, 2H, J=3.9 Hz), 2.97-2.79 (m, 2H), 2.58-2.38 (m, 1H), 2.00-1.80 (m, 2H), 1.72-1.53 (m, 2H), 1.21 (d, 6H, J=6.3 Hz); LRMS (ESI), m/z 214 (M−H).

Step 2: 1-Methylethyl 4-{[(4-bromophenyl)amino]carbonyl}-1-piperidinecarboxylate (1.86 g, 54%) was prepared as a white solid from TBTU (4.48 g, 13.95 mmol), diisopropylethylamine (2.43 mL, 13.95 mmol), 1-{[(1-methylethyl)oxy]carbonyl}-4-piperidinecarboxylic acid (2 g, 9.3 mmol), DMF (25 mL) and 6-bromo-3-pyridinamine (1.77 g, 10.23 mmol) in a manner similar to Example 172, Step 1. $^1$H NMR (400 MHz, CDCl$_3$): δ 8.32 (d, 1H, J=2.7 Hz), 8.07 (dd, 1H, J$_a$=8.7 Hz, J$_b$=2.7 Hz), 7.42 (d, 1H, J=8.7 Hz), 7.37 (bs, 1H), 4.90 (septet, 1H, J=6.3 Hz), 4.21 (dd, 2H, J$_a$=2.4 Hz, J$_b$=1.4 Hz), 2.87-2.73 (m, 2H), 2.47-2.35 (m, 1H), 1.89 (d, 2H, J=11.9 Hz), 1.80-1.66 (m, 2H), 1.22 (d, 6H, J=6.2 Hz); LRMS (ESI), m/z 370/372 (M+H).

Step 3: A mixture of 1-methylethyl 4-{[(4-bromophenyl)amino]carbonyl}-1-piperidinecarboxylate (596 mg, 1.61 mmol), [2-fluoro-4-(methylthio)phenyl]boronic acid (prepared as in Example 161, Alternative synthesis, Step 2, 300 mg, 1.61 mmol), Pd(PPh$_3$)$_2$Cl$_2$ (112 mg, 0.16 mmol), 2M Na$_2$CO$_3$ (2 mL) and DME (6 mL) was stirred at 80° C. overnight. The mixture was charged with water, and extracted with EtOAc. The organics were dried over MgSO$_4$, filtered, and the filtrate was concentrated. The crude product was purified by chromatography on a silica gel column using 0 to 70% EtOAc/hexanes, followed by purification by reverse-phase preparative HPLC using $CH_3CN:H_2O$ gradient (10:90 to 100:0) with 0.05% TFA as a modifier to give 410 mg (59%) of 1-methylethyl 4-[({6-[2-fluoro-4-(methylthio)phenyl]-3-pyridinyl}amino)carbonyl]-1-piperidinecarboxylate as a yellow solid. $^1$H NMR (400 MHz, $CDCl_3$): δ 9.03 (bs, 1H), 7.90-7.83 (m, 1H), 7.70 (t, 1H, J=8.2 Hz), 7.67-7.59 (m, 1H), 7.47 (dd, 1H, $J_a$=7.6 Hz, $J_b$=3.0 Hz), 7.13 (dd, 1H, $J_a$=8.4 Hz, $J_b$=1.7 Hz), 7.03 (dd, 1H, $J_a$=11.9 Hz, $J_b$=1.7 Hz), 4.90 (septet, 1H, J=6.2 Hz), 4.27-4.09 (m, 2H), 2.88-2.72 (m, 2H), 2.70-2.55 (m, 1H), 2.51 (s, 3H), 2.00-1.80 (m, 2H), 1.80-1.65 (m, 2H), 1.23 (d, 6H, J=6.2 Hz); LRMS (ESI), m/z 432 (M+H).

Step 4:1-Methylethyl 4-[({6-[2-fluoro-4-(methylthio)phenyl]-3-pyridinyl}amino)methyl]-1-piperidinecarboxylate (195 mg, 49%) was prepared as a yellow solid from 1-methylethyl 4-[({6-[2-fluoro-4-(methylthio)phenyl]-3-pyridinyl}amino)carbonyl]-1-piperidinecarboxylate (410 mg, 0.95 mmol), 1M $BH_3$-THF (2.85 mL, 2.85 mmol) and THF (5 mL) in a manner similar to Example 172, Step 3, except that no 1.8M $BH_3$-THF was used. $^1$H NMR (400 MHz, $CDCl_3$): δ 8.45 (bs, 1H), 7.70 (d, 1H, J=9.0 Hz), 7.64-7.56 (m, 1H), 7.35 (d, 1H, J=9.1 Hz), 7.11 (d, 1H, J=8.2 Hz), 7.01 (d, 1H, J=11.8 Hz), 4.95-4.82 (m, 1H), 4.24-4.08 (m, 2H), 3.08 (d, 2H, J=5.1 Hz), 2.80-2.60 (m, 2H), 2.50 (d, 3H, J=2.1 Hz), 1.85-1.70 (m, 2H), 1.32-1.09 (m, 8H); LRMS (ESI), m/z 418 (M+H).

Step 5: The title compound (38 mg, 35%) was prepared as a tan solid from 1-methylethyl 4-[({6-[2-fluoro-4-(methylthio)phenyl]-3-pyridinyl}amino)methyl]-1-piperidinecarboxylate (100 mg, 0.24 mmol), m-CPBA (62 mg, 0.36 mmol) in $CH_2Cl_2$ (3 mL) in a manner similar to Example 24, Step 3. $^1$H NMR (400 MHz, $CDCl_3$): δ 8.25 (t, 1H, J=7.9 Hz), 8.17 (d, 1H, J=2.4 Hz), 7.79 (dd, 1H, $J_a$=8.2 Hz, $J_b$=1.8 Hz), 7.77-7.69 (m, 2H), 6.96 (dd, 1H, $J_a$=8.6 Hz, $J_b$=2.7 Hz), 4.93 (septet, 1H, J=6.2 Hz), 4.22 (bs, 2H), 3.15-3.00 (m, 5H), 2.80-2.65 (m, 2H), 1.90-1.70 (m, 3H), 1.30-1.19 (m, 8H); LRMS (ESI), m/z 450 (M+H).

Example 182

5-[({1-[3-(1-Methylethyl)-1,2,4-thiadiazol-5-yl]-4-piperidinyl}methyl)oxy]-2-[4-(methylsulfonyl)phenyl]pyridine trifluoroacetate

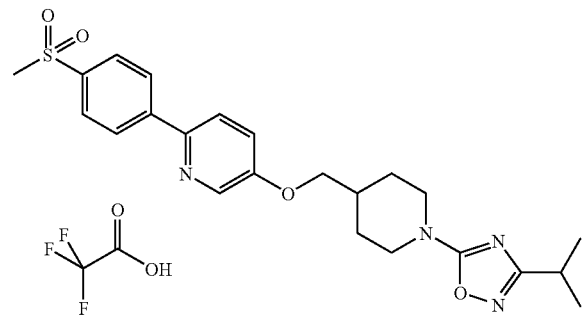

Step 1: Methanesulfonyl chloride (224 μL, 2.89 mmol) was added to a mixture of 1,1-dimethylethyl 4-(hydroxymethyl)-1-piperidinecarboxylate (519 mg, 2.41 mmol), triethylamine (504 μL, 3.62 mmol), and $CH_2Cl_2$ (10 mL) at 0° C. The mixture stirred at ambient temperature for 1 h, and was then concentrated.

Step 2: A mixture of 6-bromo-3-pyridinol (1.28 g, 7.35 mmol), [4-(methylsulfonyl)phenyl]boronic acid (1.47 g, 7.35 mmol), and 2M $Na_2CO_3$ (5 mL) in DMF (15 mL) was treated with $PdCl_2(PPh_3)_2$ (0.52 g, 0.74 mmol) and the mixture was heated at 50° C. overnight. The reaction was treated with additional catalyst ($PdCl_2(PPh_3)_2$, 0.26 g, 0.37 mmol) and was heated at 50° C. overnight, then was heated at 90° C. overnight. The reaction was allowed to cool to room temperature and was diluted with EtOAc and water and the aqueous layer was extracted with EtOAc. The combined organic extracts were dried over $MgSO_4$, filtered and concentrated. The resulting residue was treated with MeOH and cooled in an ice bath. The resulting precipitate was collected, washed with cold MeOH and air-dried and the filtrates were combined and set aside. The resulting tan solid was dissolved in 10% MeOH/$CH_2Cl_2$ and loaded onto a 220 g silica column, which was eluted with 1 to 5% MeOH/$CH_2Cl_2$ over 30 min, followed by 5% MeOH/$CH_2Cl_2$ for 30 min to provide 6-[4-(methylsulfonyl)phenyl]-3-pyridinol (0.36 g, 20%) as a tan solid. The mother liquors from the MeOH trituration step were concentrated and purified by chromatography 1 to 5% MeOH/$CH_2Cl_2$ over 20 min to provide additional product (0.24 g, 33% overall yield) as a tan solid.

Step 3: The resulting residue from Step 1 was charged with 6-[4-(methylsulfonyl)phenyl]-3-pyridinol (602 mg, 2.41 mmol), $K_2CO_3$ (666 mg, 4.82 mmol), DMF (10 mL), and was stirred at 90° C. overnight. The mixture was charged with water, and extracted with EtOAc. The organics were dried over $MgSO_4$, filtered, and the filtrate was concentrated. The crude product was purified by chromatography on a silica gel column using 25 to 75% EtOAc/hexanes to give 462 mg (43%) of 1,1-dimethylethyl 4-[({6-[4-(methylsulfonyl)phenyl]-3-pyridinyl}oxy)methyl]-1-piperidinecarboxylate as an off-white solid. $^1$H NMR (400 MHz, $CDCl_3$): δ 8.45 (bs, 1H), 8.18 (d, 2H, J=8.3 Hz), 8.06 (d, 2H, J=8.1 Hz), 7.82 (d, 1H, J=8.8 Hz), 7.51 (s, 1H), 4.27-4.11 (m, 2H), 3.95 (d, 2H, J=6.1 Hz), 3.08 (s, 3H), 2.82-2.67 (m, 2H), 2.08-1.96 (m, 1H), 1.87-1.77 (m, 2H), 1.46 (s, 9H), 1.38-1.20 (m, 2H); LRMS (ESI), m/z 447 (M+H).

Step 4: 4N HCl in 1,4-dioxane (1 mL) was added to a mixture of 1,1-dimethylethyl 4-[({6-[4-(methylsulfonyl)phenyl]-3-pyridinyl}oxy)methyl]-1-piperidinecarboxylate (462 mg, 1.03 mmol) in 1,4-dioxane (10 mL) at ambient temperature. The mixture was stirred at ambient temperature overnight. The mixture was charged with additional 4N HCl in 1,4-dioxane (1 mL), and stirred at ambient temperature overnight. The mixture was then charged with TFA (2 mL), and stirred at ambient temperature for 4 h. The mixture was concentrated, diluted with water, basified with saturated $NaHCO_3$, and extracted with EtOAc. The organics were dried over $MgSO_4$, filtered, and the filtrate was concentrated. The crude product was purified by reverse-phase preparative HPLC using $CH_3CN:H_2O$ gradient (5:95 to 75:25) with 0.05% TFA as a modifier to give 107 mg (23%) of 2-[4-(methylsulfonyl)phenyl]-5-[(4-piperidinylmethyl)oxy]pyridine trifluoroacetate as a white solid. $^1$H NMR (400 MHz, DMSO-$d_6$): δ 8.59-8.50 (m, 1H), 8.44 (d, 1H, J=2.9 Hz), 8.28 (d, 2H, J=8.6 Hz), 8.08 (d, 1H, J=8.8 Hz), 8.00 (d, 2H, J=8.6 Hz), 7.55 (dd, 1H, $J_a$=8.8 Hz, $J_b$=3.0 Hz), 4.04 (d, 2H, J=6.2 Hz), 3.40-3.25 (m, 2H), 3.25 (s, 3H), 3.00-2.86 (m, 2H), 2.16-2.06 (m, 1H), 2.05-1.90 (m, 2H), 1.56-1.40 (m, 2H); LRMS (ESI), m/z 347 (M+H).

Step 6: t-Butylnitrite (50%, 2.3 mL, 17.22 mmol) was added dropwise to a degassed solution of $CuBr_2$ (1.64 g, 7.35 mmol) in acetone (30 mL) at 0° C. under $N_2$. The mixture was stirred at ambient temperature for 90 min, then charged with a solution of 3-(1-methylethyl)-1,2,4-thiadiazol-5-amine (1 g, 7 mmol) in acetone (7 mL), and stirred at ambient temperature for 1 h. The mixture was cooled to 0° C., and was charged dropwise with 48% HBr (1.8 mL, 4.65 mmol). The mixture was stirred at 0° C. for 30 min, and then brought to ambient temperature. The mixture was charged with water (100 mL) and $CH_2Cl_2$ (75 mL), then stirred at ambient temperature for 10 min. The organics were separated, dried over $MgSO_4$, filtered, and the filtrate was concentrated. The crude product was purified by chromatography on a silica gel column using 0 to 15% EtOAc/hexane to give 1.07 g (74%) of 5-bromo-3-(1-methylethyl)-1,2,4-thiadiazole as a golden oil. $^1$H NMR (400 MHz, $CDCl_3$): δ 3.29 (septet, 1H, J=6.9 Hz), 1.37 (d, 6H, J=6.9 Hz); LRMS (ESI), m/z 207/209 (M+H).

Step 7: A mixture of 2-[4-(methylsulfonyl)phenyl]-5-[(4-piperidinylmethyl)oxy]pyridine trifluoroacetate (107 mg, 0.23 mmol), 5-bromo-3-(1-methylethyl)-1,2,4-thiadiazole (48 mg, 0.23 mmol), triethylamine (0.096 mL, 0.69 mol) and 1,2-dichloroethane (3 mL) was stirred and heated at reflux for 2 h, and the mixture was concentrated. The crude product was purified by reverse-phase preparative HPLC using $CH_3CN:H_2O$ gradient (30:70 to 70:30) with 0.05% TFA as a modifier to give 25 mg (19%) of the title compound as an off-white solid. $^1$H NMR (400 MHz, $CDCl_3$): δ 8.49 (d, 1H, J=2.6 Hz), 8.13-8.06 (m, 2H), 8.06-7.99 (m, 2H), 7.76 (d, 1H, J=8.8 Hz), 7.39 (dd, 1H, $J_a$=8.8 Hz, $J_b$=2.6 Hz), 4.06-3.94 (m, 4H), 3.27-3.17 (m, 2H), 3.12-2.99 (m, 4H), 2.23-2.08 (m, 1H), 2.05-1.95 (m, 2H), 1.65-1.50 (m, 2H), 1.31 (d, 6H, J=6.9 Hz); LRMS (ESI), m/z 473 (M+H).

Example 183

2-[2-Fluoro-4-(methylsulfonyl)phenyl]-5-[({1-[3-(1-methylethyl)-1,2,4-thiadiazol-5-yl]-4-piperidinyl}methyl)oxy]pyridine

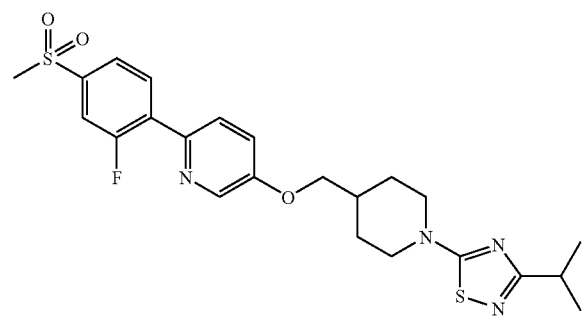

Step 1: A mixture of 4-piperidinylmethanol (115 mg, 1 mmol), 5-bromo-3-(1-methylethyl)-1,2,4-thiadiazole (Example 182, Step 6, 207 mg, 1 mmol), triethylamine (0.42 mL, 3 mmol) and $CH_2Cl_2$ (3 mL) was stirred at ambient temperature overnight. The mixture was charged with additional 4-piperidinylmethanol (58 mg, 0.5 mmol) and was stirred at ambient temperature for 3 h. The mixture was charged with water, and extracted with $CH_2Cl_2$. The organics were dried over $MgSO_4$, filtered, and the filtrate was concentrated. The crude product was purified by chromatography on a silica gel column using 0 to 10% $MeOH/CH_2Cl_2$ to give 159 mg (66%) of {1-[3-(1-methylethyl)-1,2,4-thiadiazol-5-yl]-4-piperidinyl}methanol as a golden oil. $^1$H NMR (400 MHz, $CDCl_3$): δ 3.98-3.88 (m, 2H), 3.54 (d, 2H, J=6.3 Hz), 3.20-3.05 (m, 2H), 3.02 (septet, 1H, J=6.9 Hz), 1.90-1.80 (m, 2H), 1.82-1.70 (m, 1H), 1.42-1.25 (m, 8H); LRMS (ESI), m/z 242 (M+H).

Step 2: Methanesulfonyl chloride (54 μL, 0.69 mmol) was added dropwise to a solution of {1-[3-(1-methylethyl)-1,2,4-thiadiazol-5-yl]-4-piperidinyl}methanol (159 mg, 0.66 mmol) and triethylamine (0.102 mL, 0.73 mmol) in $CH_2Cl_2$ (5 mL) at 0° C. The mixture was stirred at 0° C. for 1 h, washed with water, and the organics were concentrated. The resulting crude material was charged with 6-bromo-3-pyridinol (115 mg, 0.66 mmol), $K_2CO_3$ (184 mg, 1.32 mmol), DMF (3 mL), and then stirred at 90° C. overnight. The mixture was charged with water, and extracted with $CH_2Cl_2$. The organics were dried over $MgSO_4$, filtered, and the filtrate was concentrated. The crude product was purified by reverse-phase preparative HPLC using $CH_3CN:H_2O$ gradient (10:90 to 100:0) with 0.05% TFA as a modifier to give 125 mg (48%) of 2-bromo-5-[({1-[3-(1-methylethyl)-1,2,4-thiadiazol-5-yl]-4-piperidinyl}methyl)oxy]pyridine as an off-white solid. $^1$H NMR (400 MHz, $CDCl_3$): δ 8.05 (d, 1H, J=3.1 Hz), 7.37 (d, 1H, J=8.7 Hz), 7.09 (dd, 1H, $J_a$=8.7 Hz, $J_b$=3.2 Hz), 4.10-3.90 (m, 2H), 3.86 (d, 2H, J=6.2 Hz), 3.30-3.10 (m, 2H), 3.05 (septet, 1H, J=6.9 Hz), 2.20-2.00 (m, 1H), 2.00-1.90 (m, 2H), 1.60-1.40 (m, 2H), 1.30 (d, 6H, J=6.9 Hz); LRMS (ESI), m/z 397/399 (M+H).

Step 3: A mixture of 2-bromo-5-[({1-[3-(1-methylethyl)-1,2,4-thiadiazol-5-yl]-4-piperidinyl}methyl)oxy]pyridine (125 mg, 0.31 mmol), [2-fluoro-4-(methylsulfonyl)phenyl]boronic acid (69 mg, 0.31 mmol), 2M $Na_2CO_3$ (2 mL) and $Pd(PPh_3)_2Cl_2$ (22 mg, 0.031 mmol) in DME (4 mL) was stirred at 80° C. overnight. The mixture was charged with additional [2-fluoro-4-(methylsulfonyl)phenyl]boronic acid (69 mg, 0.31 mmol) and $Pd(PPh_3)_2Cl_2$ (22 mg, 0.031 mmol), and was stirred at 80° C. overnight. The mixture was charged with water, and extracted with EtOAc. The organics were dried over $MgSO_4$, filtered, and the filtrate was concentrated. The crude product was purified by reverse-phase preparative HPLC using $CH_3CN:H_2O$ gradient (10:90 to 100:0) with 0.05% TFA as a modifier to give 20 mg (13%) of the title compound as an off-white solid. $^1$H NMR (400 MHz, $CDCl_3$): δ 8.54 (d, 1H, J=2.7 Hz), 8.08 (t, 1H, J=7.7 Hz), 7.86-7.79 (m, 2H), 7.76 (dd, 1H, $J_a$=9.9 Hz, $J_b$=1.7 Hz), 7.43 (dd, 1H, $J_a$=8.8 Hz, $J_b$=2.9 Hz), 4.10-3.90 (m, 4H), 3.36-3.20 (m, 2H), 3.12-3.01 (m, 4H), 2.25-2.10 (m, 1H), 2.06-1.97 (m, 2H), 1.65-1.50 (m, 2H), 1.30 (d, 6H, J=6.9 Hz); LRMS (ESI), m/z 491 (M+H).

Example 184

5-[({1-[5-(1-Methylethyl)-1,3,4-thiadiazol-2-yl]-4-piperidinyl}methyl)oxy]-2-[4-(methylsulfonyl)phenyl]pyridine

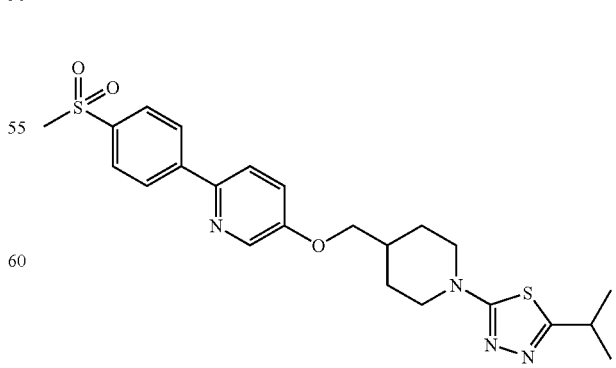

Step 1: Methanesulfonyl chloride (1.8 mL, 23.4 mmol) was added to a mixture of 1,1-dimethylethyl 4-(hydroxymethyl)-

1-piperidinecarboxylate (4.8 g, 22.3 mmol), triethylamine (3.4 mL, 24.5 mmol), and CH$_2$Cl$_2$ (100 mL) at 0° C. The mixture stirred at 0° C. for 1 h. The mixture was washed with water. The organics were dried over MgSO$_4$, filtered, and the filtrate was concentrated. The resulting residue was charged with 6-bromo-3-pyridinol (3.88 g, 22.3 mmol), K$_2$CO$_3$ (6.16 g, 44.6 mmol), DMF (50 mL), and was stirred at 90° C. overnight. The mixture was cooled to ambient temperature, and was set at ambient temperature overnight. The mixture was charged with water, and was stirred at ambient temperature for 4 h. The resulting tan precipitate was filtered, washed with water, and air-dried. The precipitate was purified by chromatography on a silica gel column using 0 to 10% MeOH/CH$_2$Cl$_2$ to give 3.6 g (43%) of 1,1-dimethylethyl 4-{[(6-bromo-3-pyridinyl)oxy]methyl}-1-piperidinecarboxylate as a white solid, and 3.5 g of 1,1-dimethylethyl 4-{[(6-bromo-3-pyridinyl)oxy]methyl}-1-piperidinecarboxylate that contained impurities. The impure batch was repurified by chromatography on a silica gel column using 0 to 2.5% MeOH/CH$_2$Cl$_2$ to give 2.8 g (34%) of 1,1-dimethylethyl 4-{[(6-bromo-3-pyridinyl)oxy]methyl}-1-piperidinecarboxylate as an off-white solid which still contained a ~17% impurity. $^1$H NMR (400 MHz, CDCl$_3$): δ 8.02 (d, 1H, J=3.0 Hz), 7.34 (d, 1H, J=8.7 Hz), 7.06 (dd, 1H, J$_a$=8.7 Hz, J$_b$=3.1 Hz), 4.15 (d, 2H, J=10.3 Hz), 3.80 (d, 2H, J=6.3 Hz), 2.72 (t, 2H, J=12.4 Hz), 2.01-1.85 (m, 1H), 1.79 (d, 2H, J=12.8 Hz), 1.44 (s, 9H), 1.32-1.13 (m, 2H); LRMS (ESI), m/z 371/373 (M+H).

Step 2: A mixture of [4-(methylsulfonyl)phenyl]boronic acid (540 mg, 2.7 mmol), 1,1-dimethylethyl 4-{[(6-bromo-3-pyridinyl)oxy]methyl}-1-piperidinecarboxylate (1 g, 2.7 mmol), Pd(PPh$_3$)$_2$Cl$_2$ (190 mg, 0.27 mmol), DME (10 mL) and 2M Na$_2$CO$_3$ (5 mL) was stirred at 80° C. overnight. The mixture was cooled to ambient temperature, charged with water, and extracted with Et$_2$O. The organics were dried over MgSO$_4$, filtered, and the filtrate was concentrated. The aqueous phase was further extracted with CH$_2$Cl$_2$. The CH$_2$Cl$_2$ extracts were combined with the Et$_2$O extracts, dried over MgSO$_4$, filtered, and the filtrate was concentrated. The crude product was purified by chromatography on a silica gel column using 0 to 1.5% MeOH/CH$_2$Cl$_2$, followed by recrystallization from MeOH. The recrystallized material and the mother liquor were combined, then concentrated to give 705 mg (58%) of 1,1-dimethylethyl 4-[({6-[4-(methylsulfonyl)phenyl]-3-pyridinyl}oxy)methyl]-1-piperidinecarboxylate as an off-white solid. This material contained a minor impurity which was carried on to the next step. $^1$H NMR (400 MHz, CDCl$_3$): δ 8.41 (d, 1H, J=2.7 Hz), 8.14 (d, 2H, J=8.4 Hz), 8.01 (d, 2H, J=8.4 Hz), 7.75 (d, 1H, J=8.7 Hz), 7.34 (d, 1H, J=8.2 Hz), 4.26-4.10 (m, 2H), 3.92 (d, 2H, J=6.3 Hz), 3.07 (s, 3H), 2.83-2.66 (m, 2H), 2.10-1.94 (m, 1H), 1.84 (d, 2H, J=12.82 Hz), 1.46 (s, 9H), 1.38-1.21 (m, 2H); LRMS (ESI), m/z 447 (M+H).

Step 3: TFA (2 mL) was added to a solution of 1,1-dimethylethyl 4-[({6-[4-(methylsulfonyl)phenyl]-3-pyridinyl}oxy)methyl]-1-piperidinecarboxylate (705 mg, 1.58 mmol) in CH$_2$Cl$_2$ (50 mL) at ambient temperature. The mixture was stirred at ambient temperature overnight. The mixture was concentrated, and the crude product was purified by chromatography on a silica gel column using 0 to 10% MeOH/CH$_2$Cl$_2$ give 460 mg (84%) of 2-[4-(methylsulfonyl)phenyl]-5-[(4-piperidinylmethyl)oxy]pyridine as a white solid. $^1$H NMR (400 MHz, DMSO-d$_6$): δ 8.44 (d, 1H, J=2.9 Hz), 8.29 (d, 2H, J=8.6 Hz), 8.08 (d, 1H, J=8.8 Hz), 8.00 (d, 2H, J=8.6 Hz), 7.55 (dd, 1H, J$_a$=8.8 Hz, J$_b$=3.0 Hz), 4.04 (d, 2H, J=6.2 Hz), 3.40-3.25 (m, 2H), 3.25 (s, 3H), 3.01-2.83 (m, 2H), 2.22-2.02 (m, 1H), 2.00-1.90 (m, 2H), 1.60-1.37 (m, 2H); LRMS (ESI), m/z 347 (M+H).

Step 4: 4-Nitrophenyl chloridocarbonate (268 mg, 1.33 mmol) was added to a mixture of 2-[4-(methylsulfonyl)phenyl]-5-[(4-piperidinylmethyl)oxy]pyridine (460 mg, 1.33 mmol), diisopropylethylamine (0.695 mL, 4 mmol) in CH$_2$Cl$_2$ (20 mL) at ambient temperature. The mixture was stirred at ambient temperature for 30 min, then concentrated, and the crude product was purified by chromatography on a silica gel column using 0 to 5% MeOH/CH$_2$Cl$_2$ give 456 mg (67%) of 4-nitrophenyl 4-[({6-[4-(methylsulfonyl)phenyl]-3-pyridinyl}oxy)methyl]-1-piperidinecarboxylate as a yellow solid. $^1$H NMR (400 MHz, CDCl$_3$): δ 8.43 (d, 1H, J=2.7 Hz), 8.25 (d, 2H, J=9.2 Hz), 8.14 (d, 2H, J=8.5 Hz), 8.02 (d, 2H, J=8.5 Hz), 7.76 (d, 1H, J=8.7 Hz), 7.37-7.27 (m, 3H), 4.45-4.30 (m, 2H), 3.98 (d, 2H, J=5.1 Hz), 3.16-3.03 (m, 4H), 3.00-2.88 (m, 1H), 2.21-2.06 (m, 1H), 2.04-1.92 (m, 2H), 1.55-1.35 (m, 2H); LRMS (ESI), m/z 512 (M+H).

Step 5: Hydrazine (0.140 mL, 4.45 mmol) was added to a mixture of 4-nitrophenyl 4-[({6-[4-(methylsulfonyl)phenyl]-3-pyridinyl}oxy)methyl]-1-piperidinecarboxylate (456 mg, 0.89 mmol) in ethanol (30 mL) at ambient temperature. The mixture was stirred at ambient temperature overnight. The mixture was charged with additional ethanol (30 mL) and hydrazine (5 mL, 159 mmol), stirred at reflux until homogeneous (15 min), then at ambient temperature overnight. The mixture was concentrated to dryness, charged with 4:1 EtOH:CH$_2$Cl$_2$ and MP-Carbonate (8 g). The mixture was stirred at ambient temperature for 2 h, filtered, washed with 4:1 EtOH:CH$_2$Cl$_2$, and the filtrate was concentrated to give 352 mg (98%) of 4-[({6-[4-(methylsulfonyl)phenyl]-3-pyridinyl}oxy)methyl]-1-piperidinecarbohydrazide as an off-white solid. $^1$H NMR (400 MHz, DMSO-d$_6$): δ 8.43 (d, 1H, J=2.9 Hz), 8.28 (d, 2H, J=8.6 Hz), 8.06 (d, 1H, J=8.9 Hz), 7.99 (d, 2H, J=8.6 Hz), 7.61 (bs, 1H), 7.54 (dd, 1H, J$_a$=8.8 Hz, J$_b$=3.0 Hz), 4.03-3.92 (m, 4H), 3.84 (d, 2H, J=3.2 Hz), 3.25 (s, 3H), 2.74-2.64 (m, 2H), 2.05-1.88 (m, 1H), 1.79-1.67 (m, 2H), 1.23-1.09 (m, 2H); LRMS (ESI), m/z 405 (M+H).

Step 6: TBTU (279 mg, 0.87 mmol) and HOBT (24 mg, 0.17 mmol) were added to a mixture of 2-methylpropanoic acid (81 μL, 0.87 mmol), diisopropylethylamine (0.758 mL, 4.35 mmol) in DMF (5 mL) at ambient temperature. The mixture was stirred at ambient temperature for 15 min. The mixture was charged with 4-[({6-[4-(methylsulfonyl)phenyl]-3-pyridinyl}oxy)methyl]-1-piperidinecarbohydrazide (352 mg, 0.87 mmol), and was stirred at ambient temperature overnight. The mixture was charged with water and set at ambient temperature overnight. The resulting tan precipitate was filtered, washed with water, and dried in a vacuum oven to give 350 mg (85%) of N'-(2-methylpropanoyl)-4-[({6-[4-(methylsulfonyl)phenyl]-3-pyridinyl}oxy)methyl]-1-piperidinecarbohydrazide as a tan solid. $^1$H NMR (400 MHz, DMSO-d$_6$): δ 9.31 (d, 1H, J=1.9 Hz), 8.44 (d, 1H, J=2.9 Hz), 8.36 (d, 1H, J=1.9 Hz), 8.29 (d, 2H, J=8.6 Hz), 8.06 (d, 1H, J=8.8 Hz), 7.99 (d, 2H, J=8.6 Hz), 7.55 (dd, 1H, J$_a$=8.8 Hz, J$_b$=3.0 Hz), 4.08-3.96 (m, 4H), 3.25 (s, 3H), 2.80-2.70 (m, 2H), 2.41 (septet, 1H, J=6.8 Hz), 2.08-1.92 (m, 1H), 1.82-1.73 (m, 2H), 1.30-1.10 (m, 2H), 1.02 (d, 6H, J=6.9 Hz); LRMS (ESI), m/z 475 (M+H).

Step 7: A mixture of N'-(2-methylpropanoyl)-4-[({6-[4-(methylsulfonyl)phenyl]-3-pyridinyl}oxy)methyl]-1-piperidinecarbohydrazide (175 mg, 0.37 mmol), [2,4-bis(4-methoxypheny)-1,3-dithia-2,4-diphosphetane-2,4-disulfide] (Lawesson's reagent, 150 mg, 0.37 mmol) and toluene (3 mL)

was stirred at reflux for 2 h. The mixture was cooled to ambient temperature and concentrated to dryness. The crude product was purified by reverse-phase preparative HPLC using CH$_3$CN:H$_2$O gradient (10:90 to 100:0) with 0.05% TFA as a modifier followed by purification by reverse-phase preparative HPLC using CH$_3$CN:H$_2$O gradient (5:95 to 90:10) with 0.05% TFA as a modifier to give 51 mg (29%) of the title compound as a white solid. $^1$H NMR (400 MHz, CDCl$_3$): δ 8.44 (d, 1H, J=2.3 Hz), 8.16-8.10 (m, 2H), 8.02 (d, 2H, J=8.4 Hz), 7.77 (d, 1H, J=8.6 Hz), 7.37 (d, 1H, J=6.9 Hz), 4.18-4.08 (m, 2H), 3.97 (d, 2H, J=5.9 Hz), 3.34-3.21 (m, 3H), 3.08 (s, 3H), 2.16 (bs, 1H), 2.07-1.98 (m, 2H), 1.68-1.51 (m, 2H), 1.36 (d, 6H, J=6.9 Hz); LRMS (ESI), m/z 473 (M+H).

Example 185

1,1-Dimethylethyl 4-[({6-[2-methyl-4-(methylsulfonyl)phenyl]-3-pyridinyl}oxy)methyl]-1-piperidinecarboxylate

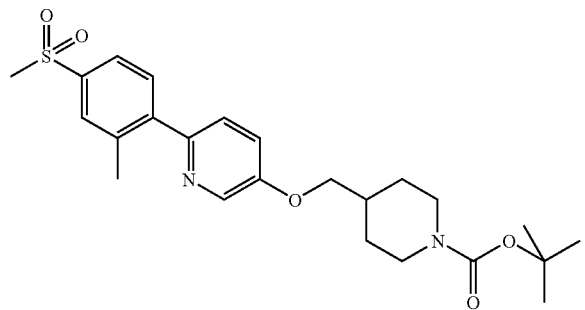

Step 1: Bromine (2.52 mL, 48.9 mmol) was added dropwise to a solution of 1-methyl-3-(methylthio)benzene (6.14 g, 44.4 mmol) in acetic acid (150 mL) at 0° C. The reaction was then stirred at ambient temperature for 2 h. The reaction was concentrated, and the resulting crude product was purified by chromatography on a silica gel column using 0 to 10% EtOAc/hexane to give 7.94 g (82%) of 1-bromo-2-methyl-4-(methylthio)benzene as a clear oil. $^1$H NMR (400 MHz, DMSO-d$_6$): δ 7.40 (d, 1H, J=8.3 Hz), 7.10 (d, 1H, J=2.1 Hz), 6.92 (dd, 1H, J$_a$=8.3 Hz, J$_b$=2.2 Hz), 2.45 (s, 3H), 2.35 (s, 3H); LRMS (ESI), m/z 218 (M+H).

Step 2: 1.7M tert-Butyllithium in pentane (6.70 mL, 11.39 mmol) was added dropwise to a solution of 1-bromo-2-methyl-4-(methylthio)benzene (1.2 g, 5.53 mmol) in diethyl ether (120 mL) at −78° C. over 15 min. The mixture was stirred at −78° C. for 2 min, then charged with trimethyl borate (0.661 mL, 5.91 mmol) dropwise over 2 min at −78° C., stirred at −78° C. for 15 min, then brought to ambient temperature. The mixture was quenched with saturated aqueous NH$_4$Cl (14 mL), stirred at ambient temperature for 15 min, charged with 1M HCl (12 mL), stirred at ambient temperature for 2 min, and the organics were separated. The organics were dried over MgSO$_4$, filtered, and the filtrate was concentrated. The crude product was purified by chromatography on a silica gel column using 20 to 100% EtOAc/hexane to give 503 mg (50%) of [2-methyl-4-(methylthio)phenyl] boronic acid as a white solid. $^1$H NMR (400 MHz, DMSO-d$_6$): δ 7.79 (d, 1H, J=7.8 Hz), 7.09-7.00 (m, 2H), 2.61 (s, 3H), 2.46 (s, 3H); LRMS (ESI), m/z 183 (M+H).

Step 3: A mixture of N-Boc-4-piperidinemethanol (4.8 g, 22.3 mmol), Et$_3$N (3.4 mL, 24.5 mmol) in CH$_2$Cl$_2$ (100 mL) at 0° C. was treated dropwise with methanesulfonyl chloride (1.8 mL, 23.4 mmol). The reaction mixture was stirred at 0° C. for 1 h, and then was washed with water twice. The CH$_2$Cl$_2$ layer was dried over MgSO$_4$, filtered, and the filtrate was concentrated. The residue was mixed with 6-bromo-3-pyridinol (3.88 g, 22.3 mmol) and K$_2$CO$_3$ (6.2 g, 44.6 mmol) in DMF (50 mL). The resulting mixture was heated at 90° C. overnight, cooled to ambient temperature, sat overnight, then was quenched with water and stirred at room temperature for 4 h. The resulting precipitate was collected, washed with water, and air-dried. The crude product was purified by chromatography on a silica gel column using 0 to 10% MeOH/CH$_2$Cl$_2$ to give 3.6 g (43%) of 1,1-dimethylethyl 4-{[(6-bromo-3-pyridinyl)oxy]methyl}-1-piperidinecarboxylate as a white solid along with some impure material. The impure material was repurified by chromatography on a silica gel column using 0 to 2.5% MeOH/CH$_2$Cl$_2$ to give an additional 2.8 g (77% overall yield) of 1,1-dimethylethyl 4-{[(6-bromo-3-pyridinyl)oxy]methyl}-1-piperidinecarboxylate as an off-white solid.

Step 4: A mixture of [2-methyl-4-(methylthio)phenyl]boronic acid (50 mg, 0.275 mmol), 1,1-dimethylethyl 4-{[(6-bromo-3-pyridinyl)oxy]methyl}-1-piperidinecarboxylate (102 mg, 0.275 mmol), Pd(PPh$_3$)$_2$Cl$_2$ (38.6 mg, 0.055 mmol), DME (2 mL) and 2M Na$_2$CO$_3$ (3 mL) was stirred at 80° C. for 2 h. The mixture was cooled to ambient temperature; the organics were separated and concentrated. The crude product was purified by reverse-phase preparative HPLC using CH$_3$CN:H$_2$O gradient (10:90 to 100:0) with 0.05% TFA as a modifier to give 101 mg (82%) of 1,1-dimethylethyl 4-[({6-[2-methyl-4-(methylthio)phenyl]-3-pyridinyl}oxy)methyl]-1-piperidinecarboxylate as a yellow oil. $^1$H NMR (400 MHz, CDCl$_3$): δ 8.67 (d, 1H, J=2.2 Hz), 7.84-7.75 (m, 1H), 7.71-7.60 (m, 2H), 7.53-7.44 (m, 2H), 4.23-4.11 (m, 2H), 4.01 (d, 2H, J=6.1 Hz), 2.83-2.68 (m, 2H), 2.50 (s, 3H), 2.36 (s, 3H), 2.10-2.01 (m, 1H), 1.90-1.75 (m, 2H), 1.47 (s, 9H), 1.38-1.22 (m, 2H); LRMS (ESI), m/z 429 (M+H).

Step 5: m-CPBA (89 mg, 0.518 mmol) was added to a solution of 1,1-dimethylethyl 4-[({6-[2-methyl-4-(methylthio)phenyl]-3-pyridinyl}oxy)methyl]-1-piperidinecarboxylate (101 mg, 0.236 mmol) in CH$_2$Cl$_2$ (3 mL) at 0° C. The mixture was stirred at 0° C. for 15 min, then at ambient temperature for 2 h. The mixture was concentrated. The crude product was purified by reverse-phase preparative HPLC using CH$_3$CN:H$_2$O gradient (5:95 to 90:10) with 0.05% TFA as a modifier to give 60 mg (55%) of the title compound as a golden oil. $^1$H NMR (400 MHz, CDCl$_3$): δ 8.57 (d, 1H, J=2.7 Hz), 7.91-7.81 (m, 2H), 7.57-7.43 (m, 3H), 4.24-4.13 (m, 2H), 3.97 (d, 2H, J=6.2 Hz), 3.08 (s, 3H), 2.85-2.70 (m, 2H), 2.39 (s, 3H), 2.10-1.97 (m, 1H), 1.88-1.79 (m, 2H), 1.47 (s, 9H), 1.40-1.20 (m, 2H); LRMS (ESI), m/z 461 (M+H).

Example 186

1-Methylethyl 4-[({6-[2-methyl-4-(methylsulfonyl) phenyl]-3-pyridinyl}oxy)methyl]-1-piperidinecarboxylate

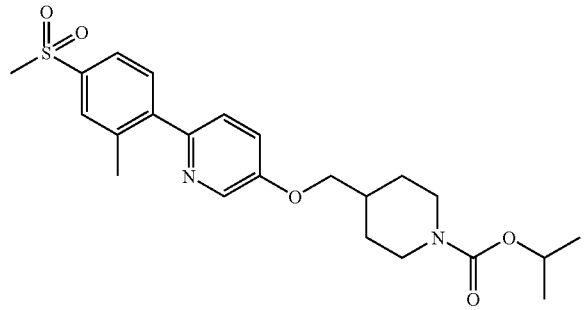

Step 1: A mixture of 1,1-dimethylethyl 4-[({6-[2-methyl-4-(methylsulfonyl)phenyl]-3-pyridinyl}oxy)methyl]-1-piperidinecarboxylate (Example 185, 57 mg, 0.124 mmol), TFA (0.095 mL, 1.24 mmol) in CH$_2$Cl$_2$ (3 mL) was stirred at ambient temperature for 3 h. The mixture was concentrated to give (80 mg, quantitative yield) of 2-[2-methyl-4-(methylsulfonyl)phenyl]-5-[(4-piperidinylmethyl)oxy]pyridine trifluoroacetate as a clear oil. $^1$H NMR (400 MHz, CDCl$_3$): δ 8.78 (d, 1H, J=2.0 Hz), 7.97-7.83 (m, 3H), 7.69 (d, 1H, J=8.7 Hz), 7.58-7.48 (m, 1H), 4.17 (d, 2H, J=5.5 Hz), 3.70-3.55 (m, 2H), 3.14-3.01 (m, 5H), 2.39 (s, 3H), 2.34-2.21 (m, 2H), 2.25-2.10 (m, 2H), 1.97-1.83 (m, 2H); LRMS (ESI), m/z 361 (M+H).

Step 2: A mixture of 2-[2-methyl-4-(methylsulfonyl)phenyl]-5-[(4-piperidinylmethyl)oxy]pyridine trifluoroacetate (80 mg, 0.169 mmol), isopropyl chloroformate (1M in toluene, 0.169 mL, 0.169 mmol), and triethylamine (0.070 mL, 0.506 mmol) in CH$_2$Cl$_2$ (3 mL) was stirred at ambient temperature for 1 h, then concentrated. The crude product was purified by reverse-phase preparative HPLC using CH$_3$CN:H$_2$O gradient (5:95 to 90:10) with 0.05% TFA as a modifier, then free-based in CH$_2$Cl$_2$ with MP-Carbonate to give 26 mg (35%) of the title compound as a clear oil. $^1$H NMR (400 MHz, CDCl$_3$): δ 8.38 (d, 1H, J=2.5 Hz), 7.86-7.76 (m, 2H), 7.55 (d, 1H, J=7.9 Hz), 7.37-7.31 (m, 1H), 7.29-7.25 (m, 1H), 4.92 (septet, 1H, J=6.2 Hz), 4.22 (bs, 2H), 3.90 (d, 2H, J=6.3 Hz), 3.05 (s, 3H), 2.90-2.70 (m, 2H), 2.43 (s, 3H), 2.09-1.95 (m, 1H), 1.95-1.80 (m, 2H), 1.39-1.22 (m, 8H); LRMS (ESI), m/z 447 (M+H).

Example 187

5-[({1-[3-(1-Methylethyl)-1,2,4-oxadiazol-5-yl]-4-piperidinyl}methyl)oxy]-2-[2-methyl-4-(methylsulfonyl)phenyl]pyridine

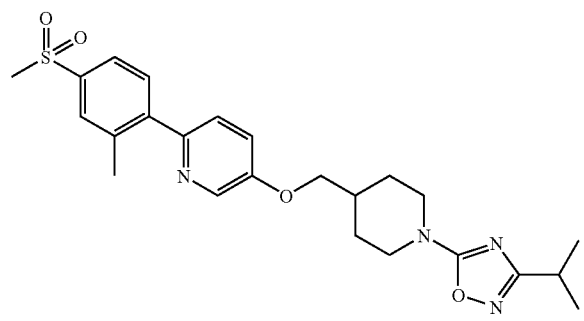

Step 1: A mixture of 6-bromo-3-pyridinol (1 g, 5.75 mmol), {1-[3-(1-methylethyl)-1,2,4-oxadiazol-5-yl]-4-piperidinyl}methyl methanesulfonate (prepared as in Example 100, Steps 1-4, 1.74 g, 5.75 mmol), potassium carbonate (1.59 g, 11.49 mmol), and DMF (15 mL) stirred at 80° C. overnight. The mixture was cooled to room temperature, charged with water (100 mL), and was extracted with EtOAc. The organics were dried over MgSO$_4$, filtered, and concentrated. The crude product was purified by chromatography on a silica gel column using 0 to 50% EtOAc/hexane to give 1.76 g (80%) of 2-bromo-5-[({1-[3-(1-methylethyl)-1,2,4-oxadiazol-5-yl]-4-piperidinyl}methyl)oxy]pyridine as a yellow solid. $^1$H NMR (400 MHz, CDCl$_3$): δ 8.03 (d, 1H, J=3.1 Hz), 7.36 (d, 1H, J=8.7 Hz), 7.07 (dd, 1H, J$_a$=8.7 Hz, J$_b$=3.1 Hz), 4.21 (dd, 2H, J$_a$=11.0 Hz, J$_b$=2.1 Hz), 3.84 (d, 2H, J=6.3 Hz), 3.09 (m, 2H), 2.94-2.83 (m, 1H), 2.12-1.98 (m, 1H), 1.92 (d, 2H, J=12.2 Hz), 1.36-1.53 (m, 2H), 1.28 (d, 6H, J=7.0 Hz); LRMS (ESI), m/z 381/383 (M+H).

Step 2: A mixture of 2-bromo-5-[({1-[3-(1-methylethyl)-1,2,4-oxadiazol-5-yl]-4-piperidinyl}methyl)oxy]pyridine (419 mg, 1.1 mmol), [2-methyl-4-(methylthio)phenyl]boronic acid (Example 185, Step 2, 200 mg, 1.1 mmol), Pd(PPh$_3$)$_2$Cl$_2$ (154 mg, 0.22 mmol), DME (6 mL) and 2M Na$_2$CO$_3$ (9 mL) was stirred at 80° C. overnight. The mixture was cooled to ambient temperature, charged with CH$_2$Cl$_2$, and the organics were separated. The organics were dried over MgSO$_4$, filtered, and the filtrate was concentrated. The crude product was purified by chromatography on a silica gel column using 0 to 50% EtOAc/hexane, followed by purification by reverse-phase preparative HPLC using CH$_3$CN:H$_2$O gradient (5:95 to 90:10) with 0.05% TFA as a modifier to give 153 mg (32%) of 5-[({1-[3-(1-methylethyl)-1,2,4-oxadiazol-5-yl]-4-piperidinyl}methyl)oxy]-2-[2-methyl-4-(methylthio)phenyl]pyridine as a clear oil. $^1$H NMR (400 MHz, CDCl$_3$): δ 8.69 (d, 1H, J=2.1 Hz), 7.66 (dd, 1H, J$_a$=8.8 Hz, J$_b$=2.0 Hz), 7.54 (d, 1H, J=8.8 Hz), 7.31 (d, 1H, J=8.6 Hz), 7.21-7.11 (m, 2H), 4.30-4.15 (m, 2H), 4.02 (d, 2H, J=6.0 Hz), 3.20-3.00 (m, 2H), 2.89 (septet, 1H, J=7.0 Hz), 2.50 (s, 3H), 2.33 (s, 3H), 2.22-2.04 (m, 1H), 2.00-1.90 (m, 2H), 1.60-1.40 (m, 2H), 1.28 (d, 6H, J=7.0 Hz); LRMS (ESI), m/z 439 (M+H).

Step 3: The title compound (84 mg, 51%) was prepared as a white solid from 5-[({1-[3-(1-methylethyl)-1,2,4-oxadiazol-5-yl]-4-piperidinyl}methyl)oxy]-2-[2-methyl-4-(methylthio)phenyl]pyridine (153 mg, 0.349 mmol), m-CPBA (132 mg, 0.767 mmol), and CH$_2$Cl$_2$ (5 mL) in a manner similar to Example 185, Step 5 with the additional step of preparing the free-base with CH$_2$Cl$_2$ and MP-Carbonate. $^1$H NMR (400 MHz, CDCl$_3$): δ 8.42 (s, 1H), 7.89-7.80 (m, 2H), 7.58 (d, 1H, J=7.9 Hz), 7.42 (bs, 2H), 4.30-4.20 (m, 2H), 3.97 (d, 2H, J=6.0 Hz), 3.20-3.05 (m, 2H), 3.06 (s, 3H), 2.95-2.82 (m, 1H), 2.45 (s, 3H), 2.18-2.05 (m, 1H), 2.00-1.90 (m, 2H), 1.60-1.40 (m, 2H), 1.28 (d, 6H, J=7.0 Hz); LRMS (ESI), m/z 471 (M+H).

Example 188

2-[({1-[3-(1-Methylethyl)-1,2,4-oxadiazol-5-yl]-4-piperidinyl}methyl)oxy]-5-[2-methyl-4-(methylsulfonyl)phenyl]pyrazine

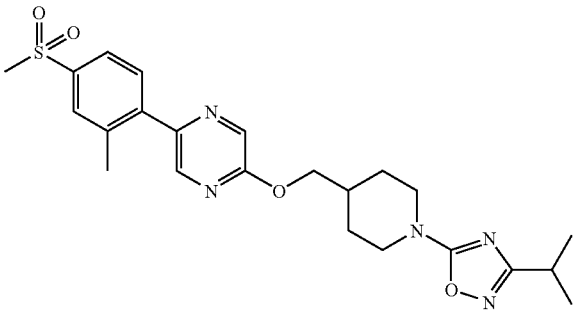

Step 1: A mixture of [2-methyl-4-(methylthio)phenyl]boronic acid (prepared as in Example 185, Step 2, 253 mg, 1.390 mmol), 5-bromo-2-pyrazinamine (242 mg, 1.390 mmol), Pd(PPh$_3$)$_2$Cl$_2$ (195 mg, 0.278 mmol), DME (5 mL) and 2M Na$_2$CO$_3$ (8 mL) was stirred at 80° C. overnight. The mixture was cooled to ambient temperature, charged with CH$_2$Cl$_2$ and water, and stirred at ambient temperature for 30 min. The mixture was filtered, the organics were separated, and the aqueous layer was washed with CH$_2$Cl$_2$. The organics were pooled, dried over MgSO$_4$, filtered, and the filtrate was concentrated. The crude product was purified by chromatography on a silica gel column using 0 to 50% EtOAc/hexane to give 190 mg (59%) of 5-[2-methyl-4-(methylthio)phenyl]-2-pyrazinamine as a white solid. $^1$H NMR (400 MHz, CDCl$_3$): δ 8.13 (s, 1H), 8.05 (s, 1H), 7.29 (d, 1H, J=8.5 Hz), 7.17-7.12 (m, 2H), 4.97-4.82 (m, 2H), 2.50 (s, 3H), 2.36 (s, 3H); LRMS (ESI), m/z 232 (M+H).

Step 2: Sodium nitrite (77 mg, 1.109 mmol) was added portionwise to concentrated sulfuric acid (2 mL) at 0° C. The mixture was stirred at 45° C. until homogeneous, cooled to 0° C., and charged with a solution of 5-[2-methyl-4-(methylthio)phenyl]-2-pyrazinamine (190 mg, 0.821 mmol) in sulfuric acid (3 mL) at 0° C. The mixture was warmed to ambient temperature, stirred at ambient temperature for 15 min, then at 45° C. for 5 h. The mixture was cooled to ambient temperature, poured into water, and the pH was adjusted to ~4 with 10N NaOH. The resulting precipitate was filtered, washed with water, and air-dried to give 100 mg (52%) of 5-[2-methyl-4-(methylthio)phenyl]-2-pyrazinol (and tautomers thereof) as a tan solid. $^1$H NMR (400 MHz, DMSO-d$_6$): δ 12.61-12.37 (m, 1H), 8.08 (d, 1H, J=1.0 Hz), 7.72-7.45 (m, 1H), 7.30 (d, 1H, J=8.1 Hz), 7.22-7.06 (m, 2H), 2.48 (s, 3H), 2.30 (s, 3H); LRMS (ESI), m/z 233 (M+H).

Step 3: A mixture of 5-[2-methyl-4-(methylthio)phenyl]-2-pyrazinol (and tautomers thereof) (100 mg, 0.430 mmol), {1-[3-(1-methylethyl)-1,2,4-oxadiazol-5-yl]-4-piperidinyl}methyl methanesulfonate (prepared as in Example 100, Steps 1-4, 131 mg, 0.430 mmol), K$_2$CO$_3$ (119 mg, 0.861 mmol) in DMF (3 mL) was stirred at 80° C. overnight. The mixture was cooled to ambient temperature, charged with water, and extracted with EtOAc. The organics were dried over MgSO$_4$, filtered, and the filtrate was concentrated. The crude product was purified by reverse-phase preparative HPLC using CH$_3$CN:H$_2$O gradient (20:80 to 100:0) with 0.05% TFA as a modifier to give 92 mg (49%) of 2-[({1-[3-(1-methylethyl)-1,2,4-oxadiazol-5-yl]-4-piperidinyl}methyl)oxy]-5-[2-methyl-4-(methylthio)phenyl]pyrazine as an off-white solid. $^1$H NMR (400 MHz, CDCl$_3$): δ 8.28 (d, 1H, J=1.3 Hz), 8.14 (d, 1H, J=1.4 Hz), 7.31 (d, 1H, J=8.1 Hz), 7.19-7.12 (m, 2H), 4.32-4.21 (m, 4H), 3.20-3.00 (m, 2H), 2.93 (septet, 1H, J=6.9 Hz), 2.50 (s, 3H), 2.36 (s, 3H), 2.18-2.05 (m, 1H), 2.05-1.90 (m, 2H), 1.60-1.40 (m, 2H), 1.30 (d, 6H, J=7.0 Hz); LRMS (ESI), m/z 440 (M+H).

Step 4: Oxone® (257 mg, 0.419 mmol) was added to a mixture of 2-[({1-[3-(1-methylethyl)-1,2,4-oxadiazol-5-yl]-4-piperidinyl}methyl)oxy]-5-[2-methyl-4-(methylthio)phenyl]pyrazine (92 mg, 0.209 mmol) in acetone (3 mL) and water (0.5 mL) at ambient temperature. The mixture was stirred at ambient temperature overnight. The mixture was quenched with saturated aqueous NaHSO$_3$, filtered, and the filtrate was concentrated. The crude product was purified by reverse-phase preparative HPLC using CH$_3$CN:H$_2$O gradient (5:95 to 90:10) with 0.05% TFA as a modifier to give 65 mg (66%) of the title compound as a white solid. $^1$H NMR (400 MHz, CDCl$_3$): δ 8.32 (d, 1H, J=1.4 Hz), 8.20 (d, 1H, J=1.4 Hz), 7.90-7.79 (m, 2H), 7.58 (d, 1H, J=7.9 Hz), 4.31-4.18 (m, 4H), 3.19-3.04 (m, 5H), 2.97-2.83 (m, 1H), 2.46 (s, 3H), 2.18-2.05 (m, 1H), 2.00-1.91 (m, 2H), 1.55-1.40 (m, 2H), 1.29 (d, 6H, J=6.9 Hz); LRMS (ESI), m/z 472 (M+H).

Compound 189

5-[({1-[2-(1-Methylethyl)-2H-tetrazol-5-yl]-4-piperidinyl}methyl)oxy]-2-[4-(methylsulfonyl)phenyl]pyridine

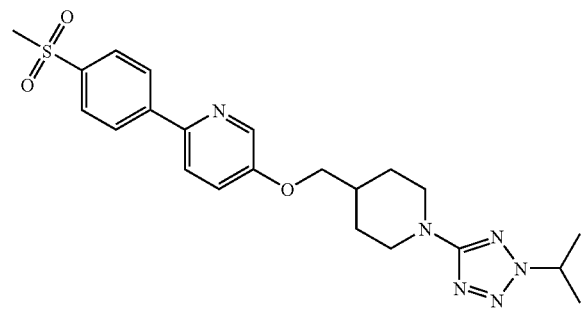

Step 1: 2-[4-(Methylsulfonyl)phenyl]-5-[(4-piperidinylmethyl)oxy]pyridine (0.50 g, 78%) was prepared from 1,1-dimethylethyl 4-[({6-[4-(methylsulfonyl)phenyl]-3-pyridinyl}oxy)methyl]-1-piperidinecarboxylate (prepared as in Example 150, Steps 1-2 and purified by chromatography on a silica gel column using 0 to 50% CH$_2$Cl$_2$/EtOAc, 0.79 g, 1.77 mmol) in a manner similar to Example 86, Step 2, except that the material was purified to give free base using a 4×10 g SCX column and eluting with CH$_2$Cl$_2$/MeOH/NH$_3$.

Step 2: A solution of 2-[4-(methylsulfonyl)phenyl]-5-[(4-piperidinylmethyl)oxy]pyridine (346 mg, 1 mmol) in MeOH (20 mL) was treated with NaOAc (574 mg, 7 mmol) then was warmed and stirred for 30 min. The suspension was then treated with a solution of cyanogen bromide (318 mg, 3 mmol) in CH$_2$Cl$_2$ (1.5 mL) at 0° C. The mixture was stirred and allowed to warm to room temperature overnight. The mixture was filtered, washed with MeOH and CH$_2$Cl$_2$, and the material was purified by chromatography on a silica gel column using 0 to 100% CH$_2$Cl$_2$/EtOAc, then 2.5% MeOH/

$CH_2Cl_2$ to afford (4-[({6-[4-(methylsulfonyl)phenyl]-3-pyridinyl}oxy)methyl]-1-piperidinecarbonitrile (250 mg, 61%).

Step 3: A solution of (4-[({6-[4-(methylsulfonyl)phenyl]-3-pyridinyl}oxy)methyl]-1-piperidinecarbonitrile (241 mg, 0.65 mmol) in DMF (3 mL) was treated with ammonium chloride (52 mg, 0.97 mmol) and sodium azide (63 mg, 0.97 mmol) at room temperature. The mixture was heated at 100° C. for 19 h. After cooling down, the solid was removed by filtration and washed with DMF. The filtrate was concentrated and a small amount of MeOH and $CH_2Cl_2$ was added to the residue. After sonication, the resulting precipitate was collected and washed with THF including a small amount of water. 2-[4-(Methylsulfonyl)phenyl]-5-({[1-(1H-tetrazol-5-yl)-4-piperidinyl]methyl}oxy)pyridine was obtained as a light gray solid (170 mg, 60%) after drying in vacuo. $^1$H NMR (400 MHz, DMSO-$d_6$): δ 8.44 (d, 1H, J=2.9 Hz), 8.28 (d, 2H, J=8.6 Hz), 8.07 (d, 1H, J=8.8 Hz), 7.99 (d, 2H, J=8.6 Hz), 7.55 (dd, 1H, $J_a$=8.8 Hz, $J_b$=2.9 Hz), 4.03 (d, 2H, J=6.3 Hz), 3.88 (d, 2H, J=12.7 Hz), 3.25 (s, 3H), 3.13-3.00 (m, 2H), 2.13-2.01 (m, 1H), 1.93-1.84 (m, 2H), 1.47-1.31 (m, 2H); LRMS (ESI), m/z 415 (M+H).

Step 4: A solution of 2-[4-(methylsulfonyl)phenyl]-5-({[1-(1H-tetrazol-5-yl)-4-piperidinyl]methyl}oxy)pyridine (157 mg, 0.38 mmol) in DMF (2 mL) and acetone (3 mL) was added potassium carbonate (105 mg, 0.76 mmol) at room temperature. After stirring for 15 min, 2-iodopropane (193 mg, 1.14 mmol) was added by syringe and the mixture was heated at 50° C. for 16 h. The salt was removed by filtration and washed with MeOH/$CH_2Cl_2$. After concentration, a small amount of MeOH/$CH_2Cl_2$ was added and the resulting precipitate was collected and washed with a small amount of MeOH. The material was dried in vacuo to give the title compound (130 mg, 71%) as a white solid. $^1$H NMR (400 MHz, DMSO-$d_6$): δ 8.44 (d, 1H, J=2.9 Hz), 8.34-8.25 (m, 2H), 8.07 (d, 1H, J=8.8 Hz), 7.99 (d, 2H, J=8.7 Hz) 7.55 (dd, 1H, $J_a$=8.8 Hz, $J_b$=2.9 Hz), 4.88 (septet, 1H, J=6.7 Hz), 4.03 (d, 2H, J=6.6 Hz), 3.98 (d, 2H, J=12.6 Hz), 3.25 (s, 3H), 3.01-2.86 (m, 2H), 2.11-1.95 (m, 1H), 1.94-1.82 (m, 2H), 1.50 (d, 6H, J=6.7 Hz), 1.46-1.30 (m, 2H); LRMS (ESI), m/z 457 (M+H).

Example 190

5-[((1S)-1-{1-[2-(1-Methylethyl)-2H-tetrazol-5-yl]-4-piperidinyl}ethyl)oxy]-2-[4-(methylsulfonyl)phenyl]

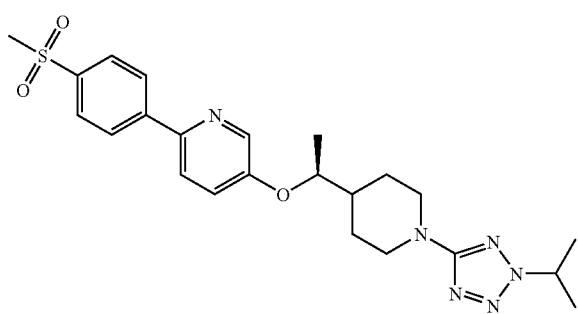

Step 1: (1R)-1-(4-Piperidinyl)ethanol acetic acid salt (Example 167, Step 1, 568 mg, 3 mmol, 94% ee) and sodium acetate (2.46 g, 30 mmol) in MeOH (30 mL) was stirred at room temperature for 15 min. A solution of cyanogen bromide (953 mg, 9 mmol) in $CH_2Cl_2$ (4 mL) was added at 0° C. The mixture was stirred from 0° C. to 25° C. for 12 h. The salt was removed by filtration and washed by $CH_2Cl_2$. After concentration, the crude product was purified by chromatography on a silica gel column using 70% EtOAc/$CH_2Cl_2$ to give 480 mg (99%) of 4-[(1R)-1-hydroxyethyl]-1-piperidinecarbonitrile as an oil. $^1$H NMR (400 MHz, CDCl$_3$): δ 3.69 (s, 1H), 3.67-3.57 (m, 1H), 3.54-3.43 (m, 2H), 3.08-2.94 (m, 2H), 1.96-1.84 (m, 1H), 1.67-1.65 (m, 1H), 1.53-1.35 (m, 3H), 1.20 (d, 3H, J=6.3 Hz).

Step 2: A solution of 4-[(1R)-1-hydroxyethyl]-1-piperidinecarbonitrile (200 mg, 1.30 mmol) in DMF (5 mL) was treated with ammonium chloride (104 mg, 1.95 mmol) and sodium azide (126 mg, 1.95 mmol) at room temperature. The mixture was heated at 100° C. for 14 h. After allowing the mixture to cool, the solid was removed by filtration and washed with DMF. The filtrate was concentrated to give (1R)-1-[1-(1H-tetrazol-5-yl)-4-piperidinyl]ethanol, which was used without further purification.

Step 3: A solution of (1R)-1-[1-(1H-tetrazol-5-yl)-4-piperidinyl]ethanol (256 mg, 1.3 mmol) in DMF (1 mL) and acetone (5 mL) was treated with potassium carbonate (359 mg, 2.59 mmol) at room temperature. After stirring for 15 min, 2-iodopropane (661 mg, 3.89 mmol) was added and the mixture was heated at 50° C. for 3 h. The salt was removed by filtration and washed by EtOAc. After concentration, the crude product was purified by chromatography on a silica gel column using MeOH/$CH_2Cl_2$ gradient (2.5% to 12.5%) to give 225 mg (69%) of (1R)-1-{1-[2-(1-methylethyl)-2H-tetrazol-5-yl]-4-piperidinyl}ethanol. $^1$H NMR (400 MHz, CDCl$_3$): δ 4.85 (septet, 1H, J=6.8 Hz), 4.24-4.07 (m, 2H), 3.63 (quint, 1H, J=6.2 Hz), 2.94-2.81 (m, 2H), 2.00-1.89 (m, 1H), 1.76-1.68 (m, 1H), 1.59 (d, 6H, J=6.8 Hz) 1.53-1.31 (m, 4H), 1.22 (d, 3H, J=6.2 Hz).

Step 4: A mixture of (1R)-1-{1-[2-(1-methylethyl)-2H-tetrazol-5-yl]-4-piperidinyl}ethanol (48 mg, 0.2 mmol), triphenylphosphine (105 mg, 0.4 mmol), di-tert-butyl azodicarboxylate (92 mg, 0.4 mmol) was dissolved in $CH_2Cl_2$ (5 mL) and treated with 6-[4-(methylsulfonyl)phenyl]-3-pyridinol (prepared as in Example 100, Step 5, 50 mg, 0.2 mmol) and the mixture was stirred at room temperature for 14 h. The reaction was extracted with $CH_2Cl_2$, washed with 2M $Na_2CO_3$, and then the organic layer was treated with SCX column. The MeOH/$CH_2Cl_2$/$NH_3$ elution was concentrated and the residue was purified by chromatography on a silica gel column using EtOAc/$CH_2Cl_2$ gradient (0 to 100%) to give 55 mg (55%) of the title compound as a white solid. Enantiomeric excess was not determined. $^1$H NMR (400 MHz, DMSO-$d_6$): 8.42 (d, 1H, J=3.0 Hz), 8.34-8.23 (m, 2H), 8.04 (d, 1H, J=8.8 Hz), 7.99 (d, 2H, J=8.6 Hz), 7.56 (dd, 1H, $J_a$=8.8 Hz, $J_b$=3.0 Hz), 4.88 (septet, 1H, J=6.7 Hz), 4.52 (quint, 1H, J=6.1 Hz), 4.11-3.91 (m, 2H), 3.25 (s, 3H), 2.97-2.77 (m, 2H), 1.93 (d, 1H, J=13.2 Hz) 1.89-1.71 (m, 2H), 1.49 (d, 6H, J=6.7 Hz), 1.46-1.31 (m, 2H), 1.27 (d, 3H, J=6.1 Hz); LRMS (ESI), m/z 471 (M+H).

Compound 191

2-[((1S)-1-{1-[2-(1-Methylethyl)-2H-tetrazol-5-yl]-4-piperidinyl}ethyl)oxy]-5-[4-(methylsulfonyl)phenyl]pyrazine

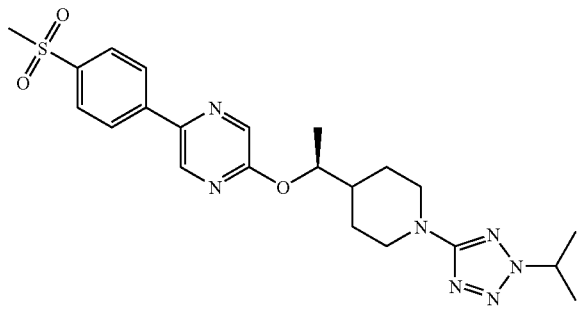

The title compound (145 mg, 58%) was prepared from 5-[4-(methylsulfonyl)phenyl]-2-pyrazinol (and tautomers thereof) (prepared as in Example 145, Steps 1-2, 125 mg, 0.5 mmol) and (1R)-1-{1-[2-(1-methylethyl)-2H-tetrazol-5-yl]-4-piperidinyl}ethanol (prepared as in Example 190, Step 3, 120 mg, 0.5 mmol) in a manner similar to Example 190, Step 4. Enantiomeric excess was not determined. $^1$H NMR (400 MHz, DMSO-d$_6$): 8.91 (d, 1H, J=1.4 Hz), 8.41 (d, 1H, J=1.4 Hz), 8.34-8.26 (m, 2H), 8.07-7.99 (m, 2H), 5.13 (quint, 1H, J=6.2 Hz), 4.87 (septet, 1H, J=6.7 Hz), 4.06-3.91 (m, 2H), 3.26 (s, 3H), 2.95-2.78 (m, 2H), 1.96-1.71 (m, 3H), 1.49 (d, 6H, J=6.7 Hz), 1.45-1.35 (m, 2H), 1.32 (d, 3H, J=6.2 Hz); LRMS (ESI), m/z 472 (M+H).

Example 192

2-[2-Fluoro-4-(methylsulfonyl)phenyl]-5-[((1S)-1-{1-[2-(1-methylethyl)-2H-tetrazol-5-yl]-4-piperidinyl}ethyl)oxy]pyridine

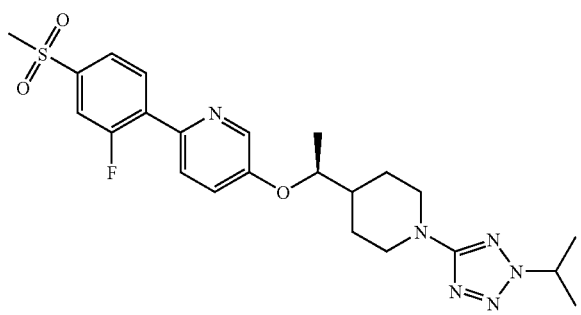

Step 1: Oxone® (9.05 g, 14.7 mmol) was added to a solution of 6-[2-fluoro-4-(methylthio)phenyl]-3-pyridinol hydrochloride (prepared as in Example 176, Step 1, 2 g, 7.4 mmol) in acetone (45 mL) and water (15 mL) at room temperature. The mixture was stirred at room temperature overnight. The reaction was filtered to remove the solid, and washed by CH$_2$Cl$_2$. The filtrate was brought to pH=7 with 2M Na$_2$CO$_3$ and was extracted with CH$_2$Cl$_2$. The organic extract was washed with brine, dried over Na$_2$SO$_4$, and evaporated to dryness. The residue was treated with a small amount of CH$_2$Cl$_2$ and sonicated, and then the solid was collected by filtration and washed with a small amount of CH$_2$Cl$_2$. The filtrate was evaporated to dryness again, treated with a small amount of CH$_2$Cl$_2$ and sonicated. The resulting solid was collected and washed by a small amount of CH$_2$Cl$_2$. The solids were combined to give 1.35 g (65%) of 6-[2-fluoro-4-(methylsulfonyl)phenyl]-3-pyridinol as a pink solid.

Step 2: The title compound (48 mg, 45%) was prepared from (55 mg, 0.21 mmol) and (1R)-1-{1-[2-(1-methylethyl)-2H-tetrazol-5-yl]-4-piperidinyl}ethanol (prepared as in Example 190, Step 3, 49 mg, 0.21 mmol) in a manner similar to Example 190, Step 4. Enantiomeric excess was not determined. $^1$H NMR (400 MHz, DMSO-d$_6$): 8.46 (d, 1H, J=2.8 Hz) 8.24-8.13 (m, 1H), 7.94-7.79 (m, 3H), 7.58 (dd, 1 H, J$_a$=8.9 Hz, J$_b$=2.8 Hz), 4.88 (septet, 1H, J=6.7 Hz), 4.52 (quint, 1H, J=6.1 Hz), 4.07-3.92 (m, 2H), 2.90-2.85 (m, 2H), 1.95-1.83 (m, 1H), 1.88-1.71 (m, 2H), 1.49 (d, 6H, J=6.7 Hz), 1.45-1.33 (m, 2H), 1.28 (d, 3H, J=6.1 Hz); LRMS (ESI), m/z 489 (M+H).

Example A

In Vivo Effects of GPR119 Agonists on Incretin Hormone Release and Glucose Homeostasis in Mice GPR119 Agonists Improves Glucose Tolerance in Normal Mice Male C57/BI6 mice of 9 weeks of age were fasted for 16 hrs and randomly grouped (n=10) to receive vehicle (0.5% HPMC/0.1% Tween), the products of Examples 77 and 83 (30 mg/kg) or a positive control (10 mg/kg), namely vildagliptin, a DPP-IV inhibitor known to stimulate glucose-dependent insulin. Vehicle or compounds were delivered orally via a gavage needle (p.o. at 10 mls/kg). The effect of the GPR119 agonists on glucose homeostasis was assessed by conducting an oral glucose tolerance test (OGTT; 2 g dextrose per kg body weight) one hour after administration of vehicle or test compounds. Whole blood glucose levels were determined prior to compound administration, immediately before and 10, 20, 30, 45, 60, 90 and 120 after glucose administration, using a Glucometer (Freestyle, Therasense).

Table 1 summarizes the glucose excursions during the OGTT as the average baseline corrected glucose area under the curve (cAUC; ±s.e.m.) from the animals in each treatment group. These results illustrate that compounds of the present invention, as demonstrated with the products of Examples 77 and 83 and the positive control DPP-IV compound significantly lowered the glucose area-under-the curve (AUC) over the 120 minute time course of the experiment:

TABLE 1

Baseline corrected Glucose area under the curve (cAUC) during an oral glucose tolerance test in C57BI6/J mice conducted one hour after oral administration of compounds or vehicle:

| Treatment | Dose (mg/kg) | Glucose cAUC (mg/dl * min) | % of Vehicle | n | P-value vs Veh |
|---|---|---|---|---|---|
| Vehicle | | 8718 ± 330 | | 10 | |
| Example 77 | 30 | 6884 ± 694 | 21% | 10 | <0.05 |
| Example 83 | 30 | 6754 ± 286 | 23% | 10 | <0.05 |
| vildagliptin | 10 | 4185 ± 455 | 52% | 10 | <0.0001 |

Example B

GPR119 Agonists Elevate GIP and GLP-1 in Normal Mice

Male C57/BI6 mice 10 weeks of age were fasted for 15 hrs and randomly grouped (n=6-10) to receive vehicle (0.5% HPMC/0.1% Tween) or a GPR119 agonists of the present invention at 30 mg/kg. 1 hr after compound administration blood was collected by cardiac-stick following iso-fluorane aneasthesia. Blood for analysis of plasma levels of total GLP-1 and total GIP was placed in a $K_2$-EDTA containing tubes supplemented with a DPP-IV inhibitor to prevent degradation of the incretin hormones (30 □M final concentration). Total GLP-1 was determined using an assay from Meso Scale Discovery (Gaithersburg, Md.). GIP was determined using an ELISA assay from Linco (St. Charles, Mo.). For each treatment group Table 2 summarizes the average plasma levels of total GLP-1 (±s.e.m.) from the number of animals in each treatment group as indicated.

TABLE 2

Total GLP-1 levels in C56BI6/J mice, one hour following oral administration of compounds or vehicle:

| Treatment | Dose (mg/kg) | Total GLP-1 (pg/ml) | P-value vs Veh | Fold change vs. Vehicle | n |
|---|---|---|---|---|---|
| Vehicle |  | 2.3 ± 1.2 |  |  | 8 |
| Example 77 | 30 | 7.5 ± 2.0 | <0.0001 | 3.3 | 10 |
| Example 83 | 30 | 6.8 ± 1.8 | <0.0001 | 3.0 | 6 |

Table 3 summarizes the average plasma levels of total GIP (±s.e.m.) from the number of animals in each treatment group as indicated.

TABLE 3

Total GIP levels in C56BI6/J mice measured one hour following oral administration of compounds or vehicle:

| Treatment | Dose (mg/kg) | Total GIP (pg/ml) | P-value vs Veh | Fold change vs. Vehicle | n |
|---|---|---|---|---|---|
| Vehicle |  | 83 ± 13 |  |  | 8 |
| Example 77 | 30 | 182 ± 12 | <0.0001 | 2.2 | 10 |
| Example 83 | 30 | 275 ± 29 | <0.0001 | 3.3 | 6 |

Review of Examples A and B

These results illustrate that the GPR119 agonists of the present invention, as illustrated by Example 77 and Example 83, increase total circulating GLP-1 and GIP levels 1 hr after giving the GPR119 compound compared to vehicle. Treatment with GPR119 agonists resulted in a 3-fold increase in total GLP-1 and 2-3 fold increase in total GIP levels. In humans treated with DPP-IV inhibitor, increases in GLP-1 and GIP levels of similar magnitudes improves β-cell function in patients with type 2 diabetes which can be expected to improved glycemic control following long term treatment.

REFERENCES

Reimer M K, Holst J J, Ahren B (2002) Long-term inhibition of dipeptidyl peptidase IV improves glucose tolerance and preserves islet function in mice. Eur J Endocrinology 146 (5):717-727

Mari A, Sallas W M, He Y L, Watson C, Ligueros-Saylan M, Dunning B E, Deacon C F, Holst J J, Foley J E. (2005) Vildagliptin, a dipeptidyl peptidase-IV inhibitor, improves model-assessed beta-cell function in patients with type 2 diabetes. J Clin Endocrinol Metab. 90(8):4888-4894

Ristic S, Byiers S, Foley J, Holmes D (2005) Improved glycaemic control with dipeptidyl peptidase-4 inhibition in patients with type 2 diabetes: vildagliptin (LAF237) dose response. Diabetes, Obesity and Metabolism 7 (6): 692-698

Example C

Tests for Agonists of GPR119

The assay consists of CHO-K1 6CRE-luciferase cells that stably express human GPR119 receptor plated at 15000 cells/well in Dulbecco's Modified Eagle Medium: Nutrient Mixture F-12 (DMEM/F12), 5% Fetal Bovine Serum (FBS), 2 mM I-glutamine in black 384-well assay plates. On the following day, the media is removed by aspiration and replaced with 20 L of DMEM/F12, 2 mM I-glutamine (no FBS) utilizing a Matrix Multidrop. Test compounds (25 μL) are then pipetted into the assay plate using a Packard Minitrak. The plates are then incubated for 5 hours at 37° C. Under subdued light conditions, 15 μL of a 1:1 solution containing SteadyLite™ and Dulbecco's Phosphate Buffered Saline with 1 mM $CaCl_2$ and 1 mM $MgCl_2$ is added to the plates using a Matrix Multidrop. Plates are then sealed with self-adhesive clear plate seals and the amount of luciferase generated is quantified in a Wallac Viewlux™. This assay system was validated using known GPR119 agonists described in WO2004/065380 A1. Compounds are also tested in the same manner against cells without the GPR119 receptor so as to check for false positives.

What is claimed is:

1. A compound 5-[({1-[3-(1-Methylethyl)-1,2,4-oxadiazol-5-yl]-4-piperidinyl}methyl)oxy]-2-[4-(methylsulfonyl)phenyl]pyridine

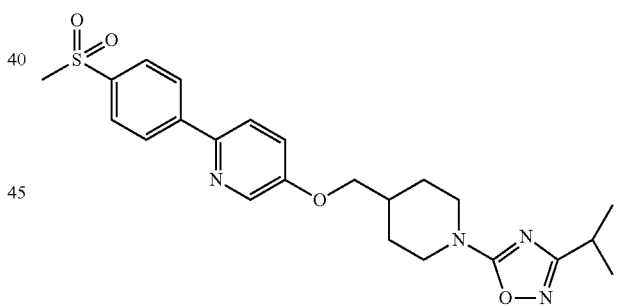

or a pharmaceutically acceptable salt thereof.

2. A pharmaceutical composition comprising 5-[({1-[3-(1-methylethyl)-1,2,4-oxadiazol-5-yl]-4-piperidinyl}methyl)oxy]-2-[4-(methylsulfonyl)phenyl]pyridine or a salt thereof and at least one pharmaceutically acceptable carrier, diluent, or excipient.

3. The pharmaceutical composition of claim 2 in a tablet.

4. A method for the treatment of metabolic disorder or condition comprising the administration of a compound according to claim 1, wherein the metabolic disorder or condition is type II diabetes.

5. A process for the preparation of a pharmaceutical composition comprising admixing a compound of claim 1 or a salt thereof with at least one pharmaceutically acceptable carrier, diluent, or excipient.

* * * * *